US011459567B2

(12) United States Patent
Elizalde et al.

(10) Patent No.: US 11,459,567 B2
(45) Date of Patent: Oct. 4, 2022

(54) SPECIFIC SIRNA MOLECULES, COMPOSITION AND USE THEREOF FOR THE TREATMENT OF TRIPLE NEGATIVE BREAST CANCER

(71) Applicant: Patricia Virginia Elizalde, C.A.B.A. Buenos Aires (AR)

(72) Inventors: Patricia Virginia Elizalde, C.A.B.A. Buenos Aires (AR); Maria Florencia Chervo, Buenos Aires (AR)

(73) Assignee: Patricia Virginia Elizalde, C.A.B.A. Buenos Aires (AR)

( * ) Notice: Subject to any disclaimer, the term of this patent is extended or adjusted under 35 U.S.C. 154(b) by 0 days.

(21) Appl. No.: 16/910,481

(22) Filed: Jun. 24, 2020

(65) Prior Publication Data

US 2021/0403914 A1 Dec. 30, 2021

(51) Int. Cl.

*C07H 21/02* (2006.01)
*C07H 21/04* (2006.01)
*C12N 15/113* (2010.01)
*A61P 35/00* (2006.01)
*A61K 9/00* (2006.01)
*A61K 31/713* (2006.01)
*A61K 45/06* (2006.01)
*C12Q 1/6886* (2018.01)

(52) U.S. Cl.

CPC ........ *C12N 15/1135* (2013.01); *A61K 9/0019* (2013.01); *A61K 31/713* (2013.01); *A61K 45/06* (2013.01); *A61P 35/00* (2018.01); *C12N 15/113* (2013.01); *C12Q 1/6886* (2013.01); *C12N 2310/14* (2013.01); *C12N 2310/315* (2013.01); *C12N 2310/32* (2013.01); *C12N 2310/321* (2013.01); *C12N 2310/3515* (2013.01); *C12N 2320/31* (2013.01); *C12N 2320/32* (2013.01); *C12Q 2600/156* (2013.01); *C12Q 2600/158* (2013.01)

(58) Field of Classification Search

CPC .......................... C12N 15/113; C12N 2310/14

See application file for complete search history.

(56) References Cited

U.S. PATENT DOCUMENTS

2004/0018176 A1 * 1/2004 Tolentino ................ A61P 17/00 424/93.21
2017/0044540 A1 * 2/2017 Saetrom et al. ..... C12N 15/113

OTHER PUBLICATIONS

Elbashir et al. (The EMBO Journal, vol. 20, No. 23, pp. 6877-6888, 2001).*
Nakanishi, K. "Anatomy of RISC: how do small RNAs and chaperones activate Argonaute proteins?" (2016) Wiley Interdiscip Rev RNA 7(5): 637-660.
Kang, M. R. et al., "Intravesical Delivery of Small Activating RNA Formulated into Lipid Nanoparticles Inhibits Orthotopic Bladder Tumor Growth" (2012) Cancer Res 72(19): 5069-79.
Ghanbarian, H. et al., "Small Activating RNAs: Towards the Development of New Therapeutic Agents and Clinical Treatments" (2021) Cells 10(3): 591.
Setten, R.L. et al., "Development of MTL-CEBPA: Small Activating RNA Drug for Hepatocel-lular Carcinoma" (2018) CurrPharm Biotechnol. 19(8): 611-621.
Li, L.C. et al., "Small dsRNAs induce transcriptional activation in human cells" (2006) Proc Natl Acad Sci USA 103(46):17337-42.
Janowski, B. A. et al., "Activating gene expression in mammalian cells with promoter-targeted duplex RNAs" (2007) Nat Chem Biol 3(3): 166-73.

* cited by examiner

*Primary Examiner* — Amy H Bowman
(74) *Attorney, Agent, or Firm* — Volpe Koenig

(57) ABSTRACT

The present invention generally relates to the field of molecular biology and RNA interference (RNAi). More specifically, the present invention relates to specific siRNA molecules, compositions and uses thereof, as well as methods of treating cancer and methods of inhibiting cancer cell proliferation, particularly methods of treating breast cancer. Yet more particularly, the methods of the present invention are methods for inhibiting growth of triple negative breast cancer (TNBC). In a preferred embodiment, the invention provides specific siRNA molecules, comprising a sequence selected from SEQ ID NO: 1 and SEQ ID NO: 2, and from any other sequence having a sequence identity greater than 90% between the siRNA and the portion of the target gene. Such siRNA molecules are suitable for the treatment of breast cancer, particularly, TNBC.

31 Claims, 47 Drawing Sheets

Specification includes a Sequence Listing.

LR-PCR1

LR-PCR2

Nested PCR

Conventional PCR

SEQUENCE LISTING

```
<160> NUMBER OF SEQ ID NOS: 53

<210> SEQ ID NO 1
<211> LENGTH: 19
<212> TYPE: RNA
<213> ORGANISM: Artificial Sequence
<220> FEATURE:
<223> OTHER INFORMATION: SpT3 siRNA #1

<400> SEQUENCE: 1

gugagauacu ucaaagauu                                                  19


<210> SEQ ID NO 2
<211> LENGTH: 19
<212> TYPE: RNA
<213> ORGANISM: Artificial Sequence
<220> FEATURE:
<223> OTHER INFORMATION: SpT3 siRNA #2

<400> SEQUENCE: 2

caaagauucc agaagauau                                                  19


<210> SEQ ID NO 3
<211> LENGTH: 40579
<212> TYPE: DNA
<213> ORGANISM: Homo sapiens

<400> SEQUENCE: 3

aagttcctgt gttctttatt ctactctccg ctgaagtcca cacagtttaa attaaagttc      60

ccggattttt gtgggcgcct gccccgcccc tcgtccccct gctgtgtcca tatatcgagg     120

cgatagggtt aagggaaggc ggacgcctga tgggttaatg agcaaactga agtgttttcc     180

atgatctttt ttgaggtagg gctgtttact gtcaccaccc ctgtcggatt ttacttccta     240

aacgtacctg taactatcca cttctctcca tctcttctgg caccaccctg gttaaagaca     300

ccatcatgtg tcgccaagac agccgcagta gcttcttaat ggctctccct gcctctactt     360

ttgcctcttc caacctgcgc tccattttga aaaattaaaa tttgcccata tcactttttt     420

tttcttaaaa ttatttactg gctcccaatt accttgggta aaatacagtc tccacaaacc     480

ctgcctgatt tggcccctgt ccactggtct ccctcactcc cttgctccag acccgcttca     540

gagggctatg tccctcaagc ttcctgactg cctggcctgg tctgaatcac tcactcttct     600
```

```
tttttcttct agtcgcaatt gaagtaccac ctcccgaggg tgattgcttc cccatgcggg    660
gtagaacctt tgctgtcctg ttcaccactc tacctccagc acagaatttg gcttatggta    720
ggcgctaact gcgtttgttt gttcttctgt ttaatgaatg aacagcatac atcaacataa    780
gaacttgaca aatccagggc tgtaaaatca tcagtatggt tctgcactga gatcggagag    840
aagtaatatt tctaggaaaa ttaggaaccc tgggaacagg acgcttgctt tagtatcctc    900
tccctgctca cctcccctgc actcccatca gcaccgaccc acacccaatc tcatagaagc    960
cttgtagcta aggatcaccc tttctcctcc cccactctcc tcaccccttg tcaacttttc   1020
tttttcgtcc tgggggttgg aatgagtaag aagtagcctg ggattccatt cactcactta   1080
acaaacattt ctgagtcctt agctctagca ccttgctaag caaggcaaaa tctccaggag   1140
gcaccattca cattgcattt tctgtgaatg gtgctctggg gagcagcatt cacattgcct   1200
tttctgtgaa tggcaaattc ttccagttaa atataacatg aatagtgtcc cctggagttg   1260
accacccaac tgatactgac tgagaagctg aaatgaacaa aacaacccct tagccctcca   1320
ggagctgacc ggaaatccag tgctaatact actttgcatc ttacagatta gttcttttac   1380
aatactgttt tttttctttt tttcatttca ttttgtcctt tctgtgactc tgggatgagt   1440
ctttttatga ggatcctcat ataaagatgg acatttagga ttaaagagga tgaaatcctg   1500
acaaaatagg gagtctcccc tttagaaaat tcctaagtaa ggctgggggt ggtggctcac   1560
gcctgtaatc ccagcacttt gggaggccga ggcggacgga tcacctgagg ttaggagttt   1620
gagaccagcc tgaccaacat ggagaaaccc catctctact aaaaatacaa aattagttgg   1680
gtgtggtggt gcatgcctgt aatcccagct actcaggagg ctgaggcagg agaatcgctt   1740
gaacccaggg aggcagaggt tgtggtgagc caagattgcg ccatcgcact ccagcctggg   1800
caacaagagc gaaactcaaa aaaaaaaaaa aaaagaaaaa gaaaattcca attttgaagg   1860
cctcatccta tattatgtca aacatactga aatgcagtaa cgccccacat taaataagat   1920
ttataaataa ctatacatat atataattca atctaattgc tgttaatagt tgacatattg   1980
ctacatttat atacatttag ttaaaaaaaa ttttttttcc cagacagcct ctcactcttt   2040
cacctagact gaagtgcagt ggcatgatca cgactcactg caacctcaac ctcccagact   2100
caagtgatcc ttccatctca gcctcctgag tagctgggac tgcagcatgc gccactatgc   2160
cctgctaatt tttttaattt tttgtagaga cacggtcttg ctatgttgcc tagactggtc   2220
tccaattcct gggctcgagt gatcctcccg cctcaacctc ccaaagtgct gggattacgg   2280
gcgtgagcca tgccacacgg ccataaaata ttaattttcg cagctttctt atattttaga   2340
actaacaatg gaaatttgtt cgggtctaaa gtatttcaga ggtccttgaa aacccatgcc   2400
tacatacctg atggaaaaag caatcctagg ttaatggtgg aagtgggagt agagacttct   2460
gttctgttga cttcttggaa gatggggtac tgtctctctg ggacagctct tgagaatttc   2520
cctgccagca cagccccaga taacaatctc tagatggcga ttacctggcc tctcttccca   2580
actttctagc ctggagcccc tagttctccc ctgagcctcc ttagcttgtc cttcttccta   2640
acttgtattt ggcttcagat gtgatccaca gtctgaaaag tcactaattc attccttcaa   2700
ctcaggctta ttgagtcctc ctgtgtatca gccattgtac tcatgggga aaaaaaagac    2760
aaagcatatg ttaatagtag agtgtgctgg acaggcacag tggctcatgc ctgtaatccc   2820
agcactttgg gagggcgagg caggtggatc atctgaggtc aggagttcga gaccagcctg   2880
acctaacatg gagaaactcc tgagatcgtg ccattgcact ccagcctggg caacaagagc   2940
```

-continued

```
aaaactccgt ttcaaaaaaa aaaaaaaaag tatagtgtgc taaaggctca acggcaagct   3000
gaccatgttc ttagatcaaa attggtagag agtctacaat gtgggttcct tattcatcaa   3060
atgtttatta agtttaccat gtgcaagtct ctgggaacag agtgatgaac aaggcactgt   3120
acttttcatg gtcagaggag ggaaacaggc cataaacaag tgtcaaacaa aagactgaag   3180
ccaggtgcgg tggctcacat ctgtaatccc agcactgtgg gaggccaagg caggcggatc   3240
atgagatcag gagatcgaga ccatcctagc caacatggtg aaaccccatc tctactaaaa   3300
atacaaaaaa attagctggg catggtggca cgtgcctgta atcccagcta ctccggaagc   3360
tgaggcagga gaattgcttg aaccagggag ttggaggttg cagtgagcct ggattatgcc   3420
actgcactcc agcctggtga cagagcgaga ctccatctac attaaaaaaa aaaatatata   3480
tatatatata tacacacaca cacacacaca cacacacata ccctctaacc caggaatttc   3540
actcctaggt atacctacat aagctccagt atacctaaac aagtgcaaat ttgtttaagt   3600
acagttattt gtggtagcat tagtcattgt tttcaatagc aagaagaaaa aggaaacaac   3660
taaatgtcca tcaataggga atgaattata ttaatggagg gagagccata caatggaagg   3720
ctgaacagaa attaatagga atggggcaga tttgtaatgt actagcatgg taaaaccttc   3780
atgatagata tagatataga tatagatata gatatagata tatatacata tacatataca   3840
tatacatata catatatata tatatatata tatatctctt gtgtctcagc ctcccgagta   3900
gctgggatta caggtgtgtg ccaccacatc cggctaattt ttgtattttt tagtagagac   3960
agggcttcac catgttggta aggctgtctt gaactcccga cctcaggtga tccacctgtc   4020
tcagcctccc aaagtgctgg gattataggc atgagccatc acacctggcc aaatattttt   4080
gataagtatc aagtgcacag tgcagaacaa aatatgtgtg tgtgtatgca tgtgtatgta   4140
cacctataca cttatataca gtaccccatg tgaagaaaaa taagggtacg tgttatgcgc   4200
gtagtattat ggttgttatt tttgagaata tatctagaaa gataaaaaag aaagtggaaa   4260
tagttcttgc ctctggtggg aagtgggact atgtgcctga tcaataggga agtaaggaac   4320
actttttttt ttttttttta aacggagttt ttgctcttgt tacccaggtt ggagtgcaat   4380
ggcgcgatct tagctcactg caacctctgc ctcccaggtt caagcgattc tgctgcctca   4440
gcctcctgag tagctgggat tataggcatg cgcctccacg cctggctaat tttgtatttt   4500
tagtaaagat ggggtttctc catgttggtc aggctggtct tgaactcccc acctcaggtg   4560
atccgtccgc ctcagcctcc caaagtgcta ggattacagg cgtgagccac cgtgcctggc   4620
caggaacgct ttttattttt gtacctttaa aagtgtgtac cgtctgtgta tataatcagt   4680
taaaaacaaa gaaaagctga gtgtggtggc tcatgcctgt aatcccagcc cttaaggagg   4740
ccgaggccgg cggcagatca cctgaggtca ggagttcaag accggcctga ccaaaacggt   4800
gaaaactcat ctctacaaaa acataaaaat tagccaggca tgatggcaag tgcctgtaat   4860
cccagctggt tgggaggctg aggtgggaga cttgcttgaa cctaggaggc agagattgca   4920
gtgagccaag actgtaccac tgcactccag cctgggcaac agagcaagtc tctgtctcaa   4980
aacaaaaaca aaaacacaaa gaaaaaatgt aaaacaattt catgcagtag caagcatcga   5040
gttaaataca gttgaccctt gaacaacaca ggtttgaatt gcacgggtcc atttatactc   5100
acatttcttc cacctctgcc acccccaaaa tagcaagacc aaccccatct cttttccttt   5160
ctcttccccc tcctcagcct actcaatgtg aagatgatga ggatgaaaac ctttgtgatg   5220
atccacttcc acttaatgaa tggtaaatat gttttttctt acttatgatt ttcttagtag   5280
cattttcttt tctctagctt cctttattgt aaaaatacag tatataacac atatcacata   5340
```

caaaatgtgt gtaaatggac tgtttgctat tgataagtat tctggtaaac agtagactat 5400
tagttttttt tgttttgtga caaggtctcc ctctgtcgcc cagcctggaa tgccgtggtg 5460
tgatcatggc tcactgcagc caaaaacttc tgggctaaag caatcctcta ctaaaaatac 5520
aaaaattagc caggcatggt ggtgcgcttc tgtaatccca gctactcagg aggctgaggc 5580
aggagaattg cttgaacccg ggaggcagag gttgcagtga gctgagattg caccgttgca 5640
ttccagcctg gacaacagag cgagactcca tctcgaaaat aaaataataa taataataat 5700
aataataata ataataataa tagggctggg tgtggtggct catgcctgta atcccagcac 5760
tttgggaggc caaggtggac agatcacctg aggtcaggag tctcaattaa aaaataaata 5820
ggccgggcac agtggctcat gcccataatc ccagcacttt gggaggccga ggtgggcaga 5880
tcacctgagg tcaggagttt gagaccagcc tggccaacac ggagaaacgc tgcctctatc 5940
aaaaatacaa aaattagctg gatgtggtgg tgcatgctat aatcccagta ataccagcta 6000
ctcggaaggc tgaggcagga gaatcactcg aatccgggac acggaggttg cagtgagccg 6060
acatcatgcc actgcgctcc agcctgggtg acagtgagac tctgtctcag aaaaaaaaaa 6120
aaaaaaaaaa aaaaaaaaaa aaaatatata tatatatata tatatatata tatatatata 6180
tatatgtgtg tatatatata tatatacaca tatatatgtg tatatatata tacacacaca 6240
catatatatg tgtatatata aaataaaata aataataata aaacatttac tttggctgct 6300
gttgctgcgg ggagaattgc agggtgtcaa aagtagcact ggtggagggg tagtgatcaa 6360
agtctggtgc tttagcccaa aggagaaatg atagagactc agactagctg gtgatggagg 6420
tagaataagc ataaatgtat caaaaagagg agttgataga tcttaaagaa tgattggatt 6480
tgaagggcaa aggaagagaa gaatcaacca ggtgggttca gtgaatgaaa ccatcagaaa 6540
cgaattgtcc cctgaaatca agactttgtg attgccatag ttgtatgctt ctcaaaggtt 6600
cctcgtctcc tcttccttgg accaaaagtc agaggcaaga atgccctcat tcatacccca 6660
gtggtctata cctccagcag caagtcgagt gagcaagtga tgtcctgaaa ggcccagtgg 6720
atcagtggaa tgaagcgggc aggaagactt agtgctcctg aaacaaggaa tccagaatcc 6780
aggagaagga tggctcagtg gggctttcaa gggacaagta tgggggttga aggggtcact 6840
gtccctatac caaatccgaa aatattgtga ccaggaacca ttctgtccaa ctcttctatt 6900
tcaggtggca aagcaaagct atattcaaga ccacatgcaa agctactccc tgagcaaaga 6960
gtcacagata aaacgggggc accagtagaa tggccaggac aaacgcagtg cagcacagag 7020
actcagaccc tggcagccat gcctgcgcag gcagtgatga gagtgacatg tactgttgtg 7080
gacatgcaca aaagtgaggt gagtcgcagg acagaagagt gctttttgtt tcagcagagc 7140
agcctgggga gagataaaag ctactcctgg ggcctgggcc tgcattcctg agatgtgggt 7200
aagaggggcc cagggtcaga gtgtctggca agcttggctc tgcccctttg ctgtcctgga 7260
gactagggct aatcctgggc tcagggagtg gcctccccat ggttaggata caagtgctca 7320
tcaagggcca cccctaggaa ggaccaattt tcctatcaga agcttctaag ttatcctcct 7380
ttggcccaaa gggacacctc aagcctactc tgaggaactc tttccaatga actaattcct 7440
acagtcactt ccccagcaac ctgtgcctca gcctcaaggc actgtggggt aggcctcagt 7500
ttgtggcctg gacatcggac tgtggaccag acgactcctc ccgatttctg tttgttttca 7560
gtcctctgac cccaagctgg ctggtgaagt aggtagaggg aggagacttt ggtgcatgca 7620
tacacacaca cacacacaca cacacacaca cacacacaca cacacacaca cacacgtctc 7680

-continued

```
ctgtgccccc cagtctccat ggctggtcaa tgattgactg gcatttcaca ggccgctggt   7740
tgcagcccca gcctgttgac ttagaggtca ccctcggaag ctagagccct gtcctgcctc   7800
ttcagtgtca gtggtcactc cactgcccac aggctggggt cttgggcaaa acacacgcat   7860
ctgccctgat ctgagtttgc tgccctctgt cccgcagtca gccccactct gttcccactc   7920
cctctcccca gcccccctagc tagacccctc tcaccagcac ccctttccct tccctgaggg   7980
tccccctcgc tgtctttgtc cctcagacat cctctttcct gggctctcct gccaggccct   8040
gctggaggga cagttaagga ggaaatcgaa tcagcagcgc ccacccctgc ccccccttcct   8100
ctcctcttgt cagacaccag acgaggtttt ttcctctggc ttcccagctc tgaatgggct   8160
cattcttttt cagaggctcg gcccctctcg agcctcctcc ccagggcgtg agttctgacc   8220
ccagctcctc cccccatccc cactccagcc ccctctccag cttgctccac cctctctacc   8280
gcccaccggg actgggcatt gtctgccagt ccgggtttct tcctgggatt tgggatgcag   8340
agaggatggg tttgcttggg cggggggggtg gagagtgaag gggggaagca ggatctttgt   8400
agagggaggg acctacagtt acctggactt ctttcctctg tctcccctct tggtaccctt   8460
gactggggct cttgagggta atgggtgaag ccaaatctgc catggctcag ttcccagctc   8520
agctctgtga ccttgggaaa gttcctttag ctcgtggaat ctcaaggctc aaggttcctc   8580
ttctgcaaaa tggggaatga taacacctgc ctcctctgga gtcttgggga ctcagtgttc   8640
tgaggaacgt ggctgtaggt cagagtggca cagagtaggg tccaatgaag catggcgtcc   8700
acagtagctt tcctgactgg actaaccttt ccggacacaa cagcagggca ggggtggggc   8760
ctggggagaa aggacacctc taaccctgat cctaacatcc cgatggcctc taaggctgcc   8820
tgcacactca tccaggtgca agccctccaa ggtgtggtgt gatgaaccag tgactcctgg   8880
agccaggtca gcgcatcctc ttcccgcagg gctgtaagct gcaggactga gaggcaggtt   8940
gaccaggtcc tgggctggat gatggggtga gagtaagggg tcagttttga tacatgccca   9000
acttttctct ctagccctaa gacatcctgg gcaaattgct tacctcagtt cccctgatcc   9060
tcaccctaac cctaacacca gctcaagaga aaatagggat attgatggcc atccagaagg   9120
gctgctgtgt tccatacaca gcaatatttc tcgaatgttt gtgacagcgg tccaaggaat   9180
aagttaattt tacattatca ctctggatac ctgtacaaaa ctccacctta tccttactat   9240
atgaatgtgc tagggttgtt tttttgtttt gttttttttt tttttttttg agacagagtt   9300
tcgctcttgt tgcccaggct ggagtacaat ggcgcgatct tggctcaccg caacctccgc   9360
ttcccaggtt caagcgattc acctgcctca gccttcccga gtagctggga ttacaggcat   9420
gcgccaccat gcccggctaa ttttgtgttt ttagtagaga cagggtttct ccatgttggt   9480
caggctggta ccaaactccc gacctcaggt gatccacctg ccttggcctc ccaaagtgct   9540
gcaattacag gcatgagcca ccgcacccag ccgtgctagg gtctttttct gttcaattcc   9600
tttctctctc ttgctctctt tctttctttc aatggagtct tactctgtca cccaggctgg   9660
agtgcagtgg caagatctca gctcactgca acctctgccc tctgagttca agcaattctc   9720
ctgcctcagc ctcccgagta gctgggatta caggtgcctg ccaccacacc tagttaattt   9780
ttgtactttt agtagagatg gggttttgtc atgttggcca ggctggtctc gaactcctga   9840
cctcgtgatc tgcctgtctt ggcctcccaa agtgctggga ttacaggcat gagccgccat   9900
actcggccaa ctttgtatta ctttcttaaa gagagtttcc caaattatat aagcttcagg   9960
ccccacaaaa cctagatctg ccccagtata actaaatctg ggaccattta ttgagcaatt  10020
attatgtgcc aagtattgcg ctgagtgctt ccagagcatt atctccttta accccagcat  10080
```

-continued

```
agtatgtcag atgctgtttt acagatgagc caactgagac cagagatgct cagtcacttg  10140
cccaaggtga catgactgat atggaataga gtcaagattt tttttttttt ttttgacacg  10200
gagtctcact ctgtctccca ggctggagtg cagaggcgca atctcagctc actgcaagct  10260
ctgcctccca ggttcacgcc attctcctgc ctcagcctcc tgagtagctg ggactacagg  10320
cacccgccac cacacctggc taattttttg tatttttagc agagacaggg tttcaccgtg  10380
ttagccagga tggtctcgat ctcctgacct cgtgatctgc ctgcctcggc ctcccaaagt  10440
gctggaatta caggtgtgag ccaccgcgac tggccagatt caagatttga acccaggtcc  10500
tcttggtccc agaggcccct gtttctcaac tccctaggat ggcatagcaa cctgtcccac  10560
aagaggtgcc tgctttaagt gtgctcagca catggaagca agtttagaaa tgcaagtgta  10620
tacctgtaaa gaggtgtggg agatgggggg gagggaagag agaaagagat gctggtgtcc  10680
ttcattctcc agtccctgat aggtgccttt gatcccttct tgaccagtat agctgcattc  10740
ttggctgggg cattccaact agaactgcca aatttagcac ataaaaataa ggaggcccag  10800
ttaaatttga atttcagata aacaatgaat aatttgttag tataaatatg tcccatgcaa  10860
tatcttgttg aaattaaaaa aaaaaaaaaa agtcttcctt ccatccccac ccctaccact  10920
aggcctaagg aatagggtca ggggctccaa atagaatgtg gttgagaagt ggaattaagc  10980
aggctaatag aaggcaaggg gcaaagaaga aaccttgaat gcattgggtg ctgggtgcct  11040
ccttaaataa gcaagaaggg tgcattttga agaattgaga tagaagtctt tttgggctgg  11100
gtgcagttgc tcgtggttgt aattccagca ctttgggagg ctgaggcggg aggatcacct  11160
gaggttggga gttcaagacc agcctcacca acgtggagaa accctgtctt tactaaaaat  11220
acaaaaaatt agctggtcat ggtggcacat gcctgtaatc ccagctgctc gggaggctga  11280
ggcaggagaa tcacttgaac cagggaggca gaggttgtgg tgagcagaga tcgcgccatt  11340
gctctccagc ctgggcaaca agagcaaaag ttcgtttaaa aaaaaaaaaa agtcctttcg  11400
atgtgactgt ctcctcccaa atttgtagac cctcttaaga tcatgctttt cagatacttc  11460
aaagattcca gaagatatgc cccgggggtc ctggaagcca caaggtaaac acaacacatc  11520
cccctccttg actatcaatt ttactagagg atgtggtggg aaaaccatta tttgatatta  11580
aaacaaatag gcttgggatg gagtaggatg caagctcccc aggaaagttt aagataaaac  11640
ctgagactta aaagggtgtt aagagtggca gcctagggaa tttatcccgg actccggggg  11700
agggggcaga gtcaccagcc tctgcattta gggattctcc gaggaaaagt gtgagaacgg  11760
ctgcaggcaa cccaggcgtc ccggcgctag gagggacgca cccaggcctg cgcgaagaga  11820
gggagaaagt gaagctggga gttgccactc ccagacttgt tggaatgcag ttggaggggg  11880
cgagctggga gcgcgcttgc tcccaatcac aggagaagga ggaggtggag gaggagggct  11940
gcttgaggaa gtataagaat gaagttgtga agctgagatt cccctccatt gggaccggag  12000
aaaccagggg agccccccgg gcagccgcgc gcccccttccc acggggccct ttactgcgcc  12060
gcgcgcccgg cccccacccc tcgcagcacc ccgcgccccg cgccctccca gccgggtcca  12120
gccggagcca tggggccgga gccgcagtga gcaccatgga gctggcggcc ttgtgccgct  12180
gggggctcct cctcgccctc ttgccccccg gagccgcgag cacccaaggt gggtctggtg  12240
tggggagggg acggagcagc ggcgggaccc tgccctgtgg atgccccgcc gaggtcccgc  12300
ggccggcggg gccagagggg cccggacgag ctctcctatc ccgaagttgt ggacagtcga  12360
gacgctcagg gcagccgggc cctggggccc tcgggcggga gggggcagtt acacggcagc  12420
```

-continued

```
ggctcgagat ggcccatcca agagactggc gctttccagg ctccgagggg ctccgggaac  12480
ttgtcaaaga agttctctga aattgttcag aaagttttcc cgcaaagggt gtattgcgta  12540
gagcgcgcgc gcgcgtttcc cccccttcttg agccccctca agctttctca aagcctttcc  12600
agttggcagc ctccgcctcc ggactggcct gggctggatt ccttgggggg gtcctctgcc  12660
ctgcccctcc tccagcccct ccccgctccc cttcagacga ttttggtttg gttgctcctg  12720
cttctggcgg ggtcgggtgt gtgtgtgtgt ggtggagtgg agggtggcat agcaacctgt  12780
cccaaccaga gccggggagg aaagggtggc ccggagggtg gcctcttgct ggggtctggg  12840
ttgggggcgg gggagacgtt tgctttgaac agattcttgg ggccagctta gggactgtgc  12900
tctgtgactt ttggagcgcg tggaccatgg aggggtgggg gtgggtttct tggggtgtaa  12960
agtgggagag ttcccagaga aggaagctaa gaaataaggc cagatgggag cctagggagg  13020
gctgcgttgt tctgctgcct tttccttggt gctgtgcgtg gggaagggtg agtgggggca  13080
gtgtgtatcc tgacccatct gtccacctgt gtgcattaat cataaaagct aacatatagc  13140
ctgggccagg tatactctgc caggaactgt ttgtggtgtt ttgcatgcat tctcctttaa  13200
tcctagaaca cccctatagt ggaagttctg ccagcattct ggactgagta gcagtccaga  13260
ggttgagtag cagctagtaa gtggtggggt caagatggga ccccaggcag tgcgaccccc  13320
aaccatgcat tcgaaatcgc tatatggatg agtgcacctg gagcaatgag ggacactgct  13380
ccctgagtca ctgggctgca ggggagacaa aatgaaagtg ttctgggagt cgtgggtggt  13440
ctccataggt cagagggtct ggggagggag tgggtgtcat cgtggctgtg tgttgcccga  13500
ggggccctct gtgagtgagt gcatggccgt gttatctctg caggtctacg ccagggtgtt  13560
cctcagttgt gtggtctttg tatttgtgtg tctgggcttt gtgttgccaa acagcagtct  13620
ctctgctgac ttggggacac aggctgaact ctgtcctctg caggaactcc cttaaggtgc  13680
tgggccagat ctgccataaa cagagggagg tagccttcta tggccacgcc ttcttgctga  13740
ggaagaaggt tcctctcttc cagggagtac atccttgccc tccctgtttc ccagacaagc  13800
atcttcacct ctcatcttct gatgagaagg gtgaggccat actgagctgt caggctgagc  13860
tgctgccctt cctcaccttg ggctgggagt tgatcaggga atggcagttg ctgcagagct  13920
ggatttgagg gctgggttct ctggatgggg cctcctcatg tcctcacccc tcaacctgca  13980
ctattgattg tgttgtgcag gagttagtta aaaagtcatt gcacagcctg ggcaacaagg  14040
caaaactctg tacaaaaaat acaaaaatta gttggatgtg attacacgtg cctgtagtcc  14100
cagctactcc ggaggctgag gcaggaggat cacctgagcc caggaagttg aggcttgcag  14160
tgagctgtga ttgcaaatgc tctccagcct gggtgacagt gtgagactcc gtttcagaaa  14220
aaaagtatac cacccagctg cctccagcac ccagatttta cccaaggggt gaggtctggg  14280
gcaggaatgt gggggaaggg gaggcctagg gggagcccca gaggggtcag gatttttctg  14340
aaatcctttc ttagaggtat gggttttaca aattgcagca aatacatcct tttaatcttg  14400
cagaactcct tcatatttta attccagtat gattcttcca acagcctcct ctctttacta  14460
tacttgggga aagtactcat tttatttgtc aagaaaaaaa caattgaaaa gatagggatc  14520
aaatgtaaaa agaaaaaaata cgtggcattc caaagtcaaa cacaaagcat gtttaatttt  14580
ctcgtggttt gggattaccc atattcctgc tgtatgaacc tgtcttgtct taacttttaa  14640
gaaatgtacg gtgtacttcc tatatgctag gtttttatcc atgctttcat ttaatctctg  14700
tgacagtcct gtgaagtagg tgcacagatg agaaaatgga agttcagaga aatgaagcaa  14760
cttatccaag gctcccagct acccagtaat gtccagggaa tttttggact ctgaagagga  14820
```

-continued

```
ggcattaaga ggtggttaga gtcttattcc agccaacaat aatgggttga acaaagcctt  14880
aggggcaggc aggtggccag atgggaggag aagcgctcct cttgttcagg cgaatgacct  14940
ttccatccac ttctctaggc tgtagaaagt ggagctgagc tgggggccct gaggttccct  15000
cttgacttca gagtcctctc ccttcctgtc cagccaatgc ctgtcttcct tttgggccct  15060
accagcatga cagggggctg cgggcaggag gggacagagg ccacgttgac acacagggct  15120
gtgggtgaga gagacagctg aagtgtcagc gtgaggggcc agtgtggggc tgcggctggg  15180
agggctgggg tggggcccag ggtagttgtg cctgtccttg ggtgatggaa tgatctggaa  15240
agagattcct tccctgccct ccacctgtga gaagcccctc tagagtgaca tctccatctt  15300
atgtttggcc acccatcctc cccctgggaa gagagccgag gtggggtaag ggatgtgtac  15360
tctttcaagg agtgggagaa ttattctagc gaatgtttgt gttgtcccag ttctgtttac  15420
aaagcctcgt catgtttaca gatggctgcg caattcatta cctcatttaa ctctcatgta  15480
cctcctctga gggagtaaga gctgttacag ccaagtttag gtcagtaaat attcaccaag  15540
ttgcaggtac tgcagggcat agagatgaat ccgatttagc ttctgccctg gaggtctggg  15600
aacttgctca agatcactca gtgagcagct gagctagggt tctcaactaa agaccctggg  15660
cccaggccct ggtctgatgt caggcctgat acaccaggtg tttgtggtcg gggaatccca  15720
gtgtcacttg aatgggctgt gacattatgg gtctgggaga gctgagcttt ggggacacag  15780
gtcattttac tgtagtattc atggaaacca agggaagtat tggcttttct gctgtgagca  15840
agaggagcag ctggggctgc aagctggtgg ggaggagaga acccacctga gagaaacctc  15900
aggactgggg tcaagtcctg accaccagag tccagagaga catgaaggac tgtgaccagc  15960
tctgagcaga gagatggatt ccatgacctc aactggtccc ttttgttcgg agactcgtga  16020
ctggacttca ttcatccact cattcattca ttcactcagc agacacttat ctagcgctcc  16080
ctgtggctgg tcctgcctca tactgtcttt gctctggaga attggaggtt ggggttcctg  16140
aggggcaggg tcctggagac aaggacactc ctgggtagaa ttaggaccta ccccccagga  16200
aatcaacggg gaccaggtgc cgtggctcac acctgtaatc ccagcacttt gggaggccga  16260
gacgggcgga tcacaaggtc agcagttcag gaccagcctg gccaacatgg tgaaacccgc  16320
ctcaactaaa aatacaaaaa ttagccaggt gtggtgtcag gcacccgtaa tcccagctac  16380
tgaggaggct gaggcaggag aattgcttga acccgggagg cagaggttgc agtgagccga  16440
gattgcgcca ctgcactcca gcctggcgac agggcgagac tccatctcaa aaaaagaaaa  16500
ccaatgggac agggcagata tggggacaat ggtaaggaga tgggagagtg ggagggaggt  16560
gtcaggaaga ccttcttgac ttcatgtagg ctggtggggg tgttagccag caagcctcca  16620
gttccctggg aaccgttctc agggtaccaa ttttaccacc tgtctgcaaa cactttaaga  16680
ttcttaatca gactcaaatt ggccacaaat caggtaaaca aactcactag tggggtgggg  16740
ctaccacccg ttctgaccct ccagcccaac ccagcccagc caccctgccc tccgtagagc  16800
ctgtggtgtt tatcggtggc attgggagaa ttagtgtgta tttatgttgg cgtggggtgt  16860
ggggtggatt tgtgtgtgtg cagttaggcc tagtggaagg aatgtgggat ctgaaggcag  16920
gccagcctga gttccagtcc tgcctgttgc tcacaagctt tatgaggcga gagctaaccc  16980
ctgccagcct cagttgtctt ctttgcaaga tggaggttgc agccccagtc tctggagcat  17040
gttatgcaga tccaccgaga gtgcctgcca ggcacacagt aggtgctcag ctcagttact  17100
gtggcggccc ccactcccca ttgttgttgt tttcctattg cctggcggcc acagctggta  17160
```

-continued

```
tcccttgaaa agggctacag ggggtggagt cggaccctgc cccagccctg tggagaccct  17220
gggcttgggc cagggcctgg ggtctgggcc tgcagacagc tgtgtctata aagcagctga  17280
agggctgagg ccgggggagg tcctggcagc agggcgttat tttgggcctg gcctgccacc  17340
cccagctcct gtttctcttg ggagtctgtt gggggaggaa gtgtggggaa gaggaggggg  17400
tgcaagtggg tgaggcatgg agtggggagg cctccctcag ggacatggac ccttgagttc  17460
tatttctgtt cctccctcct gttcctccct ctttgtcctt atctgcctag agaggtggga  17520
atagaggcca ttctgagtat cactaggaga ccaccagttt gtggccactg gccactggcc  17580
caggcaggga acctgggggc ttgccctacc agcctctccc agcaatctga aggcaggggg  17640
tacctcgtat taccccctag gatttgacct taggctccaa cttgctggga gagcagtgcc  17700
tctggtgtca gaccccaagc cagcccttgt gctgtccctg aatctgcatg tagcctgtgg  17760
gaggcggagc agtgaccggc aggaattctg ggcagctcag gcacctgtgg gcctgagggt  17820
gccctctgcc cccacccttc cgatctcctg ggcaagacac gccaggtgat tcatctcacc  17880
agagcagaaa aacaagttca actgggcact ttaatctccc ctcactggca ggcctggtgt  17940
gagctgctac cccggcgccc ctcaccaggg gtgctttacc tcctctagta ttcctgacct  18000
tagtgggcat ttctggtctc agggatacca ggctggggtc caagtgggcc aggtgtggca  18060
gttcagccct atgccccatg gctgatggct cgcgctgggc aggtatgcag ggctgacgta  18120
gtgcctttgt ggcagcagtt tcgtggcaca cattctgcca gctggttctg gagtcttgcc  18180
ctgaggaggt ggccagggtg agggtgccag cgcaggaacc tttggcgcat gcttcaccct  18240
ggcctgggat ctgcagcctg ggtccagatg cccacaactg gaatctgacg ctccttttct  18300
cttcatgggg gactcccaga ggtctctgca atgaccagag ccccggttgt cccatgcctc  18360
agctgcaact ccagctgacc ctccttcccc actctctggg tggcattacg gggtgtgga  18420
tcccttgcca agaggttggc atgtgggtgt gctggaatgg catagggaga atgcaccgag  18480
tttgtttgct tgggagaggg gcagggggta tccagaagat tcatgattcg tcatcgcctc  18540
tcttggggga tttttacccc tttgccctga gttgtgcctt tgggacaaag gaagcctttc  18600
tttgccagcc aacaccctgt actggcgggc gagctcccca gggctggcac gctggggcag  18660
cctctgaatg cacagggtgg gcctagtcag aagaagcctt tcccctgaaa tccctctact  18720
tcccaagcac gcaagctttc tcctgctgtt aaacctgcag tgtgcaaggg acatgggcgg  18780
aggggtcctt cagtcaggct tctccctgtc tgaggtggca tgacttggag tgagtttgga  18840
tggggtggcc aggtctgaga aggtcccccg ccagtgtcct ctgacccatc tgctctctcc  18900
tgccagtgtg caccggcaca gacatgaagc tgcggctccc tgccagtccc gagacccacc  18960
tggacatgct ccgccacctc taccagggct gccaggtggt gcagggaaac ctggaactca  19020
cctacctgcc caccaatgcc agcctgtcct tcctgcaggt gaggcccgtg ggcaacccag  19080
ccaggccctg cctccagctg ggctgagccc tctgtttaca ggtgggtggc agaagaaggt  19140
gccctgccct tctgtttcct ctcttgttgt ggtttctcaa ccaggaagtc ctttctaaca  19200
tctaaccccc attcatttta ctgcagaatc agttgactct ctctataacg tggctggccg  19260
aggtcatgtc tggatgggat gcgtctgtgt ttccgctaaa tcttgtgctc tcttgccagc  19320
atgatcatgt cccctgtcca cctgctccag ccactatccc tctcccactt acagcagaag  19380
aaagggctgg tgagaaaggt ggattacagg cccacttctg ccactgacga gccctatgaa  19440
tgtggcctac acccccttag cttcactggg tctcagtttc cctatctgta tattgggagc  19500
agttgtgaag ctcagaagag aaatgtctgt gaaaaggtta tgaacaggag ggagagtgga  19560
```

aaccaacctg ctggatcgtg tccacagacc ctggaatggg gccacatgct tggtttgtca 19620
aattgcagac gccggccggg tgcgatggct catgcctgta atcccagcac tttgggaggc 19680
cgaggcggac agatcacttg aggtcgggag ttcgagacca gcctgaccaa catggagaaa 19740
ccccgtctct actgaaaata caaaattagc caggcatggt ggcacatgcc tataatccca 19800
gctacttggg aaggctgagg caggagaatc acttgaacct gggagacgga ggttgtggtg 19860
agcctagatc gtgccattgt actccagcct gggcaacaag agtgaaactc cgtctcaaaa 19920
aaaaaaaatt tgcagacgcc atcccatcca ggcctttgct ttcactgatg aagaaactga 19980
gatacagaga gggcagggca cctgttcgga gtttatgaaa tgcccccccca ccattatctt 20040 tcttgatcat ataagaatct ggtgaggcaa ggtagggcgt gatctttatc tctattttat 20100
cgttttattt aagcgggaac aggactgctc agtggctggg ggccttgccc aagatctcca 20160
agtactgggg aaccccaggg aggccctggg gggtggcagt gttcctattt cagcccccact 20220 ctgcttcccc ctcccaggat atccaggagg tgcagggcta cgtgctcatc gctcacaacc 20280
aagtgaggca ggtcccactg cagaggctgc ggattgtgcg aggcacccag ctctttgagg 20340
acaactatgc cctggccgtg ctagacaatg gagacccgct gaacaatacc acccctgtca 20400
caggggcctc cccaggaggc ctgcgggagc tgcagcttcg aagcctcaca ggtggccttc 20460
accgtcattg aaaccttctc ttggttattc agagctgacc agggccactg ctaaccaggg 20520
ggaggctttg tgtgcattag aaatggtgtc ccttctgggc agacgcaggc agagcccggg 20580
aagacgccct cagaagattg gaaaaagatt ccccttcttc ctgggaagtt gtagcttgcg 20640
tcagcacata taattcaatc gtgagaatgc aggctgggtt tttgccccca cttggctgag 20700
tgaagtgtac agtgaacaac ctatgtaact atttgctggc cctggagccg actctgcccc 20760
agagtctggg tgccaggtgc tttgcccgca tggcccattt cagtcacgct gcagtcctgt 20820
caggaaaaaa tcagtgttat tctcattcta catatgagaa aactgaggct tgcagatata 20880
agggccaaaa gttacacagc tagtgagtga tggggctgag tttcagactc cacagtctct 20940
taaccaccaa gcagcatgcc cagagtagag gtgagaagga aggagagagc tgcggtccac 21000
atgagcatct ggacctagca tggacaactc actcctccct ggctctcgct ttgttcttgt 21060
tgcgggtgtg gtggtggtgg gactcaaaga cggtaaagat agctttctct cctccctggg 21120
gaatctgggg gttgtttaaa aggcctgctc ctcttttaga aggcaggagg gccccaaggg 21180
aagcagaagg tgacagaagg ggaaagggtc ctctgatcat tgctcacccc acagagatct 21240
tgaaaggagg ggtcttgatc cagcggaacc cccagctctg ctaccaggac acgattttgt 21300
ggaaggacat cttccacaag aacaaccagc tggctctcac actgatagac accaaccgct 21360
ctcgggcctg taagccatgc cctccctgc tgcctcttct ctcagacagc ctgaccccag 21420
ccgcaaactc ccaacttaca acccagtgcc tgcccgccac tgccccagcc gcctacacca 21480
cccatttcct ccctctctgt ccctcctgcc atctccctgt gcctcttcat ctctggggtt 21540
ctctgtcttg tctccctctg cttataggtt gtgcctctgg tttgggggcc tctcagcctg 21600
tctgggtccc tcccttgctg tgcagttggc ctcgtggcct ctgctgctgt ttgtgcctct 21660
ctctgttact aacccgtcct ctcgctgtta gacatctctc tcactgcctg tctctggttc 21720
tgtcctcagg ccacccctgt tctccgatgt gtaagggctc ccgctgctgg ggagagagtt 21780
ctgaggattg tcagagccgt gagtctcagg gaggcctgga gtcagggaag gggagggctg 21840
gggccgggtg gaatgcaggt gtcatacagg tgacatggga ggggtgggat aacaggcttg 21900

-continued

```
ggatgtctcc cctgggccag gtagtctccc tagaaggtga tgctgatgag ggtctggtgc  21960
ccagggcgcc actcagccct catcctgccc tttgcccaac agtgacgcgc actgtctgtg  22020
ccggtggctg tgcccgctgc aaggggccac tgcccactga ctgctgccat gagcagtgtg  22080
ctgccggctg cacgggcccc aagcactctg actgcctggt atgtgcctct gctttgtgcc  22140
caatgtgctc tacccccag gatgcaaggg gtgggcaccc tgcctggtac tgccctattg  22200
cccctggcac accagggcaa aacagcacag tgaaagccag ccacctgtcc ccccaggcct  22260
gcctccactt caaccacagt ggcatctgtg agctgcactg cccagccctg gtcacctaca  22320
acacagacac gtttgagtcc atgcccaatc ccgagggccg gtatacattc ggcgccagct  22380
gtgtgactgc ctgtccctgt gagtgccagg gagaaacaca gttttctcat tttggtgggg  22440
aggtttgttt ctgtaaatgg gagcatatgg ggagcactgt ctgcatcttg ctttgagagc  22500
tggtcatgac agttcctgcc gagctgcctt gttctttcaa cagctgtgga gcaggtggca  22560
gtaaggagag gcagctaaga gcccagactt gggagccaga ctgcctgggt ttgaaaccca  22620
gctctatcaa ttagtaggca cgtgaccctc ttgctgtgcc tcagtttcct catcagtaaa  22680
atgggggcaa gaatagtccc aactgcataa gatggttata acatttgaaa gagttaatat  22740
ttgtaaagct cttagaacgg tgcctggtat gtactaagtg ctcctaaatg ttagctttta  22800
ttctatagcc tggtgaggtc agttttacct ttcgttttgt ttttgagacc gaatttagtt  22860
agctctatcg cagtggcgcg atctcggctc actgcaacct ccgcctccca ggttcgtgct  22920
attctcgtgt ctcagcctcc tgagtagctg ggattacagg cgcccaccac catgcctcgc  22980
taaattttgt atttttagta gagacagggt ttcaccacgt tggccagact ggtctcgaac  23040
tcctgacttc aggcgatcca cctgcctcgg cctctgaaag tgctgggatt acaggcgtga  23100
gccactgcac ccggactttt tttttttgg cagagtctcg ctccattgcc caggctggag  23160
tgcagtggtg caattttggc tcactgcaac ctctgccttc cgcattcaag caattcttgt  23220
gcctcagact cttgagtagg tggaactaca ggcatgcacc accatggctg ggtaattttt  23280
gtatttttag tagagacgga gtttcactat gttggccaag ctggtctcga actcctgacc  23340
tcaagtgatc cacccgcctt ggtctcccaa agtgctggga ttacaggcat gagccatcgt  23400
gcctggccta gctcagtttt atttaacaga tcacctattt actgatgggc gtttatggac  23460
tgggctcaga cctggggaac ctctttcctc ctctcacagg aacaggagtg ggccttcaga  23520
tcctggctga ctgtgttagg gagaggacaa aatgtagagc cagaccattt gggttcaaat  23580
cctcgctcct ccactcacta gcacaatgac cttgaataat ttacagaact ctctgctttg  23640
gtctcccttt ttgcaaaatg ggaatctcac agtgctgatc ccgtctggtt gttgtgaggg  23700
gtaaatggat gtcaggtgct gatgcgtggt agggcattta agtattggtt gatattattc  23760
ttcttgtgcc tgggcacggt aatgctgctc atggtggtgc acgaagggcc agggtatgtg  23820
gctacatgtt cctgatctcc ttagacaact acctttctac ggacgtggga tcctgcaccc  23880
tcgtctgccc cctgcacaac caagaggtga cagcagagga tggaacacag cggtgtgaga  23940
agtgcagcaa gccctgtgcc cgaggtaccc actcactgcc cccgaggcca gctgcagttc  24000
ctgtccctct gcgcatgcag cctggcccag cccaccctgt cctatccttc ctcagaccct  24060
cttgggacct agtctctgcc ttctactctc tacccctggc ccccctcagc cctacaagtg  24120
tccctatatc ccctgtcagt gtggggaggg gcccggaccc tgatgctcat gtggctgttg  24180
acctgtcccg gtatgaaggc tgagacggcc ccttccccac ccacccccac ctcctcagtg  24240
tgctatggtc tgggcatgga gcacttgcga gaggtgaggg cagttaccag tgccaatatc  24300
```

-continued

```
caggagtttg ctggctgcaa gaagatcttt gggagcctgg catttctgcc ggagagcttt  24360
gatgggtaag agtgggcacg atgacctgag acagtgtcag ggcagacaga gtcctgagga  24420
tccagatgtg gcagcatctc ttggggatgg caggagacag aagtgggggg atcaagaatg  24480
caaagaaagc agatgggaga ccagaggagc agggcctttg gtgggtgggg gtgattattt  24540
ttgtaaatga catgctatcc gtgaacaagg acttgtatgg aggtcagacc atctagataa  24600
agtaaaattc cctttgagtt catagcagct ttattcaaaa tatccccaaa ttggaaataa  24660
ctcaaatgtg catcactagg tgaaggaata aacaagtggc agtgtatcca tttggtgaag  24720
ttctacttag caaccaaagg aaatgaacta ccgatacaac ataaatgaat ctcagaaaca  24780
ttacattgag caaaagaagc cagagacaag attccatact gtctgatccc ctttatgtga  24840
ggctctgaac cgaaaaaacc actctgtggt gggagagatc agaacggtgg ttgccccagg  24900
gtggggggct tcaaaaggga ggcacacaag gacatttctg gggtaataga aatgctctgt  24960
atagtgattg gggtagtgga tacatgagcg aatccatttg tcaaaactca tcaaactgtg  25020
tgataagagt ctgtgcattt tatttatttc attttatttt ttgagataga gtctcactct  25080
gtcagcaggc tggagtgcag tggtacgatc ttggctcact gcaacctctg cctcctggat  25140
tcaagcaatt ctcctgcctc agtctcctga gtagctggga ctacaggtgt gtgccaccat  25200
gcccagctaa tttttgtatt tttaatagag atggggtttc accatgttgg caaggatggt  25260
ctcgatctct tgacgtcgtg atccgcccac ctcagcctcc caaagtgctg ggattacagg  25320
catgagccac cacacccggt gcattttatt gtatataagt tatacttcaa taagaaatga  25380
attggggcca ggcacggtgg ctcacgcctg taatcccagc actttgggag gccgaggcag  25440
gcagatcact tgaggtcagg agttcaagac cagcctggcc aacatggtga aaccccatct  25500
ctactaaaaa atataaaaaa ttagccaggc ttcctggcat gcgcctatca tcccagctac  25560
ttgggaggct gaggcaggag aattgcatga actcgggagg tggaggttgt agtgagctga  25620
gatttcgcta ttgcactcca gcctgggcga cagagtgaga ccctgtctca aaaagaaaaa  25680
aaaaaaaaag ggtcaggcgc cgtggtgcac acctgtaatc ccagcacttt gggaggctga  25740
agcaggaaga ttgcttgagc ccaggaattc aagaacagcg tgggcaacat agtgagatcc  25800
catctctaca aaaaaacaca aaaaattagc cgggcatggt ggtacgcacc tgtagtctca  25860
gctactaggg agactgaggt gggagaatca cctgagcctg ggaggtggag gttgcagtgg  25920
gttgaaatca tgtcactgta ctccagcctg ggtgacagaa tgagaccctg tctcaaaaaa  25980
aaaaaaaaaa aaaaaattcc ctttcacact tcctttacct ccactcccct ttccagaggg  26040
ggccatggtt aacagtgtgt gtgttcacct agaccgttta tgcatctgta gacacacaca  26100
cagtgaagtg tggttttcgt cgttttggtg gggaggttgg tttctgtaaa tgggaacata  26160
tagggagcac tgtctgcacc ttgctttgag agccggtcat gacagttccc attgaactgc  26220
cttgttcttt caatagctgc agagcaggtg gcggcaagga gaggcagcta agagcccaga  26280
cttgggagcc agactgcctg ggtttgaaac ccggctctac cacttactag gcatgtgacc  26340
cttgtgctgt gcctcagttt cttcatctgt aaagtggggg caagaacagt cccaacttca  26400
taagatggtt ataccaccat gcctggccag atgattataa agtttgaatg agttaatatt  26460
tgtaaagctc ttagaacagt gcctggcaga tactaggtgc tcctaaatgt tggtttttat  26520
tatgtggctg ggtggctcgg ggttttattt aacagctccc ctatttacta atagacattt  26580
agatcatgtt ccattttcac tcttacaaac agttccactt tgtgtgtggc tctgggaaca  26640
```

-continued

```
tgggccagtg tctccctagg ccacattcct agaaataaga tttcttttct tttttttttt  26700
tttttgagac agagtctcgc tttatcgcca ggctggtgtg cagtagtgtg atctcggctc  26760
actgcaacct ctgcctcccg ggttcaagtg attctcctgc ctcagcctct cgagtaactg  26820
ggactatagg cgcgcggcac cacacccagc taatttttgt atttgtagta gagatggggt  26880
ttcaccatgt tggccaggat ggtctccatc tcttgacttc gtgatccgcc cgcctcggcc  26940
tcccaaagtg ctgggattac aggcgtgagc cactgagccc aggcagaaat aagatttcta  27000
gatcaaagga tataaatact gttttgatag atgttgccga actaaggcct gggctttgaa  27060
gcccaggatg ggaacagctg ggctcgatgg gcaaagggtt tgagtgaagg cattcatggt  27120
ggggagtggc tggcatggcc agtgctggga gtgatgtcca ccctgttcct ggccctgctg  27180
actcctctcc tgacccctcc agggacccag cctccaacac tgccccgctc cagccagagc  27240
agctccaagt gtttgagact ctggaagaga tcacaggtgg gctctgtctc tgcatcctgt  27300
tctgcagggg ctgggagtcc ttgtcctgtc cccactcctt taatctcacc ctctgcctgc  27360
aggttaccta tacatctcag catggccgga cagcctgcct gacctcagcg tcttccagaa  27420
cctgcaagta atccggggac gaattctgca caagtgagca ctgagaaaga gggggcctga  27480
tggggaggag tcccagggag gagtccctgt gggaagcttt gggcctgagg gagtactcct  27540
gtagcagtaa cctttccatg aaagtctgca gagtgtgctg gggatggagg aagatgagaa  27600
tagcctttgc tgaccgggaa ggggtccgtg gtaaggtgcc cacctttctc ccatagtggc  27660
gcctactcgc tgaccctgca agggctgggc atcagctggc tggggctgcg ctcactgagg  27720
gaactgggca gtggactggc cctcatccac cataacaccc acctctgctt cgtgcacacg  27780
gtgccctggg accagctctt tcggaacccg caccaagctc tgctccacac tgccaaccgg  27840
ccagaggacg agtgtggtaa gacagggagc ccagtgtgcg cactccccat ctgccagcac  27900
acagcagtgc ccagggggcc ctggcagcag cgttcttgga cttgtgcaga ctgcccgtct  27960
ctgtgcaccc ttcttgactc agcacagctc tggctggctt ggcctcttgg catggcttct  28020
ctagctgggt cctacctgcc ttggcatcct tccctccccc tctgtttctg aaatctcaga  28080
actcttcctc tccctacatc ggccccacct gtccccaccc ctccagccca cagccatgcc  28140
cacagccagt tccctggttc acttggacct ggggcctccc ctaaaagtcc cctgcggtcc  28200
cttcctcctc actgcagtgg gcgagggcct ggcctgccac cagctgtgcg cccgagggca  28260
ctgctggggt ccagggccca cccagtgtgt caactgcagc cagttccttc ggggccagga  28320
gtgcgtggag gaatgccgag tactgcaggg gtatgagggg cggaggagag ggtggctgga  28380
ggggtgcatg gggctcctct cagaccccct caccactgtc ccttctctca ggctccccag  28440
ggagtatgtg aatgccaggc actgtttgcc gtgccaccct gagtgtcagc cccagaatgg  28500
ctcagtgacc tgttttggac cggtgagctg ctggcgggct cagagctggg tggagggggg  28560
cagcgagggg gattgccagg gacttggcag gatggcgaga tgcagtaggg tgtgctatct  28620
ggtaaaatat ccctggagag ggctcagcgc tcagacctga acagcaacag agtggcagaa  28680
aaggggcctg ggggacactg gggcccttca gactatgaaa aggttctaag gaggtctgtg  28740
ttggtggctg tgactgtggc tgtgctaggg tggtgagccc tgtgggctca ggcgtcagac  28800
tacctggatt cagacccagc tcctgcttcc aaccttggtt ttttattcct aaaatgggta  28860
ttgtaataat acctaccttg ctggggtgtg gcaagaatga aattaaacag ggcttggcac  28920
agtgaagcac gggaaaggct ttctacagag cagtgactgt tgttactcgc tgttacacct  28980
taggtaatgc gttttcctct ctgggtgcct cccattttct ggctcaagtc cctgcccagg  29040
```

```
atcaagcttg gaggagggcc ccgagggagg ggccacagag actgggtgaa gagcaagggt  29100
gtttgtccca ggagcatggc gaaaattgct gctgggtggc cttgggaagc acaaagggga  29160
cccaactaag ggcctgatcc tactgccctg gggtgtcag tgccagcccc ccacaaatct  29220
tttctgcccc ccccaggagg ctgaccagtg tgtggcctgt gcccactata aggaccctcc  29280
cttctgcgtg gcccgctgcc ccagcggtgt gaaacctgac ctctcctaca tgcccatctg  29340
gaagtttcca gatgaggagg gcgcatgcca gccttgcccc atcaactgca cccactcgtg  29400
agtccaacgg tcttttctgc agaaaggagg actttccttt caggggtctt tctggggctc  29460
ttactataaa aggggaccaa ctctcccttt gtcatatctt gtttctgatg acaaaaataa  29520
cacattgtta aaattgtaaa attaaaacat gaaatataaa ttaatgccct agcagttcta  29580
tccccactgt taataatttg aaatattttt cctctagtta tttttgtctg tgcacattct  29640
aatatgtata tataagttaa catatattaa tattattctc cagttatttt tatctgtgca  29700
cattttaaca cacacacaca cacacacaca cacacacata tgtattttta gacggagttt  29760
cactctgtcg cccaggctgg agtgcagtag tacaatcttg gctcactgca gcctccacct  29820
cctgggttta agcaattctc ctgcttccgc ctcctgagta gctgggatta cgggaacgtg  29880
ctaccttgcc tggctaattt ttgtattttt agtacatagg atttcaccat gttggccagg  29940
ctggtctcga acccctgacc tcaggtgatc tgccagcctc ggtcccccaa agtgttggga  30000
ttacagcggt gagccaccat gcccagtcat atatttcttt ttaacaaata gaatcataga  30060
tcatacatat tgtttgcaaa ttgctttttc tcactttcca gaaccttgaa atgtttttcc  30120
atgttctaac atggtgatct accttattct tttaattttt cttatttagt tgtctttaca  30180
catgaaacac atgaatacat ccttgtgata aacattttca gtaacataaa agtataaatg  30240
ttacaaagcc aacgtgccct ttcactcaac tccctgtcca cccagtctct cctgtctgct  30300
gggagaacca ccgcattgac ttgtgtgttc acccttccag gctcttttct gcacacttat  30360
atagacatac tacatttata ttaggtcgag tcaaataaga ttgctgtttg tgtaaaccaa  30420
aaagtgtcaa gagcctgggc gcagtgactc acacctgtaa tcccagcact ttgggaggct  30480
gaggcaggca gatcacttga gatcaggagt tcgagaccaa tctggccaac atagcgagac  30540
cccgtctcta ctaaaaatac aaaaactagc caggtgtggt gatgctgttc tgcactttgc  30600
tttccccccg acttgaggta tcctttcttg tgagtacaga cggatctacc acctttattt  30660
ttttttaat tactcaacct gtaacatgga tgtaatttca ctttgttttt gagggatatt  30720
gagcttgttt ccctgttttt gcagtttatt gcaattgagc tccacacaca agtgagccct  30780
cttttgtatg ccccctagtg ggaatacagt gctggcaatg tttatcacaa ggatatattc  30840
atgcatttca atttaaagac aactaaatga gaaaaattaa aagaatatgg atccaggctg  30900
ggcatggtgg ctcacgcctg taatcccagc actttgggag gccgaggcag gcagatcacc  30960
tgaggtcagg agttcaagac cagcctggcc aacatggcaa aaccccgtct ctactaaaaa  31020
tacaaaaatt agccaggcgt ggtggtgggc gcctgtaatc ccagctattt gagaggttga  31080
gacaggagaa ttgcttgaac ctgggcagcg gaggttgcag tgagacgaga ttgcaccagt  31140
gcactccaac ctgggcaaca cagtgcaact ccttctcaag aaaaaaaaga aaaaaaaaaa  31200
gaatatgggt ccagatccat atggatccta gatccagatc acggtgttag aacatggaaa  31260
aacattgcaa gattctgcta agtgaaaaaa gcatttgcaa acagtatgta cagtctatat  31320
tcagaggagg aactgctggg tcatagatga tatttcatag gtattgccaa accgttctct  31380
```

-continued

```
ggagaagtgg tatgggttta ccctgggatt cttctatgga gggaatagtt gagctcccgg  31440
gcttgctctt ctgggtgccc ctccccgctt cctatccacc acaaggagct gcaggggagc  31500
ggggcatgcc ggttccttgg ctggagaagg agtctccttg tgaggtggta gaaggagcac  31560
tgacggcctt gagcccagtt tctgcctttg tcaaatgggg ataatgaccc agccacaccc  31620
ctcccagggt tgttgtgagg ctggaaaggt ggttcccaag agggtggttc ccagaattgt  31680
tgatgagact gtttctcctg cagctgtgtg gacctggatg acaagggctg ccccgccgag  31740
cagagagcca ggttggcctg gaccccagga tgtacccttc attgcccttc actcccccac  31800
tggatgctgg gtggtcactg ctgtagggag gggacccccct gacatatgtc ccttcccacc  31860
cactcttcca ctgtggaacc tcctgtcatt ttccacttca ccaagtgaca gaggacctgc  31920
tcagatgctg aggggagggg actgcaagga aagatggcta ggaaacccag tccctccaca  31980
ccctagagta acttgatgcc ttgtgaggga cacaggcaaa gttcaattcc ttggaagtca  32040
agggagactg agaagagtac agctgcagca ctgagggagt gatgaattct taactgggga  32100
tggtgggagg cttcgagtgg gaggtggcat ttgagctagg ctttgagaga ggagcaggta  32160
ttgcacttgc atttaggtag aaagcattgg ggtgcaaggt gacactggag ggggaggcat  32220
caggaaatcc aggatgtctt caaagttctg gtgtcggggg ctgttgagta agcacaggaa  32280
taagggggtc aagttagagt cagggtgggg tctgacctgg atgccatagg acctgatccc  32340
caagccacag ggtgggactt gactgggcag tggggacctt tggaaaggac tttggggaga  32400
aaaacagact ggagtctgtc ttaggcgatc atcggtccgt gaaatgagca tgtgttacag  32460
gcttggtatg taccagaccc tgtgctaagc aagggggtat ggagaggaga gggtgacaag  32520
aatattggat caacacccgg gagctccatc tatcccagga tgcactatct tttttttatt  32580
tttttgagac ggagtctcac tctgcctgca ggctggagtg cagtggctcc atctcggttc  32640
actgcaacct ctgcctcctg ggttcaagcg cttcttgtgc ctcagcctcc caagtagctg  32700
ggattacagg cacatgccac cacacccagc taatttttgt atttttagta gagacggggt  32760
ttcaccatgt tggccaggat ggtctcgatc tcttgacctc aagatccgcc caccttggcc  32820
tcccaaagtg ctgggattac agacatgagc caccgtgccc agccagatac gctatctttt  32880
tattgagtga ttgagacagg gtcttgctct cttgtccagt cttgaatgtg gtggtgtaat  32940
cacaggctca ctgcagcctt gacctcctgg gctcaagtta cccttctgca gtagctggga  33000
ctataggagc gtgccaccac gcctgggtaa tttaaaaaat ttttttgta tagacagggt  33060
ctcactatgt tgcccgagct ggtctcaaac tcgtgggctc aagtgatcct ccagttttgg  33120
cctcccaaaa tgttgggatc acaggagtga gccaccactc ctggcgatga gccaagtctt  33180
ttttttttt ttttttttt gatatggagt cttgctctgt tgcccaggct ggagtgcaat  33240
gacacgatct tggctcactg caacctctgc ctcccaggtt caagcagttc aagcaatcct  33300
cctgtctcag ccccccagta gctgggatta caggcatgcg ctaccacgtc cggctaattt  33360
ttgtattttt agtagagatg aggttttgcc atgttggcca ggctggtctt gaactgctga  33420
cctcaggtga tccacctgcc tcggcctccc aaagtgctgg gattacaggt gtgagccatc  33480
gtgcctggcg gagccgagtc ttaaaagatg accctgtgga gaaatggtgg tccaggctga  33540
agggacagcc tatgcaaaca ctgggaggtg tggaaaatca tgacctgtgg gtggaaattt  33600
tggctagaac atcaaaatca tcaggtgtac attcctgtac ccatgcagca gtcagaatct  33660
ctgggggtgg ggccccaaaa ttgtatgcat acagactgtg tgctgatttg tgatattact  33720
taggattttt tgactttaca atggtggaaa agcaataata tacattcagt ataaaccgta  33780
```

-continued ctttgaatac ccatacagcc attctgtttt tcacttttat ttttatttat ttatttattt 33840
attatttatt ttgagatgtc attttgctgt tgttacccag gctggagtgc aatggcgcag 33900
tcttggctca ccgcaacctc cacctctcag gttcaaacga ttctcctgct tcagcctcca 33960
gagtggctgg gattacaggc aggcaccacc acacccggct aattttgtat ttttagtaga 34020
gacggggttt ctccatgtta gtcaggctgg tctcgaactc gagagctcag gtgatctgcc 34080
catctcagcc tcaagccacc atgcccagcc ctactttcag tattcaataa attacatagc 34140
caggcaccgt ggctcacacc tgtaatccca gcactttagg aggccaaggt gggaggatcc 34200
tttgaggcca gaagctcgag accagcctgg gcaacatagt gagaccccat ttctacaaaa 34260
aataaaaaaa ctagctgagt gtggtggcgt gtgtctgtag tcccagctac ttgggcagct 34320
gaggtggaaa gactgcttga gcccagaggt cagggctgca gtgggccatg atctcaccac 34380
tgcactcagc ctgggcaaca cagcaaggcc ctgtctcaaa aataaataaa taaataacac 34440
aaacttattt aacagtttac tataaaatag gctttgtgtc agatgattct gcccaactgt 34500
aagctgctgg cagtgtaaat gttctgagca cgtgtaagcc aggctaggtg tcttaaatgc 34560
attttcagtt tcaacttaga attggtttat caggacgtag ccccttggtg ttgaggggca 34620
tgtgtattaa cagtctcctt agtgactttt ttttttttga gatggagtct tgcactggcc 34680
gtagtgcagt ggcacaatct cagctcactg caacctcttg tctcccgggt tcaagcgatt 34740
ctcctgcctc agtctcccaa gtagctggga ttacaggcac ccacaccacg cccagctaat 34800
ttttgtgtgt gtgtattttt agtagagacg gggtttcac tatgttggcc aggctggtct 34860
cgaactcctg accttgtgat ctgcccacct cagactctca aagtgctagg attccaggca 34920
tgagccaccg cgcccagagt ccttagtgat ttttacacca tgaattgttg aagccctaag 34980
ccagagccaa gggcaagagt atagagaatc tggagatgcg gagagggttc tgattgccta 35040
caaggagttt ggactttatt gtggaggcag cggggagcca aggcaggttt tagagtagga 35100
gagggtccaa gcctgtgggt cacccttccg acttcccttt ccgaatgcca aacaccttca 35160
tgtcccccgt gggccccctt tgtccctccc accccaaact agccctcaat ccctgaccct 35220
ggcttccgcc cccagccctc tgacgtccat catctctgcg gtggttggca ttctgctggt 35280
cgtggtcttg gggtggtct ttgggatcct catcaagcga cggcagcaga agatccggaa 35340
gtacacgatg cggagactgc tgcaggaaac ggaggtgagg cggggtgaag tcctcccagc 35400
ccgcgtgggg tctgcaccgg cccccggcac tgacccacca ccccctcacc ccagctggtg 35460
gagccgctga cacctagcgg agcgatgccc aaccaggcgc agatgcggat cctgaaagag 35520
acggagctga ggaaggtgaa ggtgcttgga tctggcgctt ttggcacagt ctacaaggtc 35580
agggccaggt cctggggtgg gcggccccag aggatggggg cggtgcctgg aggggtgtgg 35640
tcggcagttc tgatgggagg ggcaagagct ggaggcagtg tttgggggag ggcagttaca 35700
gcggagaagg gagcggggcc aagccctagg gtggtgaagg atgtttggag gacaagtaat 35760
gatctcctgg aaggcaggta ggatccagcc cacgctcttc tcactcatat cctcctcttt 35820
ctgcccaggg catctggatc cctgatgggg agaatgtgaa aattccagtg gccatcaaag 35880
tgttgaggga aaacacatcc cccaaagcca acaaagaaat cttagacgta agcccctcca 35940
ccctctcctg ctaggaggac aggaaggacc ccatggctgc aggtctgggc tctggtctct 36000
cttcattggg gtttggggag atatgactcc cgcaaaccta gactattttt ttggagacgg 36060
agtcttgctc tgtcacccag gctggagtgc agtggcgtta tctcggctca ctgcaacctc 36120
cacctcctgg actcaagcga ttttcatgcc tcaggctcct gagtagctgg gattacaagc 36180
gcccgctaat tttttttttt tttttgagac agagtctcgc tctgtcaccc aggctagagt 36240
gaaatggtgc ggtctcagct cagcctccca ggttaaagcg attcttctcc ctcagtctcc 36300
tgagtagctg ggattacagg cgcgagccac cacgcccggc taatttttgt atttttagta 36360
gagatgggat ttcaccatgt tggccaggtt ggtgtcaaac tcctgacctc atgatccgcc 36420
cgcctcggcc tcccaaagtg ctgggattac aggtgtgagc caccgtgccc ggcctaatct 36480
ttgtattttt agtagagaca gggtttcacc atgttgtcca ggctggtact ttgagccttc 36540
acaggctgtg ggccatggct gtggtttgtg atggttggga ggctgtgtgg tgtttggggg 36600
tgtgtggtct cccataccct ctcagcgtac ccttgtcccc aggaagcata cgtgatggct 36660
ggtgtgggct ccccatatgt ctcccgcctt ctgggcatct gcctgacatc cacggtgcag 36720
ctggtgacac agcttatgcc ctatggctgc ctcttagacc atgtccggga aaaccgcgga 36780
cgcctgggct cccaggacct gctgaactgg tgtatgcaga ttgccaaggt atgcacctgg 36840
gctctttgca ggtctctccg gagcaaaccc ctatgtccac aaggggctag gatggggact 36900
cttgctgggc atgtggccag gcccaggccc tcccagaagg tctacatggg tgcttcccat 36960
tccaggggat gagctacctg gaggatgtgc ggctcgtaca cagggacttg gccgctcgga 37020
acgtgctggt caagagtccc aaccatgtca aaattacaga cttcgggctg gctcggctgc 37080
tggacattga cgagacagag taccatgcag atgggggcaa ggttaggtga aggaccaagg 37140
agcagaggag gctgggtgga gtggtgtcta gcccatggga gaactctgag tggccacctc 37200
cccacaacac acagttggag gacttcctct tctgccctcc caggtgccca tcaagtggat 37260
ggcgctggag tccattctcc gccggcggtt cacccaccag agtgatgtgt ggagttatgg 37320
tgtgtgatgg ggggtgttgg gaggggtggg tgaggagcca tggctggagg gaggatgaga 37380
gctgggatgg ggagaattac ggggccacct cagcatgtga agggagggaa ggggctgcct 37440
gtgccccacc ttgcagggtc tgtgcacttc ccaggattag ggaaagaccg ggtagggtct 37500
gtctcctggc atcacatctc cccctgctac ctgccatgat gctagactcc tgagcagaac 37560
ctctggctca gtacactaaa gctccctctg gccctcccac tcctgaccct gtctctgcct 37620
taggtgtgac tgtgtgggag ctgatgactt ttggggccaa accttacgat gggatcccag 37680
cccgggagat ccctgacctg ctggaaaagg gggagcggct gccccagccc cccatctgca 37740
ccattgatgt ctacatgatc atggtcaaat gtgcgtggct gagctgtgct ggctgcctgg 37800
aggagggtgg gaggtcctgg gtggaggagc ccacaagggg catgaaaggg gaccaggatg 37860
tatgtagacc caggagccct agtatgttag gagcctcaaa accttcttgt atccctttta 37920
cagtcaaagt ccaaagccac tcttgaggaa cactcttgta caaaattaag ctgggcacag 37980
tggctcatgc ctgtaatccc agtacttttg gaggctgagg tgggaggatc ccttgaagcc 38040
aggagttcaa gaccagcctg ggcaacatag tgagatccta tctctacaaa aaataaaaaa 38100
attatctggg tgtggtggtg tgtgccagta gtcccagcta ctcaggagag gctgaggcag 38160
gaagatcact tgagcctagt ttaaggttgc agtaagctat gattgcacca ctgaaatcca 38220
gcctgggtga cagagcgaaa cctcatctca aaaaaataaa aaagcaaaca aaaagaaaaa 38280
aaaaattaaa agggaaacta gaagagatgc caaaggttct ggctgaagac cccagagtct 38340
ggtgctactt ctctaccacc tgagggcttt gggctgtccc ttgggactgt ctagaccaga 38400
ctggaggggg agtgggaggg gagaggcagc aagcacacag ggcctgggac tagcatgctg 38460
acctccctcc tgccccaggt tggatgattg actctgaatg tcggccaaga ttccgggagt 38520
tggtgtctga attctcccgc atggccaggg acccccagcg ctttgtggtc atccaggtac 38580
tgggcctctg tgccccatcc ctgcctgtgg ctaagagcac cctcctgcag agggtgggaa 38640
ggagagatga gtccagtatg ccaggcccct cacggaaggc tgcatgctgg gctggggagg 38700
ggccaccatc ctgcctctcc ttcctccaca gaatgaggac ttgggcccag ccagtccctt 38760
ggacagcacc ttctaccgct cactgctgga ggacgatgac atgggggacc tggtggatgc 38820
tgaggagtat ctggtacccc agcagggctt cttctgtcca gaccctgccc cgggcgctgg 38880
gggcatggtc caccacaggc accgcagctc atctaccagg gtcagtgccc tcggtcacac 38940
tgtgtggctg tctgcttacc tcccccaacc ccggtggact agggtccctt tctctgatgt 39000
tccctcaact gtcacctctc aaggaaaccc cattatccct acaaaaaatt cttactgcct 39060
tccaacccct gtgaccccat tctctccacg gtgactgtgt cataccccaa aggtgacctc 39120
tgtttttctc ctgtgaccct gtcaccttcc atggagtccc catcccagat ccgtgagtga 39180
cccccatcat gactttcttt cttgtcccca gagtggcggt ggggacctga cactagggct 39240
ggagccctct gaagaggagg cccccaggtc tccactggca ccctccgaag gggctggctc 39300
cgatgtattt gatggtgacc tgggaatggg ggcagccaag ggggctgcaaa gcctccccac 39360 acatgacccc agccctctac agcggtacag tgaggacccc acagtacccc tgccctctga 39420
gactgatggc tacgttgccc ccctgacctg cagcccccag cctggtatgg agtccagtct 39480
aagcagagag actgatgggc aggggaggtg ggaccttcag cccagggtcc actgtggggg 39540
cagagggagt ggcagagaca ccggggttcc ttcccctaat gggtcacctt ctcttgacct 39600
ttcagaatat gtgaaccagc cagatgttcg gccccagccc ccttcgcccc gagagggccc 39660
tctgcctgct gcccgacctg ctggtgccac tctggaaagg cccaagactc tctccccagg 39720
gaagaatggg gtcgtcaaag acgtttttgc ctttgggggt gccgtggaga accccgagta 39780
cttgacaccc cagggaggag ctgcccctca gccccaccct cctcctgcct tcagcccagc 39840
cttcgacaac ctctattact gggaccagga cccaccagag cggggggctc cacccagcac 39900
cttcaaaggg acacctacgg cagagaaccc agagtacctg ggtctggacg tgccagtgtg 39960
aaccagaagg ccaagtccgc agaagccctg atgtgtcctc agggagcagg gaaggcctga 40020
cttctgctgg catcaagagg tgggagggcc ctccgaccac ttccagggga acctgccatg 40080
ccaggaacct gtcctaagga accttccttc ctgcttgagt tcccagatgg ctggaagggg 40140
tccagcctcg ttggaagagg aacagcactg gggagtcttt gtggattctg aggccctgcc 40200
caatgagact ctagggtcca gtggatgcca cagcccagct tggccctttc cttccagatc 40260
ctgggtactg aaagccttag ggaagctggc ctgagagggg aagcggccct aagggagtgt 40320
ctaagaacaa aagcgaccca ttcagagact gtccctgaaa cctagtactg ccccccatga 40380
ggaaggaaca gcaatggtgt cagtatccag gctttgtaca gagtgctttt ctgtttagtt 40440 tttactttt ttgttttgtt tttttaaaga tgaaataaag acccaggggg agaatgggtg 40500
ttgtatgggg aggcaagtgt ggggggtcct tctccacacc cactttgtcc atttgcaaat 40560
atattttgga aaacagcta 40579

<210> SEQ ID NO 4
<211> LENGTH: 21
<212> TYPE: DNA
<213> ORGANISM: Artificial Sequence
<220> FEATURE:
<223> OTHER INFORMATION: Forward primer for LR-PCR (set 1)

-continued

<400> SEQUENCE: 4
ctgagattcc cctccattgg g 21

<210> SEQ ID NO 5
<211> LENGTH: 20
<212> TYPE: DNA
<213> ORGANISM: Artificial Sequence
<220> FEATURE:
<223> OTHER INFORMATION: Reverse primer for LR-PCR (set 1 and 2)

<400> SEQUENCE: 5
caacacccat tctccccctg 20

<210> SEQ ID NO 6
<211> LENGTH: 20
<212> TYPE: DNA
<213> ORGANISM: Artificial Sequence
<220> FEATURE:
<223> OTHER INFORMATION: Forward primer for LR-PCR (set 2)

<400> SEQUENCE: 6
gttcccggat ttttgtgggc 20

<210> SEQ ID NO 7
<211> LENGTH: 20
<212> TYPE: DNA
<213> ORGANISM: Artificial Sequence
<220> FEATURE:
<223> OTHER INFORMATION: SpT1 forward primer for Nested PCR

<400> SEQUENCE: 7
tgtgtggacc tggatgacaa 20

<210> SEQ ID NO 8
<211> LENGTH: 20
<212> TYPE: DNA
<213> ORGANISM: Artificial Sequence
<220> FEATURE:
<223> OTHER INFORMATION: SpT1 reverse primer for Nested PCR

<400> SEQUENCE: 8
ggcaacgtag ccatcagtct 20

<210> SEQ ID NO 9
<211> LENGTH: 20
<212> TYPE: DNA
<213> ORGANISM: Artificial Sequence
<220> FEATURE:
<223> OTHER INFORMATION: SpT2 forward primer for Nested PCR

<400> SEQUENCE: 9
acgcctgatg ggttaatgag 20

<210> SEQ ID NO 10
<211> LENGTH: 20
<212> TYPE: DNA
<213> ORGANISM: Artificial Sequence
<220> FEATURE:
<223> OTHER INFORMATION: SpT2 reverse primer for Nested PCR

<400> SEQUENCE: 10
cggtgcacac tcacttttgt 20

<210> SEQ ID NO 11
<211> LENGTH: 25

<212> TYPE: DNA
<213> ORGANISM: Artificial Sequence
<220> FEATURE:
<223> OTHER INFORMATION: SpT3 forward primer for Nested PCR

<400> SEQUENCE: 11
atatatcgag gcgatagggt taagg 25

<210> SEQ ID NO 12
<211> LENGTH: 21
<212> TYPE: DNA
<213> ORGANISM: Artificial Sequence
<220> FEATURE:
<223> OTHER INFORMATION: SpT3 reverse primer for Nested PCR

<400> SEQUENCE: 12
ccggggcata tcttctggaa t 21

<210> SEQ ID NO 13
<211> LENGTH: 20
<212> TYPE: DNA
<213> ORGANISM: Artificial Sequence
<220> FEATURE:
<223> OTHER INFORMATION: SpT4 forward primer for conventional PCR

<400> SEQUENCE: 13
ctggaggacg atgacatggg 20

<210> SEQ ID NO 14
<211> LENGTH: 23
<212> TYPE: DNA
<213> ORGANISM: Artificial Sequence
<220> FEATURE:
<223> OTHER INFORMATION: SpT4 reverse primer for conventional PCR

<400> SEQUENCE: 14
gctggttcac atattcctgg tag 23

<210> SEQ ID NO 15
<211> LENGTH: 18
<212> TYPE: DNA
<213> ORGANISM: Artificial Sequence
<220> FEATURE:
<223> OTHER INFORMATION: ErbB-2(DELTA)16 forward primer for conventional PCR

<400> SEQUENCE: 15
cacccactcc cctctgac 18

<210> SEQ ID NO 16
<211> LENGTH: 22
<212> TYPE: DNA
<213> ORGANISM: Artificial Sequence
<220> FEATURE:
<223> OTHER INFORMATION: ErbB-2(DELTA)16 reverse primer for conventional PCR

<400> SEQUENCE: 16
gctccaccag ctccgtttcc tg 22

<210> SEQ ID NO 17
<211> LENGTH: 20
<212> TYPE: DNA
<213> ORGANISM: Artificial Sequence
<220> FEATURE:
<223> OTHER INFORMATION: SpT4 forward primer for competitive PCR

<400> SEQUENCE: 17
agcaccttct accgctcact 20

<210> SEQ ID NO 18
<211> LENGTH: 20
<212> TYPE: DNA
<213> ORGANISM: Artificial Sequence
<220> FEATURE:
<223> OTHER INFORMATION: SpT4 reverse primer for competitive PCR

<400> SEQUENCE: 18
ctgaatgggt cgcttttgtt 20

<210> SEQ ID NO 19
<211> LENGTH: 20
<212> TYPE: DNA
<213> ORGANISM: Artificial Sequence
<220> FEATURE:
<223> OTHER INFORMATION: ErbB-2(DELTA)16 forward primer for competitive PCR

<400> SEQUENCE: 19
cggtgtgaaa cctgacctct 20

<210> SEQ ID NO 20
<211> LENGTH: 20
<212> TYPE: DNA
<213> ORGANISM: Artificial Sequence
<220> FEATURE:
<223> OTHER INFORMATION: ErbB-2(DELTA)16 reverse primer for competitive PCR

<400> SEQUENCE: 20
aagaccacga ccagcagaat 20

<210> SEQ ID NO 21
<211> LENGTH: 20
<212> TYPE: DNA
<213> ORGANISM: Artificial Sequence
<220> FEATURE:
<223> OTHER INFORMATION: ErbB-2 forward primer for RT-qPCR

<400> SEQUENCE: 21
aaaggcccaa gactctctcc 20

<210> SEQ ID NO 22
<211> LENGTH: 20
<212> TYPE: DNA
<213> ORGANISM: Artificial Sequence
<220> FEATURE:
<223> OTHER INFORMATION: ErbB-2 reverse primer for RT-qPCR

<400> SEQUENCE: 22
cctccctggg gtgtcaagta 20

<210> SEQ ID NO 23
<211> LENGTH: 20
<212> TYPE: DNA
<213> ORGANISM: Artificial Sequence
<220> FEATURE:
<223> OTHER INFORMATION: SpT3 forward primer for RT-qPCR

<400> SEQUENCE: 23
tagaatggcc aggacaaacg 20

<210> SEQ ID NO 24
<211> LENGTH: 21
<212> TYPE: DNA
<213> ORGANISM: Artificial Sequence
<220> FEATURE:
<223> OTHER INFORMATION: SpT3 reverse primer for RT-qPCR

<400> SEQUENCE: 24
ccggggcata tcttctggaa t 21

<210> SEQ ID NO 25
<211> LENGTH: 20
<212> TYPE: DNA
<213> ORGANISM: Artificial Sequence
<220> FEATURE:
<223> OTHER INFORMATION: GAPDH forward primer for RT-qPCR

<400> SEQUENCE: 25
ccagaacatc atccctgcat 20

<210> SEQ ID NO 26
<211> LENGTH: 18
<212> TYPE: DNA
<213> ORGANISM: Artificial Sequence
<220> FEATURE:
<223> OTHER INFORMATION: GAPDH reverse primer for RT-qPCR

<400> SEQUENCE: 26
gttcagctct gggatgac 18

<210> SEQ ID NO 27
<211> LENGTH: 19
<212> TYPE: RNA
<213> ORGANISM: Artificial Sequence
<220> FEATURE:
<223> OTHER INFORMATION: ErbB-2 siRNA from siRNA pool

<400> SEQUENCE: 27
ggacgaauuc ugcacaaug 19

<210> SEQ ID NO 28
<211> LENGTH: 19
<212> TYPE: RNA
<213> ORGANISM: Artificial Sequence
<220> FEATURE:
<223> OTHER INFORMATION: ErbB-2 siRNA from siRNA pool

<400> SEQUENCE: 28
gacgaauucu gcacaaugg 19

<210> SEQ ID NO 29
<211> LENGTH: 19
<212> TYPE: RNA
<213> ORGANISM: Artificial Sequence
<220> FEATURE:
<223> OTHER INFORMATION: ErbB-2 siRNA from siRNA pool

<400> SEQUENCE: 29
cuacaacaca gacacguuu 19

<210> SEQ ID NO 30
<211> LENGTH: 19
<212> TYPE: RNA
<213> ORGANISM: Artificial Sequence
<220> FEATURE:
<223> OTHER INFORMATION: ErbB-2 siRNA from siRNA pool

<400> SEQUENCE: 30
agacgaagca uacgugaug 19

<210> SEQ ID NO 31
<211> LENGTH: 19
<212> TYPE: RNA
<213> ORGANISM: Artificial Sequence
<220> FEATURE:
<223> OTHER INFORMATION: Control siRNA

<400> SEQUENCE: 31
ugguuuacau gucgacuaa 19

<210> SEQ ID NO 32
<211> LENGTH: 4940
<212> TYPE: DNA
<213> ORGANISM: Homo sapiens
<220> FEATURE:
<223> OTHER INFORMATION: ErbB-2 alternative transcript variant 3, mRNA

<400> SEQUENCE: 32
aagttcctgt gttctttatt ctactctccg ctgaagtcca cacagtttaa attaaagttc 60
ccggattttt gtgggcgcct gccccgcccc tcgtcccccct gctgtgtcca tatatcgagg 120
cgatagggtt aagggaaggc ggacgcctga tgggttaatg agcaaactga agtgttttcc 180
atgatctttt ttgagtcgca attgaagtac cacctcccga gggtgattgc ttccccatgc 240
ggggtagaac ctttgctgtc ctgttcacca ctctacctcc agcacagaat ttggcttatg 300
cctactcaat gtgaagatga tgaggatgaa aacctttgtg atgatccact tccacttaat 360
gaatggtggc aaagcaaagc tatattcaag accacatgca aagctactcc ctgagcaaag 420
agtcacagat aaaacggggg caccagtaga atggccagga caaacgcagt gcagcacaga 480
gactcagacc ctggcagcca tgcctgcgca ggcagtgatg agagtgacat gtactgttgt 540
ggacatgcac aaaagtgaga tacttcaaag attccagaag atatgccccg ggggtcctgg 600
aagccacaag tgtgcaccgg cacagacatg aagctgcggc tccctgccag tcccgagacc 660
cacctggaca tgctccgcca cctctaccag ggctgccagg tggtgcaggg aaacctggaa 720
ctcacctacc tgcccaccaa tgccagcctg tccttcctgc aggatatcca ggaggtgcag 780
ggctacgtgc tcatcgctca caaccaagtg aggcaggtcc cactgcagag gctgcggatt 840
gtgcgaggca cccagctctt tgaggacaac tatgccctgg ccgtgctaga caatggagac 900
ccgctgaaca ataccacccc tgtcacaggg gcctccccag gaggcctgcg ggagctgcag 960
cttcgaagcc tcacagagat cttgaaagga ggggtcttga tccagcggaa cccccagctc 1020
tgctaccagg acacgatttt gtggaaggac atcttccaca agaacaacca gctggctctc 1080
acactgatag acaccaaccg ctctcgggcc tgccacccct gttctccgat gtgtaagggc 1140
tcccgctgct ggggagagag ttctgaggat tgtcagagcc tgacgcgcac tgtctgtgcc 1200
ggtggctgtg cccgctgcaa ggggccactg cccactgact gctgccatga gcagtgtgct 1260
gccggctgca cgggccccaa gcactctgac tgcctggcct gcctccactt caaccacagt 1320
ggcatctgtg agctgcactg cccagccctg gtcacctaca acacagacac gtttgagtcc 1380
atgcccaatc ccgagggccg gtatacattc ggcgccagct gtgtgactgc ctgtccctac 1440
aactaccttt ctacggacgt gggatcctgc accctcgtct gcccccctgca caaccaagag 1500 gtgacagcag aggatggaac acagcggtgt gagaagtgca gcaagccctg tgcccgagtg 1560
tgctatggtc tgggcatgga gcacttgcga gaggtgaggg cagttaccag tgccaatatc 1620

-continued

```
caggagtttg ctggctgcaa gaagatcttt gggagcctgg catttctgcc ggagagcttt   1680
gatggggacc cagcctccaa cactgccccg ctccagccag agcagctcca agtgtttgag   1740
actctggaag agatcacagg ttacctatac atctcagcat ggccggacag cctgcctgac   1800
ctcagcgtct tccagaacct gcaagtaatc cggggacgaa ttctgcacaa tggcgcctac   1860
tcgctgaccc tgcaagggct gggcatcagc tggctggggc tgcgctcact gagggaactg   1920
ggcagtggac tggccctcat ccaccataac acccacctct gcttcgtgca cacggtgccc   1980
tgggaccagc tctttcggaa cccgcaccaa gctctgctcc acactgccaa ccggccagag   2040
gacgagtgtg tgggcgaggg cctggcctgc caccagctgt gcgcccgagg gcactgctgg   2100
ggtccagggc ccacccagtg tgtcaactgc agccagttcc ttcggggcca ggagtgcgtg   2160
gaggaatgcc gagtactgca ggggctcccc agggagtatg tgaatgccag gcactgtttg   2220
ccgtgccacc ctgagtgtca gccccagaat ggctcagtga cctgttttgg accggaggct   2280
gaccagtgtg tggcctgtgc ccactataag gaccctccct tctgcgtggc ccgctgcccc   2340
agcggtgtga aacctgacct ctcctacatg cccatctgga agtttccaga tgaggagggc   2400
gcatgccagc cttgccccat caactgcacc cactcctgtg tggacctgga tgacaagggc   2460
tgccccgccg agcagagagc cagccctctg acgtccatca tctctgcggt ggttggcatt   2520
ctgctggtcg tggtcttggg ggtggtcttt gggatcctca tcaagcgacg gcagcagaag   2580
atccggaagt acacgatgcg gagactgctg caggaaacgg agctggtgga gccgctgaca   2640
cctagcggag cgatgcccaa ccaggcgcag atgcggatcc tgaaagagac ggagctgagg   2700
aaggtgaagg tgcttggatc tggcgctttt ggcacagtct acaagggcat ctggatccct   2760
gatggggaga atgtgaaaat tccagtggcc atcaaagtgt tgagggaaaa cacatccccc   2820
aaagccaaca aagaaatctt agacgaagca tacgtgatgg ctggtgtggg ctccccatat   2880
gtctcccgcc ttctgggcat ctgcctgaca tccacggtgc agctggtgac acagcttatg   2940
ccctatggct gcctcttaga ccatgtccgg gaaaaccgcg gacgcctggg ctcccaggac   3000
ctgctgaact ggtgtatgca gattgccaag gggatgagct acctggagga tgtgcggctc   3060
gtacacaggg acttggccgc tcggaacgtg ctggtcaaga gtcccaacca tgtcaaaatt   3120
acagacttcg ggctggctcg gctgctggac attgacgaga cagagtacca tgcagatggg   3180
ggcaaggtgc ccatcaagtg gatggcgctg gagtccattc tccgccggcg gttcacccac   3240
cagagtgatg tgtggagtta tggtgtgact gtgtgggagc tgatgacttt tggggccaaa   3300
ccttacgatg ggatcccagc ccgggagatc cctgacctgc tggaaaaggg ggagcggctg   3360
ccccagcccc ccatctgcac cattgatgtc tacatgatca tggtcaaatg ttggatgatt   3420
gactctgaat gtcggccaag attccgggag ttggtgtctg aattctcccg catggccagg   3480
gacccccagc gctttgtggt catccagaat gaggacttgg gcccagccag tcccttggac   3540
agcaccttct accgctcact gctggaggac gatgacatgg gggacctggt ggatgctgag   3600
gagtatctgg taccccagca gggcttcttc tgtccagacc ctgcccccggg cgctgggggc   3660
atggtccacc acaggcaccg cagctcatct accaggagtg gcggtgggga cctgacacta   3720
gggctggagc cctctgaaga ggaggccccc aggtctccac tggcaccctc cgaaggggct   3780
ggctccgatg tatttgatgg tgacctggga atgggggcag ccaaggggct gcaaagcctc   3840
cccacacatg accccagccc tctacagcgg tacagtgagg accccacagt acccctgccc   3900
tctgagactg atggctacgt tgccccccctg acctgcagcc cccagcctga atatgtgaac   3960
```

```
cagccagatg ttcggcccca gcccccttcg ccccgagagg gccctctgcc tgctgcccga   4020

cctgctggtg ccactctgga aaggcccaag actctctccc cagggaagaa tggggtcgtc   4080

aaagacgttt ttgcctttgg gggtgccgtg gagaaccccg agtacttgac accccaggga   4140

ggagctgccc ctcagcccca ccctcctcct gccttcagcc cagccttcga caacctctat   4200

tactgggacc aggacccacc agagcggggg gctccaccca gcaccttcaa agggacacct   4260

acggcagaga acccagagta cctgggtctg gacgtgccag tgtgaaccag aaggccaagt   4320

ccgcagaagc cctgatgtgt cctcagggag cagggaaggc ctgacttctg ctggcatcaa   4380

gaggtgggag ggccctccga ccacttccag gggaacctgc catgccagga acctgtccta   4440

aggaaccttc cttcctgctt gagttcccag atggctggaa ggggtccagc ctcgttggaa   4500

gaggaacagc actggggagt ctttgtggat tctgaggccc tgcccaatga gactctaggg   4560

tccagtggat gccacagccc agcttggccc tttccttcca gatcctgggt actgaaagcc   4620

ttagggaagc tggcctgaga ggggaagcgg ccctaaggga gtgtctaaga acaaaagcga   4680

cccattcaga gactgtccct gaaacctagt actgcccccc atgaggaagg aacagcaatg   4740

gtgtcagtat ccaggctttg tacagagtgc ttttctgttt agtttttact ttttttgttt   4800

tgttttttta aagatgaaat aaagacccag gggagaatg ggtgttgtat ggggaggcaa   4860

gtgtgggggg tccttctcca cacccacttt gtccatttgc aaatatattt tggaaaacag   4920

ctaaaaaaaa aaaaaaaaaa                                                4940
```

<210> SEQ ID NO 33
<211> LENGTH: 1240
<212> TYPE: PRT
<213> ORGANISM: Homo sapiens
<220> FEATURE:
<223> OTHER INFORMATION: ErbB-2 isoform c, protein

<400> SEQUENCE: 33

```
Met Pro Arg Gly Ser Trp Lys Pro Gln Val Cys Thr Gly Thr Asp Met
1               5                   10                  15

Lys Leu Arg Leu Pro Ala Ser Pro Glu Thr His Leu Asp Met Leu Arg
            20                  25                  30

His Leu Tyr Gln Gly Cys Gln Val Val Gln Gly Asn Leu Glu Leu Thr
        35                  40                  45

Tyr Leu Pro Thr Asn Ala Ser Leu Ser Phe Leu Gln Asp Ile Gln Glu
    50                  55                  60

Val Gln Gly Tyr Val Leu Ile Ala His Asn Gln Val Arg Gln Val Pro
65                  70                  75                  80

Leu Gln Arg Leu Arg Ile Val Arg Gly Thr Gln Leu Phe Glu Asp Asn
                85                  90                  95

Tyr Ala Leu Ala Val Leu Asp Asn Gly Asp Pro Leu Asn Asn Thr Thr
            100                 105                 110

Pro Val Thr Gly Ala Ser Pro Gly Gly Leu Arg Glu Leu Gln Leu Arg
        115                 120                 125

Ser Leu Thr Glu Ile Leu Lys Gly Gly Val Leu Ile Gln Arg Asn Pro
    130                 135                 140

Gln Leu Cys Tyr Gln Asp Thr Ile Leu Trp Lys Asp Ile Phe His Lys
145                 150                 155                 160

Asn Asn Gln Leu Ala Leu Thr Leu Ile Asp Thr Asn Arg Ser Arg Ala
                165                 170                 175

Cys His Pro Cys Ser Pro Met Cys Lys Gly Ser Arg Cys Trp Gly Glu
            180                 185                 190
```

-continued

```
Ser Ser Glu Asp Cys Gln Ser Leu Thr Arg Thr Val Cys Ala Gly Gly
        195                 200                 205

Cys Ala Arg Cys Lys Gly Pro Leu Pro Thr Asp Cys Cys His Glu Gln
    210                 215                 220

Cys Ala Ala Gly Cys Thr Gly Pro Lys His Ser Asp Cys Leu Ala Cys
225                 230                 235                 240

Leu His Phe Asn His Ser Gly Ile Cys Glu Leu His Cys Pro Ala Leu
                245                 250                 255

Val Thr Tyr Asn Thr Asp Thr Phe Glu Ser Met Pro Asn Pro Glu Gly
            260                 265                 270

Arg Tyr Thr Phe Gly Ala Ser Cys Val Thr Ala Cys Pro Tyr Asn Tyr
        275                 280                 285

Leu Ser Thr Asp Val Gly Ser Cys Thr Leu Val Cys Pro Leu His Asn
    290                 295                 300

Gln Glu Val Thr Ala Glu Asp Gly Thr Gln Arg Cys Glu Lys Cys Ser
305                 310                 315                 320

Lys Pro Cys Ala Arg Val Cys Tyr Gly Leu Gly Met Glu His Leu Arg
                325                 330                 335

Glu Val Arg Ala Val Thr Ser Ala Asn Ile Gln Glu Phe Ala Gly Cys
            340                 345                 350

Lys Lys Ile Phe Gly Ser Leu Ala Phe Leu Pro Glu Ser Phe Asp Gly
        355                 360                 365

Asp Pro Ala Ser Asn Thr Ala Pro Leu Gln Pro Glu Gln Leu Gln Val
    370                 375                 380

Phe Glu Thr Leu Glu Glu Ile Thr Gly Tyr Leu Tyr Ile Ser Ala Trp
385                 390                 395                 400

Pro Asp Ser Leu Pro Asp Leu Ser Val Phe Gln Asn Leu Gln Val Ile
                405                 410                 415

Arg Gly Arg Ile Leu His Asn Gly Ala Tyr Ser Leu Thr Leu Gln Gly
            420                 425                 430

Leu Gly Ile Ser Trp Leu Gly Leu Arg Ser Leu Arg Glu Leu Gly Ser
        435                 440                 445

Gly Leu Ala Leu Ile His His Asn Thr His Leu Cys Phe Val His Thr
    450                 455                 460

Val Pro Trp Asp Gln Leu Phe Arg Asn Pro His Gln Ala Leu Leu His
465                 470                 475                 480

Thr Ala Asn Arg Pro Glu Asp Glu Cys Val Gly Glu Gly Leu Ala Cys
                485                 490                 495

His Gln Leu Cys Ala Arg Gly His Cys Trp Gly Pro Gly Pro Thr Gln
            500                 505                 510

Cys Val Asn Cys Ser Gln Phe Leu Arg Gly Gln Glu Cys Val Glu Glu
        515                 520                 525

Cys Arg Val Leu Gln Gly Leu Pro Arg Glu Tyr Val Asn Ala Arg His
    530                 535                 540

Cys Leu Pro Cys His Pro Glu Cys Gln Pro Gln Asn Gly Ser Val Thr
545                 550                 555                 560

Cys Phe Gly Pro Glu Ala Asp Gln Cys Val Ala Cys Ala His Tyr Lys
                565                 570                 575

Asp Pro Pro Phe Cys Val Ala Arg Cys Pro Ser Gly Val Lys Pro Asp
            580                 585                 590

Leu Ser Tyr Met Pro Ile Trp Lys Phe Pro Asp Glu Glu Gly Ala Cys
        595                 600                 605
```

-continued

```
Gln Pro Cys Pro Ile Asn Cys Thr His Ser Cys Val Asp Leu Asp Asp
    610                 615                 620

Lys Gly Cys Pro Ala Glu Gln Arg Ala Ser Pro Leu Thr Ser Ile Ile
625                 630                 635                 640

Ser Ala Val Val Gly Ile Leu Leu Val Val Val Leu Gly Val Val Phe
                645                 650                 655

Gly Ile Leu Ile Lys Arg Arg Gln Gln Lys Ile Arg Lys Tyr Thr Met
            660                 665                 670

Arg Arg Leu Leu Gln Glu Thr Glu Leu Val Glu Pro Leu Thr Pro Ser
        675                 680                 685

Gly Ala Met Pro Asn Gln Ala Gln Met Arg Ile Leu Lys Glu Thr Glu
    690                 695                 700

Leu Arg Lys Val Lys Val Leu Gly Ser Gly Ala Phe Gly Thr Val Tyr
705                 710                 715                 720

Lys Gly Ile Trp Ile Pro Asp Gly Glu Asn Val Lys Ile Pro Val Ala
                725                 730                 735

Ile Lys Val Leu Arg Glu Asn Thr Ser Pro Lys Ala Asn Lys Glu Ile
            740                 745                 750

Leu Asp Glu Ala Tyr Val Met Ala Gly Val Gly Ser Pro Tyr Val Ser
        755                 760                 765

Arg Leu Leu Gly Ile Cys Leu Thr Ser Thr Val Gln Leu Val Thr Gln
    770                 775                 780

Leu Met Pro Tyr Gly Cys Leu Leu Asp His Val Arg Glu Asn Arg Gly
785                 790                 795                 800

Arg Leu Gly Ser Gln Asp Leu Leu Asn Trp Cys Met Gln Ile Ala Lys
                805                 810                 815

Gly Met Ser Tyr Leu Glu Asp Val Arg Leu Val His Arg Asp Leu Ala
            820                 825                 830

Ala Arg Asn Val Leu Val Lys Ser Pro Asn His Val Lys Ile Thr Asp
        835                 840                 845

Phe Gly Leu Ala Arg Leu Leu Asp Ile Asp Glu Thr Glu Tyr His Ala
    850                 855                 860

Asp Gly Gly Lys Val Pro Ile Lys Trp Met Ala Leu Glu Ser Ile Leu
865                 870                 875                 880

Arg Arg Arg Phe Thr His Gln Ser Asp Val Trp Ser Tyr Gly Val Thr
                885                 890                 895

Val Trp Glu Leu Met Thr Phe Gly Ala Lys Pro Tyr Asp Gly Ile Pro
            900                 905                 910

Ala Arg Glu Ile Pro Asp Leu Leu Glu Lys Gly Glu Arg Leu Pro Gln
        915                 920                 925

Pro Pro Ile Cys Thr Ile Asp Val Tyr Met Ile Met Val Lys Cys Trp
    930                 935                 940

Met Ile Asp Ser Glu Cys Arg Pro Arg Phe Arg Glu Leu Val Ser Glu
945                 950                 955                 960

Phe Ser Arg Met Ala Arg Asp Pro Gln Arg Phe Val Val Ile Gln Asn
                965                 970                 975

Glu Asp Leu Gly Pro Ala Ser Pro Leu Asp Ser Thr Phe Tyr Arg Ser
            980                 985                 990

Leu Leu Glu Asp Asp Asp Met Gly Asp Leu Val Asp Ala Glu Glu Tyr
        995                 1000                1005

Leu Val Pro Gln Gln Gly Phe Phe Cys Pro Asp Pro Ala Pro Gly Ala
    1010                1015                1020

Gly Gly Met Val His His Arg His Arg Ser Ser Ser Thr Arg Ser Gly
```

-continued

```
1025                1030                1035                1040

Gly Gly Asp Leu Thr Leu Gly Leu Glu Pro Ser Glu Glu Glu Ala Pro
                1045                1050                1055

Arg Ser Pro Leu Ala Pro Ser Glu Gly Ala Gly Ser Asp Val Phe Asp
            1060                1065                1070

Gly Asp Leu Gly Met Gly Ala Ala Lys Gly Leu Gln Ser Leu Pro Thr
        1075                1080                1085

His Asp Pro Ser Pro Leu Gln Arg Tyr Ser Glu Asp Pro Thr Val Pro
    1090                1095                1100

Leu Pro Ser Glu Thr Asp Gly Tyr Val Ala Pro Leu Thr Cys Ser Pro
1105                1110                1115                1120

Gln Pro Glu Tyr Val Asn Gln Pro Asp Val Arg Pro Gln Pro Pro Ser
                1125                1130                1135

Pro Arg Glu Gly Pro Leu Pro Ala Ala Arg Pro Ala Gly Ala Thr Leu
            1140                1145                1150

Glu Arg Pro Lys Thr Leu Ser Pro Gly Lys Asn Gly Val Val Lys Asp
        1155                1160                1165

Val Phe Ala Phe Gly Gly Ala Val Glu Asn Pro Glu Tyr Leu Thr Pro
    1170                1175                1180

Gln Gly Gly Ala Ala Pro Gln Pro His Pro Pro Pro Ala Phe Ser Pro
1185                1190                1195                1200

Ala Phe Asp Asn Leu Tyr Tyr Trp Asp Gln Asp Pro Pro Glu Arg Gly
                1205                1210                1215

Ala Pro Pro Ser Thr Phe Lys Gly Thr Pro Thr Ala Glu Asn Pro Glu
            1220                1225                1230

Tyr Leu Gly Leu Asp Val Pro Val
        1235                1240


<210> SEQ ID NO 34
<211> LENGTH: 915
<212> TYPE: DNA
<213> ORGANISM: Homo sapiens
<220> FEATURE:
<223> OTHER INFORMATION: ErbB-2 transcript variant 1, BT-474 cells
      primer forward sequencing

<400> SEQUENCE: 34

tggggcttcg acagagagca gccctctgac gtccatcatc tctgcggtgg ttggcattct      60

gctggtcgtg gtcttggggg tggtctttgg gatcctcatc aagcgacggc agcagaagat     120

ccggaagtac acgatgcgga gactgctgca ggaaacggag ctggtggagc cgctgacacc     180

tagcggagcg atgcccaacc aggcgcagat gcggatcctg aaagagacgg agctgaggaa     240

ggtgaaggtg cttggatctg gcgcttttgg cacagtctac aagggcatct ggatccctga     300

tggggagaat gtgaaaattc cagtggccat caaagtgttg agggaaaaca catcccccaa     360

agccaacaaa gaaatcttag acgaagcata cgtgatggct ggtgtgggct ccccatatgt     420

ctcccgcctt ctgggcatct gcctgacatc cacggtgcag ctggtgacac agcttatgcc     480

ctatggctgc ctcttagacc atgtccggga aaaccgcgga cgcctgggct cccaggacct     540

gctgaactgg tgtatgcaga ttgccaaggg gatgagctac ctggaggatg tgcggctcgt     600

acacagggac ttggccgctc ggaacgtgct ggtcaagagt cccaaccatg tcaaaattac     660

agacttcggg ctggctcggc tgctggacat tgacgagaca gagtaccatg cagatggggg     720

caaggtgccc atcaagtgga tggcgctgga gtccattctc cgccggcggt tcacccacca     780

tagtgatgtg tggagttatg gtgtgactgt gtggaagctg atgactttttg ggggcaaacc     840
```

tttacgatgg tatcctgccc cgggtagatc ccagacctgc gtgttaaacg cagagcgggt 900
gacaacagcc accca 915

<210> SEQ ID NO 35
<211> LENGTH: 1497
<212> TYPE: DNA
<213> ORGANISM: Homo sapiens
<220> FEATURE:
<223> OTHER INFORMATION: ErbB-2 transcript variant 1, BT-474 cells
primer reverse sequencing

<400> SEQUENCE: 35
cccaccggtt taaagggacc ccccaaattt tctctggggg ggttgggcca catttaaccg 60
gggttcgggt ttttaggggg gagtttcctt tgggaattct ccttcaaagg gacgggcgca 120
ccaaagaatt tccggaaatt tccccgatgg cggggaagct tttttcccgg aaaaccggaa 180
atttgtgtga accccccttgt caccccttag gggaagcggt tgcccaatcc aggggccgga 240
ttgcggatcc ctgaaaagga accggaattt gaggaaaggt gaaaggtgcc ttggatcttg 300
gcggcttttt ggccacagtt tatcaaaggg cattctggat tccctgatgg ggaagaaagg 360
tgaaaatttc cagtggccca tccaaagtgt tgagggaaaa acacatcccc ccaaaaccca 420
acaaagaaat tcttagacga aggcatacgt gatggctggg tgtgggctcc cccataagtt 480
ttcccgcctt ctggggcatc tgcctgacat tccacggtgc agctggtgac acagcttatg 540
ccctatggct gcctcttaga ccatgtccgg gaaaaccgcg gacgcctggg ctccccagga 600
cctgctgaac tggtgtatgc agattgccaa ggggatgagc tacctggagg atgtgcggct 660
cgtacacagg gacttggccg ctcggaacgt gctggtcaag agtcccaacc atgtcaaaat 720
tacagacttc gggctggctc ggctgctgga cattgacgag acagagtacc atgcagatgg 780
gggcaaggtg cccatcaagt ggatggcgct ggagtccatt ctccgccggc ggttcaccca 840
ccagagtgat gtgtggagtt atggtgtgac tgtgtgggag ctgatgactt ttggggccaa 900
accttacgat gggatcccag cccgggagat ccctgacctg ctggaaaagg gggagcggct 960
gccccagccc cccatctgca ccattgatgt ctacatgatc atggtcaaat gttggatgat 1020
tgactctgaa tgtcggccaa gattccggga gttggtgtct gaattctccc gcatggccag 1080
ggacccccag cgctttgtgg tcatccagaa tgaggacttg ggcccagcca gtcccttgga 1140
cagcaccttc taccgctcac tgctggagga cgatgacatg gggggacctgg tggatgctga 1200 ggagtatctg gtaccccagc agggcttctt ctgtccagac cctgccccgg gcgctggggg 1260
catggtccac cacaggcacc gcagctcatc taccaggagt ggcggtgggg acctgacact 1320
agggctggag ccctctgaag aggaggcccc caggtctcca ctggcaccct ccgaaggggc 1380
tggctccgat gtatttgatg gtgacctggg aatgggggca gccaaggggc tgcaaagcct 1440
ccccacacat gaccccagcc ctctacagcg gtacagtgag accccacaac ccctcac 1497

<210> SEQ ID NO 36
<211> LENGTH: 957
<212> TYPE: DNA
<213> ORGANISM: Homo sapiens
<220> FEATURE:
<223> OTHER INFORMATION: ErbB-2 transcript variant 1, HCC-70 cells
primer forward sequencing

<400> SEQUENCE: 36
gaagctacga cgagagcagc cctctgacgt ccatcatctc tgcggtggtt ggcattctgc 60
tggtcgtggt cttgggggtg gtctttggga tcctcatcaa gcgacggcag cagaagatcc 120
ggaagtacac gatgcggaga ctgctgcagg aaacggagct ggtggagccg ctgacaccta 180
gcggagcgat gcccaaccag gcgcagatgc ggatcctgaa agagacggag ctgaggaagg 240
tgaaggtgct tggatctggc gcttttggca cagtctacaa gggcatctgg atccctgatg 300
gggagaatgt gaaaattcca gtggccatca aagtgttgag ggaaaacaca tcccccaaag 360
ccaacaaaga aatcttagac gaagcatacg tgatggctgg tgtgggctcc ccatatgtct 420
cccgccttct gggcatctgc ctgacatcca cggtgcagct ggtgacacag cttatgccct 480
atggctgcct cttagaccat gtccgggaaa accgcggacg cctgggctcc caggacctgc 540
tgaactggtg tatgcagatt gccaagggga tgagctacct ggaggatgtg cggctcgtac 600
acagggactt gggcgctcgg aacgtgctgg tcaagagtcc caaccatgtc aaaattacag 660
acttcgggct ggctcggctg ctggacattg acgagacaga gtaccatgca gatgggggca 720
aggtgcccat caagtggatg gcgctggagt ccattctccg ccggcggttc acccaccaaa 780
atgaagtgtg gaaattatga tgttggctgt gtgggaaccg gatgacttat gggggccaag 840
tcttatgatg ggaatgccag gcccgggagc tctccgtatt ttgttggtga atgggggaag 900
aacttgtccc tggctctcct atttgtgcta agtttttgtt tgagttggac aagggtc 957

<210> SEQ ID NO 37
<211> LENGTH: 1253
<212> TYPE: DNA
<213> ORGANISM: Homo sapiens
<220> FEATURE:
<223> OTHER INFORMATION: ErbB-2 transcript variant 1, HCC-70 cells primer reverse sequencing

<400> SEQUENCE: 37
accaggcccg ggtggggggt ttccgaaaag gacgggaggt tgaggaaggt tagggggctt 60
tgaatttggg gggtatttgg cccagttctt caaaggcatt ctggattccc tgatggggaa 120
gaattggaaa attccccatg gccattcaaa gtgttgaggc gaaaacacat tcccccaaag 180
ccaacaaaga aatctttgac gaagcctacg tgatggctgg tgtgggctcc ccctaagttt 240
tctcgccttc tgggcatctg cctgacatcc cacggtgcag ctggtgacac agcttatgcc 300
ctatggctgc cttttagacc atgtccggga aaaccgcgga cgcctgggct cccaggacct 360
gctgaactgg tgtatgcaga ttgccaaggg gatgagctac ctggaggatg tgcggcttgt 420
acacagggac ttggccgctc ggaacgtgct ggtcaagagt cccaaccatg tcaaaattac 480
agacttcggg ctggctcggc tgctggacat tgacgagaca gagtaccatg cagatggggg 540
caaggtgccc atcaagtgga tggcgctgga gtccattctc cgccggcggt tcacccacca 600
gagtgatgtg tggagttatg gtgtgactgt gtgggagctg atgacttttg gggccaaacc 660
ttacgatggg atcccagccc gggagatccc tgacctgctg gaaaaggggg agcggctgcc 720
ccagcccccc atctgcacca ttgatgtcta catgatcatg gtcaaatgtt ggatgattga 780
ctctgaatgt cggccaagat tccgggagtt ggtgtctgaa ttctcccgca tggccaggga 840
cccccagcgc tttgtggtca tccagaatga ggacttgggc ccagccagtc ccttggacag 900
caccttctac cgctcactgc tggaggacga tgacatgggg gacctggtgg atgctgagga 960
gtatctggta ccccagcagg gcttcttctg tccagaccct gccccgggcg ctgggggcat 1020
ggtccaccac aggcaccgca gctcatctac caggagtggc ggtggggacc tgacactagg 1080
gctggagccc tctgaagagg aggcccccag gtctccactg gcaccctccg aaggggctgg 1140

```
ctccgatgta tttgatggtg acctgggaat gggggcagcc aaggggctgc aaagcctccc   1200

cacacatgac cccagccctc tacagcggta cagtgagacc ccacaaccct cac          1253


<210> SEQ ID NO 38
<211> LENGTH: 407
<212> TYPE: DNA
<213> ORGANISM: Homo sapiens
<220> FEATURE:
<223> OTHER INFORMATION: ErbB-2 transcript variant 2, MDA-MB-468 cells
      primer forward sequencing

<400> SEQUENCE: 38

gacgtttctg atcttttttg agtctcattg tgttaccacc tcccgagggt gattgcttcc     60

ccatgcgggg tagaaccttt gctgtcctgt tcaccactct acctccagca cagaatttgg    120

cttatgccta ctcaatgtga agatgatgag gatgaaaacc tttgtgatga tccacttcca    180

cttaatgaat ggtggcaaag caaagctata ttcaagacca catgcaaagc tactccctga    240

gcaaagagtc acagataaaa cgggggcacc agtagaatgg gcgggacgaa ctcattgctg    300

cacagagact cacaccctgg tagccatgcc tgcgcaggca gtgatgagag tgacatgtac    360

tgttgtggac atgctcaaaa ttgagtgtgc tccgaaattt ttttttc                  407


<210> SEQ ID NO 39
<211> LENGTH: 402
<212> TYPE: DNA
<213> ORGANISM: Homo sapiens
<220> FEATURE:
<223> OTHER INFORMATION: ErbB-2 transcript variant 2, MDA-MB-468 cells
      primer reverse sequencing

<400> SEQUENCE: 39

tttttaacgc ctgatgggtt aatgagcaaa ctgaagtgtt ttccatgatc ttttttgagt     60

cgcaattgaa gtaccacctc ccgagggtga ttgcttcccc atgcggggta gaacctttgc    120

tgtcctgttc accactctac ctccagcaca gaatttggct tatgcctact caatgtgaag    180

atgatgagga tgaaaacctt tgtgatgatc cacttccact taatgaatgg tggcaaagca    240

aagctatatt caagaccaca tgcaaagcta ctccctgagc aaagagtcac agataaaacg    300

ggggcaccag tagaatggcc aggacaaacg cagtgcagca cagagactca gaccctggca    360

gccatgcctg cgcaggcagt gatgagagga cagttacgaa cc                       402


<210> SEQ ID NO 40
<211> LENGTH: 424
<212> TYPE: DNA
<213> ORGANISM: Homo sapiens
<220> FEATURE:
<223> OTHER INFORMATION: ErbB-2 transcript variant 2, MDA-MB-231 cells
      primer forward sequencing

<400> SEQUENCE: 40

gaacgttttt ctgatctttt ttgagtcgca attgaagtac cacctcccga gggtgattgc     60

ttccccatgc ggggtagaac ctttgctgtc ctgttcacca ctctacctcc agcacagaat    120

ttggcttatg cctactcaat gtgaagatga tgaggatgaa aacctttgtg atgatccact    180

tccacttaat gaatggtggc aaagcaaagc tatattcaag accacatgca aagctactcc    240

ctgagcaaag agtcacagat aaaacggggg cacggtgata atggccagga caaacgttct    300

ggttcttcca gactcaaccc tggtattatg cctgctgtac cccggatgag agcgacgtga    360

tctggttgct acatgcacag atcggtgtga ccgtgggtga aatcgctttc tccctttta    420
```

-continued aata 424

<210> SEQ ID NO 41
<211> LENGTH: 402
<212> TYPE: DNA
<213> ORGANISM: Homo sapiens
<220> FEATURE:
<223> OTHER INFORMATION: ErbB-2 transcript variant 2, MDA-MB-231 cells primer reverse sequencing

<400> SEQUENCE: 41
aaaatttggt cgcctgatgg gttaatgagc aaactgaagt gttttccatg atcttttttg 60
agtcgcaatt gaagtaccac ctcccgaggg tgattgcttc cccatgcggg gtagaacctt 120
tgctgtcctg ttcaccactc tacctccagc acagaatttg gcttatgcct actcaatgtg 180
aagatgatga ggatgaaaac ctttgtgatg atccacttcc acttaatgaa tggtggcaaa 240
gcaaagctat attcaagacc acatgcaaag ctactccctg agcaaagagt cacagataaa 300
acgggggcac cagtagaatg gccaggacaa acgcagtgca gcacagagac tcagaccctg 360
gcagccatgc ctgcgcaggc agtgatgaga ggacagtacg cc 402

<210> SEQ ID NO 42
<211> LENGTH: 403
<212> TYPE: DNA
<213> ORGANISM: Homo sapiens
<220> FEATURE:
<223> OTHER INFORMATION: ErbB-2 alternative transcript variant 3, MDA-MB-468 cells primer forward sequencing

<400> SEQUENCE: 42
ctcacggagc tgatgggtta tgagcaactg aagtgttttc catgatcttt tttgagtcgc 60
aattgaagta ccacctcccg agggtgattg cttccccatg cggggtagaa cctttgctgt 120
cctgttcacc actctacctc cagcacagaa tttggcttat gcctactcaa tgtgaagatg 180
atgaggatga ccgccttcgc tccccgcgaa ctaaagtcac gatccggtcg aagaaaggga 240
cgcaatgcgg cgtcttattc gtacggcgcg cgcctcgaga ccgtccttcg catgcttttc 300
tttcgaggcg gagcacacgc ctcgcgtgaa cgccaaagcg tggaacgcag acagaggctt 360
ccccttcgtc tttggcatgt gggaaacgtt caggttattt tga 403

<210> SEQ ID NO 43
<211> LENGTH: 375
<212> TYPE: DNA
<213> ORGANISM: Homo sapiens
<220> FEATURE:
<223> OTHER INFORMATION: ErbB-2 alternative transcript variant 3, MDA-MB-468 cells primer reverse sequencing

<400> SEQUENCE: 43
tctttttgag tcgcaattga agtaccacct cccgagggtg attgcttccc catgtggggt 60
agaacctttg ctgtcctgtt caccactcta cctccagcac agaatttggc ttatgcctac 120
tcaatgtgaa gatgatgagg atgaaaacct ttgtgatgat ccacttccac ttaatgaatg 180
gtggcaaagc aaagctatat tcaagaccac atgcaaagct actccctgag caaagagtca 240
cagataaaac gggggcacca gtagaatggc caggacaaac gcagtgcagc acagagactc 300
agaccctggc agccatgcct gcgcaggcag tgatgagagt gacatgtact gttgtggaca 360
gcacaaaagt aggcg 375

<210> SEQ ID NO 44

<211> LENGTH: 313
<212> TYPE: DNA
<213> ORGANISM: Homo sapiens
<220> FEATURE:
<223> OTHER INFORMATION: ErbB-2 alternative transcript variant 3, MDA-MB-231 cells primer forward sequencing

<400> SEQUENCE: 44

```
ttaatagcga gctgatgggt atgagcaact gagagttttc atgatctttt ttgactcgca     60

attggctacc ggatccattg ggggattgtt ccccaatgcg gggttctgcc ctcgtcccga    120

tgtcccatat cttatcttcc tcctgcgatt ctttcccccg aatcttgaag ctgattcctc    180

gtctgctgtt tccttcttcc ctgctctcac tgcgcactgc tcgtacacga tgctccgttg    240

cccttctcct cttcttcgtg ttcaagcctt ttcgttttaa atcgccgtta ctttgtcccg    300

ttcctcaaac ctc                                                       313
```

<210> SEQ ID NO 45
<211> LENGTH: 317
<212> TYPE: DNA
<213> ORGANISM: Homo sapiens
<220> FEATURE:
<223> OTHER INFORMATION: ErbB-2 alternative transcript variant 3, MDA-MB-231 cells primer reverse sequencing

<400> SEQUENCE: 45

```
tttgtattac tatcatgtac aacagtgtgg tccagcaaaa aatttggagt aaccttacaa     60

agaatgaaga tgatgaggat gaaaacctgt gtgatgatcc acttccactt aatgaatggt    120

ggcaaagcaa agctatattc aagaccacat gcaaagctac tccctgagca aagagtcaca    180

gataaaacgg gggcaccagt agaatggcca ggacaaacgc agtgcagcac agagactcag    240

accctggcag ccatgcctgc gcaggcagtg atgagagtga catgtactgt tgtggacagc    300

acataagagt cttttac                                                   317
```

<210> SEQ ID NO 46
<211> LENGTH: 129
<212> TYPE: DNA
<213> ORGANISM: Homo sapiens
<220> FEATURE:
<223> OTHER INFORMATION: ErbB-2?16, HCC-70 cells primer forward sequencing

<400> SEQUENCE: 46

```
ctgggcgtgg tggcttctgc tggtcgtggt cttgggggtg gtctttggga tcctcatcaa     60

gcgacggcag cagaagatcc ggaagtacac gatgcggaga ctgctgcagg aaacggagct    120

ggtggagca                                                            129
```

<210> SEQ ID NO 47
<211> LENGTH: 128
<212> TYPE: DNA
<213> ORGANISM: Homo sapiens
<220> FEATURE:
<223> OTHER INFORMATION: ErbB-2?16, HCC-70 cells primer reverse sequencing

<400> SEQUENCE: 47

```
cacccactcc cctctgacgt ccatcatctc tgcggtggtt ggcattctgc tggtcgtggt     60

cttgggggtg gtctttggga tcctcatcaa gcgacggcag cagaagatcc ggaagtacac    120

gagcgagc                                                             128
```

-continued

<210> SEQ ID NO 48
<211> LENGTH: 131
<212> TYPE: DNA
<213> ORGANISM: Homo sapiens
<220> FEATURE:
<223> OTHER INFORMATION: ErbB-2?16, MDA-MB-453 cells primer forward sequencing

<400> SEQUENCE: 48
cccgtgggtg gttggcattc tgctggtcgt ggtcttgggg gtggtctttg ggatcctcat 60
caagcgacgg cagcagaaga tccggaagta cacgatgcgg agactgctgc aggaaacgga 120
gctggtggag c 131

<210> SEQ ID NO 49
<211> LENGTH: 128
<212> TYPE: DNA
<213> ORGANISM: Homo sapiens
<220> FEATURE:
<223> OTHER INFORMATION: ErbB-2?16, MDA-MB-453 cells primer reverse sequencing

<400> SEQUENCE: 49
cacccactcc cctctgacgt ccatcgtctc tgcggtggtt ggcattctgc tggtcgtggt 60
cttgggggtg gtctttggga tcctcatcaa gcgacggcag cagaagatcc ggaagtacac 120
gagcgagt 128

<210> SEQ ID NO 50
<211> LENGTH: 53
<212> TYPE: DNA
<213> ORGANISM: Homo sapiens
<220> FEATURE:
<223> OTHER INFORMATION: Exon 2 skipping, MDA-MB-468 cells SpT2 primer forward sequencing

<400> SEQUENCE: 50
gaacgttttc tgatcttttt tgagcctact caatgtgaag atgatgagga tga 53

<210> SEQ ID NO 51
<211> LENGTH: 295
<212> TYPE: DNA
<213> ORGANISM: Homo sapiens
<220> FEATURE:
<223> OTHER INFORMATION: Exon 2 skipping, MDA-MB-468 cells SpT2 primer reverse sequencing

<400> SEQUENCE: 51
aatttaacgc ctgatgggtt aatgagcaaa ctgaagtgtt ttccatgatc ttttttgagc 60
ctactcaatg tgaagatgat gaggatgaaa acctttgtga tgatccactt ccacttaatg 120
aatggtggca aagcaaagct atattcaaga ccacatgcaa agctactccc tgagcaaaga 180
gtcacagata aaacgggggc accagtagaa tggccaggac aaacgcagtg cagcacagag 240
actcagaccc tggcagccat gcctgcgcag gcagtgatga gaggacagta caacc 295

<210> SEQ ID NO 52
<211> LENGTH: 83
<212> TYPE: DNA
<213> ORGANISM: Homo sapiens
<220> FEATURE:
<223> OTHER INFORMATION: Exon 2 skipping, BT-474 cells SpT3 primer forward sequencing

<400> SEQUENCE: 52
tccagccgga gctgatgggt tatgagcaac tgaagtgttt tccatgatct tttttgagcc 60

-continued

```
tactcaatgt gaagatgatg agg                                          83


<210> SEQ ID NO 53
<211> LENGTH: 414
<212> TYPE: DNA
<213> ORGANISM: Homo sapiens
<220> FEATURE:
<223> OTHER INFORMATION: Exon 2 skipping, BT-474 cells SpT3 primer
      reverse sequencing

<400> SEQUENCE: 53

ttttaaaaaa atggggaaag attggatgtc acccagggta ccacggattt ttaggatagc     60

aacatcataa ctttggcctg ggcggagtac acgtttttta atattgtcgg taatttgggg    120

aataacctga atggtaccac taaagtattt gagcctactc aatgtgaaga tgatgaggat    180

gaaaaccttt gtgatgatcc acttccactt aatgaatggt ggcaaagcaa agctatattc    240

aagaccacat gcaaagctac tccctgagca aagagtcaca gataaaacgg gggcaccagt    300

agaatggcca ggacaaacgc agtgcagcac agagactcag accctggcag ccatgcctgc    360

gcaggcagtg atgagagtga catgtactgt tgtggacagc acaaaagtag ttgg          414
```

SPECIFIC SIRNA MOLECULES, COMPOSITION AND USE THEREOF FOR THE TREATMENT OF TRIPLE NEGATIVE BREAST CANCER

REFERENCE TO A SEQUENCE LISTING SUBMITTED VIA EFS-WEB

The content of the ASCII text file of the sequence listing named 132912a.seq.app.txt, which is 99 kb in size was created on Nov. 16, 2020 and electronically submitted via EFS-Web herewith, the application is incorporated herein by reference in its entirety.

FIELD OF THE INVENTION

The present invention generally relates to the field of molecular biology and RNA interference (RNAi). More specifically, the methods of the present invention relates to specific double stranded RNA (dsRNA) molecules, referred to as small (or short) interfering RNAs (siRNAs), its composition and use thereof, as well as a method of treating cancer and methods of inhibiting cancer cell proliferation, particularly a method of treating breast cancer.

Yet more particularly, the method of the present invention is a method for inhibiting in vitro proliferation of triple negative breast cancer (TNBC) cells and for the blockade of in vivo grow of TN breast tumors. In a preferred embodiment, the invention provides specific siRNA molecules, comprising nucleotide sequences as depicted in SEQ ID NO: 1 and SEQ ID NO: 2. Such siRNA molecules are suitable for the treatment of breast cancer, particularly, TNBC. Aspects of the invention also relate to methods for detecting a diagnostic marker in a sample of a subject suspected of having a TNBC tumor, the methods comprising providing a diagnostic sample of the subject, contacting the diagnostic sample of the subject with the siRNA molecules of the invention, and determining the presence of a diagnostic marker in said sample.

BACKGROUND OF THE INVENTION

Double stranded RNA (dsRNA) has the capacity to inhibit protein expression, which represents an extraordinary therapy for a large number of human diseases. Actually, therapeutic dsRNA, are emerging as a new class of drugs. The mechanism of RNA induced silencing (RNA interference, or RNAi) in mammalian cells consists on the catalytic degradation of a homologous host messenger RNA (mRNA). It has been well demonstrated that the introduction of short (18-30 bp) RNA duplexes (small interfering RNAs, siRNAs) into cultures of mammalian cells results in sequence-specific inhibition of target mRNA. Mechanism of action and several examples of siRNAs use can be found in the following publications: Elbashir, S. M. et al. (2001) *Duplexes of 21-nucleotide RNAs mediate RNA interference in cultured mammalian cells*. Nature 411, 494-498; Fire, A. et al. (1998) *Potent and specific genetic interference by double-stranded RNA in Caenorhabditis elegans*. Nature 391, 806-811; Hutvagner, G. et al. (2002) *A microRNA in a multiple-turnover RNAi enzyme complex*. Science 297, 2056-2060; and Provost, P. et al. (2002) *Ribonuclease activity and RNA binding of recombinant human Dicer*. The EMBO journal 21, 5864-5874.

The advantages of therapeutic siRNAs compared to small-molecule inhibitors or antibody-based drugs, include: i) ease of design, straightforward identification of appropriate drug candidates based on sequence information; ii) ability to target disease genes previously considered "undruggable" by traditional drug discovery strategies. Thus, an siRNA-based drug can target any mRNAs of interest, regardless of the cellular location of the translated proteins; iii) the sequence-specific basis of RNAi allows to target any mRNA and to discriminate against different alleles and alternatively spliced isoforms of protein-coding mRNAs (Goldberg, M. S. et al. (2012) *Pyruvate kinase M2-specific siRNA induces apoptosis and tumor regression*. J Exp Med 209, 217-224; Kisielow, M. et al. (2002) *Isoform-specific knockdown and expression of adaptor protein ShcA using small interfering RNA*. The Biochemical journal 363, 1-5), a fact relevant for the present invention; iv) high potency and unusually sustained activity; v) siRNAs can be chemically synthesized, thus leading to cheaper and more easily manufactured drugs than biologics; and vi) easy to combine into drug cocktails, providing flexibility for personalized drugs (Lieberman, J. (2018) *Tapping the RNA world for therapeutics*. Nature structural & molecular biology 25, 357-364). Clinical success is dependent on their efficient delivery to disease tissues.

siRNAs are especially advantageous for therapeutic applications in heterogeneous diseases that lack common molecular signatures. Within this class of diseases is included triple-negative breast cancer (TNBC), which refers to tumors that do not express clinically significant levels of the steroid hormone receptors estrogen (ER) and progesterone (PR), and lack overexpression at the cytoplasmic membrane of ErbB-2/HER2 (MErbB-2), a member of the ErbBs family of receptor tyrosine kinases (EGFR/ErbB-1, ErbB-2, ErbB-3, ErbB-4) or ERBB2 gene amplification. Clinical biomarkers and targeted therapies for this disease remain elusive so chemotherapy has been the standard of care for early and metastatic TNBC (reviewed in Garrido-Castro, A. C. et al. (2019) *Insights into Molecular Classifications of Triple-Negative Breast Cancer: Improving Patient Selection for Treatment*. Cancer discovery 9, 176-198). The IMpassion130 trial (NCT02425891) showed that the combination of atezolizumab, a programmed death ligand 1 (PD-L1) antibody, with chemotherapy prolonged progression-free survival among patients with metastatic TNBC in the entire population and in the PD-L1-positive subgroup (Schmid, P. et al. (2018) Atezolizumab and Nab-Paclitaxel in Advanced Triple-Negative Breast Cancer. N Engl J Med 379, 2108-2121). These results led to the recent Food and Drug Administration (FDA) approval of said combination for patients with locally advanced or metastatic TNBC, whose tumors express PD-L1-positive immune cells. However, continued approval will require a confirmatory trial. Gene expression (GE) profile studies in TNBC cohorts revealed that this subtype is indeed a heterogeneous group and identified six different GE profile clusters: basal-like 1 (BL1), basal-like 2 (BL2), immunomodulatory (IM), mesenchymal (M), mesenchymal stem-like (MSL) and luminal androgen receptor (LAR) (Lehmann, B. D. et al. (2011) *Identification of human triple-negative breast cancer subtypes and preclinical models for selection of targeted therapies*. JClinInvest 121, 2750-2767). Further studies showed that IM and MSL subtypes were defined by expression of genes from infiltrating lymphocytes and tumor-associated stromal cells and thus TNBC molecular subtypes were refined to four subtypes (TNBC-4type: BL1, BL2, M and LAR) (Lehmann, B. D. et al. (2016) *Refinement of Triple-Negative Breast Cancer Molecular Subtypes: Implications for Neoadjuvant Chemotherapy Selection*. PloS one 11, e0157368; Prat, A. et al. (2013a) *Molecular characterization*

*of basal-like and non-basal-like triple-negative breast cancer*. The oncologist 18, 123-133). Another study on TNBC transcriptomes identified four subtypes: LAR, M, basal-like immune suppressed (BLIS), and BL immune activated (BLIA) (Burstein, M. D. et al. (2015) *Comprehensive genomic analysis identifies novel subtypes and targets of triple-negative breast cancer*. ClinCancer Res. 21, 1688-1698). Correlation of the transcriptional profiles of TN tumors to those of the intrinsic BC molecular subtypes (luminal A (LumA), luminal B (LumB), basal-like (BL), and ErbB-2-enriched (ErbB-2E)) (Perou, C. M. et al. (2000) *Molecular portraits of human breast tumours*. Nature 406, 747-752; Prat, A. et al. (2013b) *Characterization of cell lines derived from breast cancers and normal mammary tissues for the study of the intrinsic molecular subtypes*. Breast cancer research and treatment 142, 237-255) revealed that TNBC is composed by all the intrinsic subtypes (Lehmann, B. D. et al. (2016) op. cit.; Prat, A. et al. (2013a) op. cit.). Most TN tumors were identified as basal-like (50 to 78%) (Lehmann, B. D. et al. (2016) op. cit.; Prat, A. et al. (2013a) op. cit.). Furthermore, specific subsets of TN tumors showed undistinguishable overall gene expression profiles when compared to ErbB-2E or luminal A/B subtypes. Interestingly, 5-8% of TNBCs segregated into the ErbB-2E subtype, which is defined by MErbB-2 overexpression and/or ERBB2 gene amplification (Prat, A. et al. (2013a) op. cit.). TNBCs that segregated into the ErbB-2E subtype (TN/ErbB-2E) showed only five genes significantly downregulated as compared to ErbB-2E tumors, including ErbB-2 (Prat, A. et al. (2013a) op. cit.).

MErbB-2 role as a potent inducer of BC growth and metastasis is well acknowledged (Henderson, I. C. et al. (1998) *The relationship between prognostic and predictive factors in the management of breast cancer*. Breast Cancer ResTreat 52, 261-288; Ross, J. S. et al. (2009) *The HER-2 receptor and breast cancer: ten years of targeted anti-HER-2 therapy and personalized medicine*. Oncologist 14, 320-368; Slamon, D. J. et al. (1989) *Studies of the HER-2/neu proto-oncogene in human breast and ovarian cancer*. Science 244, 707-712). Also, compelling findings, including those of the inventors, demonstrated that MErbB-2 migrates to the nucleus (NErbB-2) of BC cells where it binds promoters/enhancers of target genes and functions as a transcription factor (TF) or as a coactivator to promote BC growth, metastasis and resistance to anti-MErbB-2 therapies (Beguelin, W. et al. (2010) *Progesterone receptor induces ErbB-2 nuclear translocation to promote breast cancer growth via a novel transcriptional effect: ErbB-2 function as a coactivator of Stat3*. MolCell Biol 30, 5456-5472; Cordo Russo, R. I. et al. (2015) *Targeting ErbB-2 nuclear localization and function inhibits breast cancer growth and overcomes trastuzumab resistance*. Oncogene 34, 3413-3428; Diaz Flaque, M. C. et al. (2013a) *Progesterone receptor assembly of a transcriptional complex along with activator protein 1, signal transducer and activator of transcription 3 and ErbB-2 governs breast cancer growth and predicts response to endocrine therapy*. Breast Cancer Res 15, R118; Diaz Flaque, M. C. et al. (2013b) *Progestin drives breast cancer growth by inducing p21 (CIP1) expression through the assembly of a transcriptional complex among Stat3, progesterone receptor and ErbB-2*. Steroids 78, 559-567; Kim, H. P. et al. (2009) *Lapatinib, a dual EGFR and HER2 tyrosine kinase inhibitor, downregulates thymidylate synthase by inhibiting the nuclear translocation of EGFR and HER2*. PLoSOne 4, e5933; Li, L. Y. et al. (2011) *Nuclear ErbB2 enhances translation and cell growth by activating transcription of ribosomal RNA genes*. Cancer Res 71, 4269-4279; Li, X. et al. (2012) *The atypical histone macroH2A1.2 interacts with HER-2 protein in cancer cells*. JBiolChem 287, 23171-23183; Venturutti, L. et al. (2016) *Stat3 regulates ErbB-2 expression and co-opts ErbB-2 nuclear function to induce miR-21 expression, PDCD4 downregulation and breast cancer metastasis*. Oncogene 35, 2208-2222; Wang, S. C. et al. (2004) *Binding at and transactivation of the COX-2 promoter by nuclear tyrosine kinase receptor ErbB-2*. Cancer Cell 6, 251-261).

The inventor's clinical studies in a Latin American cohort of primary invasive BCs revealed for the first time a role for nuclear ErbB-2 as an independent prognostic factor of poor clinical outcome in membrane ErbB-2-positive tumors (ErbB-2E subtype) (Schillaci, R. et al. (2012) *Clinical relevance of ErbB-2/HER2 nuclear expression in breast cancer*. BMCCancer 12, 74).

"ErbB-2" as used herein refers to the tyrosine kinase receptor ErbB-2 that belongs to the epidermal growth factor receptor family. ErbB-2 can be natural or synthetic (e.g., derived from PCR and/or recombinant DNA techniques). ErbB-2 can be from a mammal, such as a human. An exemplary wild-type ErbB-2 nucleic acid sequence is NCBI GenBank Accession No. NG_007503.1 (SEQ ID NO: 3).

SUMMARY OF THE INVENTION

As disclosed herein, the present inventors have revealed the differential presence of wild-type (WT) ErbB-2 and of an ErbB-2 isoform having a molecular weight (MW) of 165 kDa on sodium dodecyl sulfate polyacrylamide gel electrophoresis (SDS-PAGE) (herein also referred to as p165ErbB-2) in cell lines from the four TNBC subtypes identified at present.

MDA-MB-453 cells (luminal androgen receptor, LAR subtype) express wild-type (WT) ErbB-2 (MW of 185 kDa, also referred to as p185ErbB-2). MDA-MB-468 cells (basal-like 1, BL1 subtype) express only p165ErbB-2. HCC-70 (basal-like 2, BL2 subtype) and MDA-MB-231 cells (mesenchymal, M subtype) express both p185ErbB-2 (WTErbB-2) and p165ErbB-2.

According to extensive work carried out by the present inventors, ErbB-2 protein variants are placed in a new and unanticipated scenario: the nucleus of TNBC. Their findings on ErbB-2 alternative splicing events, using a polymerase chain reaction (PCR)-based sequencing, as well as the RNA interference (RNAi) approach envisioned by the present inventors, with specific siRNAs, show that ErbB-2 isoform c (NP_001276865), encoded by the ErbB-2 alternative transcript 3 (SpT3, NM_001289936), is the contributor to the low MW variant p165ErbB-2. This is the first report of the expression of the non-canonical ErbB-2 isoform c in any normal or malignant cell type. The inventors' discoveries also revealed that ErbB-2 isoform c is located in the nucleus. Consequently, specific siRNAs targeting ErbB-2 isoform c were designed by the inventors and it was surprisingly found that silencing ErbB-2 isoform c expression results in the blockade of the proliferation of TNBC expressing either ErbB-2 isoform c alone or both ErbB-2 isoform c and p185ErbB-2 (WTErbB-2), indicating that isoform c is the major driver of TNBC proliferation. Most important for the field of drug development was the inventors' discovery that silencing of isoform c blocks proliferaction of in vivo tnbc models. Therefore, through RNA interference methodology, the present inventors have designed novel and specific siRNA molecules that target the abovementioned alternative transcript variant encoding isoform c of ErbB-2 and propose the use of said specific siRNAs for the treatment of breast cancer, in particular, triple negative breast cancer.

Therefore, the present invention provides a new alternative for treating cancer and methods of inhibiting cancer cell proliferation, more particularly, for the treatment of triple negative breast cancer, through specific siRNAs directed against the ErbB-2 isoform c.

It is therefore a first object of the present invention to provide a kit for gene silencing, wherein said kit is comprised of at least two siRNA duplexes, wherein one strand of each duplex comprises at least eighteen contiguous bases that are complementary to a region of one target messenger RNA (mRNA). According to this embodiment, the present invention provides specific siRNA molecules targeting ErbB-2 alternative transcript variant 3 (SpT3) which encodes the non-canonical ErbB-2 isoform c, including, but not restricted to those having the sequences depicted in SEQ ID NO: 1 and SEQ ID NO: 2. More specifically, according to this embodiment, the present invention provides a specific siRNA molecule targeted to ErbB-2 alternative transcript variant 3 (SpT3, NM_001289936, SEQ ID NO: 32), which encodes the non-canonical isoform c (NP_001276865) of ErbB-2 having a MW of ~165 kDa on SDS-PAGE, said siRNA molecule comprising a sequence as depicted in SEQ ID NO: 1 or in SEQ ID NO: 2 or any other sequence having a sequence identity greater than 90% between the siRNA and the portion of the target gene.

More specifically the aforesaid siRNA molecule is composed by a duplex region and displays either no overhangs or at least one overhang, wherein each overhang has up to six or fewer nucleotides, wherein the duplex region comprises a sense strand and an antisense strand, wherein said sense strand and said antisense strand together form said duplex region and said duplex region is 18-30 base pairs in length and said antisense strand comprises a sequence that is complementary to the target RNA, SEQ ID NO: 32.

More particularly, the sense strand and the antisense strand each comprise one or more chemically-modified nucleotides; or the sense strand and the antisense strand each consists of chemically-modified nucleotides.

A second object of the present invention is to provide a pharmaceutical composition comprising a siRNA molecule as disclosed herein, in particular an effective amount thereof, together with a pharmaceutically acceptable excipient or carrier.

According to a third object of the present invention, it is also provided a pharmaceutical composition comprising an effective amount of a siRNA molecule as disclosed herein, in particular an effective amount thereof, further comprising an additional anti-cancer agent, and a pharmaceutically acceptable excipient or carrier.

The present invention also provides the use of the siRNAs disclosed herein for the manufacture of a medicament for the treatment of breast cancer. In a preferred aspect, the breast cancer is triple negative breast cancer.

According to another object of the present invention, a method for the treatment of triple negative breast cancer is provided, comprising administration of one or more of the siRNA molecules according to the invention, or a composition comprising said siRNAs according to the invention and a pharmaceutically acceptable excipient or carrier, or a composition comprising said siRNAs, an additional anti-cancer agent, and a pharmaceutically acceptable excipient or carrier.

In a preferred embodiment of the method of treatment of triple negative breast cancer, SpT3 siRNA #2 (SEQ ID NO: 2) is used.

In another embodiment of the method of treatment of triple negative breast cancer SpT3 siRNA #1 is used Another aspect of the present invention involves the administration of a pool of the two siRNAS designed by the inventors: SEQ ID NO: 1 and SEQ ID NO: 2 to increase the gene silencing activity. Further, other specific siRNAs with sequencings targeting isoform c, in addition to SEQ ID NO: 1 and SEQ ID NO: 2, may be used either alone or as a pool.

Also provided are methods for detecting a diagnostic marker in a sample of a subject suspected of having a TNBC tumor, the methods comprising providing a diagnostic sample of the subject, contacting the diagnostic sample of the subject with the siRNA molecules of the invention, and determining the presence of a diagnostic marker in said sample. In particular, the diagnostic marker is alternative transcript variant 3 (SpT3), which encodes isoform c of ErbB-2, having a MW of 165 kDa on SDS-PAGE (p165ErbB-2).

According to another aspect of the method for detecting a diagnostic marker as disclosed in the present invention, said method is based on the ability of a siRNA molecular beacon (MB) to recognize a unique mRNA sequence at the 5' UTR and 5' coding region of SpT3, the transcript variant encoding ErbB-2 isoform c which displays a MW of 165 kDa (p165ErbB-2). The siRNA molecules of the invention having the sequences depicted in SEQ ID NO: 1 or SEQ ID NO: 2 are targeted to this unique region.

It is therefore another object of the invention to provide a kit for detection of ErbB-2 alternative transcript variant 3 (SpT3), which comprises a siRNA molecular beacon (SpT3 MB) displaying either SpT3 siRNA #1 or SpT3 siRNA #2 (having the sequences depicted in SEQ ID NO: 1 and SEQ ID NO: 2, respectively) for detection of ErbB-2 alternative transcript variant 3 (SpT3) diagnostic marker.

Yet another object of the present invention is directed to a binary molecular beacon consisting of SpT3 MB displaying SpT3 siRNA #1 of SEQ ID NO: 1 and SpT3 MB displaying SpT3 siRNA #2 of SEQ ID NO: 2.

MBs may include also other specific siRNAs sequences targeting SpT3 as explained above.

In another aspect of the present invention, the method for detecting a diagnostic marker involves the use of a highly sensitive, branched fluorescence in situ hybridization (FISH) technology named RNAscope® (Wang, F. et al. (2012) *RNAscope: a novel in situ RNA analysis platform for formalin-fixed, paraffin-embedded tissues*. JMD 14, 22-29) for determining the presence of alternative ErbB-2 transcripts in breast cancer, in particular TNBC. This purpose is achieved by selecting a series of RNA target probe sets including, but not restricted to those having the sequences depicted in SEQ ID NO: 1 and SEQ ID NO: 2 to be used in the RNAscope® techniques. The target probes of the RNAscope® assays are designed to specifically recognize a unique mRNA sequence at the 5' UTR and 5' coding region of SpT3, the transcript variant encoding ErbB-2 isoform c which displays a MW of 165 kDa (p165ErbB-2).

RNAscope® is the subject for the following issued patents, incorporated by reference into this application: U.S. Pat. Nos. 7,709,198; 8,604,182; 8,658,361; 8,951,726; 7,709,198; 8,658,361; and 7,709,198.

It is therefore another object of the invention to provide a kit for detection of ErbB-2 alternative transcript variant 3 (SpT3), comprising agents for conducting an RNA ISH assay including, but not restricted to, one or more target probe sets having the sequences depicted in SEQ ID NO: 1 and SEQ ID NO: 2, for detection of ErbB-2 alternative transcript variant 3 (SpT3) diagnostic marker. In a preferred embodiment, the aforementioned ISH assay is an RNAscope® assay."

Further objects of the invention are a method for inhibiting in vitro proliferation of triple negative breast cancer (TNBC) cells, by using the aforesaid siRNA molecules; a method for the blockade of in vivo grow of TN breast tumors, comprising the administration to a patient of the aforesaid siRNA molecules.

BRIEF DESCRIPTION OF THE DRAWINGS

The following figures form part of the present disclosure and are included to further illustrate certain aspects of the present invention.

FIGS. 5A-5B. N-glycosylation pattern of ErbB-2 in TNBC cells. (5A) NetNGlyc 1.0 server (http:// www.cbs.dtu.dk/services/NetNGlyc/) was used to predict N-glycosylation sites by analyzing the Asn-Xaa-Ser/Thr sequons defined as a pre-requisite for N-glycosylation (Blom, N. et al. (2004) *Prediction of post-translational glycosylation and phosphorylation of proteins from the amino acid sequence*. Proteomics 4, 1633-1649). Each graph illustrates putative N-glycosylation sites across the protein chain of different ErbB-2 isoforms (https://www.ncbi.nlm-.nih.gov/refseq/). X-axis represents protein length from N- to C-terminal. A position with a vertical grey line crossing the threshold (black horizontal line at 0.5) is predicted to be N-glycosylated. (5B) BT-474 and MDA-MB-468 cells were treated with tunicamycin (10 μg/ml) or DMSO as control for 15 h. ErbB-2 expression was then evaluated by WB with the C-18 antibody. MW calculation of protein bands was performed using the relative migration distance (Rf) method.

Figure 6A:
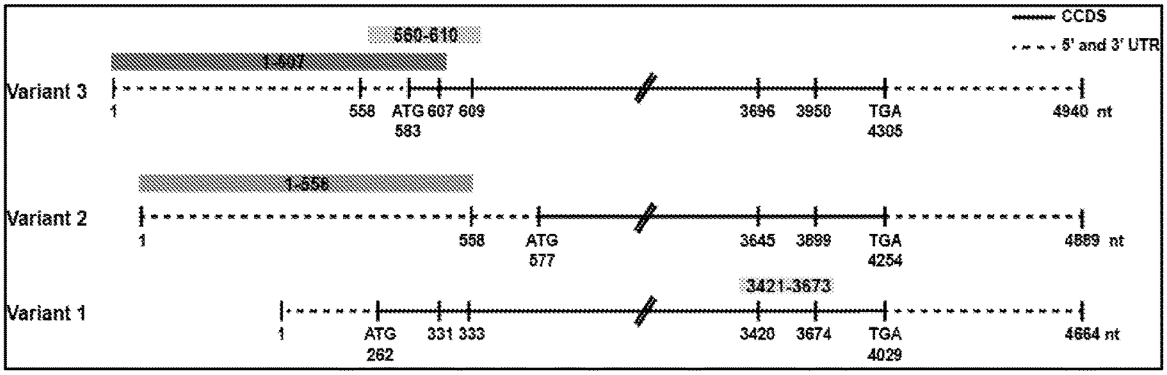
Figure 6B:
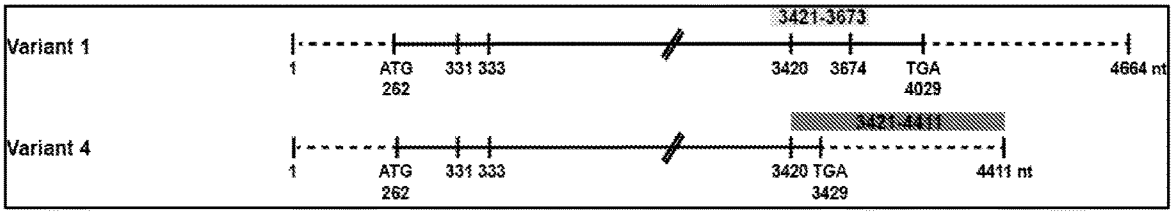
Figure 6C:
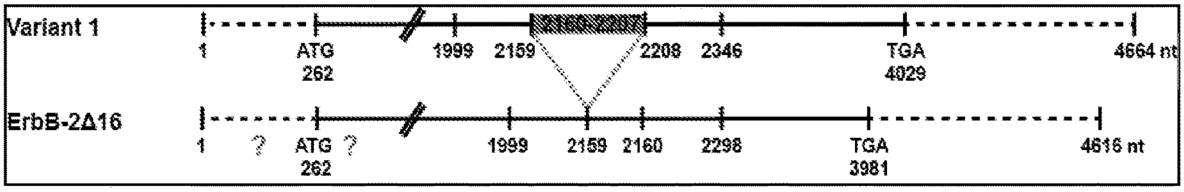

FIGS. 6A-6C. Schematic representation of protein-coding ErbB-2 transcript variants annotated on RefSeq database (NCBI RefSeq, 2020 https://www.ncbi.nlm.nih.gov/refseq/). Consensus coding sequences (CCDSs) and untranslated regions (5' and 3' UTRs) are represented as lines and dashed lines, respectively. Numbers inside boxes and below lines indicate the sequence length in nucleotides (nt). The position of the translation start site (ATG) and the translation stop codon (TGA) are also shown. (6A) Variant 1 (SpT1) corresponds to the canonical sequence that encodes the ErbB-2 isoform a, p185ErbB-2 (WTErbB-2). Variant 2 (SpT2) differs in the 5' UTR, it lacks a portion of the 5' CCDS, initiating translation at a downstream start codon. The box indicating region from position 1 to position 558 nt shows the differential region of variant 2 compared to variant 1. Variant 3 (SpT3) has an alternate 5' UTR and 5' CCDS. The box indicating region from position 1 to position 607 nt indicates the differential region of variant 3 with respect to the canonical transcript. Variant 3 also presents a unique sequence of 51 nt (exon 5) spanning its 5' UTR and 5' CCDS (box indicating region from position 560 to position 610 nt). (6B) Variant 4 (SpT4) lacks the sequence that corresponds to exon 26 in the 3' CCDS of variant 1 (box indicating region from position 3421 to position 3673 nt) resulting in a translational frameshift. The box indicating region from position 3421 to position 4411 nt shows the differential 3' UTR and 3' CCDS region of variant 4. (6C) Schematic representation of ErbB-2Δ16 spliced transcript compared with variant 1. Skipping of exon 16 (box indicating region from position 2160 to position 2207 nt) is represented in ErbB-2Δ16 transcript by the diagonal dashed lines. Question marks (?) indicate an undetermined 5' UTR and translation start site in ErbB-2Δ16 splice variant.

Figure 7:
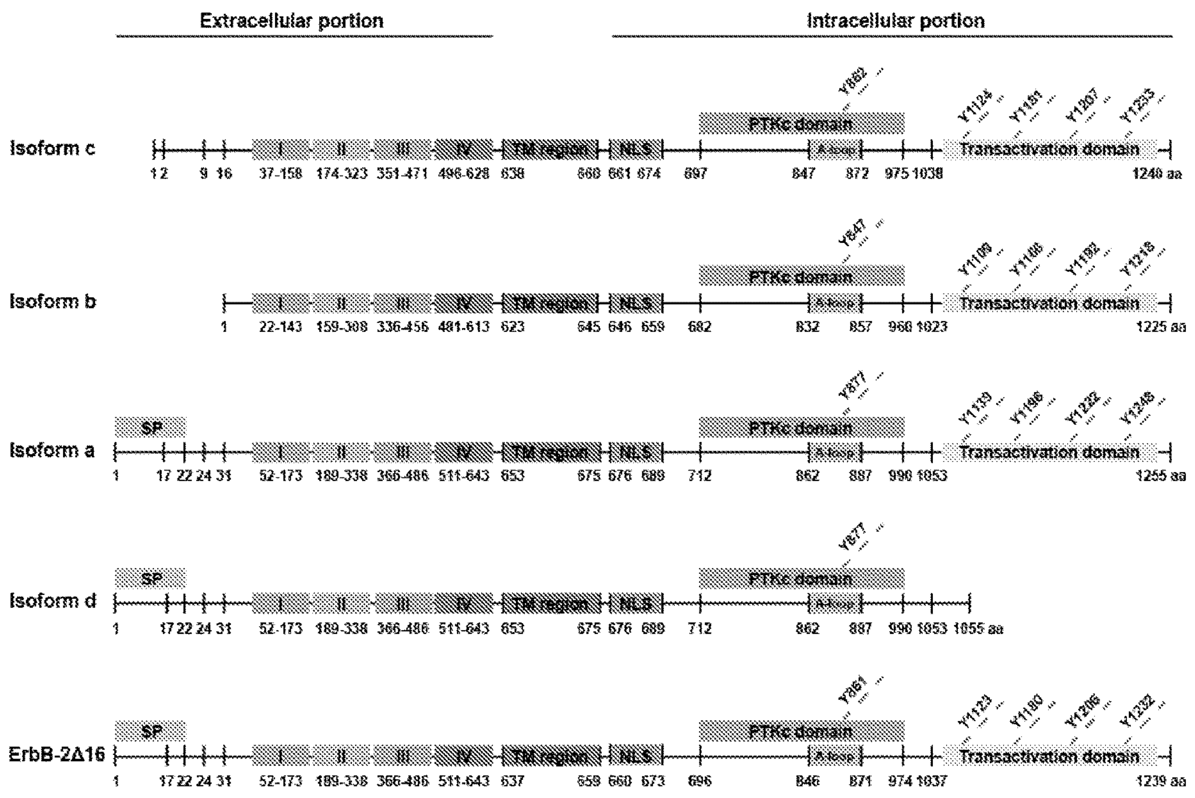

FIG. 7. Schematic representation of ErbB-2 isoforms. The regions that are relevant to ErbB-2 function are depicted as grey boxes. Numbers below lines indicate the protein length in amino acids (aa). The extracellular portion is composed by 4 domains (I-IV): two leucine-rich (L) ligand-binding domains, I/LI and III/LII, and two cysteine-rich (C) domains, II/CI and TV/CII, which facilitate the formation of disulfide bonds. The position of the signal peptide (SP) in the amino-terminus is also shown. ErbB-2 contains a transmembrane domain (TM region) and a juxtamembrane domain, which bears the nuclear localization sequence (NLS). The intracellular portion includes the catalytic protein tyrosine kinase domain (PTKc domain) which contains the activation loop (A-loop), and a proline-rich transactivation domain near the carboxy-terminus. The major phosphorylation sites are indicated (grey dashed lines).

Figure 8:
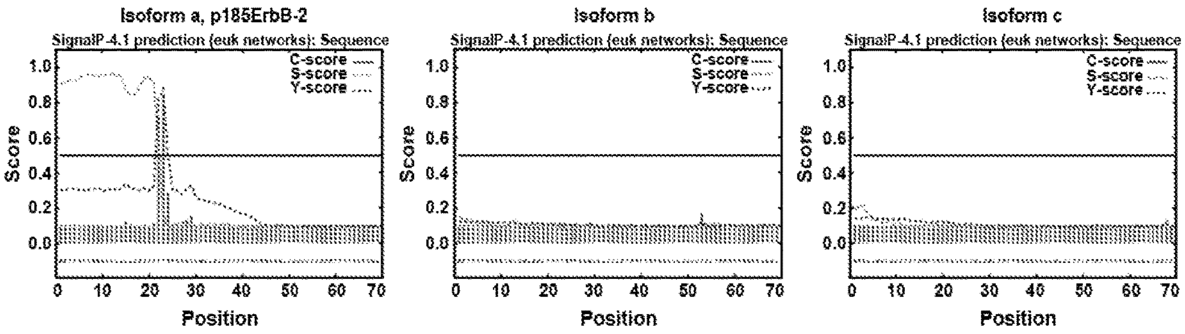
Figure 9A:
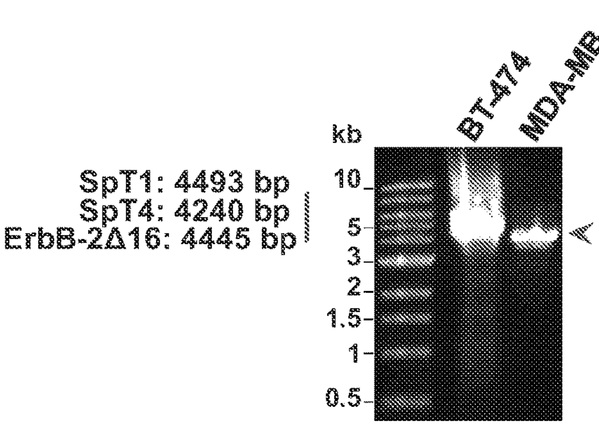
Figure 9B:
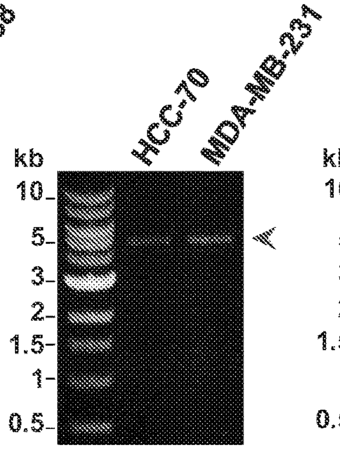
Figure 9C:
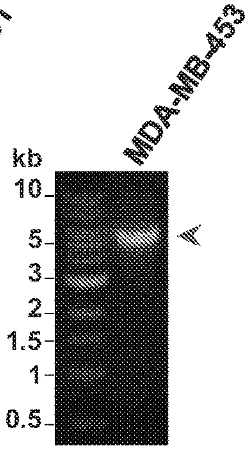
Figure 9D:
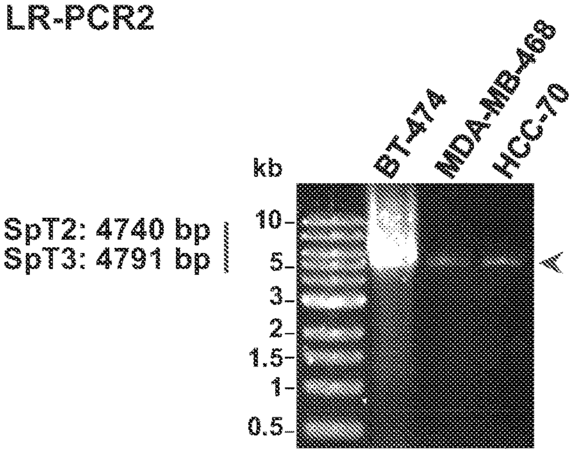
Figure 9E:
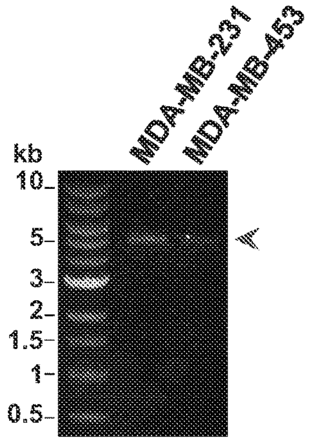

FIG. 8. Signal peptide prediction. Graphical output of SignalP 4.1 Server (http://www.cbs.dtu.dk/services/SignalP/) for signal peptide (SP) prediction (Nielsen, H. (2017) *Predicting Secretory Proteins with SignalP*. Methods in molecular biology 1611, 59-73; Emanuelsson, O. et al. (2007) *Locating proteins in the cell using TargetP, SignalP and related tools*. Nature protocols 2, 953-971). C-score (raw cleavage site score, dark grey continuous line) is the output from the cleavage site networks, which distinguish the location in which SP is cleaved and removed from mature protein. The C-score is trained to be high at the position immediately after the cleavage site (the first residue in the mature protein). S-score (signal peptide score, light grey dashed line) is the output from the signal peptide networks, which distinguish positions within SPs from positions in the mature part of the proteins and from proteins without SPs. Y-score (combined cleavage site score, dark grey dotted line) is a combination (geometric average) of the C-score and the slope of the S-score, resulting in a better cleavage site prediction than the raw C-score alone.

FIGS. 9A-9E. Amplification of the entire coding region of ErbB-2 transcript variants by long range (LR)-PCR. LR-PCRs were performed with RANGER DNA polymerase using cDNA as template and two sets of primers: (9A, 9B, 9C) forward primer of SEQ ID NO: 4 and reverse primer of SEQ ID NO: 5, spanning the complete coding region of variants 1, 4 and ErbB-2Δ16 on one side (LR-PCR1), and on the other, (9D, 9E) forward primer of SEQ ID NO: 6 and reverse primer of SEQ ID NO: 5, spanning the complete coding region of variants 2 and 3 (LR-PCR2). Analysis of LR-PCR products on 0.7% agarose gels showed fragments ranging between ~4 to 5 kb long (indicated by arrows) corresponding to the size of expected products, which are indicated.

Figure 10A:
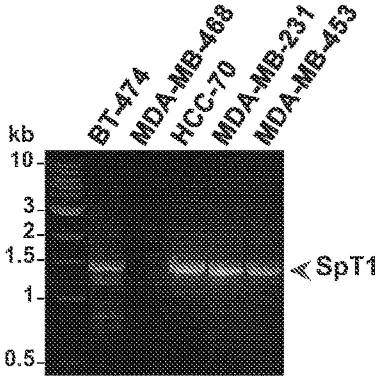
Figure 10B:
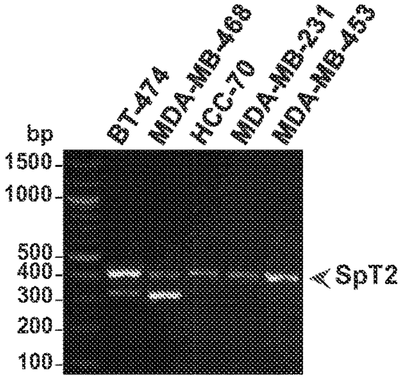
Figure 10C:
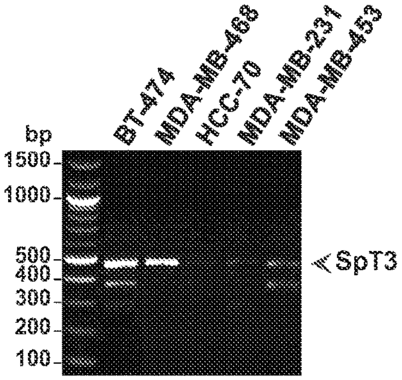

FIGS. 10A-10C. Representative gel images for the nested PCR strategy. LR-PCR1 product was used as template for nested PCR with primers for SpT1, and LR-PCR2 product as template for nested PCR with primers for SpT2 and SpT3. (10A) SpT1 expression was studied using primers spanning its differential region between exons 16 to 26 (forward primer of SEQ ID NO: 7 and reverse primer of SEQ ID NO: 8). Expression of SpT2 (10B) and SpT3 (10C) was assessed using variants specific primers spanning their differential region between exons 1 to 5. Primers for SpT2 are depicted as SEQ ID NOs: 9 and 10, and primers for SpT3 have SEQ ID NOs: 11 and 12.

Figure 11A:
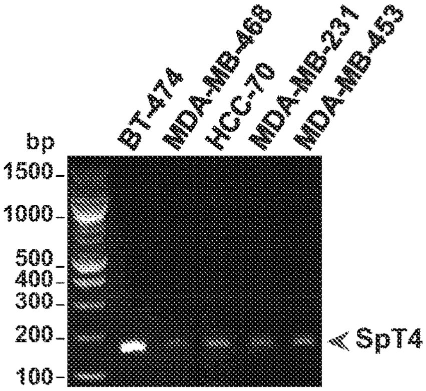
Figure 11B:
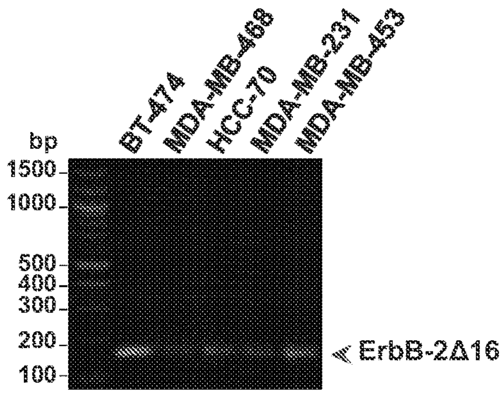

FIGS. 11A-11B. Representative gel images for the conventional PCR strategy. Expression of SpT4 (11A) and of ErbB-2Δ16 (11B) was studied by conventional PCR using spliced-specific primers: for SpT4 primers of SEQ ID NOs: 13 and 14; and primers for ErbB-2Δ16 have SEQ ID NOs: 15 and 16.

FIGS. 12A-12D. Representative gel images of the competitive PCR strategy. (12A) The relative abundance of SpT4 (black arrow) as compared to transcripts with exon 26 inclusion (grey arrow) was studied using primers of SEQ ID NOs: 17 and 18. (12B) ErbB-2Δ16 levels (black arrow) in comparison to those of transcripts with exon 16 inclusion (grey arrow) were determined by using primers of SEQ ID NOs: 19 and 20. Quantification of SpT4 (12C) and of ErbB-2Δ16 (12D) expression levels relative to total ErbB-2 mRNA. Amplification products corresponding to competitors (variants with exon 26 or 16 inclusion) and targets (SpT4 or ErbB-2Δ16, respectively) were quantified by densitometry and plotted as % of total ErbB-2 mRNA levels. For b vs a: N.S. (not significant), by one-way ANOVA test.

Figure 13:
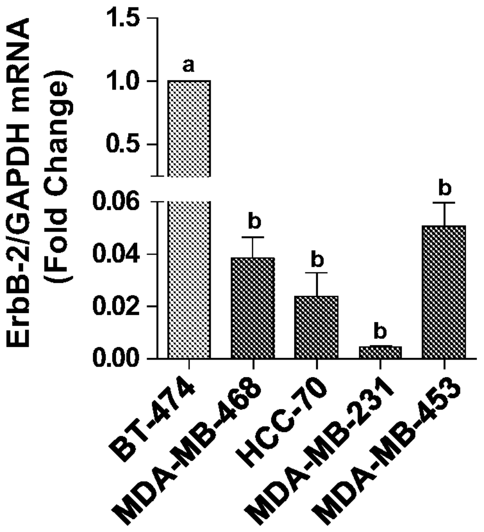

FIG. 13. Total ErbB-2 mRNA levels assessed by Reverse Transcriptase (RT)-quantitative PCR (qPCR). Fold change was calculated by normalizing the absolute levels of ErbB-2 mRNA to those of GAPDH, used as an internal control, setting the value of BT-474 cells to 1. Data are presented as mean±S.D. For b vs a: P<0.001. Primers for total ErbB-2 are depicted as SEQ ID NOs: 21 and 22, and primers for GAPDH have SEQ ID NOs: 25 and 26.

Figure 14A:
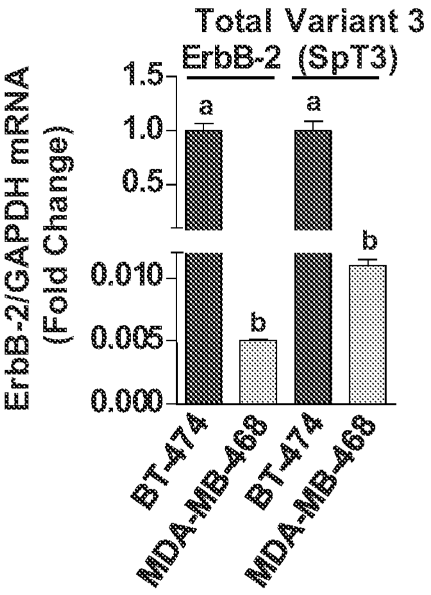
Figure 14B:
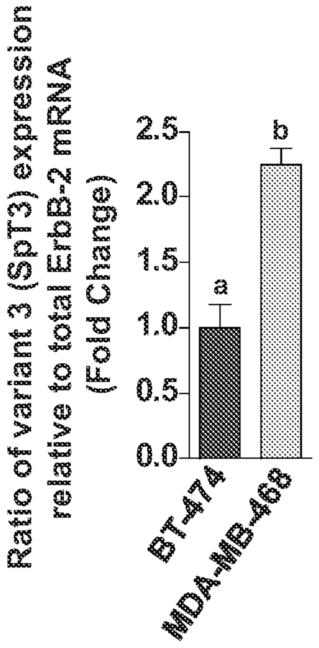

FIGS. 14A-14B. SpT3 expression levels assessed by RT-qPCR. (14A) Total ErbB-2 and SpT3 mRNA levels were measured by RT-qPCR. Fold change was calculated by normalizing the absolute levels of total ErbB-2 or SpT3 mRNA to those of GAPDH, used as an internal control, setting the value of BT-474 cells to 1. Data are presented as mean±S.D. For b vs a: P<0.001. (14B) Relative expression of SpT3 mRNA compared with total ErbB-2 transcripts. Normalized SpT3 and total ErbB-2 mRNA levels from FIG. 14A were expressed as a ratio relative to BT-474 cells, which was defined as 1. For b vs a: P<0.001. Results in FIGS. 14A and 14B are representative of three experiments with similar results. Primers for total ErbB-2 are depicted as SEQ ID NOs: 21 and 22. Primers for SpT3 are depicted as SEQ ID NOs: 23 and 24. Primers for GAPDH have SEQ ID NOs: 25 and 26.

FIGS. 15A-15G. siRNAs targeting the common coding region of transcript variants 1 to 4, and of ErbB-2Δ16 are unable to silence p165ErbB-2 expression. (15A) Schematic diagram of the target sequences of a pool of 4 siRNAs (ErbB-2 siRNA, siGENOME SMARTpool siRNAs for human ErbB-2 (2064) cat #M-0031126-04-0020, Dharmacon, Lafayette, Colo., USA) designed to target the common coding region of all ErbB-2 variants analyzed in the present application (grey boxes indicating regions between nucleotides (nt): 1080-1098, 1558-1576, 1559-1577, and 2565-2583). As an example, only the canonical transcript (SpT1) is illustrated. Consensus coding sequences (CCDSs) and untranslated regions (5' and 3' UTRs) are represented as lines or dashed lines, respectively. Numbers below the lines indicate the sequence length of mRNA in nt. Shown are the position of the translation start site (ATG) and the translation stop codon (TGA). The pool of siRNAs targeting ErbB-2 (ErbB-2 siRNA) have the sequences: GGACGAAUUCUGCACAAUG (SEQ ID NO: 27); GACGAAUUCUGCACAAUGG (SEQ ID NO: 28); CUACAACACAGACACGUUU (SEQ ID NO: 29) and AGACGAAGCAUACGUGAUG (SEQ ID NO: 30). (15B) BT-474 and TNBC cells (MDA-MB-468, HCC-70, MDA-MB-231 and MDA-MB-453) were transfected with either Control siRNA (siGENOME Non-Targeting siRNA #5, cat #D-001210-05-20, Dharmacon, Lafayette, Colo., USA), shown in the sequence listing as SEQ ID NO: 31 (UGGUUUACAUGUCGACUAA), or with the abovementioned pool of 4 siRNAs (ErbB-2 siRNA) at a final concentration of 100 nM. Protein extracts (50 μg) were examined for ErbB-2 isoforms expression with the C-18 antibody. β-tubulin was used as a loading control. Signal intensities of p185ErbB-2 (15C) and p165ErbB-2 (15D) were analyzed by densitometry from three independent WBs performed as in FIG. 15B. Fold change was calculated by normalizing the absolute levels of each ErbB-2 isoform to those of 6-tubulin, setting the value of Control siRNA-transfected cells to 1. For b vs a: P<0.001. MDA-MB-468 (15E), MDA-MB-231 (15F) and MDA-MB-453 (15G) cells were transfected with ErbB-2 siRNA (SEQ ID NOs: 27 to 30) or Control siRNA (SEQ ID NO: 31) as in FIG. 15B and total ErbB-2 mRNA levels were measured by RT-qPCR using primers of SEQ ID NOs: 21 and 22. Fold change was calculated by normalizing the absolute levels of ErbB-2 mRNA to those of GAPDH, used as an internal control, setting the value of Control siRNA-transfected cells to 1. Data represent mean±S.D. of three independent experiments. For b vs a: P<0.001.

FIGS. 16A-16J. ErbB-2 siRNA pool had no effect on NErbB-2 levels in TNBC cells only expressing p165ErbB-2. Cell lines were transfected with control siRNA (SEQ ID NO: 31) (upper panels) or with ErbB-2 siRNA pool (SEQ ID NOs: 27-30) (lower panels) at a final concentration of 100 nM. Nuclei were stained with propidium iodide (PI). ErbB-2 levels were visualized by IF and confocal microscopy using the ErbB-2 C-18 antibody in BT-474 (16A) and TNBC cell lines: MDA-MB-468 (16B), HCC-70 (16C), MDA-MB-231 (16D) and MDA-MB-453 (16E). Quantitative analysis of ErbB-2 expression in confocal images from FIGS. 16A to 16E was performed. Fluorescence intensities from membrane (grey) and nuclear (black) compartments were quantified in 50 cells from BT-474 (16F) and TNBC cell lines: MDA-MB-468 (16G), HCC-70 (16H), MDA-MB-231 (16I) and MDA-MB-453 (16J), and plotted (mean±S.D.). For b vs a, and d vs c: P<0.001. Experiments in FIGS. 16A to 16E and its quantification were repeated thrice with similar results.

FIGS. 17A-17E. ErbB-2 siRNA pool blocks proliferation in BC cells expressing only p185ErbB-2. BT-474 (17A), MDA-MB-468 (17B), HCC-70 (17C), MDA-MB-231 (17D) and MDA-MB-453 (17E) cells were transfected with Control siRNA (SEQ ID NO: 31) or with the ErbB-2 siRNA pool (SEQ ID NOs: 27-30) at a final concentration of 100 nM and proliferation was assessed by [$^3$H]-thymidine uptake. Data are presented as mean±S.D. of three independent experiments. For b vs a: P <0.001.

FIGS. 18A-18D. siRNAs targeting variant 3 (SpT3) which encodes the non-canonical isoform c, silence p165ErbB-2 expression. (18A) Schematic representation of SpT3 mRNA showing the target sequences of two specific siRNAs: SpT3 siRNA #1 (SEQ ID NO: 1) and SpT3 siRNA #2 (SEQ ID NO: 2), designed to target its differential region (gray box indicating exon 5 sequence between nucleotides 560-610) comprising both the 5' UTR and 5' CCDS. SpT3 siRNAs have the sequences: GUGAGAUACUUCAAAGAUU (SEQ ID NO: 1) and CAAAGAUUCCAGAAGAUAU (SEQ ID NO: 2). Consensus coding sequences (CCDSs) and untranslated regions (5' and 3' UTRs) are represented as full lines and dashed lines, respectively. Numbers below lines indicate the sequence length of mRNA in nucleotides (nt). The position of the translation start site (ATG) and the translation stop codon (TGA) are also shown. Target sequences of SpT3 siRNA #1 (SEQ ID NO: 1) and SpT3 siRNA #2 (SEQ ID NO: 2) are depicted as a dark grey box indicating region between nt 555-573, and as a black box indicating region between nt 566-584, respectively. (18B) BT-474 and TNBC cells (MDA-MB-468, HCC-70, MDA-MB-231 and MDA-MB-453) were transfected with Control siRNA (SEQ ID NO: 31) or with SpT3 siRNA #2 (SEQ ID NO: 2) targeting SpT3, at a final concentration of 100 nM. Protein extracts (10 μg) were examined for ErbB-2 isoforms expression with the C-18 antibody. β-tubulin was used as a loading control. Signal intensities of (18C) p185ErbB-2 and (18D) p165ErbB-2 (ErbB-2 isoform c) were analyzed by densitometry from three independent WBs performed as in FIG. 18B. Fold change was calculated by normalizing the absolute levels of each ErbB-2 isoform to those of 6-tubulin, setting the value of Control siRNA-transfected cells to 1. For b vs a: P<0.001.

FIGS. 19A-19F. SpT3 siRNA #2 reduces nuclear ErbB-2 levels in TNBC cells expressing only p165ErbB-2 (ErbB-2 isoform c) or both p165ErbB-2 (ErbB-2 isoform c) and p185ErbB-2. TNBC cell lines were transfected with Control siRNA (SEQ ID NO: 31) (upper panels) or with SpT3 siRNA #2 (SEQ ID NO: 2) (lower panels) at a final concentration of 100 nM. Nuclei were stained with DAPI. ErbB-2 levels were visualized by IF and confocal microscopy using the ErbB-2 C-18 antibody in MDA-MB-468 (19A), MDA-MB-231 (19B) and MDA-MB-453 cells (19C). Quantitative analysis of NErbB-2 expression in confocal images from FIGS. 19A to 19C was performed. Fluorescence intensities from nuclear compartment (black bars) were quantified in 50 cells from MDA-MB-468 (19D), MDA-MB-231 (19E) and MDA-MB-453 (19F), and plotted (mean±S.D.). For b vs a: P<0.001. Experiments in FIGS. 19A to 19C and its quantification were repeated thrice with similar results.

FIGS. 20A-20E. SpT3 siRNA #2 inhibits in vitro proliferation of TNBC cells expressing only p165ErbB-2 (ErbB-2 isoform c) or both p165ErbB-2 (ErbB-2 isoform c) and p185ErbB-2. (20A) BT-474, (20B) MDA-MB-468, (20C) HCC-70, (20D) MDA-MB-231 and (20E) MDA-MB-453 cells were transfected with Control siRNA (SEQ ID NO: 31) or with SpT3 siRNA #2 (SEQ ID NO: 2) targeting SpT3, at a final concentration of 100 nM and proliferation was assessed by [$^3$H]-thymidine uptake. Data are presented as mean±S.D. of three independent experiments. For b vs a: P<0.001.

FIGS. 21A-21F. Effects of SpT3 siRNA #1. (21A) BT-474 and TNBC cells (MDA-MB-468, HCC-70, MDA-MB-231 and MDA-MB-453) were transfected with Control siRNA (SEQ ID NO: 31) or with SpT3 siRNA #1 (SEQ ID NO: 1) at a final concentration of 100 nM. Protein extracts (50 μg) were examined for ErbB-2 isoforms expression with the C-18 antibody. β-tubulin was used as a loading control. Images shown are representative of three independent experiments. Numbers under each blot represent the corresponding densitometric quantification of p185ErbB-2 and p165ErbB-2 (ErbB-2 isoform c). Fold change of protein levels was calculated by normalizing the absolute levels of each ErbB-2 band to those of 6-tubulin, setting the value of Control siRNA-transfected cells to 1. BT-474 (21B), MDA-MB-468 (21C), HCC-70 (21D), MDA-MB-231 (21E), and MDA-MB-453 (21F) were transfected as in FIG. 21A and proliferation was assessed by [$^3$H]-thymidine uptake. Data are presented as mean±S.D. of three independent experiments. For b vs a: P<0.001.

Figure 22:
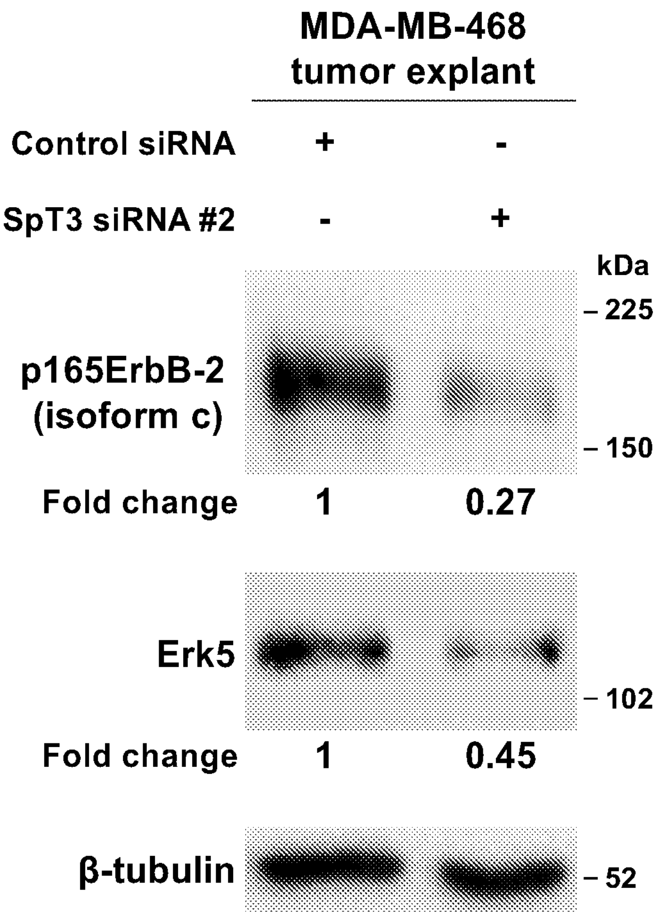

FIG. 22. Effects of SpT3 siRNA #2 on tumor explants. Triple negative tumor explants established from MDA-MB-468 xenografts were cultured with medium containing SpT3 siRNA #2 (SEQ ID NO: 2) or Control siRNA (SEQ ID NO: 31) at a final concentration of 100 nM. WB analyses of p165ErbB-2 (ErbB-2 isoform c) and Erk5 were performed in tumor lysates after 24 hours of transfection. Numbers under each blot represent the corresponding densitometric quantification. Fold change of protein levels was calculated by normalizing the absolute levels of p165ErbB-2 (ErbB-2 isoform c) and Erk5 bands to those of 6-tubulin, used as loading control, setting the value of control siRNA-transfected tumors to 1.

Figure 23A:
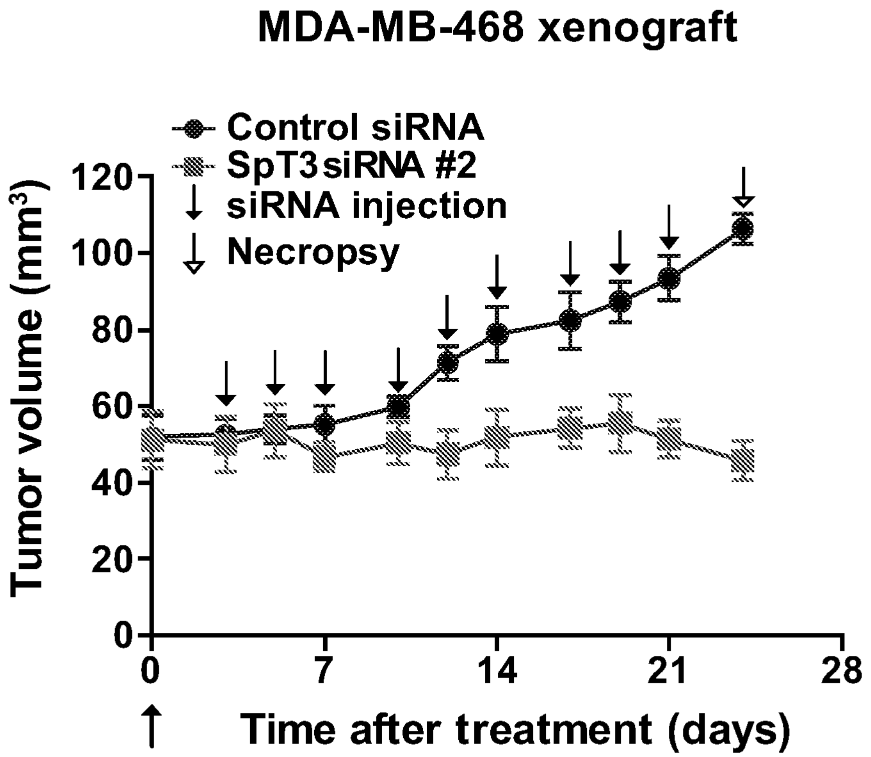
Figure 23B:
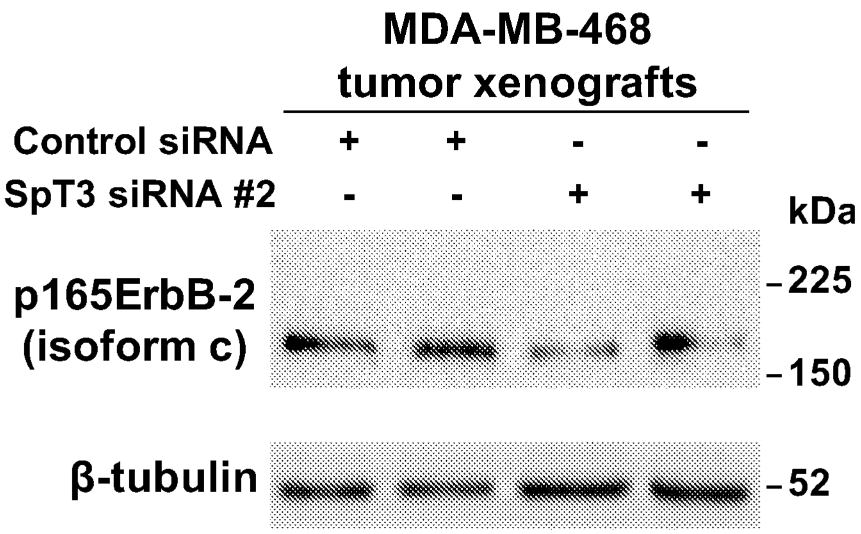

FIG. 23A-23B. Preclinical model of the blockade of p165ErbB-2 (ErbB-2 isoform c) expression with SpT3 siRNA #2. (23A) Female NIH(S)-nude mice were inoculated in the mammary fat pad with MDA-MB-468 cells. Once tumors were established (average tumor volume of 50-70 mm$^3$), mice received Control siRNA (SEQ ID NO: 31) or SpT3 siRNA #2 (SEQ ID NO: 2) intratumoral injections (1 mg/kg) three times a week for three weeks. Each point represents the mean volume ±S.D. (n=6). See Table 8. (23B) Mice were sacrificed two days after the last treatment and tumor lysates were analyzed by WB with the C-18 antibody. Shown are two representative tumors from each group.

Figure 24A:
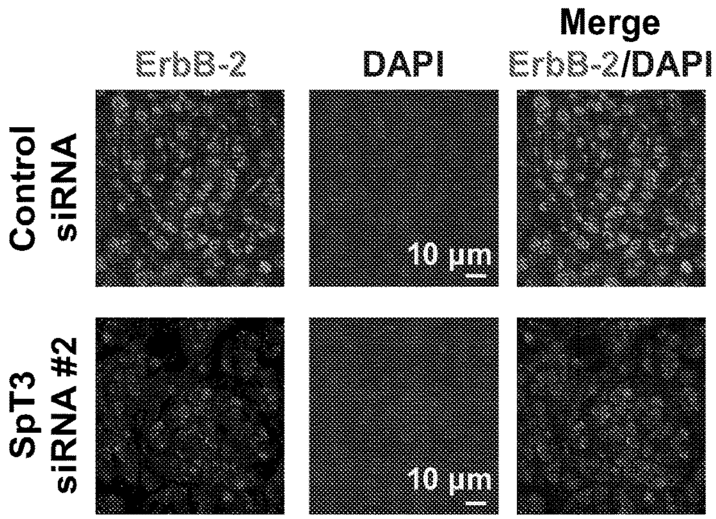
Figure 24B:
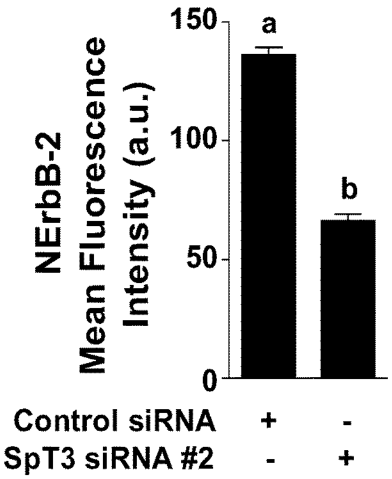
Figure 25A:
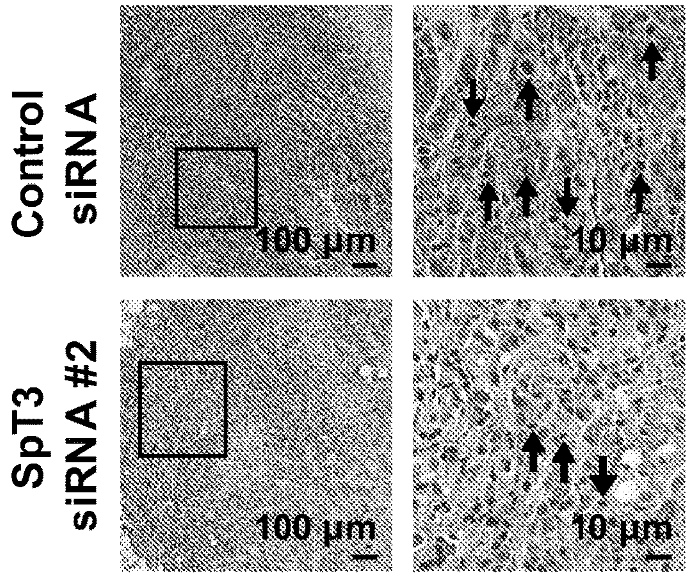
Figure 25B:
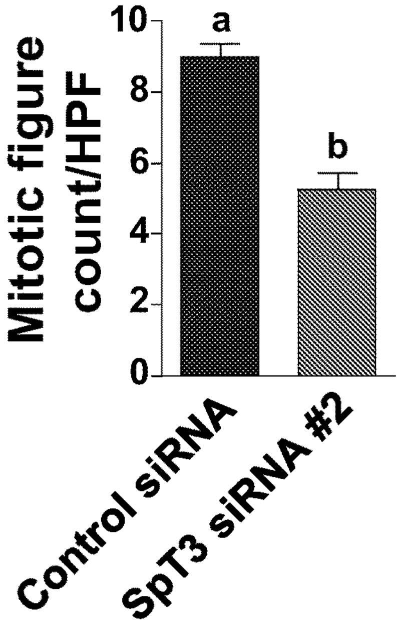
Figure 25C:
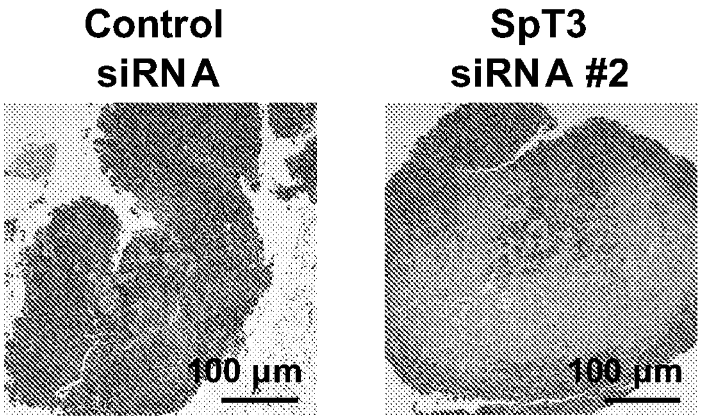
Figure 25D:
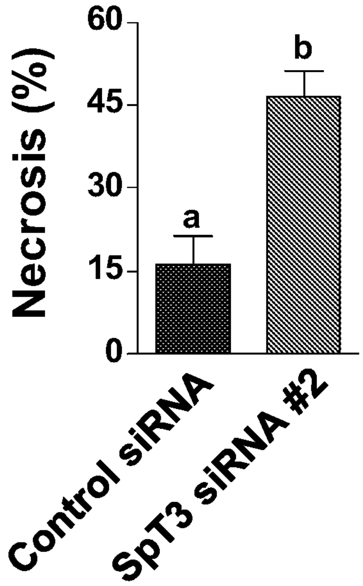
Figure 26A:
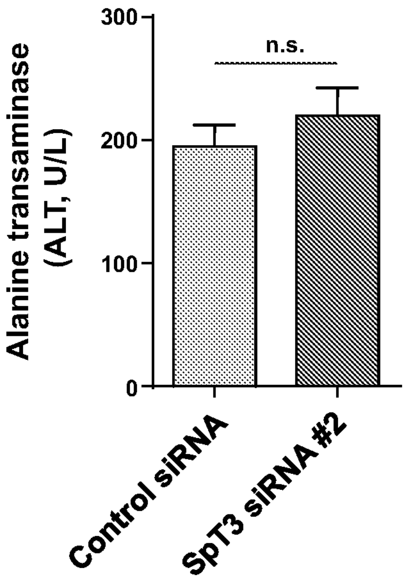
Figure 26B:
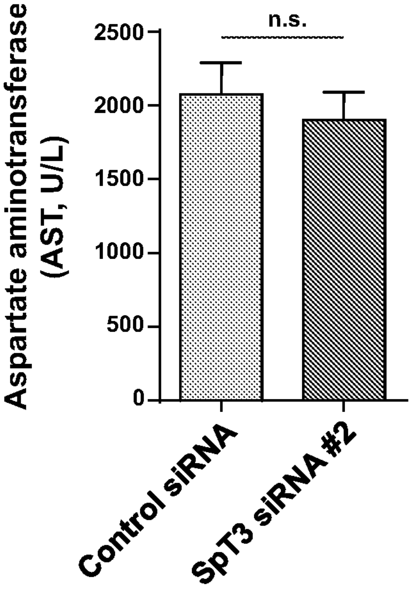
Figure 26C:
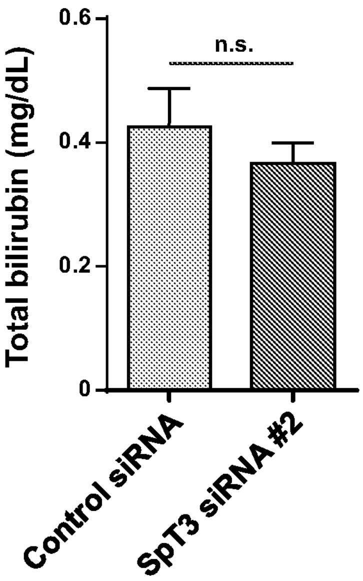
Figure 26D:
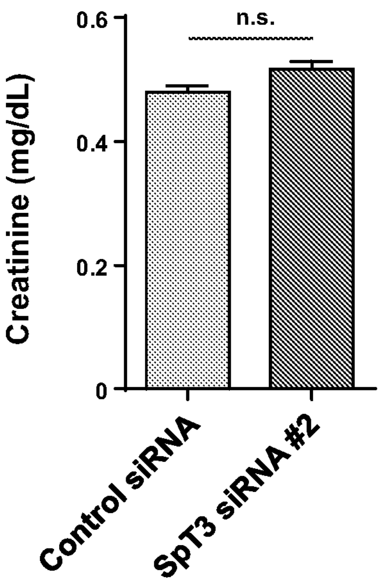

FIGS. 24A-24B. Silencing of p165ErbB-2 (ErbB-2 isoform c) with SpT3 siRNA #2 in the MDA-MB-468 preclinical model reduces nuclear ErbB-2 expression. (24) IF and confocal microscopy of histological sections from MDA-MB-468 tumors excised at the end of the experiment. ErbB-2 was detected using the C-18 antibody, followed by incubation with an IgG-Alexa Fluor 488 secondary antibody. Nuclei were stained with DAPI. Representative images are shown. (24B) Quantitative analysis of NErbB-2 expression in images from FIG. 24A. Fluorescence intensities from nuclear compartment (black bars) were quantified in 50 cells from each group and plotted (mean±S.D.). For b vs a: P<0.001. Experiment in FIG. 24A and its quantification were repeated thrice with similar results.

FIGS. 25A-25D. Histopathological analysis. (25A) Representative hematoxylin and eosin (H&E) staining of histological sections from MDA-MB-468 tumors excised at the end of the experiment. Mitotic figures are indicated with black arrows. (25B) Tumor proliferation was quantified by mitotic figures count per high power field (HPF) in MDA-MB-468 histological sections. Data are presented as mean±S.D. For b vs a: P<0.001. (25C) Representative H&E staining of histological sections from MDA-MB-468 tumors showing areas with extensive necrosis (pale eosinophilic areas) after SpT3 siRNA #2 treatment. (25D) Percentage of necrosis was measured at lower magnification in MDA-MB-468 tumors. Data are presented as mean±S.D. For b vs a: P<0.001.

are presented as mean±S.D. For b vs a: P<0.001.

FIGS. 26A-26D. Preclinical toxicological analysis of animal blood samples. (26A) Alanine transaminase (ALT), (26B) aspartate aminotransferase (AST) and (26C) total bilirubin levels were determined for evaluating hepatotoxicity in SpT3 siRNA #2 injected mice. (26D) Creatinine levels were also measured to assess SpT3 siRNA #2 effects on renal function. n.s., non-significant by unpaired Student's t test.

Figure 27:
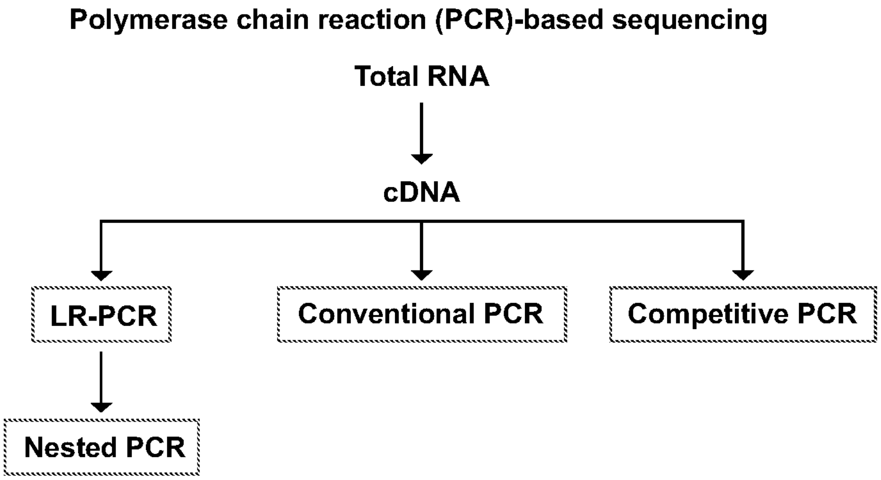

FIG. 27 shows a Polymerase Chain Reaction (PCR)-based sequence scheme.

DETAILED DESCRIPTION OF THE INVENTION

Definitions

As used herein, a "nucleotide base," or "nucleobase," is a heterocyclic pyrimidine or purine compound that is a component of a nucleotide, and includes the primary purine bases adenine (A) and guanine (G), and the primary pyrimidine bases cytosine (C), thymine (T), and uracil (U). A nucleobase may further be modified to include, without limitation, universal bases, hydrophobic bases, promiscuous bases, size-expanded bases, and fluorinated bases. (See. e.g., Modified Nucleosides in Biochemistry, Biotechnology and Medicine, Herdewijn, P. ed. Wiley-VCH, 2008). The synthesis of such modified nucleobases (including phosphoramidite compounds that include modified nucleobases) is known in the art.

As used herein, the term "nucleoside" refers to a molecule made up of a nucleotide base and its sugar.

As used herein, the term "nucleotide" refers to a nucleoside having a phosphate group on its 3' or 5' sugar hydroxyl group.

As used herein, the terms "oligonucleotide", "polynucleotide" and "nucleic acid" mean a polymer of linked nucleotides each of which can be independently modified or unmodified. The polynucleotides can be "deoxyribonucleic acid" (DNA), "ribonucleic acid" (RNA), or derivatives or modified versions thereof. The polynucleotide may be single-stranded or double-stranded.

The term "deoxynucleotide" refers to a nucleotide or polynucleotide lacking a hydroxyl group (OH group) at the 2' and/or 3' position of a sugar moiety. Instead, it has a hydrogen bonded to the 2' and/or 3' carbon. Within an RNA molecule that comprises one or more deoxynucleotides, "deoxynucleotide" refers to the lack of an OH group at the 2' position of the sugar moiety, having instead a hydrogen bonded directly to the 2' carbon.

The terms "deoxyribonucleotide" and "DNA" refer to a nucleotide or polynucleotide comprising at least one sugar moiety that has an H, rather than an OH, at its 2' and/or 3' position.

The term "ribonucleotide" and the phrase "ribonucleic acid" (RNA), refer to a modified or unmodified nucleotide or polynucleotide comprising at least one ribonucleotide unit. A ribonucleotide unit comprises an hydroxyl group attached to the 2' position of a ribosyl moiety that has a nitrogenous base attached in N-glycosidic linkage at the 1' position of a ribosyl moiety, and a moiety that either allows for linkage to another nucleotide or precludes linkage As used herein, the term "3' end" refers to the end of a nucleic acid that contains an unmodified hydroxyl group at the 3' carbon of its ribose ring.

As used herein, the term "5' end" refers to the end of a nucleic acid that contains a phosphate group attached to the 5' carbon of its ribose ring.

As used herein, the term "messenger RNA (mRNA)" and "mRNA transcripts", include, but are not limited to pre-mRNA transcript(s), transcript processing intermediates, mature mRNA(s) ready for translation and transcripts of the gene or genes, or nucleic acids derived from the mRNA transcript(s). Processing of pre-mRNA transcripts, along with the possible use of alternative promoters and alternative polyadenylation sites, allows a single gene to generate many different mature RNAs, by varying the pattern of splicing in a process known as alternative splicing. Alternative splicing can also introduce or remove regulatory elements to affect mRNA translation, localization or stability. These alternatively spliced mRNAs are translated into alternative splice form proteins, here referred to as protein isoforms, that contain different amino acid sequences than the corresponding wild-type or canonical protein produced by normally spliced mRNA.

As used herein, an "RNAi agent" and "RNA silencing agent" means a composition that contains an RNA or RNA-like (e.g., chemically modified RNA) oligonucleotide molecule that is capable of degrading or inhibiting (e.g., degrades or inhibits under appropriate conditions) translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action.

Specifically, the term "small (or short) interfering RNA" or "siRNA" as used herein refers to exogenously synthesized RNA duplexes. siRNAs consist of two RNA strands, an antisense (or guide) strand and a sense (or passenger) strand. These molecules display generally between 18-30 basepairs and contain varying degrees of complementarity to their target mRNA in the antisense strand. Some, but not all, siRNAs include structures with overhangs. Overhangs have been described to be advantageous and may be present on the 5' ends or on the 3' ends of either strand as they reduce recognition by RNAses. Some authors recommend including overhangs on both 3' ends of the molecules, whereas others consider one overhang to be sufficient. Others have described the use of blunt-ended structures with specific modification patterns (EP 1527176, WO 2008/104978, and many others). These overhangs are said to further enhance resistance to nuclease (RNase) degradation. As used herein, the term "overhang" or "tail" refers to 3, 4, 5, 6, 7, 8, 9, 10, 11, 12, 13, 14, 15, 16, 17, 18, 19, 20 or more sequential nucleotides at the 3' end of one or both of the sense strand and the antisense strand that are single-stranded.

The term "siRNA" includes duplexes of two separate strands, as well as single strands that can form hairpin structures comprising a duplex region.

As used herein, the term "antisense (or guide) strand" refers to the strand of an siRNA duplex that contains some degree of complementarity to a target gene or mRNA and contains complementarity to the sense strand of the siRNA duplex.

As used herein, the term "sense (or passenger) strand" refers to the strand of an siRNA duplex that contains complementarity to the antisense strand of the siRNA duplex.

As used herein, the term "duplex region" refers to the region in two complementary or partially complementary polynucleotides (e.g., a sense strand or an antisense strand) that form base pairs with one another.

The term "complementary" refers to the hybridization or base-pairing between nucleotides. A base pair (bp) is a unit consisting of two nucleobases connected by hydrogen bonds. According to Watson-Crick base-pairing, DNA contains four bases: the two purines adenine (A) and guanine (G) and the two pyrimidines cytosine (C) and thymine (T). Within the DNA molecule, A bonds only with T and C bonds only with G. As persons skilled in the art are aware, in RNA thymine is replaced by uracil (U). Non-Watson-Crick base-pairing models display alternative hydrogen-bonding patterns; examples are Hoogsteen base pairs, which are A-T or C-G analogues.

As used herein, the terms "chemically modified nucleotide" or "nucleotide analog" or "altered nucleotide" or "modified nucleotide" refer to a non-standard nucleotide, including non-naturally occurring ribonucleotides or deoxyribonucleotides.

Within the meaning of the present invention any position of the nucleotide analogs may be modified to change chemical properties of the nucleotide, maintaining the ability of the nucleotide analog to perform its function. Nucleotide analogs include nucleotides having modifications in the chemical structure of the base, sugar and/or phosphate.

Specifically, the nucleobase moiety may be modified by the replacement or addition of one or more atoms or groups. A pyrimidine base may be modified at the 2, 3, 4, 5, and/or 6 position of the pyrimidine ring. The exocyclic amine of cytosine may also be modified. A purine base may be modified at the 1, 2, 3, 6, 7, or 8 position. The exocyclic amine of adenine may also be modified. Base modifications are known to those of ordinary skill in the art. Some examples include alkylated, halogenated, thiolated, aminated, amidated, or acetylated bases, or other heterocycles. Nucleobase modifications in small amounts (up to 10%) could reduce immune reactions and improve the thermodynamic siRNA profile. Some examples of nucleobases substitutions (Reviewed in Chernikov, I. V. et al. (2019) *Current Development of siRNA Bioconjugates: From Research to the Clinic*. Frontiers in pharmacology 10, 444) with various modified analogs (pseudouridine, 2'thiouridine, dihydrouridine, 2,4-difluorobenzene, 4-methylbenzimidazole, hypoxanthine, 7-deazaguanin, N2-alkyl-8-oxoguanine, N2-benzylguanine, and 2,6-diaminopurine) may be used to increase the thermal stability of the siRNA duplex.

Non-limiting examples of modified bases are described in U.S. Pat. Nos. 10,011,836; 8,008,474; 7,816,512 and 7,977,471, all of which are incorporated herein by reference.

Within the meaning of the present invention nucleotide analogs may also display modifications at the sugar moiety. Sugar moieties include natural, unmodified sugars, e.g., monosaccharide (such as pentose, e.g., ribose, deoxyribose), modified sugars and sugar analogs. In general, modifications of sugar moiety include substitutions in the 2'-position, as the 2'OH group participates in the cleavage of RNA by endoribonucleases. Some examples of said modifications include but are nor limited to, the replacement of the 2'OH group by a group selected from H, OR, R, F, Cl, Br, I, SH, SR, NH2, NHR, NR2, COOR, or OR, wherein R is substituted or unsubstituted C1-C6 alkyl, alkenyl, alkynyl, aryl, etc, as described in U.S. Pat. No. 9,080,171 and U.S. Pat. Application No. 2019/0024082, all of which are incorporated herein by reference. Specific 2'-substitutions such as 2'-O-methyl (2'O-Me), 2'-O-methoxyethyl (2'O-MOE), 2'-fluoro (2'F) and/or alternating combinations thereof, may be used to achieve metabolic stabilization of siRNA molecules. Ribose modifications are not limited to substitutions in structure. Nucleotide analogs with a modified structure of the furanose cycle, such as derivatives containing 6-membered (hexitol (HNA), cyclohexenic (CeNA) and altritol (ANA) nucleic acids), and 7-membered rings (oxepanic nucleic acid (ONA)), bicyclic (locked nucleic acids (LNA), 2'-deoxymethanocarbanucleosides (MCs)), tricyclic (tricyclo-DNA (tc-DNA)), and acyclic (unlocked nucleic acid (UNA)) derivatives, can be used.

Within the meaning of the present invention, nucleotide analogs may also display non-natural phosphodiester linkages such as methylphosphonates, phosphorothioates and peptides.

Within the meaning of the present invention, nucleotide analogs may also comprise hydrophobic modifications at the base moiety. Non-limiting examples of hydrophobic modifications are phenyl, indolyl, isobutyl, butyl, aminobenzyl, benzyl, thiophene, ethynyl, and imidazole.

As used herein, the term "nucleotide" also includes what are known in the art as universal bases. These nucleotide analogues lack hydrogen bonding sites and are generally hydrophobic aromatic base residues. Some examples are 3-nitropyrrole 5-nitroindole, or nebularine. The term "nucleotide" is also meant to include the nucleotide analogues N3' to P5' phosphoramidates. These compounds contain 3'-amino group replacing the ribosyl 3'-O-atom.

In addition, the term "nucleotide" also includes those species that have a detectable label, such as for example a radioactive or fluorescent moiety, or mass label attached to the nucleotide.

As used herein, "gene silencing" or "knockdown" refers to a process by which the expression of a specific gene product is lessened or attenuated. As used herein, the terms "silenced" or "knockdown", when referring to expression of a given gene, mean that the expression of the gene, as measured by the level of RNA transcribed from the gene or the level of polypeptide, protein, alternative isoform of a given protein, e.g. ErbB-2, or protein subunit translated from the mRNA in a cell, group of cells, tissue, organ, or subject in which the gene is transcribed, is reduced when the cell, group of cells, tissue, organ, or subject is treated with the siRNA is described herein as compared to a second cell, group of cells, tissue, organ, or subject that has not or have not been so treated.

The phrases "off-target silencing" and "off-target interference" are defined as degradation of mRNA other than the intended target mRNA due to overlapping and/or partial homology with secondary mRNA messages. Such off-target effects are primarily mediated by the sequence-specific interaction between the siRNA seed regions (position 2-8 of either siRNA strand counting from the 5'-end) and complementary sequences in the 3' UTR of off-targets (Bramsen, J. B. et al. (2010) *A screen of chemical modifications identifies position-specific modification by UNA to most potently reduce siRNA off-target effects*. Nucleic acids research 38, 5761-5773).

The term "siRNA score" refers to a number determined by applying any of the design algorithms or formulas (e.g., siDESIGN Center, Dharmacon, Lafayette, Colo., USA) to a given siRNA sequence. According to one embodiment, the present invention provides specific siRNA molecules for use to silence a particular mRNA (e.g., ErbB-2 alternative transcript variant 3, SpT3) which have been selected on the basis of this method.

Within the meaning of the present invention, "Target mRNA" refers to a messenger RNA (mRNA) to which a given siRNA can be directed against. "Target sequence" refers to a contiguous portion of the nucleotide sequence of a target mRNA molecule formed during the transcription of a target gene, including mRNA that is a product of RNA processing of a primary transcription product. The term "siRNA target" can refer to the gene, mRNA, or protein against which an siRNA is directed.

As used herein, "Non-targeting siRNA", "Control siRNA" (siGENOME Non-Targeting siRNA #5 cat #D-001210-05-20, Dharmacon, Lafayette, Colo., USA), refers to a highly functional, chemically synthesized negative control siRNA duplex for experiments in human, mouse, and rat cells. The control siRNA oligonucleotide used herein does not target any known mammalian gene. Neither the mRNA nor protein level of the experimental gene is affected by this control siRNA. Cell viability as well as cell phenotype of samples treated with the control siRNA remains comparable to those of untreated samples. In the present invention, control siRNA does not bind to ErbB-2 alternative transcript variant 3 (SpT3), which encodes isoform c of ErbB-2. The control siRNA used in the assays carried out in the present invention consists of the sequence UGGUUUACAUGUCGACUAA shown as SEQ ID NO: 31.

The present invention will next be described in connection with preferred embodiments. These embodiments are presented in order to aid in an understanding of the present invention and are intended and should not be construed to limit the invention in any way. Rather these embodiments are provided so that this disclosure will be through and complete, and will fully convey the scope of the invention to those skilled in the art.

Chemical Modificatons:

In certain embodiments of the present invention, an RNA silencing agent (or any portion thereof), e.g., the siRNA molecules of the present invention targeting ErbB-2 alternative transcript SpT3 which encodes ErbB-2 isoform c, as described herein, may be modified such that the activity of the RNA silencing agent is further improved. For example, the RNA silencing agents described in the present invention may be modified with any of the modifications described herein. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

Within the meaning of the present invention, certain modifications may be incorporated to facilitate preferential selection of the antisense strand of the siRNA molecule by the cellular RNAi machinery, such that the antisense strand preferentially guides cleavage or translational repression of a target mRNA, and thus increasing the efficiency of target cleavage and silencing. Non-limiting examples of structural and chemical modifications used to achieve preferential strand selection, include the development of internally destabilized duplexes, asymmetric duplexes and 2'OMe modifications of the two nucleotides at the 5' end of the sense strand.

In certain embodiments, the siRNAs of the invention may be substituted with a destabilizing nucleotide. Non-limiting examples include acyclic nucleotide residues which decrease the stability when incorporated into RNA duplexes. Unlocked nucleic acid (UNA) is reported to destabilize RNA-RNA interactions and can be strategically used in siRNA design to induce local thermodynamical destabilization (Bramsen, J. B. et al. (2010) op. cit.)

In certain embodiments, the siRNAs of the invention may be altered according to asymmetry design rules. Asymmetric siRNA compounds have previously been developed. Non-limiting examples include: i) siRNAs with deletions at the sense and/or antisense strand, with a duplex region of 16 nucleotides (nt) (Chu, C. Y. and Rana, T. M. (2008) *Potent RNAi by short RNA triggers*. Rna 14, 1714-1719); ii) asymmetric interfering RNA (aiRNA) compounds with a short sense strand (12-15 nt) and a regular length antisense strand (21 nt) (Sun, X. et al. (2008) *Asymmetric RNA duplexes mediate RNA interference in mammalian cells*. Nature biotechnology 26, 1379-1382); and iii) a new class of small, hydrophobic, asymmetric RNAi compounds, termed "self-delivering rxRNAs" (sd-rxRNA®, U.S. Pat. No. 9,080,171). sd-rxRNA® are extensively modified siRNAs compounds, with a small duplex region of <15 nt, and a fully phosphorothioated single-stranded tail. Importantly, sd-rxRNAs are functional in vitro and in vivo without the aid of any delivery vehicle (Byrne, M. et al. (2013) *Novel hydrophobically modified asymmetric RNAi compounds* (*sd-rxRNA*) *demonstrate robust efficacy in the eye*. J Ocul Pharmacol Ther 29, 855-864).

In certain embodiments, modifications that increase or decrease sugar flexibility, including locked nucleic acid (LNA) and unlocked nucleic acid (UNA), may be used to introduce chemical asymmetry into duplex siRNAs (Reviewed in Khvorova, A. and Watts, J. K. (2017) *The chemical evolution of oligonucleotide therapies of clinical utility*. Nature biotechnology 35, 238-248).

In certain embodiments, siRNA molecules of the present invention may be modified at various locations in order to promote metabolic stability and enhance silencing activity. Examples of said modifications include, but are not limited to: a) sugar modifications such as 2' ribo modifications, including particularly combinations of 2'-O-methyl (2'OMe), 2'-fluoro (2'F), 2'-deoxy and others; modifications that increase or decrease sugar flexibility, including locked nucleic acid (LNA) and unlocked nucleic acid (UNA); b) backbone modifications such as phosphorothioate internucleotide linkages (referred to as phosphorothioate modifications) at both ends of both strands of the siRNA duplex; and methylation of the 5' carbon to give (S)-5'-C-methyl-RNA; and c) 5'-phosphate stabilization of the siRNA guide strand by incorporation of phosphate analogs such as 5'E-vinyl phosphonate (5'-E-VP), 5'-methyl phosphonate, 5'-C-methyl analog, and phosphorothioate (Reviewed in Khvorova, A. and Watts, J. K. (2017) op. cit.).

The use of 2'-O-methyl (2'OMe) and 2'-fluoro (2'F) modifications may also be beneficial in circumstances in which it is desirable to avoid siRNA-induced immune response. However, the introduction of these chemical modifications in siRNAs is limited by inhibition of its interfering activity (Manoharan, M. et al. (2011) *Unique gene-silencing and structural properties of* 2'-*fluoro-modified siRNAs*. Angew Chem Int Ed Engl 50, 2284-2288) and toxicity (Janas, M. M. et al. (2017) *Impact of Oligonucleotide Structure, Chemistry, and Delivery Method on In Vitro Cytotoxicity. Nucleic acid therapeutics* 27, 11-22).

In other circumstances, immune stimulation may be beneficial for the treatment of cancer and siRNAs with both RNAi and immunostimulatory activity (isiRNAs) (Poeck, H. et al. (2008) 5'-*triphosphate-siRNA: turning gene silencing and Rig-I activation against melanoma*. Nature Medicine 14, 1256-1263) will be designed. As example, 5'-triphosphate modifications, known to activate the cytosolic antiviral helicase retinoic acid-induced protein I (Rig-I) and, therefore induce innate immunity, may be introduced to the siRNAs of the present invention (Poeck, H. et al. (2008) op.cit.).

In certain embodiments, siRNA molecules of the present invention may be associated with a hydrophobic moiety for targeting and/or delivery of the molecule to a cell. In certain embodiments, the hydrophobic moiety is associated (covalently or non-covalently) with the nucleic acid molecule through a linker. Any linker known in the art may be used to associate the nucleic acid with the hydrophobic moiety. In certain embodiments, the linker is capable of being cleaved from the nucleic acid under physiological conditions (e.g., acid labile linkers are cleaved in the acidic endosomal/lysosomal compartments, and disulfide linkers are cleaved at the reductive environment of cytosolic space). In certain embodiments, the linker is capable of being cleaved by an enzyme (e.g., an esterase or phosphodiesterase). Non-limiting examples of linkers employed for hydrophobic/lipid conjugation include: trans-4-hydroxyprolinol linker, disulfide linker, aminohexyl linker, triethyl glycol (TEG) linker and 2-aminobutyl-1-3-propanediol (C7) linker.

In certain embodiments, the hydrophobic moiety is linked at various positions of the siRNA molecule. In a preferred embodiment, the hydrophobic moiety is linked to either the 3' or 5' end of the sense strand. In an exemplary embodiment, the hydrophobic moiety is selected from the group consisting of saturated fatty acids (e.g. docosanoic acid (DCA)), non-saturated fatty acids (e.g. docosahexaenoic acid (DHA, 22:6 n-3) and eicosapentaenoic acid (EPA, 20:5 n-3)), sterols (e.g. cholesterol (Chol) and lithocholic acid (LA)) and vitamins (e.g. retinoic acid (RA) and α-tocopheryl succinate (TS)), or cationic dyes (e.g., Cy3) (Biscans, A. et al. (2019)

*Diverse lipid conjugates for functional extra-hepatic siRNA delivery in vivo*. Nucleic acids research 47, 1082-1096).

In certain embodiments, the siRNA molecules of the present invention contain 5'- and/or 3'-end overhangs. The number and/or sequence of nucleotides overhang on one end of the polynucleotide may be the same or different from the other end of the polynucleotide. In certain embodiments, one or more of the overhang nucleotides may contain chemical modification(s), such as phosphorothioate or 2'OMe modification.

In certain embodiments, the 3' and 5' end of the siRNA molecules of the present invention can be substantially protected from nucleases by modifying the 3' or 5' linkages (e.g., U.S. Pat. No. 5,849,902 and WO 98/13526). "End-blocking groups" or "exonuclease blocking groups" may also be used to protect the 5' and 3' end of the oligonucleotides. Such groups include modified nucleotides and non-nucleotide exonuclease resistant structures. Exemplary end-blocking groups are described in U.S. Pat. No. 9,080,171.

Delivery/Carrier:

Oligonucleotides and oligonucleotide compositions of the present invention are contacted with (i.e., brought into contact with, also referred to herein as administered or delivered to) and taken up by one or more cells. The term "cells" includes eukaryotic cells, preferably vertebrate cells, and, more preferably, mammalian cells. In a preferred embodiment, the oligonucleotide compositions of the invention are contacted with human cells.

The siRNAs of the present invention can be delivered or administered to a cell (e.g., a cancer cell) in vitro, in vivo, or ex vivo. The novel siRNAs disclosed herein are suitable for any known delivery method, including intratumor or systemic routes.

Delivery of the siRNAs of the present invention to an organelle, cell, tissue, and/or organism can be done by any method known to those skilled in the art. One exemplary means of delivering or introducing siRNAs into a cell is by transfection or transduction procedures. "Transfection" refers to the acquisition by a cell of siRNAs by incorporation of added siRNAs molecules. Transfection can occur by physical or chemical methods. Transduction refers to the process of transferring nucleic acid into a cell using a DNA or RNA virus. Such methods for delivering siRNAs to an organelle, cell, tissue, and/or organism include, but are not limited to, direct delivery of RNA such as by ex vivo transfection, by injection, including microinjection; by electroporation; by calcium phosphate precipitation; by using DEAE-dextran followed by polyethylene glycol; by direct sonic loading; by liposome mediated transfection and receptor-mediated transfection; by microprojectile bombardment; by agitation with silicon carbide fibers; by Agrobacterium-mediated transformation; by PEG-mediated transformation of protoplasts; by desiccation/inhibition-mediated RNA uptake, naked plasmid adsorption, and any combination of such methods. Through the application of techniques such as these, organelle(s), cell(s), tissue(s) or organism(s) may be stably or transiently transformed.

A vector may be used in some embodiments as a carrier for the siRNA. The vector may comprise deoxyribonucleic acids (DNA) and/or ribonucleic acids (RNA). Vectors include plasmids, cosmids, viruses (bacteriophage, animal viruses, and plant viruses), and artificial chromosomes (e.g., YACs). One of skill in the art would be well equipped to construct a vector through standard recombinant techniques. Non-limiting examples of vectors include plasmid vectors such as *E. coli*; phage vectors; and viral vectors such as adenoviral vectors, adeno-associated virus (AAV) vectors, retroviral vectors, vaccinia viruses, and Semliki Forest virus vectors.

In another embodiment of the invention, an oligonucleotide is associated with a carrier or vehicle. In yet further embodiments, the siRNAs of the present invention can be delivered or administered to a cell by suitable art recognized methods including but not limited to: a) lipid-based siRNA delivery, b) polymer-based siRNA delivery, c) bioconjugated siRNA delivery, d) inorganic nanoparticles, and e) extracellular vesicles.

Lipid-based systems for delivering siRNAs embody varied lipid nanoparticles, including liposomes, micelles, emulsions, and solid lipid nanoparticles. For the delivery of siRNAs using lipid-based systems, lipid composition, drug-to-lipid ratio, particle size, and the manufacturing process should be optimized.

It is therefore another object of the present invention to provide liposomal formulations of the compounds disclosed herein and compositions thereof. Liposomal formulations containing the compounds (e.g., siRNAs), disclosed herein or compositions thereof may be lyophilized, to produce a lyophilizate, which may be reconstituted with a pharmaceutically acceptable carrier, such as water, to regenerate a liposomal suspension.

Cationic liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The diameters of the liposomes generally range from about 15 nm to about 5 microns. The components mainly include cationic lipids and neutral adjuvant lipids. Cationic lipids can be readily mixed and complexed with negatively charged siRNA molecules to form nanoparticles by electrostatic interaction. Diphenol phthalocyanine ethanolamine (DOPE) and cholesterol are commonly used as neutral auxiliary lipid molecules.

The technology for forming liposomal suspensions is well known in the art. When the compound or composition thereof is an aqueous-soluble composition, using conventional liposome technology, the same may be incorporated into lipid vesicles. In such an instance, due to the water solubility of the compound or composition, the compound or composition will be substantially entrained within the hydrophilic center or core of the liposomes. The lipid layer employed may be of any conventional composition and may either contain cholesterol or may be cholesterol-free. When the compound or composition of interest is water-insoluble, again employing conventional liposome formation technology, the composition may be substantially entrained within the hydrophobic lipid bilayer that forms the structure of the liposome. In either instance, the liposomes that are produced may be reduced in size, as through the use of standard sonication and homogenization techniques.

In certain embodiments of the invention, cationic liposomes are stable nucleic acid lipid particles (SNALPs). In SNALPs, the siRNA is surrounded by a lipid bilayer containing a mixture of cationic lipids, fused lipids, cholesterol, and polyethylene glycol (PEG)-modified neutral lipids.

In certain embodiments, nucleic acids associated with the invention can be hydrophobically modified and can be encompassed within neutral nanotransporters (further description of neutral nanotransporters is incorporated in U.S. Pat. No. 10,138,485). Such particles enable quantitative oligonucleotide incorporation into non-charged lipid mixtures. The lack of toxic levels of cationic lipids in such neutral nanotransporter compositions is an important feature.

The neutral nanotransporters compositions enable efficient loading of oligonucleotide into neutral fat formulation. The composition includes an oligonucleotide that is modified in a manner such that the hydrophobicity of the molecule is increased (for example a hydrophobic molecule is attached (covalently or no-covalently) to a hydrophobic molecule on the oligonucleotide terminus or a non-terminal nucleotide, base, sugar, or backbone), the modified oligonucleotide being mixed with a neutral fat formulation (for example containing at least 25% of cholesterol and 25% of 1,2-dioleoyl-sn-glycero-3-phosphatidylcholine (DOPC) or analogs thereof). A cargo molecule, such as another lipid can also be included in the composition. This composition, where part of the formulation is build into the oligonucleotide itself, enables efficient encapsulation of oligonucleotide in neutral lipid particles.

In some embodiments of the present invention lipid-like delivery molecules, termed lipidoids may also be used to deliver the siRNAs of the invention (Akinc, A. et al. (2008) *A combinatorial library of lipid-like materials for delivery of RNAi therapeutics*. Nature biotechnology 26, 561-569).

In other embodiments of the present invention, a cationic polymer-based delivery system may be used for siRNA administration. In polymer-based delivery, the siRNA is condensed within different kinds of cationic polymers that form nanoparticles, and the surface of the nanoparticles is decorated with PEG and targeting moieties. Said molecules include, but are not limited to, natural polymer materials such as chitosan, beta-cyclodextrin, hyaluronic acid, and gelatin, and synthetic polymers such as poly-L-lysine (PLL), poly-L-glutamic acid (PGA), and polyethyleneimine (PEI).

In certain embodiments of the present invention, dendrimers may be used for siRNA administration. Dendrimers are synthetic, highly branched macromolecules with three-dimensional nanometric structure. Dendrimers have high surface charge density, which also uses electrostatic interactions to load siRNA drugs effectively. Cationic dendrimers have proven useful in masking the charge of siRNA long enough for in vivo delivery. Commonly used dendrimers are polyamidoamine dendrimers (PAMAM), polylylamine dendrimers (poly-L-lysine dendrimers), and polypropylene imine dendrimers (polypropylenimine dendrimers), among others.

In other embodiments of the present invention, the delivery of siRNAs can also be improved by targeting the siRNAs to a cellular receptor. The targeting moieties can be conjugated to the oligonucleotides or attached to a carrier group (i.e., poly(L-lysine) or liposomes) linked to the oligonucleotides. This method is well suited to cells that display specific receptor-mediated endocytosis.

Non-limiting examples of targeting moieties linked to oligonucleotides include 6-phosphomannosylated proteins and nucleic-acid aptamers.

Non-limiting examples of specific ligands linked to the polylysine component of polylysine-based delivery systems include transferrin-polylysine, adenovirus-polylysine, and influenza virus hemagglutinin HA-2 N-terminal fusogenic peptides-polylysine conjugates.

In other embodiments, targeting ligands may be included in the siRNA delivery vehicles, e.g., the use of fusion proteins made by an antibody and the cationic protein protamine (De Paula, D. et al. (2007) *Hydrophobization and bioconjugation for enhanced siRNA delivery and targeting*. RNA 13, 431-456).

In certain embodiments of the invention, a liposome may be complexed with a hemagglutinating virus (HVJ). This has been shown to facilitate fusion with the cell membrane and promote cell entry of liposome-encapsulated DNA. In other embodiments, a liposome may be complexed or employed in conjunction with nuclear non-histone chromosomal proteins (HMG-1). In yet further embodiments, a liposome may be complexed or employed in conjunction with both HVJ and HMG-1. In other embodiments, a delivery vehicle may comprise a ligand and a liposome.

In certain embodiments, siRNAs can also be conjugated with cell-penetrating peptides (CPPs), which can enhance the internalization of siRNAs into cells. In one embodiment, the composition includes an oligonucleotide which is complementary to a target nucleic acid molecule encoding the protein, and a covalently attached CPP. CPPs are cationic or amphiphilic peptides, usually up to 30 amino acids. CPPs may be natural or synthetic and can cross the plasma membrane and the blood-brain barrier.

Non-limiting examples of CPPs include: HIV TAT transcription factor, lactoferrin, Herpes VP22 protein, fibroblast growth factor 2, penetratin and transportan.

Partially or fully chemically modified molecules associated with the present invention may be also optimized for cellular uptake. In the siRNA molecules described herein, the guide and/or passenger strands can be attached to a conjugate. In certain embodiments the conjugate is hydrophobic. In some instances the hydrophobic molecule is or includes a lipophilic group. Conjugation with lipids may enhance siRNA uptake via receptor-mediated endocytosis or by an increased membrane permeability of the otherwise negatively charged siRNA. The presence of such conjugate can influence the ability of the siRNA molecule to be taken into a cell with or without a lipid transfection reagent.

In some aspects, molecules associated with the invention are "self-delivering" RNA (sdRNA) including rxRNA® (RXi Therapeutics). As used herein, "self-delivery" refers to the ability of a molecule to be delivered into a cell without the need for an additional delivery vehicle such as a transfection reagent. Further description of self-delivering siRNAs are incorporated by reference from U.S. Patent Application Nos. 2019/0024082 and 2016/0319278 and U.S. Pat. No. 9,080,171.

In other embodiments of the present invention, the delivery of siRNAs can also be achieved using inorganic nanoparticles. A number of inorganic nanoparticles have been emerging as potential siRNA delivery systems devised for therapeutic purposes. They include but are not limited to: gold nanoparticles (AuNPs), magnetic nanoparticles (MNPs), mesoporous silica nanoparticles (MSNPs), carbon nanotubes (CNTs) and quantum dots (QDs).

In other embodiments, siRNAs of the present invention can also be delivered by extracellular vesicles (EVs). EVs are bilayer membrane-coated vesicles, 30-100 nm in diameter, which are secreted by cells. In certain embodiments EVs are "exosomes".

Methods generally used to load therapeutic siRNA into the exosomes include but are not limited to: (1) plasma membrane anchors are used to induce a high degree of protein oligomerization on the surface of exosomes; (2) a zipper-like sequence is added to the non-coding region of the mRNA to promote mRNA loading into the exosomes; (3) siRNA is over-expressed in the donor cell, which positively loads it into the exosomes; (4) exosomes are infected with an AAV containing therapeutic information; or (5) small molecule drugs or siRNA are loaded into exosomes via physical methods, including mixing (e.g., for curcumin) and electroporation.

In certain embodiments, hydrophobically modified siRNAs can efficiently be loaded into exosomes upon simple co-incubation without altering vesicle size distribution or intactness (Didiot, M. C. et al. (2016) *Exosome-mediated Delivery of Hydrophobically Modified siRNA for Huntingtin mRNA Silencing*. Mol Ther 24, 1836-1847).

Pharmaceutical Compositions/Administration:

In one aspect, provided herein is a pharmaceutical composition comprising a therapeutically effective amount of one or more siRNA compounds as described herein, and a pharmaceutically acceptable carrier.

In another aspect, provided herein is a method of treating or managing breast cancer, particularly TNBC, comprising administering to a patient in need of such treatment or management a therapeutically effective amount of an active agent, siRNA, or nucleic acid as described herein, or a pharmaceutical composition comprising said active agent, siRNA, or nucleic acid.

As used herein "administration" refers to contacting cells with siRNAs of the present invention and can be performed in vitro, in vivo or ex vivo.

As used herein "effective amount" refers to the amount of a therapeutic active agent (e.g., siRNA) that produces the desired therapeutic result when administered or delivered to a subject by an appropriate dose and regimen.

As used herein "pharmaceutically acceptable" means that the active agent is suitable for administration or delivery to a subject to achieve the treatments described herein, without unduly deleterious side effects in light of the severity of the disease and necessity of the treatment.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The active agents and/or compositions thereof described herein may be formulated for administration or delivery together with a pharmaceutically acceptable excipient or carrier in accordance with known techniques in the art (See, e.g., Remington, The Science and Practice of Pharmacy (9.sup.th Ed. 1995)). In the manufacture of a pharmaceutical formulation according to the invention, the active compound (s) (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound(s) as a unit-dose formulation, for example, a tablet, which may contain from 0.01 or 0.5% to 95% or 99% by weight of the active compound. One or more active compounds may be incorporated in the formulations of the invention, which may be prepared by any of the well-known techniques of pharmacy comprising admixing the components, optionally including one or more accessory ingredients.

The formulations of the present invention can be administered to a patient in a variety of forms adapted to the chosen route of administration, e.g., parenterally, orally, or intraperitoneally. Parenteral administration, which in some instances is preferred, includes administration by the following routes: intravenous; intramuscular; interstitially; intraarterially; subcutaneous; intrasynovial; intradermal; intracerebroventricular; intrathecal; transepithelial, including transdermal; pulmonary via inhalation; sublingual and buccal; topically, including dermal; vaginal; rectal; and nasal inhalation via insufflation. The most suitable route in any given case will depend on the nature and severity of the condition being treated and on the nature of the particular active compound which is being used.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes that render the formulation isotonic with the blood of the intended recipient. Aqueous and non-aqueous sterile suspensions may include suspending agents and thickening agents. The formulations may be presented in unitary-dose or multi-dose containers, for example sealed ampoules and vials, and may be stored in a freeze-dried (lyophilized) form requiring only the addition of the sterile liquid carrier, for example, saline or water-for-injection, immediately prior to use. Extemporaneous injection solutions and suspensions may be prepared from sterile powders, granules and tablets of the kind previously described. For example, in one aspect of the present invention, there is provided an injectable, stable, sterile composition comprising an active compound or composition in a unit dosage form in a sealed container. The compound or composition is provided in the form of a lyophilizate that is capable of being reconstituted with a suitable pharmaceutically acceptable carrier to form a liquid composition suitable for injection thereof into a subject. When the compound or composition is substantially water-insoluble, a sufficient amount of emulsifying agent that is physiologically acceptable may be employed in sufficient quantity to emulsify the compound or composition in an aqueous carrier. One such useful emulsifying agent is phosphatidyl choline.

In addition to active compounds, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

Oligonucleotides of the present invention may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

Liposomal formulations containing the compounds (e.g., siRNAs), disclosed herein or compositions thereof may be lyophilized, as disclosed above, to produce a lyophilizate, which may be reconstituted with a pharmaceutically acceptable carrier, such as water, to regenerate a liposomal suspension.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are particularly suitable. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies typically within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The active agent of the present invention, the siRNAs, may optionally be administered in conjunction with other compounds and/or therapies useful in the treatment of cancer.

The siRNAs of the present invention may be administered in both the neoadjuvant and adjuvant settings of a patient's treatment.

In some embodiments of the present invention, other therapies, including but not limited to cancer therapies, can be used in combination with the siRNAs of the present invention. Exemplary therapies include, but are not limited to, radiotherapeutic agents and factors; surgery; antibiotics such as doxorubicin, daunorubicin, mitomycin, actinomycin D, and bleomycin; chemotherapeutic agents such as cisplatin, VP16, adriamycin, verapamil, and podophyllotoxin; tumor necrosis factor; plant alkaloids such as taxol, vincristine, and vinblastine; and alkylating agents such as carmustine, melphalan, cyclophosphamide, chlorambucil, busulfan, and lomustine.

Other cancer therapies for TNBC, which may be used in conjunction to siRNAs disclosed herein include, but are not limited to, standard anthracycline- and/or taxane-based chemotherapy. Additional therapies for TNBC which may be used alone and/or with anthracycline and/or taxane chemotherapeutic regimens, include: a) chemotherapy treatments with carboplatin, capecitabine and cyclophosphamide; b) anti-androgen receptor (AR) therapies using bicalutamide or enzalutamide; c) treatment with the anti-PD-11 antibodies nivolumab, pembrolizumab, atezolizumab, avelumab and durvalumab; d) endocrine therapy for estrogen receptor-beta-positive TNBC, using toremifene or anastrozole; e) immunotherapy with the PVX-410 multi-peptide vaccine; treatment with: 0 the anti-EGF-R antibody cetuximab; g) the Hedgehog signaling inhibitor vismodegib; h) the anti-vascular endothelial growth factor receptor (VEGF-R) monoclonal antibody bevacizumab; i) the poly (ADP Ribose) polymerase inhibitors olaparib, talazoparib and veliparib; j) phosphoinositide 3-kinase (PI3K), AKT and mammalian target of rapamycin (mTOR) inhibitors, such as the pan-PI3K inhibitor buparlisib (BKM120), the mTOR inhibitor everolimus, and the three AKT isoforms inhibitor Ipatasertib; k) MEK Inhibitors such as cobimetinib.

The other compounds and/or therapies may optionally be administered concurrently or sequentially. The active agents may be mixed prior to administration or delivery, or may be administered or delivered at the same point in time but at different anatomic sites and/or by using different routes of administration.

In other embodiments of the present invention, the siRNA is delivered as a single-agent therapy to treat the TNBC. A "single-agent therapy," as used herein, is one in which no other agent or therapy is utilized to treat the TNBC or to sensitize the cancer cell to the siRNA, i.e., the siRNA, is administered or delivered as a single therapeutic or agent to treat the TNBC. In some embodiments the siRNA, is delivered as a single-agent therapy in the first-line therapeutic approach. The expressions "first-line therapeutic approach", "first-line therapy" and grammatical variations thereof, as used herein, refer to a therapeutic utilized in the initial treatment of a disease or disorder. The first-line therapeutic approach as used herein is not limited to single-agent therapies, but may also apply to combination therapies. Thus, in some embodiments the siRNAs are utilized as a first-line therapy for the initial treatment of cancer, wherein the siRNAs are delivered as single-agent therapy or as a combination therapy. In other embodiments, the siRNAs are utilized as a therapeutic in the second-line therapeutic approach or in any subsequent therapeutic approach. The second-line therapeutic approach and any subsequent therapeutic approaches refer to therapeutic approaches after the initial therapeutic approach, i.e., the first-line therapeutic approach. These approaches may be the same as or different from the first-line therapeutic approach and may comprise a single-agent therapy or a combination therapy.

The present invention also relates to vectors expressing the nucleic acids of the invention, and cells comprising such vectors or the nucleic acids. The cell may be a mammalian cell in vivo or in culture, such as a human cell. The invention further relates to compositions comprising the RNAi constructs, and a pharmaceutically acceptable carrier or diluent. Another aspect of the invention provides a method for inhibiting the expression of a target gene in a mammalian cell, comprising contacting the mammalian cell with any of the RNAi constructs. The method may be carried out in vitro, ex vivo, or in vivo. The target cells (e.g., breast cancer cells) may be contacted in the presence of a delivery reagent, such as a lipid (e.g., a cationic lipid) or a liposome.

In another aspect, siRNAs of the present invention are targeted to a neoplasm or neoplastic cells of epithelial origin. In one embodiment, the neoplasm of epithelial origin is breast cancer. In another embodiment, breast cancer is triple negative breast cancer (TNBC).

"Treatment," or "treating," as used herein, is defined as the application or administration of a therapeutic agent (e.g., a RNAi agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

Treatment of cells, or contacting cells, can be performed in vitro (e.g., by culturing the cell with the agent), in vivo (e.g., by administering the agent to a subject), or ex vivo (e.g., by administering the agent to cells removed from a subject).

For ex vivo treatment, cells are isolated from an animal (e.g., a human), transformed (i.e., transduced or transfected in vitro) with a delivery vehicle containing the siRNA and then administered to a recipient. Procedures for removing cells from mammals are well known to those of ordinary skill in the art. In addition to cells, tissue or (whole or parts of) organs may be removed, treated ex vivo and then returned to the patient. Thus, cells, tissue or organs may be cultured, bathed, perfused and the like under conditions for introducing the siRNAs of the invention into the desired cells.

For in vivo treatment, cells of a subject are transformed in vivo with the siRNAs of the invention. The in vivo treatment may involve, but is not limited to, systemic intravenous treatment, local internal treatment such as by localized perfusion or topical treatment, and the like.

In some embodiments, the siRNAs are delivered to the cell or subject by injection. The injection (e.g., needle injection) may comprise one or more injections and can be, for example, subcutaneous, intradermal, intramuscular, intervenous, intraperitoneal, intrathecal, and/or intratumor. Methods of injection are well known to those of ordinary skill in the art (e.g., injection of a composition comprising a saline solution). Further embodiments of the present invention include the introduction of the siRNAs by direct microinjection.

Chemically modified siRNAs of the present invention can be administered by any known delivery method, including local (intratumoral) or systemic routes.

In some instances, the siRNAs are delivered directly to the neoplasm, for example, by injection using a needle and syringe. Injection into the neoplasm permits large quantities of the siRNAs to be delivered directly to the target cells while minimizing delivery to systemic sites. By direct injection into the neoplasm, an effective amount to promote RNA interference by the siRNAs is distributed throughout at least a substantial volume of the neoplasm. In some instances, delivery of the siRNAs requires a single injection into the neoplasm. In other instances, delivery of the siRNAs requires multiple injections into separate regions of the neoplasm such that the entire mass of the neoplasm is invested with an effective amount to promote RNA interference by the siRNAs. See U.S. Pat. Nos. 5,162,115 and 5,051,257, each of which is incorporated herein by reference.

The total dose, concentration, volume of the siRNAs delivered, and rate of delivery can be optimized for a given neoplasm type, size and architecture. The zone of RNA interference can be controlled by optimizing these parameters. The volume and concentration of the siRNAs delivered into the neoplasm must be sufficient to promote RNA interference throughout the tumor. Depending on the number of injections, and their placement with respect to neoplasm architecture, it can be useful to administer total siRNAs volumes less than the neoplasm volume, greater than the neoplasm volume, or approximately equal to the neoplasm volume.

In some instances, the siRNAs are delivered directly to the neoplasm using an implantable device.

In some instances siRNAs injection into a neoplasm can be accompanied by ultrasound guidance.

In other instances, the siRNAs are administered systemically, for example, intravenously, intraarterially, intramuscularly, or subcutaneously.

Further aspects of the invention relate to delivery of siRNA to brain tumors. Any appropriate delivery mechanism for delivering an siRNA to the brain or spinal cord can be applied. In some embodiments, delivery to the brain or spinal cord occurs by infusion, intrathecal delivery, parenchymal delivery, intravenous delivery or direct injection into the brain or spinal cord. In some embodiments, an siRNA is delivered to a specific region of the brain. An siRNA can be modified or formulated appropriately to pass the blood-brain barrier. In other embodiments, an siRNA is administered in such a way that it does not need to cross the blood-brain barrier.

Administration of an "effective amount" of an oligonucleotide of the present invention is defined as an amount, at dosages and for periods of time necessary to achieve the desired result. For example, an effective amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms.

In general, the initial pharmaceutically effective amount of the active compound or composition administered parenterally (e.g., intravenous or subcutaneous administration) may be in the range of about 0.1 to 50 mg/kg of patient body weight per day. The desired dosage can be delivered by a single bolus administration, by multiple bolus administrations, by continuous infusion administration, or by intermittent infusion administration of active compound, depending on the pattern of pharmacokinetic decay that the practitioner wishes to achieve.

The active compound(s) is/are administered to the patient at one time or over a series of treatments. Depending on the type and severity of the disease, about 1 mg/kg to 15 mg/kg of active compound(s) is an initial candidate dosage for administration to the patient. A typical daily dosage might range from about 0.1, 0.5, 1, 10 or 100 micrograms/kg up to 100, 200 or 500 mg/kg, or more, including any intermediate values, depending on the factors mentioned above.

For repeated administrations over several days or longer, depending on the condition, the treatment is sustained until a desired suppression of disease symptoms occurs. A more particular dosage of the active compound will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g., such that the patient receives from about two to about twenty, e.g. about six doses of siRNA). An initial higher loading dose, followed by one or more lower doses may be administered. An exemplary dosing regimen comprises administering an initial loading dose of about 0.5 to 10 mg/kg, followed by a weekly maintenance dose of about 0.5 to 10 mg/kg of the active compound. However, other dosage regimens may be useful. The progress of this therapy can be monitored by conventional techniques and assays.

Subjects treated by the methods of the present invention can also be administered one or more additional therapeutic agents. Chemotherapeutic agents may be administered by methods well known to the skilled practitioner, including systemically, direct injection into the cancer, or by localization at the site of the cancer by associating the desired chemotherapeutic agent with an appropriate slow release material or intra-arterial perfusing of the tumor. The preferred dose may be chosen by the practitioner based on the nature of the cancer to be treated, and other factors routinely considered in administering.

Subjects may also be treated by radiation therapy, including, but not limited to, external beam radiotherapy, which may be at any suitable dose (e.g., 20 to 70 Gy or more per tumor, typically delivered over a fractionated schedule).

Methods of Diagnostic:

It is another object of the present invention to provide a method for detecting a diagnostic marker in a sample of a subject suspected of having a TNBC tumor, the method comprising providing a diagnostic sample of the subject, contacting the diagnostic sample of the subject with the siRNA molecules of the invention, and determining the presence of a diagnostic marker in said sample. In particular, the diagnostic marker is alternative transcript variant 3 (SpT3), which encodes isoform c of ErbB-2, having a MW of 165 kDa on SDS-PAGE (p165ErbB-2).

The expressions "sample", "biological sample", "diagnostic sample", and the like refer to a material known or suspected of expressing or containing one or more polynucleotide or polypeptide cancer markers. The diagnostic sample may be any cell, tissue or organ and may be removed by standard biopsy. Exemplary tissues for use in methods described herein include, but are not limited to, blood, bone, brain tissue, endometrial tissue, kidney tissue, stomach tissue, mammary tissue, mammary gland tissue, muscle tissue, nervous tissue and soft tissue. The diagnostic sample may also be a bodily fluid, including, but not limited to, cerebrospinal fluid, pericardial fluid, peritoneal fluid, saliva, serum, and urine.

In one aspect, the diagnostic method disclosed herein is based on the ability of a siRNA molecular beacon (SpT3 MB) to recognize the unique mRNA sequence at the 5' UTR and 5' coding region of SpT3, the transcript variant encoding the isoform c of ErbB-2, which displays a MW of 165 kDa (p165ErbB-2). To this unique region are targeted siRNA molecules including, but not limited to, those of the present invention, comprising the sequences depicted in SEQ ID NO: 1 or SEQ ID NO: 2. A binary MB approach may also be used consisting of the simultaneous contact of the diagnostic sample with both the SpT3 MB displaying SEQ ID NO: 1 and the SpT3 MB displaying SEQ ID NO: 2. The SpT3 MB is designed to have a stem-loop structure, with the nucleotides in the stem complementary to each other forming a four to seven base pairs double stranded stem and the loop consisting of SEQ ID NO: 1 or SEQ ID NO: 2. Furthermore, conjugated to the 5' and 3' ends of this molecular beacon are a fluorophore and a quencher, respectively. Replacement of the organic fluorophores with other brighter signaling materials, such as quantum dots and fluorescent polymers is also considered. Chemical modifications to promote metabolic stability and improve target cell penetration may be introduced to the SpT3 MBs, including but not limited to 2'OMe-modified siRNAs. The diagnostic method disclosed in the present invention enables the detection of gene expression in fixed as well as viable cells, thus allowing identification of the expression of SpT3 in clinical samples.

In another aspect, the diagnostic method disclosed herein concerns an RNA in situ hybridization (ISH) assay for determining the presence of alternative ErbB-2 transcripts (e.g., SpT3). In a preferred embodiment, the aforementioned ISH assay is an RNAscope® assay. RNAscope® platform presents a unique probe design strategy that allows simultaneous signal amplification and background suppression to achieve single-molecule visualization while preserving tissue morphology. Importantly, RNAscope® is compatible with routine formalin-fixed, paraffin embedded (PE) tissue specimens and can use either conventional chromogenic dyes for bright-field microscopy or fluorescent dyes for multiplex analysis (Wang, F. et al. (2012) op. cit.).

Target probes for the RNAscope® assay displaying, but not limited to, the sequences depicted in SEQ ID NO: 1 or SEQ ID NO: 2 may be designed to specifically recognize a unique mRNA sequence at the 5' UTR and 5' coding region of SpT3, the transcript variant encoding ErbB-2 isoform c which displays a MW of 165 kDa (p165ErbB-2).

It is therefore another object of the invention to provide a kit for detection of ErbB-2 alternative transcript variant 3 (SpT3), comprising agents for conducting an RNAscope® assay including one or more target probe sets having the sequences depicted in SEQ ID NO: 1 and SEQ ID NO: 2, or other specific sequences, for detection of ErbB-2 alternative transcript variant 3 (SpT3) diagnostic marker.

A series of target probes to hybridize SpT3 may be designed according to methods described in published U.S. Pat. Nos. 7,709,198; 8,604,182; 8,658,361; 8,951,726; 7,709,198; 8,658,361 and 7,709,198. For example, each target probe may contain an 18 to 25-base region complementary to the target mRNA (e.g., SpT3), a spacer sequence, and a 14-base tail sequence (conceptualized as Z). A pair of target probes (double Z), each possessing a different type of tail sequence, may hybridize contiguously to a target region (~50 bases). The two tail sequences together form a 28-base hybridization site for the preamplifier, which contains 20 binding sites for the amplifier, which, in turn, contains 20 binding sites for the label probe. Typically, a 1 kb region on the RNA molecule could be targeted by 20 probe pairs; thus, sequential hybridizations with the preamplifier, amplifier, and label probe can theoretically yield up to 8000 labels for each target RNA molecule. The label probe can be either fluorescently labeled for direct visualization under an epifluorescent microscope or conjugated to an alkaline phosphatase or horseradish peroxidase (HRP) molecule for chromogenic reactions (Fast Red with alkaline phosphatase and 3,3'-diaminobenzidine (DAB) with HRP). The alkaline phosphatase or HRP-labeled probes have an added advantage, in that chromogen-stained slides can be viewed under a standard bright-field microscope similar to immunohistochemistry (IHC) procedures, making RNAscope® assay results easier to read and archive in a clinical setting. Multiple mRNA species could be measured simultaneously in two ways: the target probes for different ErbB-2 transcripts could have the same tail sequence recognized by the same signal amplification system, generating a pooled signal; alternatively, multiple signal amplification systems with different label probes can be used to detect each mRNA species, allowing for multiplex detection of multiple target RNAs.

Hybridization, chromogenic detection and estimation of mRNA copy number may be performed as described (Wang, F. et al. (2012), op. cit.).

EXAMPLES

As demonstrated in the experimental section of the present invention, ErbB-2 isoform c, encoded by SpT3, is the major contributor to the p165ErbB-2 protein isoform.

Based on the assays carried out, the present inventors were able to conclude that the ErbB-2 isoform c, encoded by alternative transcript 3 (SpT3):

has a MW on SDS-PAGE of 165 kDa, is located at the nucleus of basal (BL) and mesenchymal (M) TNBC, and drives proliferation of basal (BL) and mesenchymal (M) TNBC subtypes.

Accordingly, ErbB-2 was placed in a new and unanticipated scenario, i.e., the nucleus of TNBC. Also, it was revealed that alternative ErbB-2 transcript 3 (SpT3), encoding ErbB-2 isoform c, is the major oncogenic driver of TNBC proliferation. The authors' clinical findings also identified nuclear ErbB-2 as a biomarker of poor clinical outcome in TNBC.

It is therefore proposed by the present inventors that TNBC needs to be further sub-classified as either nuclear ErbB-2-positive or nuclear ErbB-2-negative. Also, nuclear wild-type (WT) ErbB-2 (p185ErbB-2, WTErbB-2) is postulated as a novel common biomarker and as a target of therapy for LAR TNBC subtype and ErbB-2E tumors. Furthermore, the nuclear ErbB-2 isoform c is postulated as a novel common biomarker and target of therapy in BL and M TNBC subtypes.

The invention is further illustrated by the following Examples, which are not intended to limit the scope thereof. Instead, the examples set forth below should be understood only as exemplary embodiments for better taking into practice the present invention.

Example 1—NErbB-2 Correlates with Poor Prognosis in TNBC

Figure 1A:
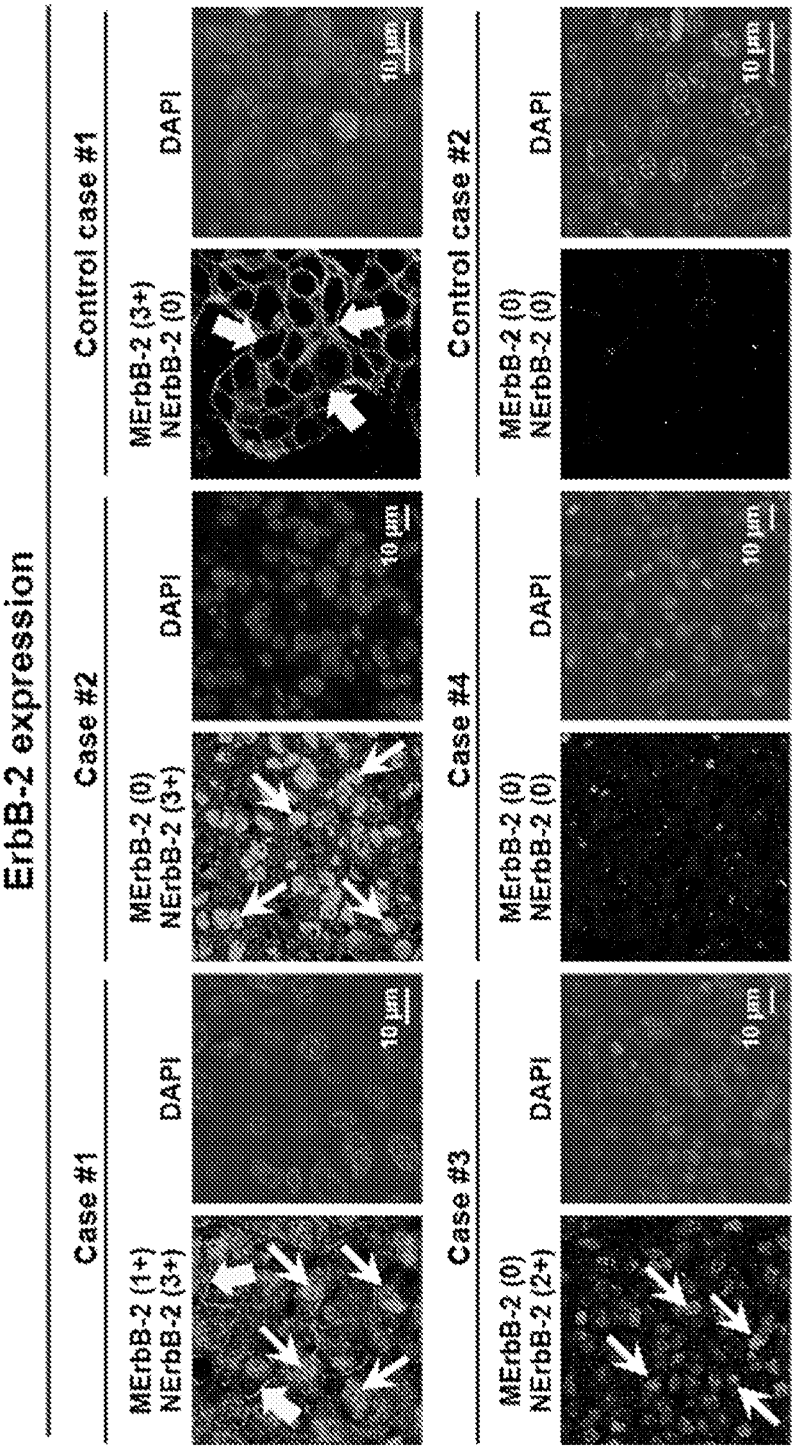
FIGS. 1A-1C. NErbB-2 expression in TNBC patients. (1A) NErbB-2 levels were evaluated by immunofluorescence (IF) and confocal microscopy using the C-18 ErbB-2 polyclonal antibody, raised against the human ErbB-2 carboxy (C) terminal region (amino acids 1242 to 1255). NErbB-2 was scored as previously reported (Schillaci, R. et al. (2012) op. cit.), considering both the percentage of positive cells and the staining intensity. A score of 0 represents faint or no staining in less than 10% of cells, 1+ weak nuclear staining in 10-25%, 2+ moderate staining in 26-50%, and 3+ strong staining in >50% of cells. Scores of 2+ and 3+ were considered positive for NErbB-2. Left and middle panels: shown are representative samples of tumors displaying 0 to 3+ NErbB-2 staining (Cases #1 to #4). Low membrane ErbB-2 (MErbB-2) levels (1+ score) are not considered as membrane ErbB-2 overexpression in the clinical setting. Right panels (control cases #1 and #2): as control of specificity, NErbB-2-negative BC samples were used either lacking MErbB-2 or displaying 3+ MErbB-2 score. Thick arrows indicate MErbB-2 and slim arrows, NErbB-2. Nuclei were stained with DAPI. (1B) NErbB-2 IF staining using the C-18 ErbB-2 polyclonal antibody (upper panel) or the ErbB-2 A-2 monoclonal antibody raised against amino acids 1180-1197 at the ErbB-2 C-terminus (lower panel). One representative tumor displaying 3+ NErbB-2 score is shown. Nuclei were stained with DAPI. (1C) NErbB-2 expression was detected with the C-18 antibody by IF, as described in FIG. 1A, or by immunohistochemistry (IHC). Shown are representative images of tumors displaying 3+ NErbB-2 score. Boxed areas in the IHC staining are shown in detail in the inset (400×).
Figure 1B:
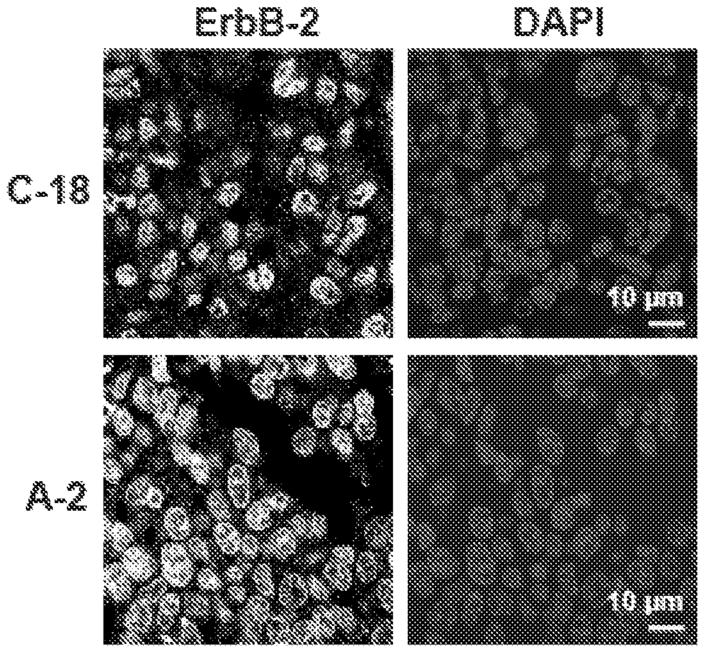
Figure 1C:
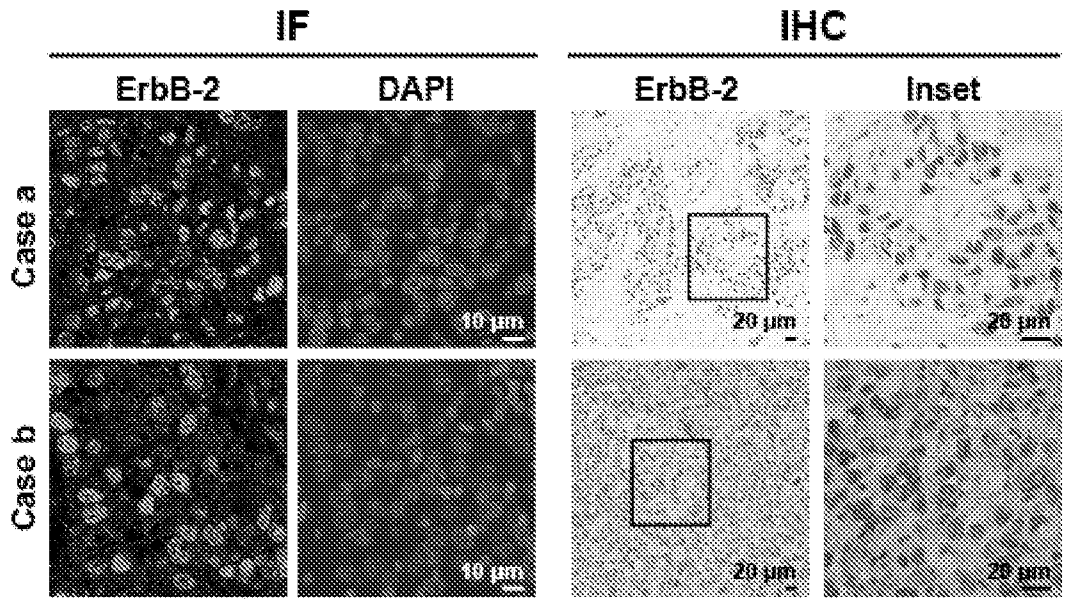

The role of NErbB-2 in TNBC remains completely unknown. The present inventors explored NErbB-2 presence and clinical relevance in a large cohort of 99 TNBC samples (see Table 1 below). Samples were stained by immunofluorescence (IF) with the C-18 polyclonal antibody, raised against the human ErbB-2 C-terminal region. This protocol shows significantly higher sensitivity for detection of NErbB-2 than immunohistochemistry (IHC) procedures, while its specificity and sensitivity to detect MErbB-2 are comparable to those of IHC (Shillaci, R. et al. (2012) op. cit.). High NErbB-2 expression (2+ and 3+ according to the scoring system described by the present inventors (Shillaci, R. et al. (2012) op. cit.) was found in 38.4% of the tumors (FIG. 1A and Table 3). Either absence (85.9% of the samples) or low MErbB-2 levels (1+ score, 14.1% of the samples), which would not be considered as membrane overexpression in the clinical setting, were found in the TN tumors (FIG. 1A and Table 1). Similar scores of NErbB-2 were found when selected TN samples were stained with an ErbB-2 monoclonal antibody, ErbB-2 A-2, raised against the C-terminal domain of human ErbB-2 (FIG. 1B). The present inventors also explored NErbB-2 by IHC using the same antibody as in IF and found substantial to excellent overall concordance regarding NErbB-2 positivity detected by both techniques (91.4%, κ=0.82, Table 2 below) (FIG. 1C).

Figure 2A:
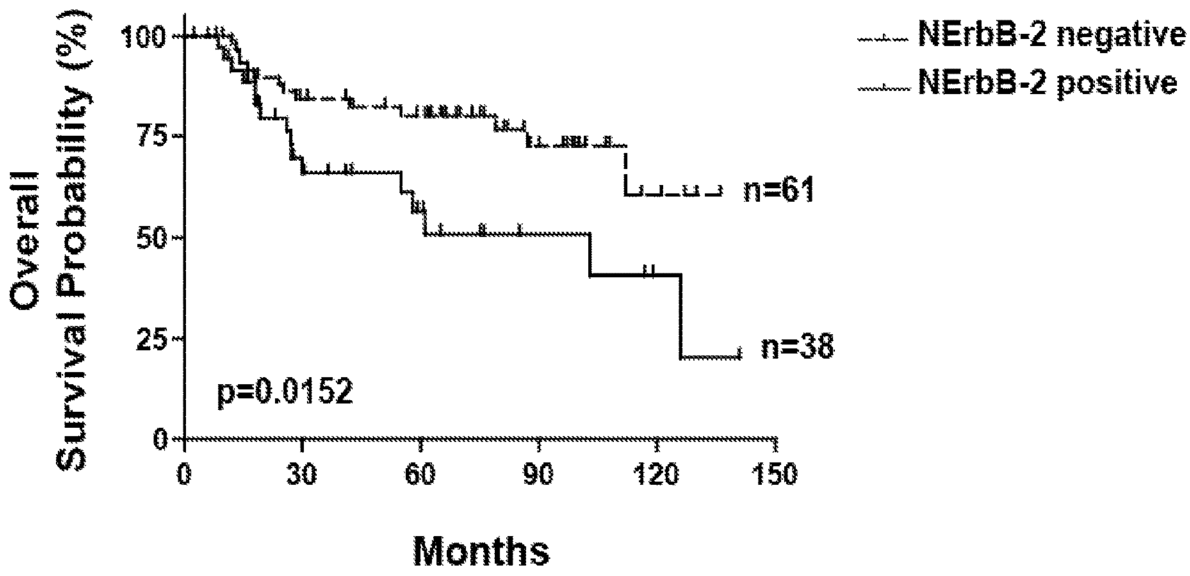
FIGS. 2A-2D. NErbB-2 shows clinical relevance in TNBC. Relationship between NErbB-2 positivity and survival in terms of overall survival (2A), disease-free survival (2B), local relapse-free survival (2C) and distant metastasis-free survival (2D) probabilities (%), as assessed by a Kaplan-Meier analysis and log-rank test. The TNBC clinical study is based on the monitoring of 99 patients, 38 therefrom being NErbB-2-positive (full line) and 61 NErbB-2-negative (dotted line).
Figure 2B:
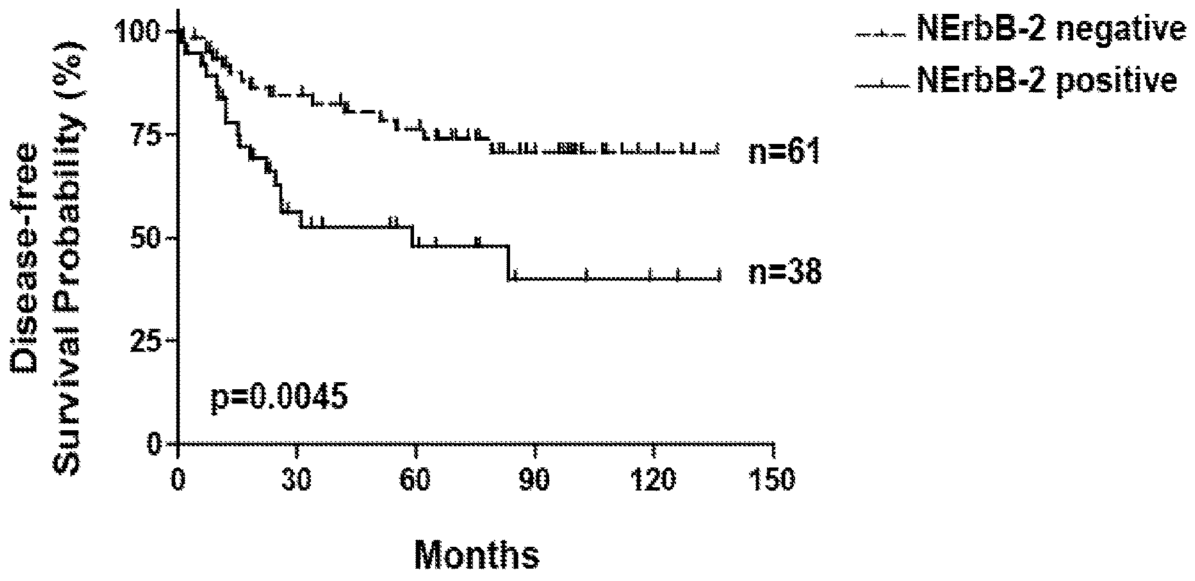
Figure 2C:
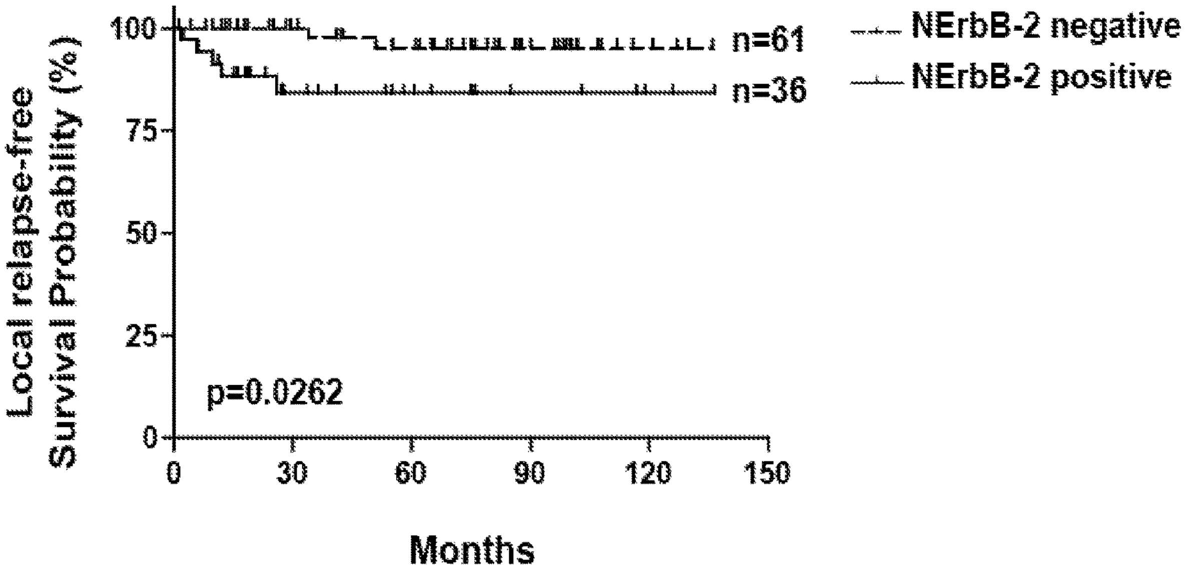
Figure 2D:
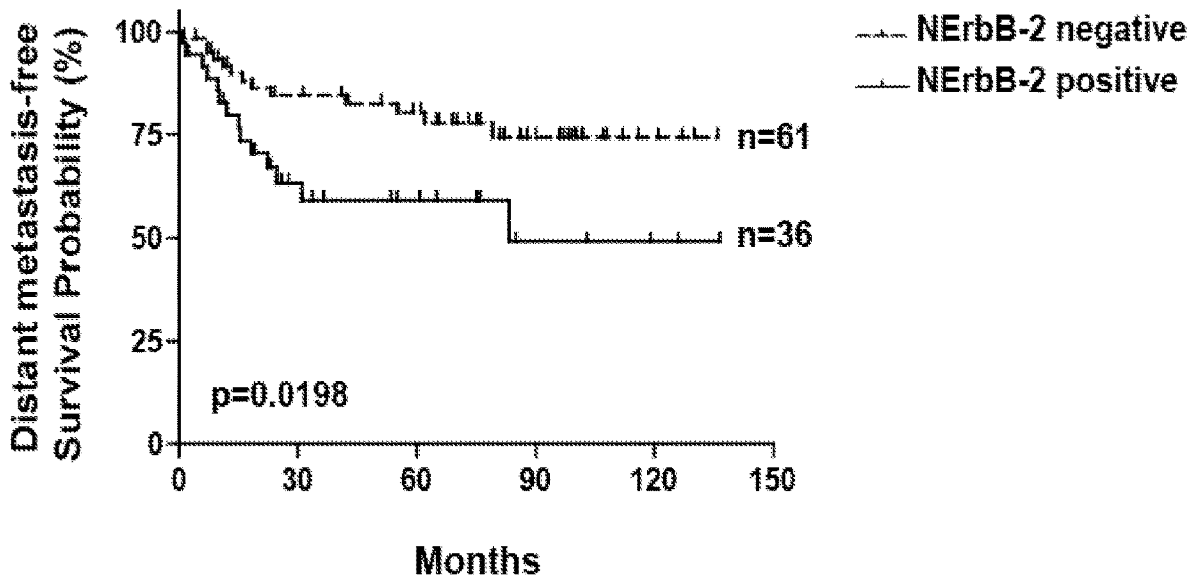

Kaplan-Meier analysis revealed that TNBC patients bearing NErbB-2-positive tumors showed significantly shorter overall survival (OS) and disease-free survival (DFS) compared to patients whose tumors lacked NErbB-2 (FIG. 2A and FIG. 2B). Local relapse-free survival (LRFS) and distant metastasis-free survival (DMFS) were also lower in NErbB-2-positive tumors than in NErbB-2-negative ones (FIG. 2C and FIG. 2D). Univariate analysis revealed that NErbB-2 and higher clinical stage were associated with lower OS, DFS and DMFS (see Table 4 below). Higher lymph node status was also associated with shorter OS and DMFS. In addition, multivariate analysis adjusted for the clinical stage identified NErbB-2 as an independent predictor of shorter OS (HR, 2.54; 95% CI, 1.22-5.28; P=0.013), DFS (HR, 2.91; 95% CI, 1.44-5.87; P=0.003), and DMFS (HR, 2.59; 95% CI, 1.20-5.60; P=0.015) in TNBC.

TABLE 1

Clinicopathological characteristics of TNBC patients. NErbB-2 presence was explored in a cohort of 99 TNBC samples by IF and confocal microscopy:

| Characteristic | No patients | % |
|---|---|---|
| Total number of patients | 99 | |
| Age (years) | | |
| Mean | 53.51 | |
| SD | 11.93 | |
| Range | 28-81 | |
| Length of follow up (months) | | |
| Median | 58.50 | |
| Range | 2.4-140.90 | |
| Menopausal status | | |
| Premenopausal | 41 | 41.41 |
| Postmenopausal | 58 | 58.59 |
| Tumor size | | |
| T1 | 16 | 16.16 |
| T2 | 45 | 45.46 |
| T3 | 26 | 26.26 |
| T4 | 9 | 9.09 |
| Not documented | 3 | 3.03 |
| Lymph node status | | |
| N0 | 55 | 55.56 |
| N1 | 19 | 19.19 |
| N2 | 17 | 17.17 |
| N3 | 8 | 8.08 |
| Distant metastasis at diagnosis | | |
| M0 | 99 | 100.00 |
| M1 | 0 | 0.00 |
| Clinical Stage | | |
| I | 8 | 8.08 |
| II | 50 | 50.51 |
| III | 41 | 41.41 |
| IV | 0 | 0.00 |
| Tumor grade | | |
| 1 | 2 | 2.02 |
| 2 | 24 | 24.24 |
| 3 | 70 | 70.71 |
| Not documented | 3 | 3.03 |

TABLE 1-continued

Clinicopathological characteristics of TNBC patients. NErbB-2 presence was explored in a cohort of 99 TNBC samples by IF and confocal microscopy:

| Characteristic | No patients | % |
|---|---|---|
| Membrane ErbB-2 Status (IHC)[a] | | |
| 0 | 85 | 85.86 |
| 1+ | 14 | 14.14 |
| 2+ | 0 | 0.00 |
| 3+ | 0 | 0.00 |
| Operation | | |
| Breast conserving surgery | 44 | 44.44 |
| Mastectomy | 54 | 54.55 |
| Not documented | 1 | 1.01 |
| Chemotherapy (Anthracycline-containing regimen) | | |
| No | 0 | 0 |
| Yes | 99 | 100 |
| Radiotherapy | | |
| No | 19 | 19.19 |
| Yes | 79 | 79.80 |
| Not documented | 1 | 1.01 |
| Events during follow up | | |
| No | 66.00 | 66.67 |
| Yes | 33.00 | 33.33 |
| Events description | | |
| Local recurrence plus metastasis | 3.00 | 9.09 |
| Only local recurrence | 4.00 | 12.12 |
| Only metastasis | 24.00 | 72.73 |
| Not documented | 2.00 | 6.06 |

[a]IHC: immunohistochemistry.

TABLE 2

Concordance between detection of NErbB-2 expression by immunofluorescence and immunohistochemistry. NErbB-2 expression determined by immunohistochemistry (IHC) using the C18 antibody shows substantial to excellent overall concordance regarding NErbB-2 positivity detected by both techniques (91.4%, K = 0.82):

| NErbB-2 (IHC[b] C-18), n (%) | NErbB-2 (IF[a] C-18), n (%) Negative | Positive | Total N[c] (%) | Overall concordance (%) | κ statistics[e] |
|---|---|---|---|---|---|
| Negative | 12 (34.3)[d] | 1 (2.9) | 13 (37.1) | 91.4 | 0.82 |
| Positive | 2 (5.7) | 20 (57.1) | 22 (62.9) | | |

[a]IF: Immunofluorescence.
[b]IHC: Immunohistochemistry.
[c]Concordance between detection of NErbB-2 expression by IF and IHC was evaluated in 35 patients from our cohort.
[d]Percentage of the total number of patients analyzed by both IF and IHC.
[e]κ statistics (with a value of 1.0 indicating perfect agreement and a value of −1.0 indicating perfect disagreement) revealed almost perfect levels of concordance between detection of NErbB-2 positivity by IF and IHC with C-18 antibody.

TABLE 3

Univariate analysis of clinicopathological characteristics of 99 TNBC patients in relation to NErbB-2 expression positivity using Odds ratio model.

| Variable | Characteristics | NErbB-2 expression Negative N = 61 | Positive N = 38 | OR (Odds ratio) | 95% CI (Confidence interval) | p value |
|---|---|---|---|---|---|---|
| Menopausal status | Premenopausal | 27 | 14 | 1.36 | 0.59-3.12 | 0.53 [a] |
| | Postmenopausal | 34 | 24 | | | |
| Tumor size | ≤20 mm | 9 | 7 | 0.77 | 0.26-2.29 | 0.78 [a] |
| | >20 mm | 50 | 30 | | | |
| Lymph node status | Negative | 33 | 22 | 0.86 | 0.38-1.94 | 0.84 [a] |
| | Positive | 28 | 16 | | | |
| Clinical Stage | I + II | 36 | 22 | 1.05 | 0.46-2.38 | 1.00 [a] |
| | III | 25 | 16 | | | |
| Tumor grade | Well to moderately differentiated [c] | 19 | 8 | 2.04 | 0.76-5.47 | 0.17 [a] |
| | Poorly differentiated | 40 | 29 | | | |

[a] Chi-Square Test
[b] Fisher's exact test
[c] Well to moderately differentiated: tumor grade 1 + 2, poorly differentiated: tumor grade 3

TABLE 4

Univariate and multivariate analyses of overall survival (OS), disease-free survival (DFS) and distant metastasis-free survival (DMFS) in TNBC patients. Multivariate analysis adjusted for the clinical stage identified NErbB-2 positivity as a significant and independent predictor of shorter OS (HR, 2.54; 95% CI, 1.22-5.28; P = 0.013), DFS (HR, 2.91; 95% CI, 1.44-5.87; P = 0.003), and DMFS (HR, 2.59; 95% CI, 1.20-5.60; P = 0.015):

| | OS | | | DFS | | | DMFS | | |
|---|---|---|---|---|---|---|---|---|---|
| Variable | HR[a] | 95% CI[b] | p value | HR[a] | 95% CI[b] | p value | HR[a] | 95% CI[b] | p value |
| Univariate analysis | | | | | | | | | |
| Menopausal status (Premenopausal vs postmenopausal) | 0.885 | 0.431-1.818 | 0.739 | 0.654 | 0.330-1.297 | 0.224 | 0.727 | 0.341-1.548 | 0.408 |
| Tumor size (≤20 mm vs >20 mm) | 1.690 | 0.512-5.581 | 0.389 | 1.023 | 0.395-2.654 | 0.962 | 1.019 | 0.352-2.950 | 0.972 |
| Lymph node status (Negative vs Positive) | 2.244 | 1.084-4.648 | 0.030 | 1.867 | 0.940-3.711 | 0.075 | 2.242 | 1.039-4.841 | 0.040 |
| Clinical Stage (I + II vs III) | 2.352 | 1.121-4.939 | 0.024 | 2.197 | 1.105-4.369 | 0.025 | 2.475 | 1.146-5.343 | 0.021 |
| Tumor grade (well to moderately vs poorly differentiated)[c] | 0.498 | 0.234-1.059 | 0.070 | 0.576 | 0.276-1.199 | 0.140 | 0.687 | 0.297-1.585 | 0.378 |
| NErbB-2 (Negative vs Positive) | 2.383 | 1.156-4.913 | 0.019 | 2.621 | 1.314-5.228 | 0.006 | 2.400 | 1.122-5.135 | 0.024 |
| Multivariate analysis | | | | | | | | | |
| Clinical Stage (I + II vs III) | 2.514 | 1.184-5.340 | 0.016 | 2.470 | 1.231-4.952 | 0.011 | 2.650 | 1.220-5.755 | 0.014 |
| NErbB-2 (Negative vs Positive) | 2.535 | 1.218-5.275 | 0.013 | 2.912 | 1.444-5.874 | 0.003 | 2.590 | 1.198-5.597 | 0.015 |

[a]HR: Hazard ratio
[b]CI: Confidence interval
[c]Well to moderately differentiated: tumor grade 1 + 2, poorly differentiated: tumor grade 3

In conclusion, based on the clinical findings described above, the present inventors identified nuclear ErbB-2 as a biomarker of poor clinical outcome in TNBC.

Example 2—ErbB-2 Protein Variants Expression and Activation in TNBC Cells

Figure 3A:
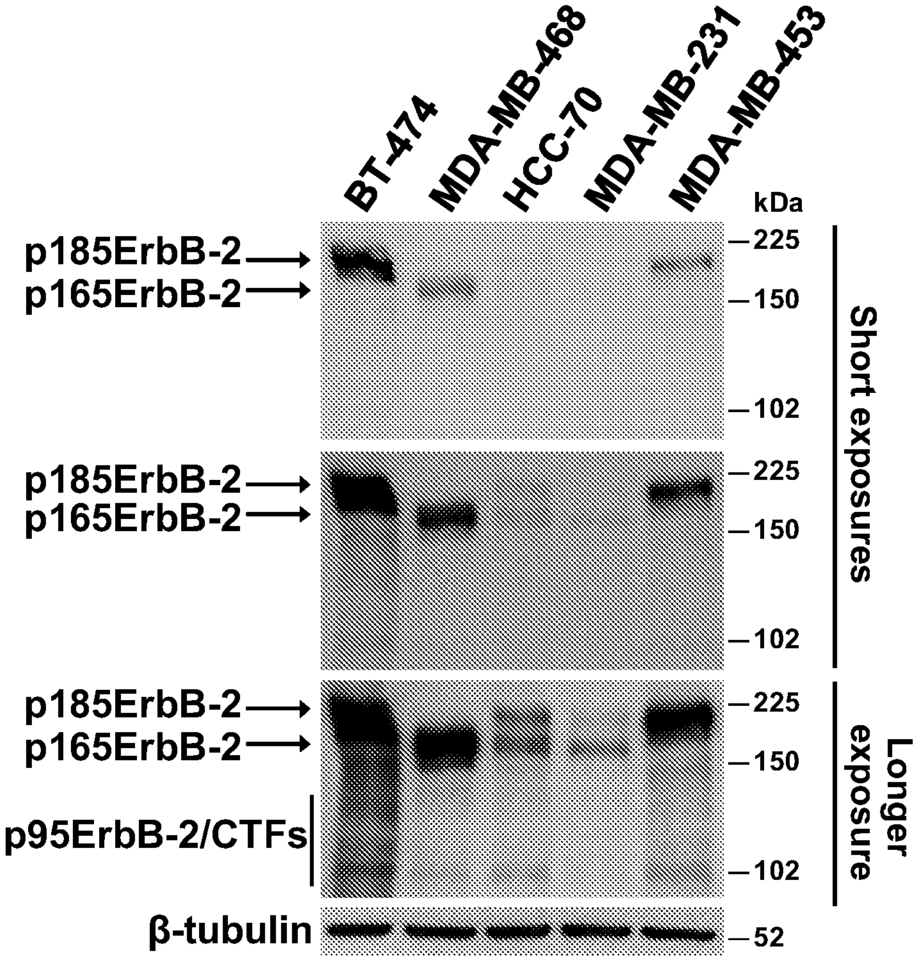
FIGS. 3A-3I. ErbB-2 isoforms expression and activation in BC cells. (3A) Representative Western Blot (WB) of ErbB-2 expression in BC cells (50 μg of protein). Total cell lysates were analyzed with the ErbB-2 C-18 antibody. MDA-MB-453 cells (LAR subtype) expressed full-length ErbB-2 (185 kDa, p185ErbB-2, WTErbB-2) comparable to the canonical ErbB-2 present in BT-474 cells, used as a control. MDA-MB-468 (BL1 subtype) showed an ErbB-2 variant of lower MW (~165 kDa, p165ErbB-2). HCC-70 and MDA-MB-231 cells (BL2 and M subtype, respectively) presented both p185ErbB-2 (WTErbB-2) and p165ErbB-2. Additionally, the ErbB-2 truncated isoforms p95ErbB-2/CTFs (~90-115 kDa) produced by proteolytic cleavage and alternative initiation of translation were observed. (3B) Signal intensities of p185ErbB-2 (black bars) and p165ErbB-2 (grey bars) in four independent WBs performed as in FIG. 3A, were analyzed by densitometry and normalized to β-tubulin protein bands. Densitometry was performed at different exposures to assure quantification within the linear detection range, preventing signal saturation. Data are presented as mean±S.D. One-way ANOVA test with Dunnett's multiple comparisons was applied to determine significant differences between BT-474 and TNBC cells. For b vs a: P<0.001. (3C) Signal intensities of p95ErbB-2/CTFs (white bars) were quantified and plotted as in FIG. 3B. For b vs a: P<0.001. (3D) Proportion of each ErbB-2 isoform (p185ErbB-2, black bars; p165ErbB-2, grey bars; and p95ErbB-2/CTFs, white bars) among BC cell lines. Mean values obtained in FIGS. 3B-3C were represented as percentage relative to total ErbB-2. (3E) Representative WB analysis, performed as in FIG. 3A, in a panel of BC lines. (3F) Unsupervised hierarchical clustering of BC cells carried out on quantification profiles of p185, p165 and p95ErbB-2/CTFs protein bands from three independent WBs performed as in FIG. 3E. Color scale of heatmap represents the logarithm of mean protein intensities normalized to 8-tubulin. (3G) WB analysis of ErbB-2 isoforms expression using the monoclonal antibody A-2 raised against amino acids 1180-1197 located at the C-terminus of p185ErbB-2. (3H) WB analysis of ErbB-2 isoforms expression using the monoclonal antibody C-3 raised against amino acids 251-450 located at the N-terminus of p185ErbB-2. (3I) Total cell lysates were analyzed by WB using the anti-phospho-ErbB-2 Tyr877 antibody or with the total ErbB-2 C-18 antibody. BT-474 cells were used as a control of ErbB-2 expression and activation. The experiments shown in FIGS. 3G to 3I are representative of three independent ones with similar results.

The present inventors explored the presence and activation state of ErbB-2 in TNBC cell lines from all four TNBC molecular subtypes (TNBC-4type). While ErbB-2 expression was detected in cell lysates from all lines, using the C-18 antibody, ErbB-2 variants of different molecular weight (MW) where found among subtypes. Comparable to control BT-474 cells, from the ErbB-2-enriched (ErbB-2E) intrinsic BC subtype, MDA-MB-453 cells (LAR subtype) express wild-type (WT) ErbB-2 (MW of 185 kDa, p185ErbB-2) (FIG. 3A). MDA-MB-468 cells (BL1 subtype) express only an isoform with a SDS-PAGE MW of 165 kDa (p165ErbB-2) (FIG. 3A). HCC-70 (BL2 subtype) and MDA-MB-231 (M subtype) display both p185ErbB-2 and p165ErbB-2 (FIG. 3A). Consistent with the inventors' finding on the expression of p165ErbB-2, ErbB-2 bands between 130-170 kDa were previously detected in clinically ErbB-2-negative BC samples (Gautrey, H. et al. (2015) *SRSF3 and hnRNP H1 regulate a splicing hotspot of HER2 in breast cancer cells*. RNABiol 12, 1139-1151).

Figure 3B:
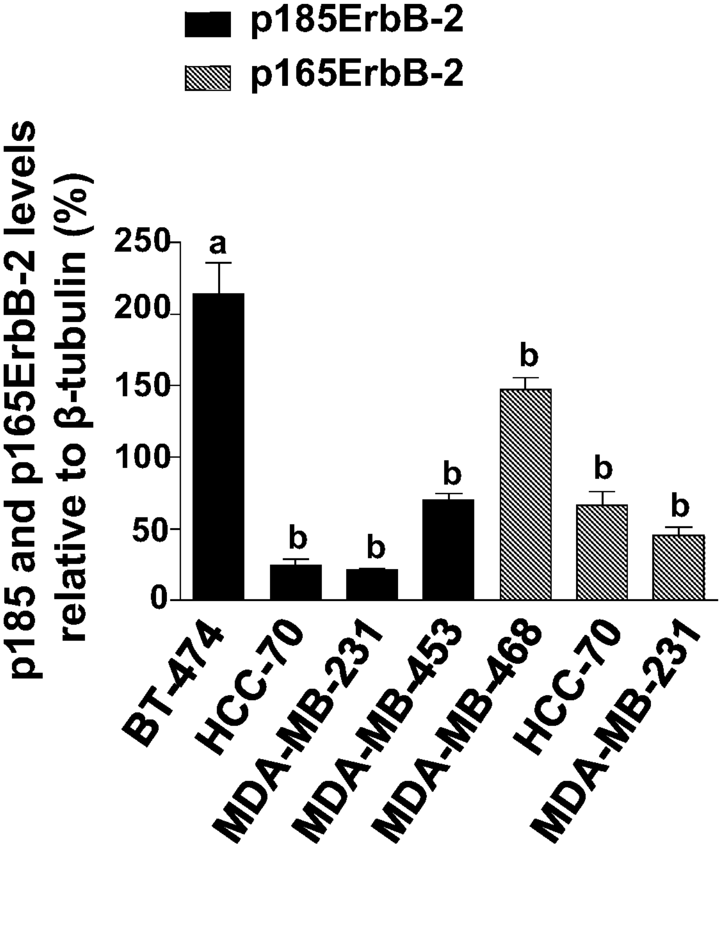
Figure 3C:
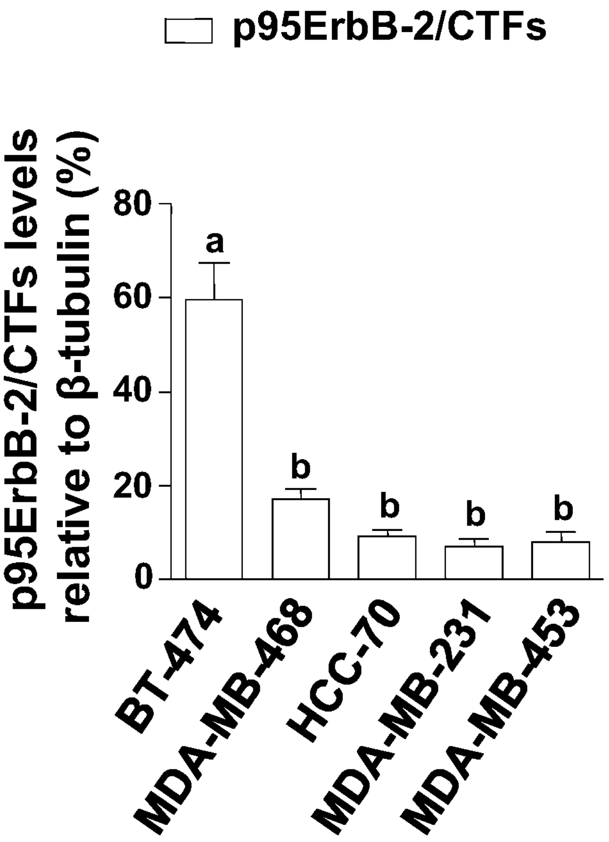
Figure 3D:
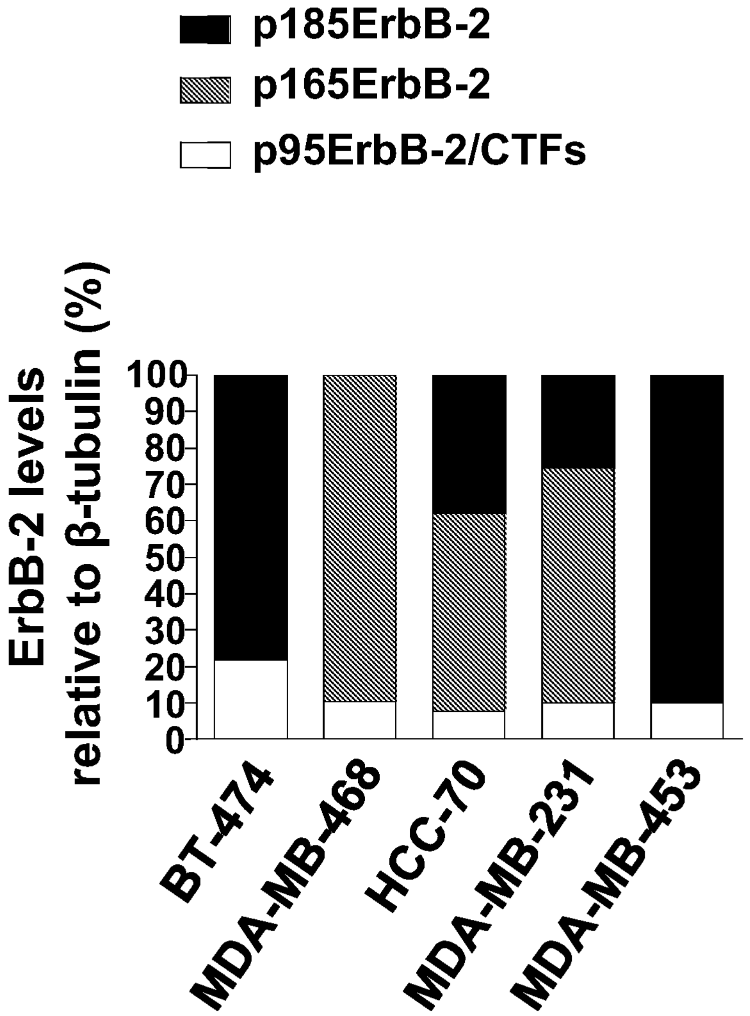
Figure 3E:
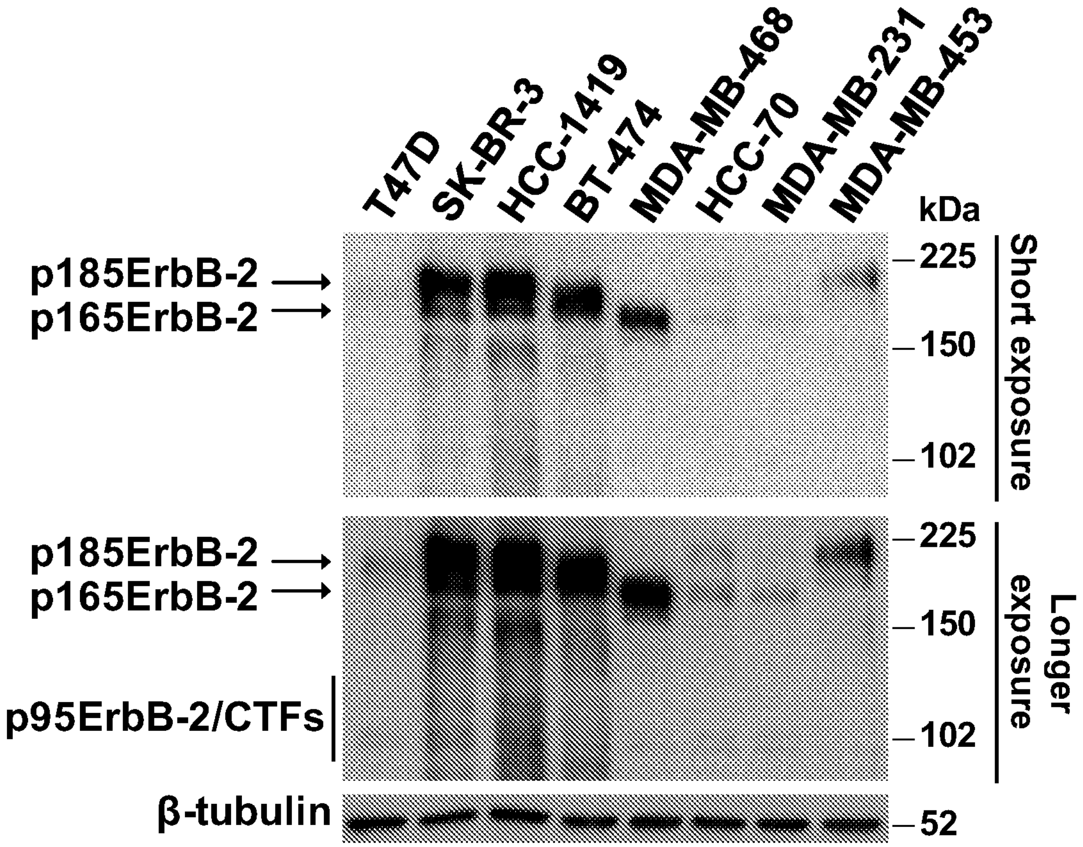
Figure 3F:
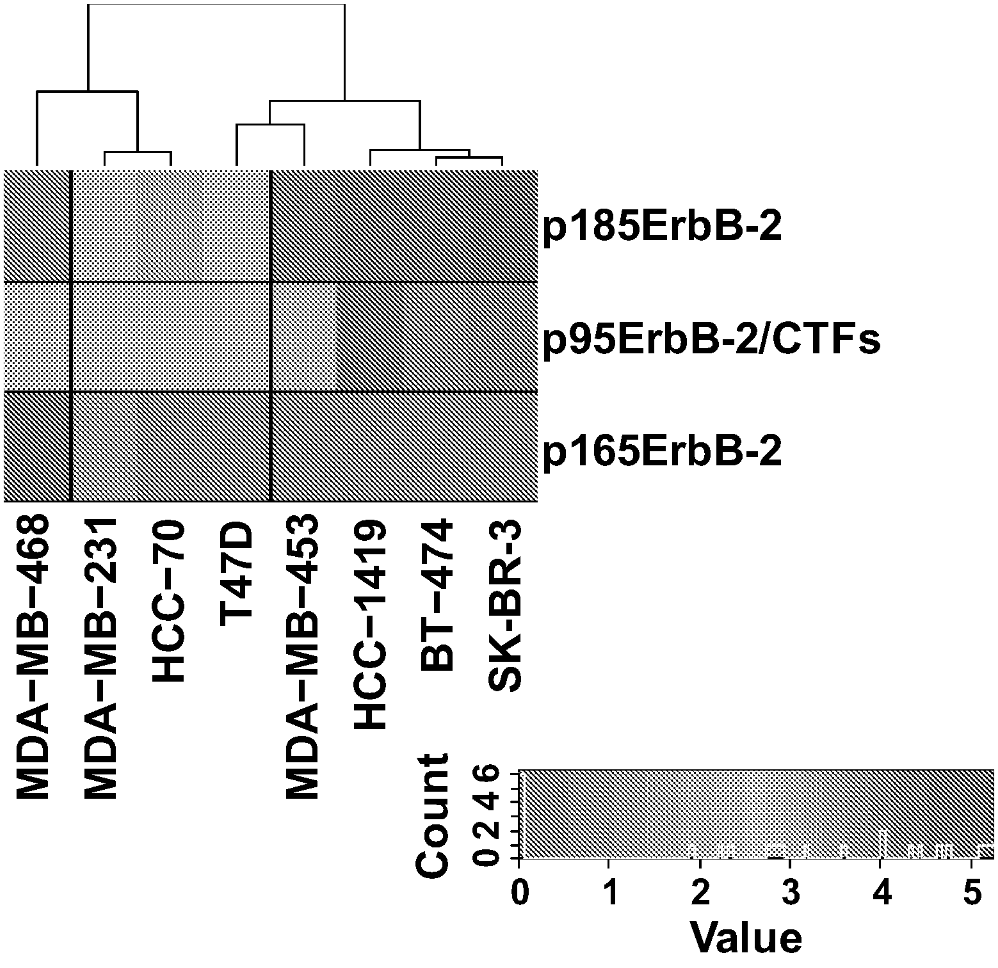
Figure 3G:
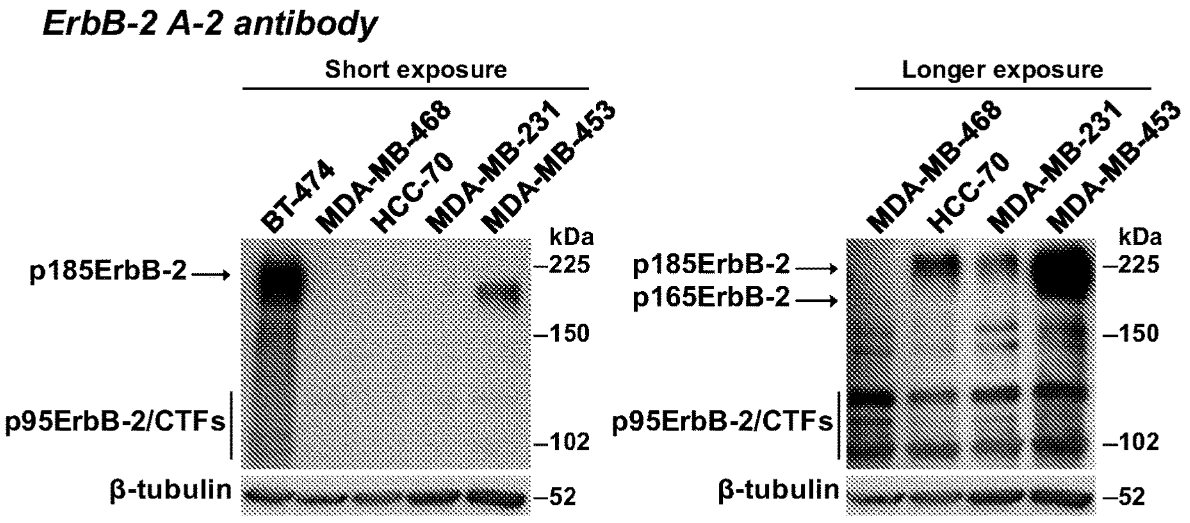
Figure 3H:
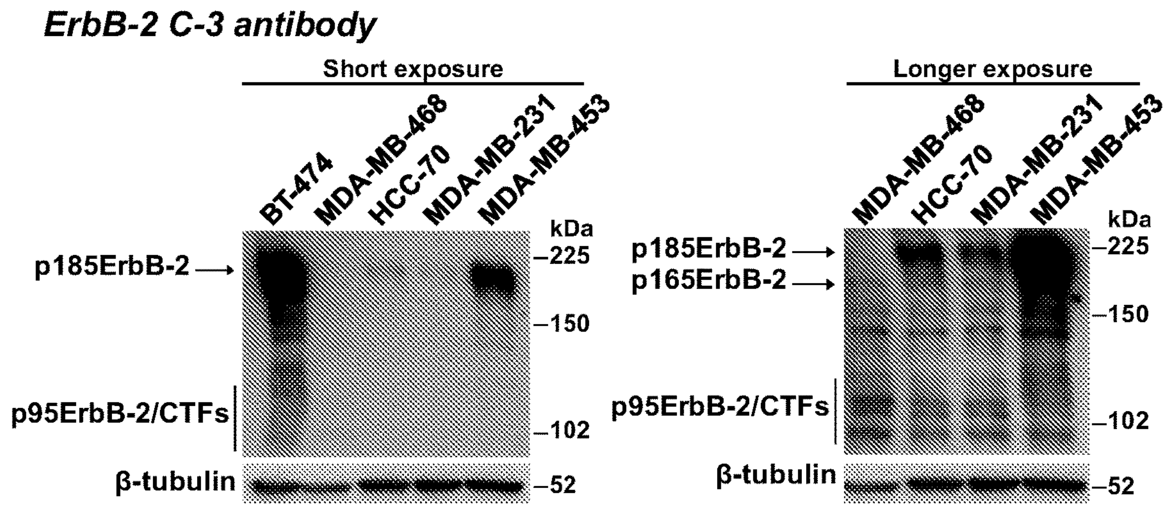
Figure 3I:
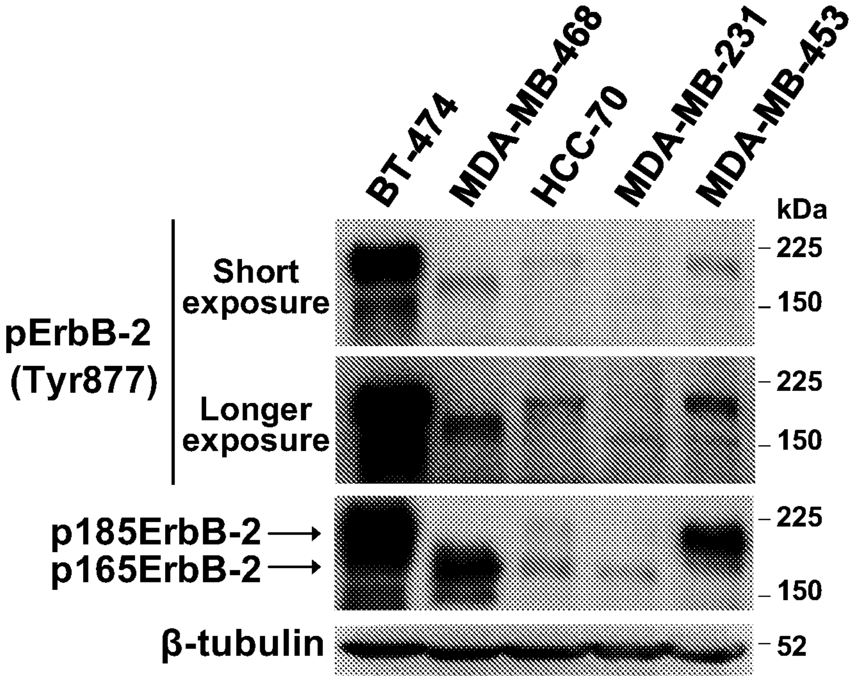

As reported (Brand, T. M. et al. (2014) *Nuclear epidermal growth factor receptor is a functional molecular target in triple-negative breast cancer*. Molecular cancer therapeutics 13, 1356-1368), TNBC lines express significantly lower p185ErbB-2 levels than those in BT-474 cells (FIG. 3A and FIG. 3B). Levels of p165ErbB-2 isoform in MDA-MB-468, HCC-70 and MDA-MB-231 cells were also lower than those of p185ErbB-2 in BT-474 cells (FIG. 3A and FIG. 3B). Proteolytic cleavage and alternative initiation of translation of ErbB-2 result in carboxy-terminal fragments from 90 to 115 kDa in BC cells and tumors, collectively referred to as p95ErbB-2/CTFs variants (Anido, J. et al. (2006) *Biosynthesis of tumorigenic HER2 C-terminal fragments by alternative initiation of translation*. EMBO J 25, 3234-3244), which are associated with nodal metastasis, resistance to anti-MErbB-2 and to endocrine therapies (Anido, J. et al. (2006) op. cit.; Scaltriti, M. et al. (2007) *Expression of p95HER2, a truncated form of the HER2 receptor, and response to anti-HER2 therapies in breast cancer*. J Natl Cancer Inst 99, 628-638; Warri, A. M. et al. (1996) *Anti-oestrogen stimulation of ERBB2 ectodomain shedding from BT-474 human breast cancer cells with ERBB2 gene amplification*. Eur J Cancer 32A, 134-140). Upon longer exposition of the blots, p95ErbB-2 variants were detected in all TNBC cells, again at levels significantly lower than those in BT-474 cells (FIG. 3A and FIG. 3C). Proportional representation of ErbB-2 isoforms highlights that in TNBC cells which express p165ErbB-2, this is the highest represented variant (FIG. 3D). Similar results on ErbB-2 isoforms and levels of expression were found when TNBC lines were compared with additional ErbB-2E cells (SK-BR-3 and HCC-1419) (FIG. 3E). Also, it was found that in T47D cells, from the luminal B (LumB) intrinsic BC subtype, p185ErbB-2 levels were comparable to or even lower than those in TNBC lines (FIG. 3E). T47D cells do not express of p165ErbB-2 (FIG. 3E). Unsupervised hierarchical clustering based on differential expression of ErbB-2 isoforms showed that ErbB-2E lines clustered together (FIG. 3F). T47D and MDA-MB-453 were placed together in a cluster which forms another major one with the ErbB-2E lines (FIG. 3F). MDA-MB-468, MDA-MB-231 and HCC-70 segregated in another major cluster (FIG. 3F). The present inventors found similar results when expression of ErbB-2 isoforms was investigated using the monoclonal antibodies A-2 and C-3 raised against ErbB-2 C- and N-terminus, respectively (FIG. 3G and FIG. 3H). These antibodies showed lower sensitivity to detect p165ErbB-2 than C-18, likely because polyclonal antibodies, such as C-18, recognize a broad range of epitopes, amplifying the signal from proteins with low expression levels. The present inventors previously reported that in ErbB-2E BC cells, NErbB-2 is phosphorylated at tyrosine (Tyr) 877 (Beguelin, W. et al. (2010) op. cit.; Cordo Russo, R. I. et al. (2015) op. cit.), a site different from the autophosphorylation ones, located at the kinase domain (Guo, W. et al. (2006) *Beta* 4 *integrin amplifies ErbB*2 *signaling to promote mammary tumorigenesis*. Cell 126, 489-502; Xu, W. et al. (2007) *Loss of Hsp*90 *association up-regulates Src-dependent ErbB*2 *activity*. MolCell Biol 27, 220-228). This phosphorylation appears to be mandatory for ErbB-2 nuclear migration in said cells (Beguelin, W. et al. (2010) op. cit.; Cordo Russo, R. I. et al. (2015) op. cit.). As shown herein, ErbB-2 Tyr877 phosphorylation was found in all TNBC cells at both p165 and p185 ErbB-2 (FIG. 3I).

Figure 4A:
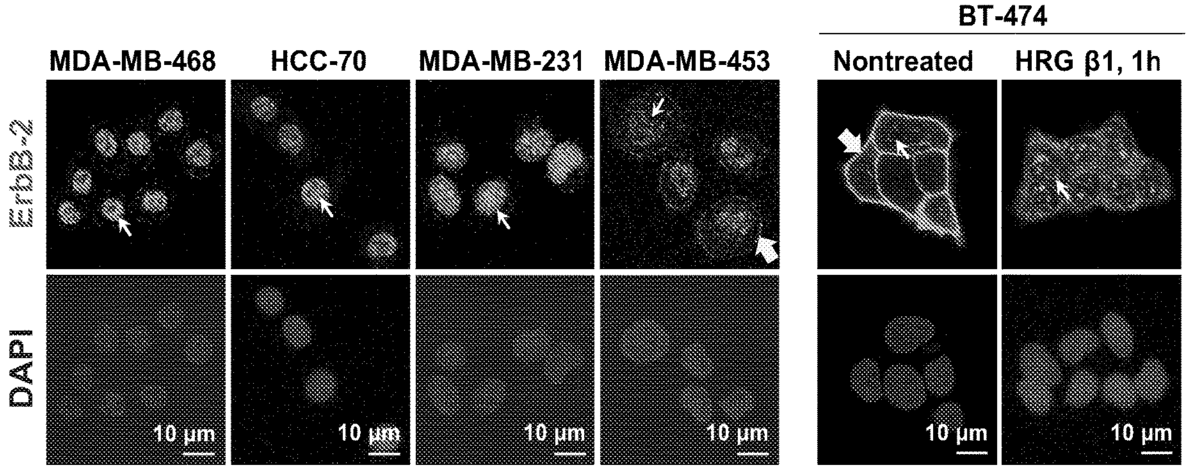
FIGS. 4A-4D. ErbB-2 subcellular localization in BC cells. (4A) ErbB-2 localization was studied by IF and confocal microscopy using the ErbB-2 C-18 antibody followed by incubation with an IgG-Alexa Fluor 488 secondary antibody. Thick arrows indicate the presence of MErbB-2 and slim ones show NErbB-2 presence in TNBC cell lines and in the control BT-474 cells upon heregulin (HRG) stimulation. Nuclei were stained with DAPI. (4B) Percentage of nuclear ErbB-2 presence in confocal images from FIG. 4A. Integrated density (mean fluorescence intensity per unit area) of subcellular compartments was quantified in 50 cells from each cell line and was analyzed as percentages (mean±SD), relative to the total content (integrated density) of ErbB-2 in each cell, which was set to 100%. One-way ANOVA with Dunnett's multiple comparisons test was applied to determined significant differences between control and HRG-β1-treated cells. For b vs a, and c vs a: P<0.001. (4C) Nuclear ErbB-2 expression was analyzed in BT-474 and MDA-MB-468 cells by IF and confocal microscopy using the ErbB-2 A-2 and C-3 antibodies, followed by incubation with an IgG-Alexa Fluor 488 secondary antibody. Nuclei were stained with propidium iodide (PI). (4D) p185ErbB-2 and p165ErbB-2 are located in the nucleus of TNBC cells. Cytosolic (C), Nuclear (N) and Membrane (M) protein lysates were analyzed by WB with the ErbB-2 C-18 antibody. Total (T) protein lysates were blotted in parallel. Histone H3 and β-tubulin were used to control cellular fractionation efficiency. The experiments shown in FIGS. 4A to 4D are representative of three independent ones.
Figure 4B:
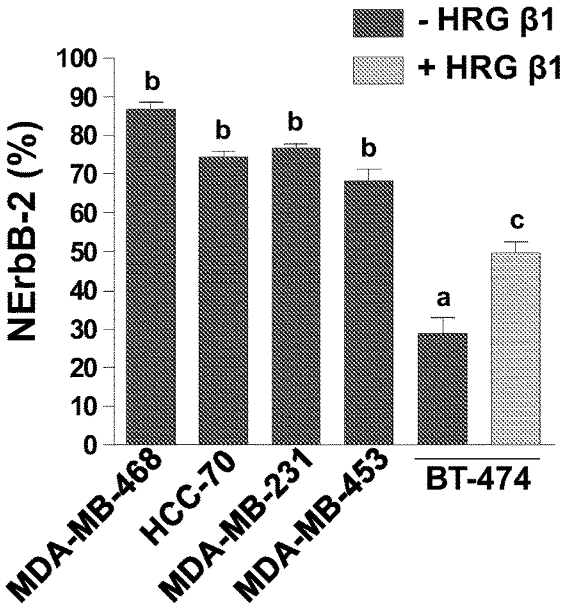
Figure 4C:
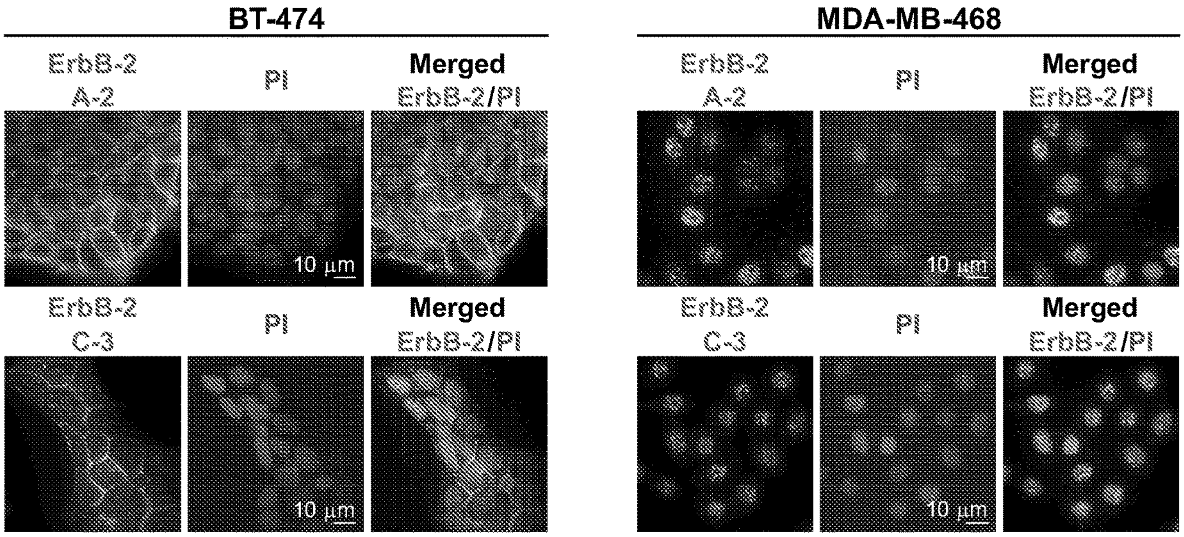
Figure 4D:
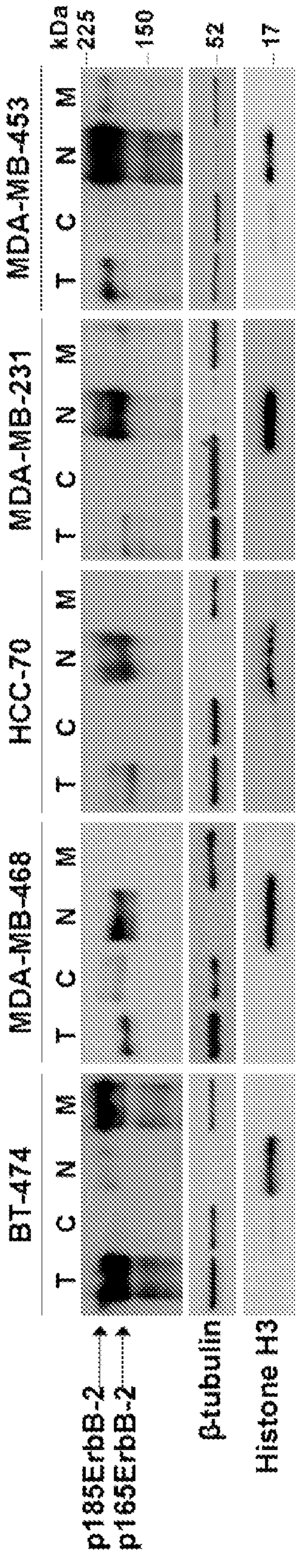

The present inventors also explored NErbB-2 presence in TNBC cells by immunofluorescence (IF) and confocal microscopy with the C-18 antibody. NErbB-2 presence was found in all lines, at levels comparable to those in BT-474 cells treated with heregulin (HRG), an ErbBs' ligand which induces ErbB-2 nuclear migration (Cordo Russo, R. I. et al. (2015) op. cit.) (FIG. 4A and FIG. 4B). TNBC cells also display very low to moderate levels of MErbB-2 staining (FIG. 4A and FIG. 4B). The inventors found comparable results using the anti-ErbB-2 A-2 and C-3 antibodies (FIG. 4C, shows results in MDA-MB-468 and BT-474 cells). Subcellular fractionation and immunoblotting studies, using C-18 antibody showed that the major ErbB-2 nuclear isoform reflects its abundance in each cell type (FIG. 4D).

Figure 5A:
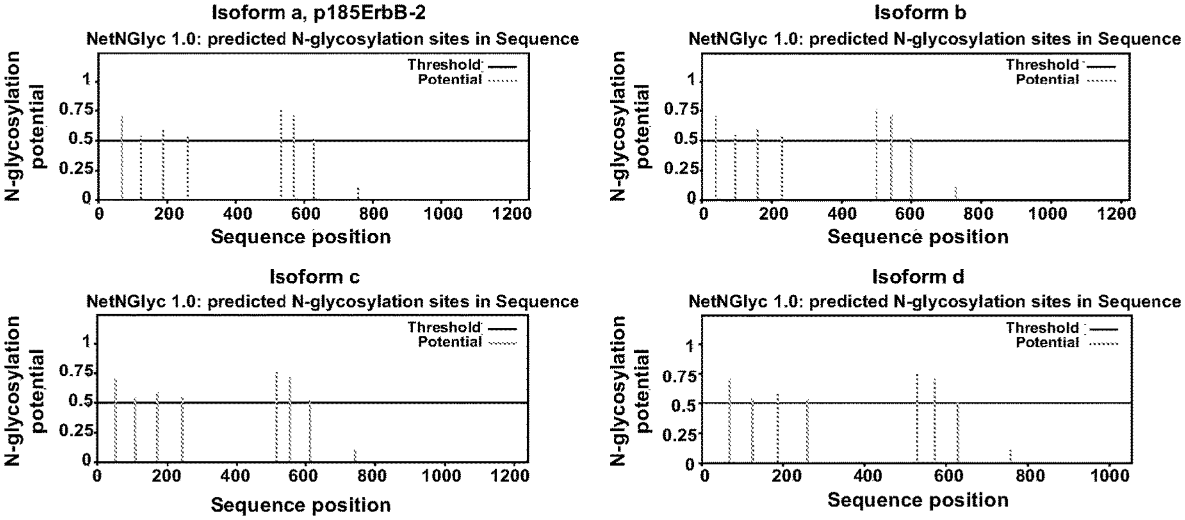
Figure 5B:
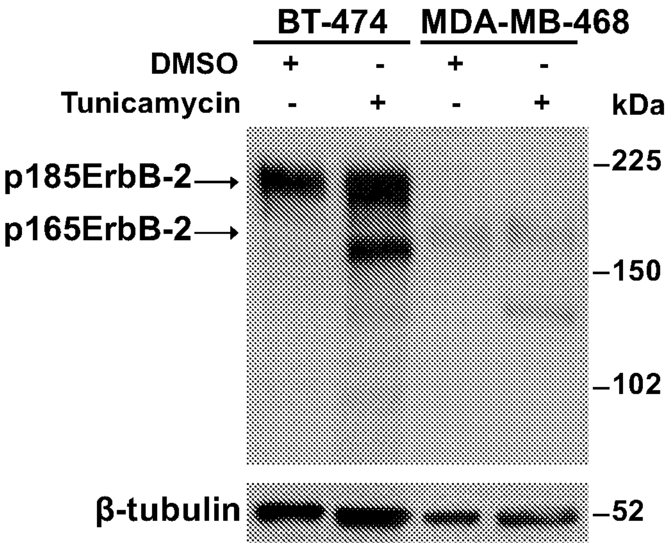

The extracellular domain of ErbB-2 displays 7 putative sites for N-glycosylation (FIG. 5A), 5 of which were validated in BC cells (Frei, A. P. et al. (2012) *Direct identification of ligand-receptor interactions on living cells and tissues*. Nature biotechnology 30, 997-1001; Watanabe, M. et al. (2013) *Improvement of mass spectrometry analysis of glycoproteins by MALDI-MS using* 3-*aminoquinoline/alpha-cyano*-4-*hydroxycinnamic acid*. Analytical and bioanalytical chemistry 405, 4289-4293). This posttranslational modification alters the migration pattern of proteins on SDS-PAGE. We found that inhibition of de novo N-glycosylation by tunicamycin treatment of BT-474 and MDA-MB-468 cells reduced p185ErbB-2 and p165ErbB-2 levels, generating protein bands with MWs ~38-43 kDa lower than those of the respective full-length isoform (FIG. 5B). This indicates that p165ErbB-2 is not a product of variations in the glycosylation of WT ErbB-2.

Example 3—Differentially Expressed ErbB-2 Splice Variants in TNBC Cell Lines

To identify the p165ErbB-2 isoform, the present inventors explored the expression of ErbB-2 transcript variants in TNBC lines and compared them to those in BT-474 cells, used as control. In order to obtain reliable and high quality data, the inventors based on NCBI RefSeq (release 95) (https://www.ncbi.nlm.nih.gov/refseq/, 2019), Ensembl (release94) (https://www.ensembl.org/index.html, 2018) and Uniprot (release 2019/06) (http://www.uniprot.org/, 2019) databases (see Table 5 below).

TABLE 5

Protein-coding ErbB-2 transcripts and their respective protein isoforms as annotated in the indicated databases. Shown are transcript length in nucleotides (nt) and translation length in amino acids (aa).

| | RefSeq Transcript ID | RefSeq Protein ID | | Transcript length (nt) | Translation length (aa) | Ensembl Transcript ID | Ensembl Protein ID | UniProt ID |
|---|---|---|---|---|---|---|---|---|
| Variant 1 | NM_004448 | Isoform a, WTErbB-2 | NP_004439 | 4864 | 1255 | ENST00000269571.9 | ENSP00000269571.4 | P04626-1 |
| Variant 2 | NM_001005862 | Isoform b | NP_001005862 | 4889 | 1225 | ENST00000584601.5 | ENSP00000462438.1 | P04626-5 |
| Variant 3 | NM_001289936 | Isoform c | NP_001278865 | 4940 | 1240 | ENST00000541774.5 | ENSP00000446466.1 | P04626-4 |
| Variant 4 | NM_001289937 | Isoform d | NP_001278888 | 4411 | 1055 | ENST00000584450.5 | ENSP00000463714.1 | J3QLU9 |

The inventors focused on coding variants whose translation might produce a protein of ~165 kDa. As used herein, spliced transcripts (SpTs) are referred to by numbers and protein isoforms (SpPs) are referred to by letters, as labelled in Refseq (Table 5). Alternative transcript variant 3 (SpT3) is the longest one (FIG. 6A). Transcript variant 2 (SpT2), arises from the same transcriptional start site (TSS) than SpT3, but differs from SpT3 in that it excludes the exon 5 by alternative splicing (FIG. 6A). The transcriptional unit of ERBB2 has another TSS, downstream of the one that generates SpT2 and SpT3, from which other ErbB-2 transcripts are generated, among them, SpT1 and SpT4 (FIG. 6B). Actually SpT1, is considered the canonical transcript which translates into p185ErbB-2 WTErbB-2, herein referred as isoform a (FIG. 7). SpT4 lacks the penultimate exon (26, considering the order of exons in SpT1), and uses an alternative 3' splice site in the last exon (27, according to the order in SpT1) (FIG. 6B). The protein encoded by SpT4 (isoform d) has a shorter C-terminus compared to isoform a (and FIG. 7). On the other hand, translation of SpT2 and SpT3 give rise to proteins (isoforms b and c, respectively) with the same C-termini as isoform a, but with shorter N-termini, lacking the signal peptide (SP) (FIG. 7 and FIG. 8). The absence of the SP in isoforms b and c makes them particularly interesting for the present study since this could result in their non-canonical localization at the nucleus. This is consistent with inventors' findings on NErbB-2 presence in TNBC (FIGS. 4A-4D). Antibodies against ErbB-2 C- and N-terminus would recognize isoforms b and c (see Table 6 below).

In addition, an alternative-spliced ErbB-2 isoform (ErbB-2Δ16) was detected in BC and associated with high oncogenic and metastatic potential (Castiglioni, F. et al. (2006) *Role of exon-16-deleted HER2 in breast carcinomas*. Endocr Relat Cancer 13, 221-232; Kwong, K. Y. and Hung, M. C. (1998) A novel splice variant of HER2 with increased transformation activity. Mol Carcinog 23, 62-68; Mitra, D. et al. (2009) *An oncogenic isoform of HER2 associated with locally disseminated breast cancer and trastuzumab resistance*. Molecular cancer therapeutics 8, 2152-2162; Turpin, J. et al. (2016) *The ErbB2DeltaEx16 splice variant is a major oncogenic driver in breast cancer that promotes a pro-metastatic tumor microenvironment*. Oncogene 35, 6053-6064). ErbB-2Δ16 lacks exon 16 (considering the order of exons in SpT1) (FIG. 6C). The exclusion of this exon results in an in-frame deletion of 16 amino acids (aa) at the juxtamembrane domain (FIG. 7). There is no mRNA sequence of ErbB-2Δ16 logged to any publicly available databases. Although several works showed that ErbB-2Δ16 protein runs slightly faster than p185ErbB-2 on SDS-PAGE, in a position comparable to that of p165ErbB-2, its MW was not disclosed. Therefore, the inventors also investigated whether ErbB-2Δ16 protein contributes to the p165ErbB-2 band detected by WB. ErbB-2 C- and N-terminal antibodies would recognize ErbB-2Δ16, which displays intact C- and N-terminus (see Table 6 below).

TABLE 6

Anti-ErbB-2 antibodies used in this study. Target amino acids sequences (aa) corresponding to the amino- and carboxy-terminus of all ErbB-2 isoforms are indicated.

| | Anti-ErbB-2 antibody | | |
|---|---|---|---|
| ErbB-2 isoform | ErbB-2 C-18 aa | ErbB-2 A-2 aa | ErbB-2 C-3 aa |
| Isoform a | 1248-1255 | 1180-1197 | 251-450 |
| Isoform b | 1218-1225 | 1150-1167 | 221-420 |
| Isoform c | 1233-1240 | 1165-1182 | 236-435 |
| Isoform d | — | — | 251-450 |
| ErbB-2A16 | 1232-1239 | 1164-1181 | 251-450 |

For the analysis of ErbB-2 transcript variants the present inventors used a polymerase chain reaction (PCR)-based sequencing approach. Said strategy is depicted in FIG. 27.

First, total RNA from all cells was reverse transcribed. Due to the high sequence homology among ErbB-2 transcripts, the first strategy used by the present inventors was to use cDNA for long-range (LR)-PCR. Two sets of primers were used: one of them amplifies the entire coding region of transcripts 1, 4, and ErbB-2Δ16 (LR-PCR1: forward primer SEQ ID NO: 4; reverse primer SEQ ID NO: 5) while the other, amplifies the entire coding region of transcripts 2 and 3 (LR-PCR2: forward primer SEQ ID NO: 6; reverse primer SEQ ID NO: 5).

Forward primer for LR-PCR1 (SEQ ID NO: 4) anneal to the common 5' end of SpT1, SpT4 and ErbB-2Δ16. Forward primer for LR-PCR2 (SEQ ID NO: 6) anneal to the common 5' end of SpT2 and SpT3. The same reverse primer (SEQ ID NO: 5), which anneals to the common 3' end of all five transcripts, was used for both LR-PCRs.

Sets of Primers Used for Long Range PCR (LR-PCR):

Set 1 (Long Range PCR1): for transcripts 1, 4, and ErbB-2Δ16.

```
Fw primer (SEQ ID NO: 4):
CTGAGATTCCCCTCCATTGGG

Rv primer (SEQ ID NO: 5):
CAACACCCATTCTCCCCCTG
```

Set 2 (Long Range PCR2): for transcripts 2 and 3.

```
Fw primer (SEQ ID NO: 6):
GTTCCCGGATTTTTGTGGGC

Rv primer (SEQ ID NO: 5)
CAACACCCATTCTCCCCCTG
```

For each LR-PCR, the inventors obtained a single band with the expected size of the amplicons (FIGS. 9A-9E).

Next, each of the LR-PCR products were purified and used as templates for nested PCR with variant specific primers for SpTs 1, 2 or 3. To detect SpT1 expression in the LR-PCR1 product, the inventors designed forward and reverse primers annealing to exons 16 and 26, respectively. To assess SpT2 and SpT3 expression in the LR-PCR2 product, the inventors designed two set of primers spanning their differential region between exons 1 to 5 (additional exons upstream of the canonical exon 1).

SpT1 was detected in all cell lines where expression of p185ErbB-2 (WT ErbB-2) was found, but not in TNBC MDA-MB-468 cells, which only express the p165ErbB-2 isoform (FIG. 10A). Direct Sanger sequencing in both directions of the PCR products confirmed SpT1 identity in BT-474 (SEQ IDs 34 and 35) and HCC-70 cells (SEQ IDs 36 and 37). SpT2 and SpT3 were present in all TNBC lines and in BT-474 cells (FIGS. 10B and 10C). Sequencing of the corresponding amplicons verified transcript identities. An exemplary sequencing of the SpT2 PCR products is shown for MDA-MB-468 (SEQ IDs 38 and 39) and MDA-MB-231 cells (SEQ IDs 40 and 41). Representative sequences were also obtained from SpT3 PCR products in MDA-MB-468 (SEQ IDs 42 and 43) and MDA-MB-231 (SEQ IDs 44 and 45) cells. Notably, slightly lower bands were observed for some of the cell lines when using primers for SpT2 and SpT3 (FIGS. 10B and 10C). These amplicons were attributed to exon 2 skipping (according to the order in SpT2 and SpT3), of 104 nt in length. Exon 2 skipping events were confirmed by sequencing of the PCR products in MDA-MB-468 (SEQ ID NOs 50 and 51) and BT-474 cells (SEQ ID NOs 52 and 53).

Sets of Primers Used for Nested PCR:

For transcript SpT1:

```
Fw primer (SEQ ID NO: 7):
TGTGTGGACCTGGATGACAA

Rv primer (SEQ ID NO: 8):
GGCAACGTAGCCATCAGTCT
```

For transcript SpT2:

```
Fw primer (SEQ ID NO: 9):
ACGCCTGATGGGTTAATGAG

Rv primer (SEQ ID NO: 10):
CGGTGCACACTCACTTTTGT
```

For transcript SpT3:

```
Fw primer (SEQ ID NO: 11):
ATATATCGAGGCGATAGGGTTAAGG

Rv primer (SEQ ID NO: 12):
CCGGGGCATATCTTCTGGAAT
```

In addition, conventional PCR was performed on the cDNAs using primers spanning the novel splice junctions between exons 25 and 27, for the detection of SpT4, and between exons 15 and 17 for ErbB-2Δ16. Expression of SpT4 and ErbB-2Δ16 was detected in all cell lines (FIGS. 11A and 11B). An exemplary sequencing of the ErbB-2Δ16 PCR products is shown for HCC-70 (SEQ IDs 46 and 47) and MDA-MB-453 cells (SEQ IDs 48 and 49).

Sets of Primers Used for Conventional PCR
For transcript SpT4:

```
Fw primer (SEQ ID NO: 13):
CTGGAGGACGATGACATGGG

Rv primer (SEQ ID NO: 14):
GCTGGTTCACATATTCCTGGTAG
```

For transcript ErbB-2Δ16:

```
Fw primer (SEQ ID NO: 15):
CACCCACTCCCCTCTGAC

Rv primer (SEQ ID NO: 16):
GCTCCACCAGCTCCGTTTCCTG
```

Direct Sanger sequencing in both directions of the PCR products confirmed transcript variants identity.

Figure 12A:
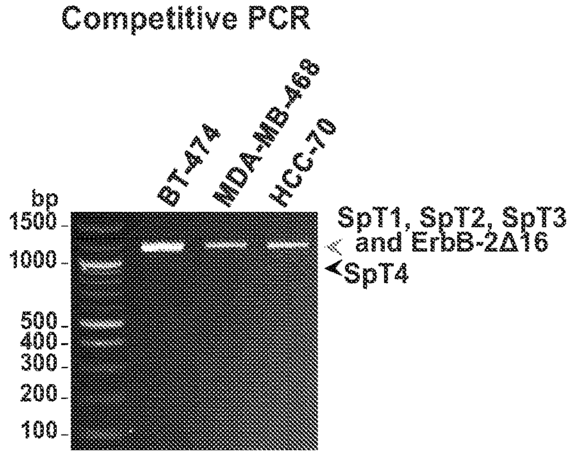
Figure 12B:
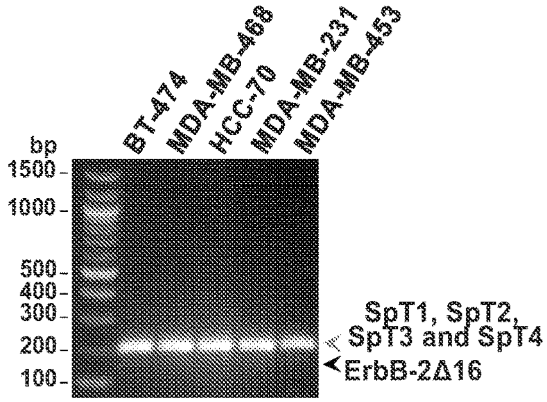
Figure 12C:
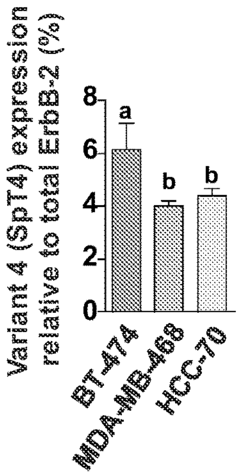
Figure 12D:
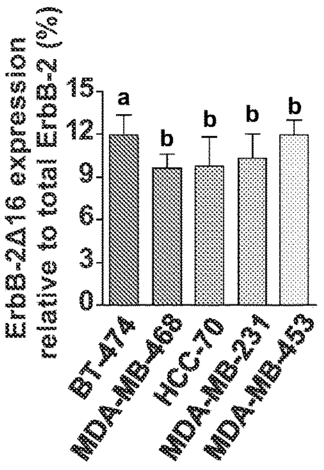

Next, cDNAs from all cell lines were used for competitive PCR to quantify the relative abundance of SpT4 in comparison to those of variants that include exon 26 using primers that amplify the region between exons 25 and 27. All cell lines express SpT4 which represents 4 to 6% of the total ErbB-2 mRNA (FIGS. 12A and 12C). The inventors also performed competitive PCR to quantify the relative levels of ErbB-2Δ16 in comparison to those of variants that include exon 16 using primers spanning exons 15 and 17. ErbB-2Δ16 transcript accounts for 9 to 12% of total ErbB-2 mRNA (FIGS. 12B and 12D).

Sets of Primers Used for Competitive PCR
For transcript SpT4:

```
Fw primer (SEQ ID NO: 17):
AGCACCTTCTACCGCTCACT
```

```
Rv primer (SEQ ID NO: 18):
CTGAATGGGTCGCTTTTGTT
```

For transcript ErbB-2Δ16:

```
Fw primer (SEQ ID NO: 19):
CGGTGTGAAACCTGACCTCT

Rv primer (SEQ ID NO: 20):
AAGACCACGACCAGCAGAAT
```

Furthermore, the inventors studied the expression levels of SpT3 by reverse transcriptase (RT)-quantitative PCR (qPCR) in BT-474 and MDA-MB-468 cells. Consistent with their findings of lower total ErbB-2 message in TNBC as compared with ErbB-2E cells (FIG. 13), SpT3 expression was decreased in MDA-MB-468 cells with respect to BT-474 (FIG. 14A). However, the ratio of SpT3/total ErbB-2 was higher in MDA-MB-468 cells (FIG. 14B).

Sets of Primers Used for Reverse Transcriptase (RT)-Quantitative PCR (qPCR)
For total ErbB-2 mRNA (transcripts SpT1, SpT2, SpT3, SpT4 and ErbB-2Δ16):

```
Fw primer (SEQ ID NO: 21):
AAAGGCCCAAGACTCTCTCC

Rv primer (SEQ ID NO: 22):
CCTCCCTGGGGTGTCAAGTA
```

For transcript SpT3:

```
Fw primer (SEQ ID NO: 23):
TAGAATGGCCAGGACAAACG

Rv primer (SEQ ID NO: 24):
CCGGGGCATATCTTCTGGAAT
```

For Glyceraldehyde-3-Phosphate Dehydrogenase (GAPDH):

```
Fw primer (SEQ ID NO: 25):
CCAGAACATCATCCCTGCAT

Rv primer (SEQ ID NO: 26):
GTTCAGCTCTGGGATGAC
```

The table below (Table 7) shows the ErbB-2 transcript variants identified by the present inventors in BT-474 and TNBC cells.

TABLE 7

ErbB-2 transcript variants identified in the present invention.

| Transcript variants | RefSeq Transcript ID | Protein Isoforms | RefSeq Protein ID | BT-474 | MDA-MB-468 | HCC-70 | MDA-MB-231 | MDA-MB-453 |
|---|---|---|---|---|---|---|---|---|
| Variant 1 (SpT1) | NM_004448 | Isoform a, WT ErbB-2 | NP_004439 | ✓ | — | ✓ | ✓ | ✓ |
| Variant 2 (SpT2) | NM_001005862 | Isoform b | NP_001005862 | ✓ | ✓ | ✓ | ✓ | ✓ |
| Variant 3 (SpT3) | NM_001289936 | Isoform c | NP_001276865 | ✓ | ✓ | ✓ | ✓ | ✓ |
| Variant 4 (SpT4) | NM_001289937 | Isoform d | NP_001278888 | ✓ | ✓ | ✓ | ✓ | ✓ |
| ErbB-2Δ16 | — | ErbB-2Δ16 | — | ✓ | ✓ | ✓ | ✓ | ✓ |

The present results reveal that MDA-MB-468 cells, only displaying p165ErbB-2 at the nucleus, express SpT2 and SpT3, and very low levels of SpT4 and ErbB-2Δ16. Compelling evidence showed that ErbB-2Δ16 is a membrane bound isoform (Mitra, D. et al. (2009) op. cit.; Turpin, J. et al. (2016) op. cit.), which precludes its contribution to p165ErbB-2. On the other hand, the C-terminus of isoform d, encoded by SpT4, lacks the epitope recognized by C-18 antibody (Table 6). This indicates that p165ErbB-2 protein band, the only one recognized by C-18 in MDA-MB-468 cells, could not be isoform d.

Figure 15A:
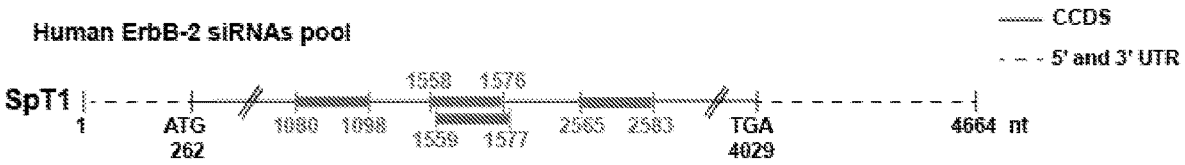
Figure 15B:
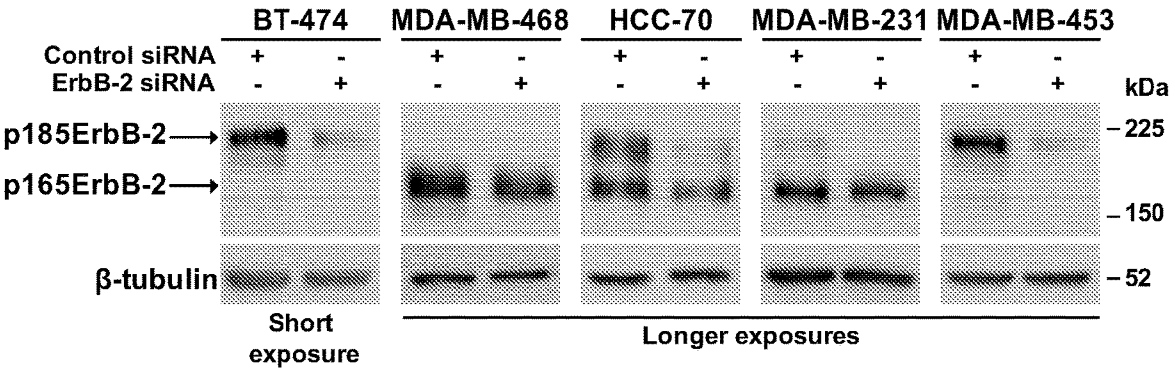
Figure 15C:
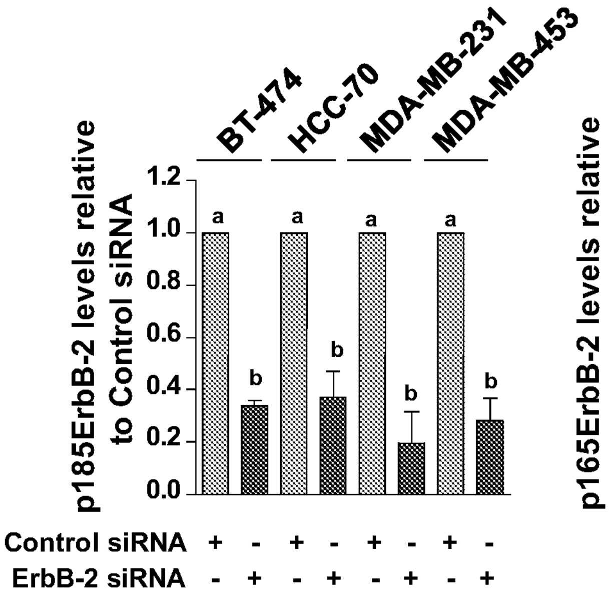
Figure 15D:
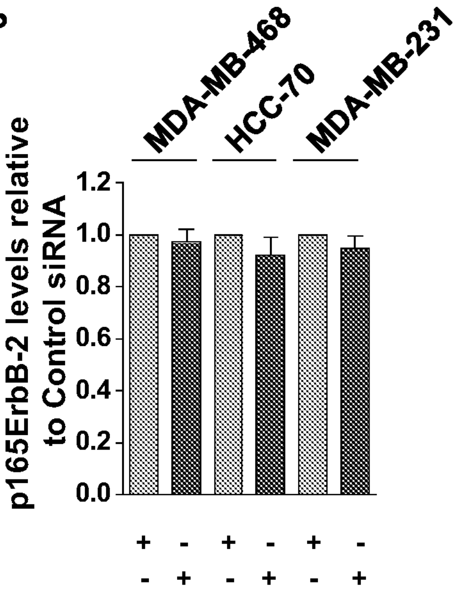
Figure 15E:
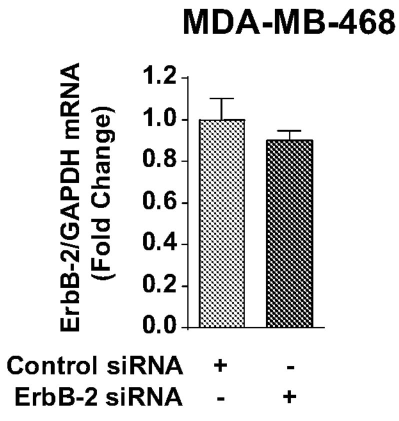
Figure 15F:
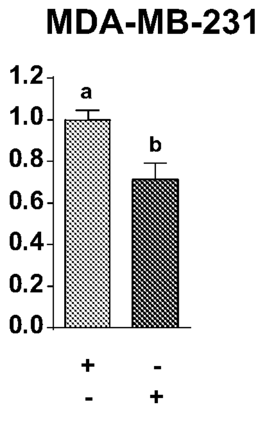
Figure 15G:
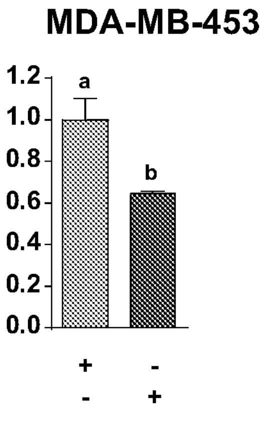

Example 4—Nuclear ErbB-2 Isoform c Induces Proliferation of TNBC of Basal and Mesenchymal Subtypes To further dissect the identity of the p165ErbB-2 protein, a pool of 4 different siRNAs (siGENOME SMARTpool Human ERBB2, Dharmacon, Lafayette, Colo., USA), herein referred as ErbB-2 siRNA (FIG. 15A) was used. These siRNAs target the common coding region of transcript variants 1 to 4, and ErbB-2Δ16. Unexpectedly, these series of siRNAs silenced only p185ErbB-2 but were ineffective to knockdown p165ErbB-2 (FIGS. 15B-15D). Levels of ErbB-2 mRNA were silenced in cells expressing p185ErbB-2 (FIG. 15G) or both p185 and p165ErbB-2 (FIG. 15F), but remained unaffected in cells which only express p165ErbB-2 (FIG. 15E).

Figures 16A, 16B:
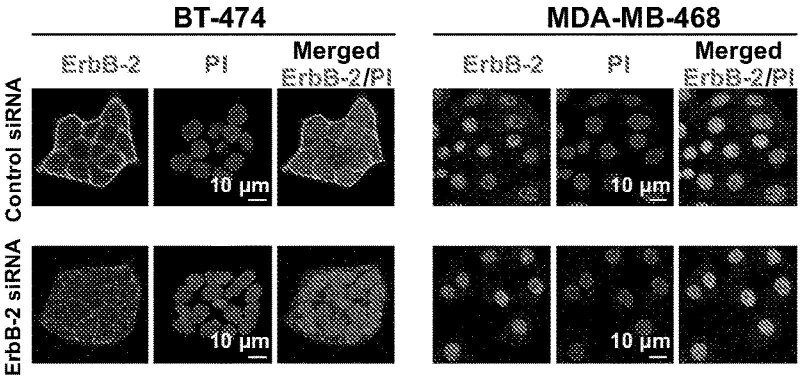
Figures 16C, 16D, 16E:
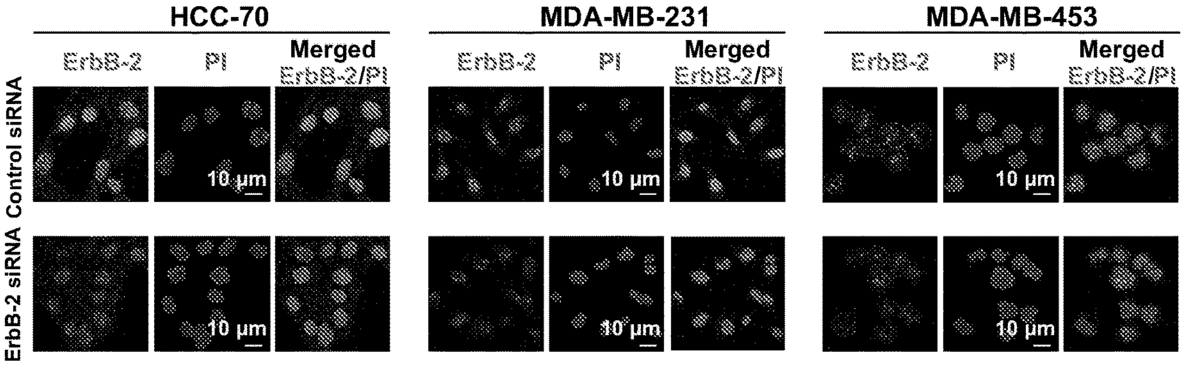
Figures 16F, 16G, 16H, 16I, 16J:
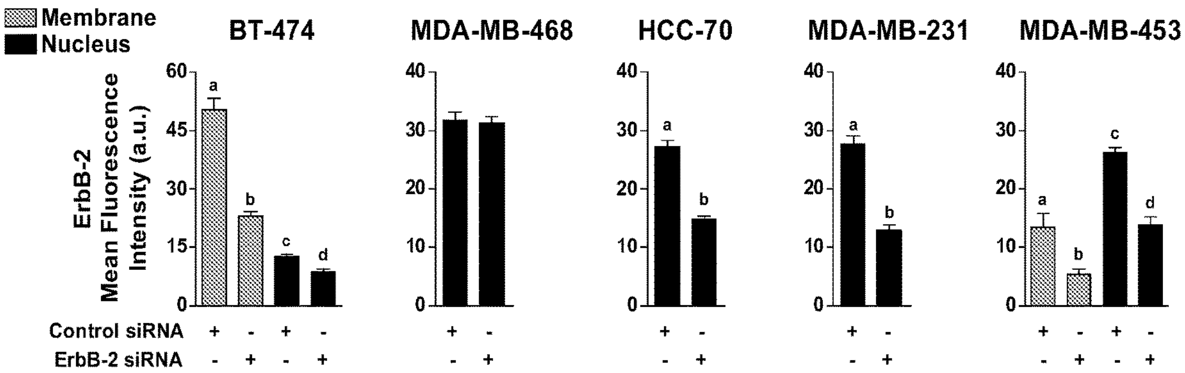
Figures 17A, 17B, 17C, 17D, 17E:
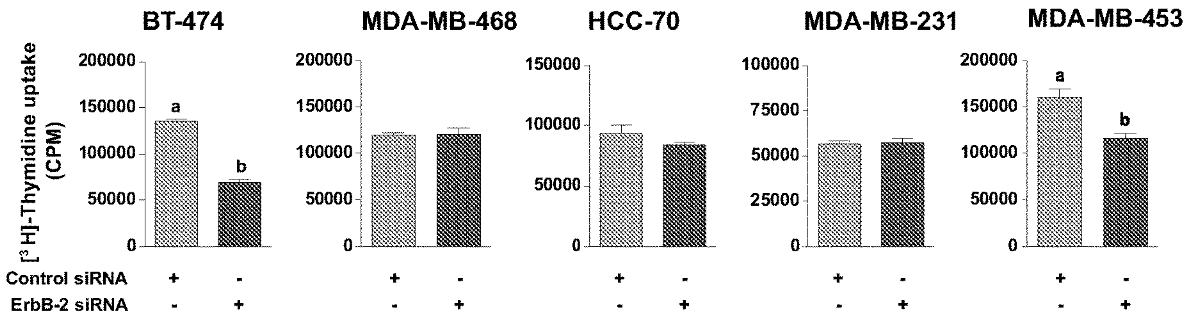

IF and confocal microscopy also showed that in MDA-MB-468 cells, which only express p165ErbB-2, these siRNAs had no effect on the levels of NErbB-2 (FIGS. 16B and 16G). By the contrary, in BT-474 (FIGS. 16A and 16F) and MDA-MB-453 cells (FIGS. 16E and 16J), which only express p185ErbB-2, as well as in HCC-70 (FIGS. 16C and 16H) and MDA-MB-231 cells (FIGS. 16D and 16I), which express both p185 and p165ErbB-2, it was shown that these siRNAs reduced NErbB-2 levels. In addition, they blocked in vitro proliferation of cells that only express p185ErbB-2 (FIGS. 17A and 17E) but were unable to inhibit proliferation of TNBC cells which express p165ErbB-2 (FIG. 17B) or both p165 and p185ErbB-2 (FIGS. 17C and 17D).

Figure 18A:
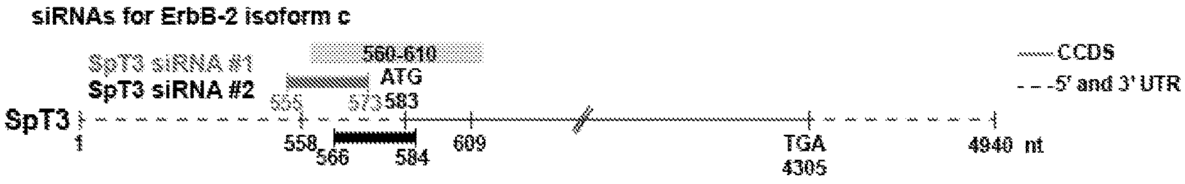
Figure 18B:
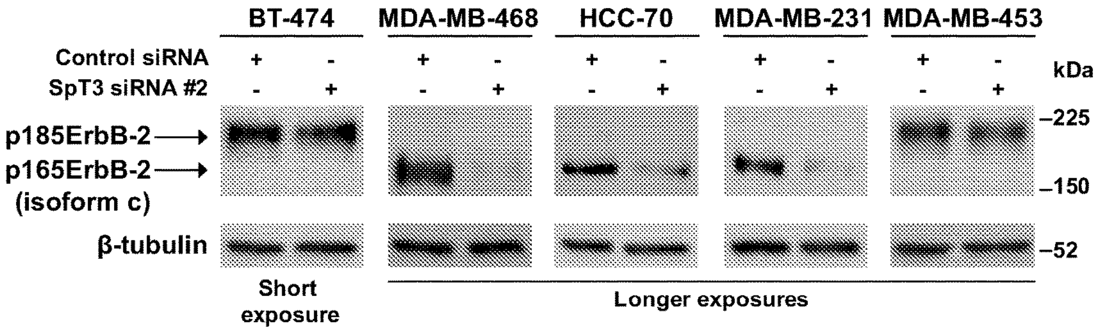
Figure 18C:
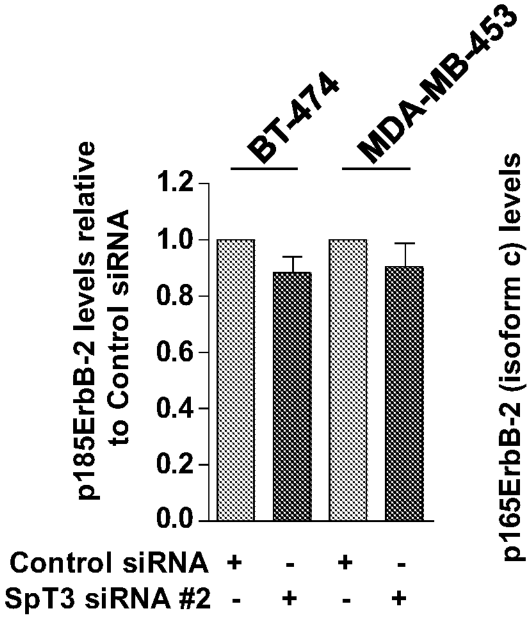
Figure 18D:
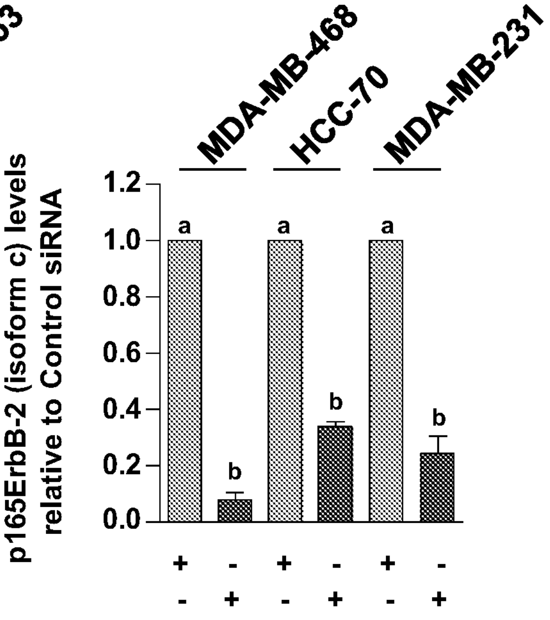
Figures 19A, 19B, 19C:
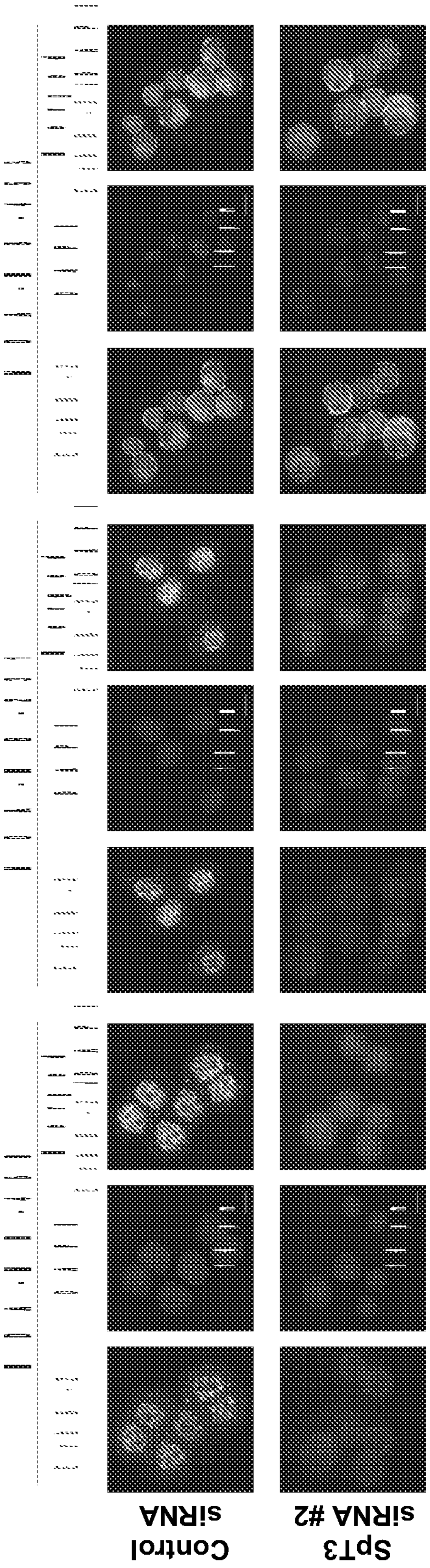
Figures 19D, 19E, 19F:
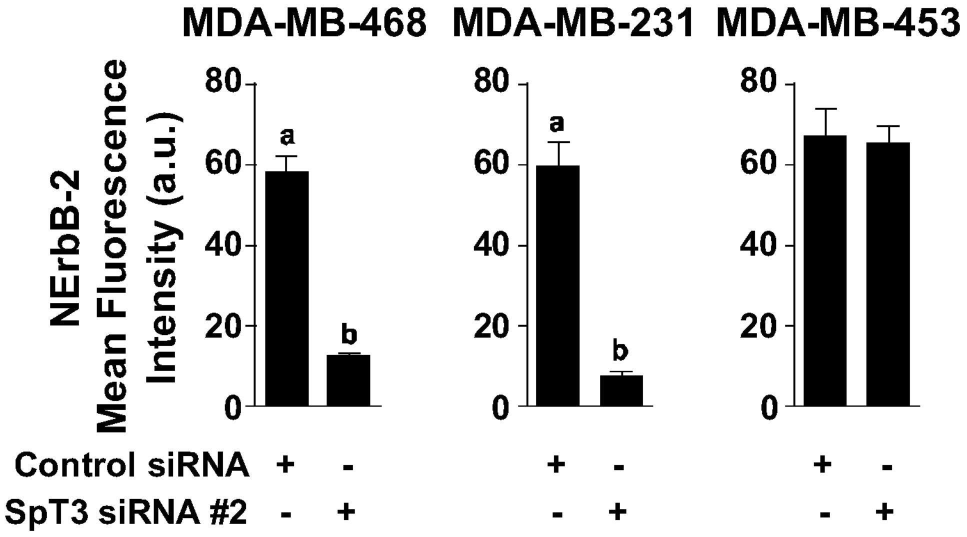
Figures 20A, 20B, 20C, 20D, 20E:
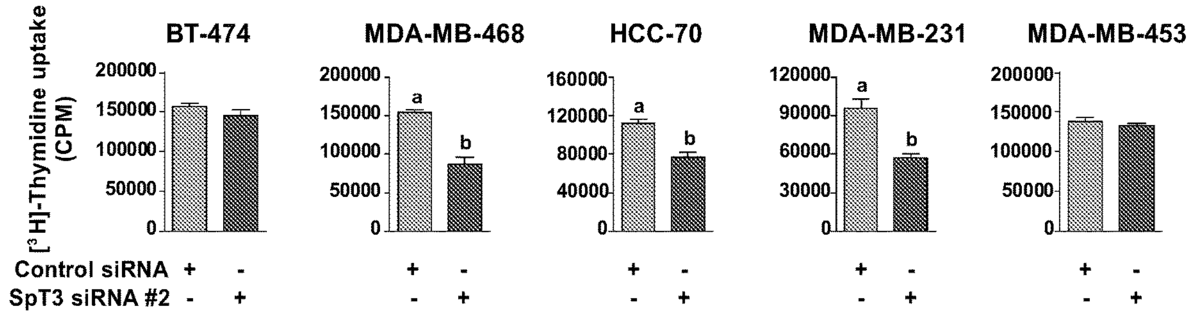

According to the PCR-sequencing approach used herein, SpTs 2 and 3 were identified as the main contributors to the p165ErbB-2 protein. However, since the secondary structure of said variants remains unknown, the use of total ErbB-2 siRNAs was possibly inappropriate to target them. As shown in FIGS. 6A-6C, SpT3 includes a specific exon (5, according to the order of exons in SpT3), spanning its 5' UTR and 5' coding region from nucleotides (nt) 560 to 610, which is neither present in any of the other transcripts here studied. This allowed the present inventors to design two pairs of siRNAs (SpT3 siRNAs) targeting this unique region using siDESIGN Center (https://dharmacon.horizondiscovery-.com/design-center/) from Dharmacon (Lafayette, Colo., US), an advanced siRNA design tool which significantly improves the likelihood of identifying functional siRNAs targeting particular transcript variants (FIG. 18A). Transfection of all BC cell lines with SpT3 siRNA #2 (SEQ ID NO: 2) resulted in up to 95% inhibition of the levels of p165ErbB-2 (FIGS. 18B and 18D) while it did not affect the levels of p185ErbB-2 (FIGS. 18B and 18C). These findings show that p165ErbB-2 protein band corresponds to isoform c. IF and confocal microscopy also showed that SpT3 siRNA #2 (SEQ ID NO: 2) strikingly reduced nuclear ErbB-2 levels in TNBC lines expressing only isoform c (FIGS. 19A and 19D) or both isoform c and WT ErbB-2 (FIGS. 19B and 19E), but had no effect on cells which only display WT ErbB-2 (FIGS. 19C and 19F). Similarly, SpT3 siRNA #2 (SEQ ID NO: 2) abrogated in vitro growth in cells displaying isoform c (FIG. 20B) or both isoform c and WT ErbB-2 (FIGS. 20C and 20D), but did not block growth of cells which only display WT ErbB-2 (FIGS. 20A and 20E).

Numerous commercial entities, such as Dharmacon, provide access to algorithms on their website (e.g., siDESIGN Center) for selecting one, or more than one, siRNA in order to optimize specific silencing. Because the ability of siRNA to function is dependent on the sequence of the RNA, greater than 90% sequence identity, e.g., 91%, 92%, 93%, 94%, 95%, 96%, 97%, 98%, 99% or even 100% sequence identity, between the siRNA and the portion of the target gene is preferred.

Preferably, at least two optimized siRNAs that have been selected according to the aforementioned algorithms are used to silence a gene, more preferably at least three and most preferably at least four. The siRNAs may be used individually or together in a pool or kit. Further, they may be applied to a cell simultaneously or separately. Preferably, the at least two siRNAs are applied simultaneously. Pools are particularly beneficial for many research applications. However, for therapeutics, it may be more desirable to employ a single siRNA.

In the present invention, siDESIGN Center was used for identifying functional siRNAs against ErbB-2 alternative transcript variant 3 (SpT3) (SEQ ID NO: 32), which encodes the non-canonical isoform c (SEQ ID NO: 33). siRNA molecules include, but are not limited to those having the sequences depicted in SEQ ID NO: 1 and SEQ ID NO: 2.

Within the meaning of the present invention any other sequence selection algorithm or method may be used for optimizing siRNAs for specific targets (e.g., ERBB2 alternative transcript variant 3, NM_001289936, SEQ ID NO: 32).

Within the meaning of the present invention any other sequence selection algorithm or method may be used for optimizing siRNAs for specific targets (e.g., ERBB2 alternative transcript variant 3, NM_001289936, SEQ ID NO: 32).

The first step of siDESIGN Center comprises selecting the target nucleotide sequence for evaluation by the siDESIGN algorithm. There are four options for identifying the target sequence: i) Accesion Number: the preferred accession numbers are found in the NCBI Reference Sequence (RefSeq) database (https://www.ncbi.nlm.nih.gov/refseq/) ii) Nucleotide Sequence: RNA or cDNA sequences up to 10,000 nucleotides represented using the standard nucleic acids codes: A, C, G, T, and U, according to FASTA format; iii) Gene ID: a unique identifying number in the NCBI RefSeq database; and iv) GI Number (GenInfo Identifier): a series of digits that are assigned consecutively to each sequence record processed by NCBI. Advanced options were selected by the present inventors in order to perform isoform or gene variant-specific siRNA design. These options may greatly reduce the number of siRNA designs generated due to the increased stringency of the design parameters. As a result, a "Target Gene Variants Table" with the Accession number(s) for all known RefSeq variants associated with the target gene (e.g., ERBB2 human) was displayed. Specific variant(s) were selected in the Target Gene Variants Table (e.g., ERBB2 alternative transcript variant 3, NM_001289936) and targeted by resulting siRNA designs. Particular regions of the target mRNA (i.e., 5' UTR, open reading frame (ORF), 3' UTR) and BLAST analysis were also considered to further enhance target specificity. In addition to user-specified design criteria, candidate siRNA design regions are also selected by the siDESIGN algorithm with other important criteria. Several of these key criteria include the exclusion of: i) motifs correlated with toxicity; ii) known miRNA seed region motifs and iii) known single nucleotide polymorphisms (SNPs). Following analysis, up to 50 candidates are presented as a list according to the siRNA score, an algorithmic indicator of the likelihood of successful silencing with this siRNA design. This score does not quantify expected percent knockdown.

As a result of siDESIGN analysis performed by the present inventors, two individual siRNAs were identified for ErbB-2 alternative transcript variant 3 (SpT3): SpT3 siRNA #1, score=86 (SEQ ID NO: 1) and SpT3 siRNA #2, score=80 (SEQ ID NO: 2). In addition to the scoring, BLAST analysis revealed that both siRNAs were highly sequence specific (100% sequence identity between each siRNA and SpT3), targeting SpT3 mRNA at positions 555-573 (SpT3 siRNA #1, SEQ ID NO: 1) and 566-584 (SpT3 siRNA #2, SEQ ID NO: 2) (FIG. 18A).

Figure 21A:
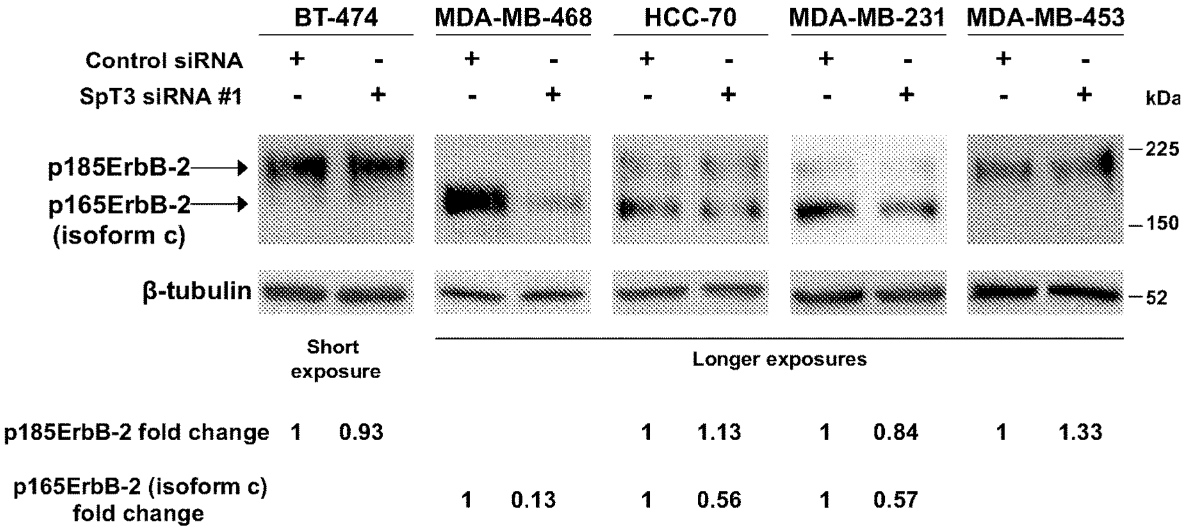
Figures 21B, 21C, 21D, 21E, 21F:
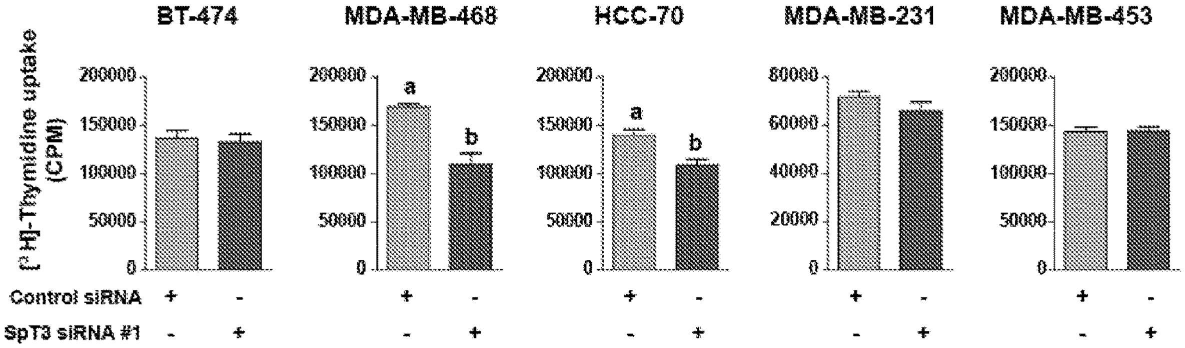

In general a higher scored siRNA should be used. However, although SpT3 siRNA #1 was predicted to be more successful silencing ErbB-2 isoform c than SpT3 siRNA #2, WB analysis showed reduced capacity of SpT3 siRNA #1 as compared to siRNA #2 to block isoform c expression in TNBC cells displaying both isoform c and WTErbB-2 (FIG. 21A). Consistently, SpT3 siRNA #1 had less effect on cell proliferation in TNBC subtypes expressing both isoform c and WTErbB-2 (FIGS. 21B-21F).

Example 5—SpT3 siRNA #2 of the Present Invention Abrogates Tumor Growth in TNBC Having demonstrated the in vitro efficacy of SpT3 siRNAs, the present inventors evaluated the effect of silencing in triple negative tumors the expression of p165ErbB-2 (isoform c) with the siRNA #2. They used an ex vivo methodology to culture MDA-MB-468 human tumor xenografts. This procedure is a modified version of a previously reported technique (Centenera, M. M. et al. (2012) *Evidence for efficacy of new Hsp*90 *inhibitors revealed by ex vivo culture of human prostate tumors*. Clin Cancer Res 18, 3562-3570; Dean, J. L. et al. (2012) *Therapeutic response to CDK*4/6 *inhibition in breast cancer defined by ex vivo analyses of human tumors*. Cell cycle 11, 2756-2761; Ochnik, A. M. et al. (2014) *Antiandrogenic actions of medroxyprogesterone acetate on epithelial cells within normal human breast tissues cultured ex vivo*. Menopause 21, 79-88; Dean, J. L. et al. (2012) op. cit.) Preclinical models like this, that retain the architecture, biomarkers and histological features of original tumours, are much sought after in the field of cancer drug discovery and development. They can predict outcomes in the clinic. Importantly, the inventors established a human TN breast tumor explant that allowed to study, on one hand, TNBC response to their invented siRNAs drugs and, on the other, to reveal in the preclinical setting the role of ErbB-2 isoform c as biomarker in TN tumors. Briefly, two-month-old female NIH(S)-nude mice (La Plata National University, Argentina) were inoculated into their inguinal mammary fat pad with MDA-MB-468 cells ($5\times10^6$/mouse) resuspended in 1:1 v/v DMEM F12: Matrigel (Becton Dickinson, Franklin Lakes, N.J., USA). Once MDA-MB-468 tumors were established (volumes of 50-70 $mm^3$), they were surgically removed and dissected into approximately 1-$mm^3$ using a scalpel. Four tumor pieces were placed on a presoaked gelatin sponge (Johnson and Johnson) in 6-well plates containing 1 mL DMEM F12 with 10% FBS. Tumor explants were cultured at 37° C. in a 5% $CO_2$-enriched atmosphere for 6 hours. Subsequently, medium was removed and tumor explants were treated for 24 hours with SpT3 siRNA #2 (SEQ ID NO: 2), or Control siRNA (SEQ ID NO: 25) at a final concentration of 100 nM, by using DharmaFECT transfection reagent (Dharmacon) according to the manufacturer's instructions. After siRNAs treatment, cultured tumor explants were lysed in ice-cold radioimmunoprecipitation assay buffer (10 mmol/L Tris-HCl, 150 mmol/L NaCl, 1 mmol/L EDTA, 1% Triton X-100) containing protease inhibitor cocktail (Sigma), using the Precellys24 tissue homogenizer (Bertin Technologies). Proteins were then analyzed by immunoblotting with the ErbB-2 C-18 antibody as indicated above. Consistent with inventors' previous results, SpT3 siRNA #2 significantly reduced p165ErbB-2 (isoform c) expression in triple negative tumors (FIG. 22). Next, it was assessed whether modulation of p165ErbB-2 (ErbB-2 isoform c) in primary tumors was associated with TNBC proliferation. For that purpose, Erk5/MAPK7 expression was evaluated. Erk5 is a cancer-related kinase which is overexpressed in TNBC (Al-Ejeh, F. et al. (2014) *Kinome profiling reveals breast cancer heterogeneity and identifies targeted therapeutic opportunities for triple negative breast cancer*. Oncotarget 5, 3145-3158; Hsu, Y. H. et al. (2014) *Definition of PKC-alpha, CDK*6, *and MET as therapeutic targets in triple-negative breast cancer*. Cancer research 74, 4822-4835) and has been associated with TNBC growth (Montero, J. C. et al. (2009) *Expression of Erk*5 *in early stage breast cancer and association with disease free survival identifies this kinase as a potential therapeutic target*. PLoSOne 4, e5565; Ortiz-Ruiz, M. J. et al. (2014) *Therapeutic potential of ERK*5 *targeting in triple negative breast cancer*. Oncotarget 5, 11308-11318). Notably, silencing of p165ErbB-2 (ErbB-2 isoform c) expression in MDA-MB-468 tumor explants strongly decreased Erk5 levels (FIG. 22).

Example 6—SpT3 siRNA #2 of the Present Invention Abrogates TNBC Growth In Vivo In order to determine the in vivo activity of SpT3 siRNA #2 of the present invention, tumor xenografts were developed in nude mice using MDA-MB-468 cells. Mice received intratumoral injections of SpT3 siRNA #2 (SEQ ID NO: 2), or Control siRNA (SEQ ID NO: 31), thrice a week. Tumor volume was measured as a function of time (days) in the xenografts generated for this assay (FIG. 23A and Table 8 below).

TABLE 8

Tumor growth analysis of MDA-MB-468 xenografts treated with either SpT3 siRNA #2 (SEQ ID NO: 2), or Control siRNA (SEQ ID NO: 31).

| | Mean tumor volume ($mm^3$) ± S.D. | Mean growth rate[a] ($mm^3$/day) ± S.D. | % Growth inhibition |
|---|---|---|---|
| Control siRNA | 114.7 ± 7.54* | 2.409 ± 0.2058* | |
| SpT3 siRNA #2 | 44.37 ± 3.49# | 0.022 ± 0.2552# | 61.31[b] |

[a]Growth rates were calculated as the slopes of growth curves.

Volumes and percentage of growth inhibition were calculated at the end of the experiment.

For # vs

*P < 0.001.

[b]With respect to Control siRNA, P < 0.001.

At the end of the experiment, p165ErbB-2 (ErbB-2 isoform c) levels in tumors injected with SpT3 siRNA #2 were significantly knocked down (FIG. 23B) and NErbB-2 levels were decreased as compared with those in tumors injected with Control siRNA (FIGS. 24A and 24B). Histopathological analysis revealed that tumors injected with SpT3 siRNA #2 have significantly lower mitotic figures count per HPF (FIGS. 25A and 25B) and larger percentages of necrosis (FIGS. 25C and 25D) than those injected with Control siRNA.

Importantly, we found no weight loss or signs of overt toxicity in mice that received SpT3 siRNA #2 injections. No significant changes in the hematological parameters (Table 9 below), levels of liver enzymes (FIGS. 26A and 26B), bilirubin and renal function (FIGS. 26C and 26D) were found in SpT3 siRNA #2 treated mice when compared to the control group. Histological examination of major organs such as kidney, liver, lungs, heart, spleen, pancreas and brain did not reveal any pathological changes after SpT3 siRNA #2 treatment'

TABLE 9

Hematological parameters of representative mice treated with either SpT3 siRNA #2 (SEQ ID NO: 2), or Control siRNA (SEQ ID NO: 31).

| Treatment group | Hematocrit (%) | RBC ($\times10^6$ $mm^3$) | WBC ($\times10^3$ $mm^3$) | Hemoglobin (g %) | PLT ($\times10^3$ $mm^3$) | MCV (fl) | MCH (%) | MCHC (g/dL) | DLC (no of cells/100 leukocytes) N(%) | L(%) | M(%) | B(%) | E(%) |
|---|---|---|---|---|---|---|---|---|---|---|---|---|---|
| Control | 36 | 6.37 | 1.6 | 10.8 | 842 | 56.40 | 16.90 | 30.00 | 12 | 80 | 8 | 0 | 0 |
| siRNA | 37 | 6.98 | 1.0 | 12.1 | 893 | 53.70 | 17.40 | 32.40 | 80 | 17 | 3 | 0 | 0 |
| | 40 | 6.57 | 0.7 | 11.9 | 484 | 60.20 | 18.10 | 30.00 | 66 | 21 | 0 | 0 | 13 |
| SpT3 | 37 | 6.70 | 0.6 | 11.3 | 974 | 54.60 | 16.90 | 30.90 | 60 | 36 | 1 | 0 | 3 |
| siRNA | 38 | 6.43 | 0.7 | 10.8 | 213 | 58.30 | 16.90 | 28.90 | 79 | 16 | 0 | 0 | 5 |
| #2 | 28 | 5.17 | 0.6 | 8.1 | 195 | 53.10 | 15.60 | 29.40 | Not reported | | | | |

RBC: Red blood cell (erythrocyte) count; WBC: White blood cell (leukocyte) count; PLT: Platelet count; MCV: Mean corpuscular volume; MCH: Mean corpuscular hemoglobin; MCHC: Mean corpuscular hemoglobin concentration; DLC: Differential leukocyte count; N: Neutrophils; L: Lympocytes; M: Monocytes; B: Basophils, E: Eosinophils.

Additionally, according to this example, it was revealed that ErbB-2 isoform c, encoded by SpT3 and displaying a SDS-PAGE MW of 165 kDa, is located in the nucleus and drives in vitro and in vivo growth of BL and M TNBC subtypes. Accordingly, SpT3 siRNA #2 of the invention proves to be an excellent therapy for TNBC tumors.

Materials and Methods

Patients

The Review Boards on Human Research from Universidad de La Frontera-Hospital de Temuco (Chile) and Hospital General de Agudos "Juan A. Fernández" (Argentina) reviewed and approved the collection of tumor specimens, the survey data, and all clinical and pathological information, as well as the retrospective biomarker analysis on anonymized specimens from their corresponding archival cohorts. Paraffin-embedded tissue sections from 99 consecutively archived triple negative invasive breast carcinomas were selected from the files of the Histopathology Department of Hospital Temuco (from 2001 to 2008) and of Hospital Fernandez (from 2003 to 2015). The median follow-up time was 58.5 months (range 2.4-140.9 months). Pre-established patient inclusion criteria: women aged 18-85 (alive or deceased), diagnosed with stage I-III TNBC as primary tumor, treated with surgery, who received radiotherapy and/or standard chemotherapy with anthracyclins, taxanes and/or platinum compounds in the adjuvant setting. This study was conducted according to the provisions of the Declaration of Helsinki and informed written consents were obtained from all patients before inclusion. The primary endpoints were disease-free survival (DFS), distant metastasis-free survival (DMFS), and local relapse-free survival (LRFS). DFS was defined as the time from BC diagnosis to the first recording of a recurrence or death, whichever came first. DMFS and LRFS were defined as the time from BC diagnosis to the first recording of a distant metastasis or a local recurrence, respectively. Local relapse was defined as recurrences of BC occurring in the ipsilateral breast, regional lymph nodes, and skin from the breast. Distant relapse was defined as recurrences of BC occurring beyond the confines of the ipsilateral breast, chest wall, or regional lymph nodes. Sites of distant relapse included: brain (and central nervous system), liver, lung, bone, pleural/peritoneal, and supraclavicular nodes. The secondary endpoint was the overall survival (OS). Pre-treatment patient staging was classified according to the American Joint Committee on Cancer (AJCC) system (Singletary, S. E. et al. (2002) *Revision of the American Joint Committee on Cancer staging system for breast cancer.* JClinOncol 20, 3628-3636) through the Elston and Ellis histological grading system (Page, D. L. et al. (1995) Histologic grading of breast cancer. Let's do it. *AmJClinPathol* 103, 123-124). Clinicopathological data of the cohort is shown in Table 1.

Cell Lines and Treatments

MDA-MB-468, HCC-70, MDA-MB-231, BT-474, SK-BR-3 and T47D cells were obtained from American Type Culture Collection (Manassas, Va., USA). MDA-MB-453 and HCC-1419 were a gift from DJ Slamon (University of California, Los Angeles, Calif., USA). Luciferase-expressing MDA-MB-231 cells (MDA-MB-231-luc) were kindly provided by MC Hung (University of Texas, M.D. Anderson Cancer Center, Houston, Tex., USA). BT-474, SK-BR-3 and T47D cells were cultured as described previously (Beguelin, W. et al. (2010) op. cit.; Cordo Russo, R. I. et al. (2015) op. cit.; Diaz Flaque, M. C. et al. (2013a) op. cit.; Proietti, C. J. et al. (2009) *Activation of Stat*3 *by heregulin/ErbB*-2 *through the co-option of progesterone receptor signaling drives breast cancer growth.* MolCell Biol 29, 1249-1265; Rivas, M. A. et al. (2010) *Transactivation of ErbB*-2 *induced by tumor necrosis factor alpha promotes NF-kappaB activation and breast cancer cell proliferation.* Breast Cancer ResTreat 122, 111-124). MDA-MB-453 and HCC-1419 cells were cultured as described by DJ Slamon (O'Brien, N. A. et al. (2010) *Activated phosphoinositide* 3-*kinase/AKT signaling confers resistance to trastuzumab but not lapatinib.* MolCancer Ther 9, 1489-1502). MDA-MB-468, HCC-70 and MDA-MB-231 were maintained according to the supplier's instructions. MDA-MB-231-luc cells were cultured as described by MC Hung (Xie, X. et al. (2012) *Targeted expression of BikDD eliminates breast cancer with virtually no toxicity in noninvasive imaging models.* Molecular cancer therapeutics 11, 1915-1924). All cell lines were authenticated by short tandem repeat DNA profiling and were routinely tested for mycoplasma infection. All experiments were performed in complete media. In experiments assessing the effects of heregulin β1 (HRG β1) on ErbB-2 nuclear migration, BT-474 cells were starved in 0.1% charcoalized fetal calf serum for 48 h before stimulation with HRG β1 (40 ng/ml) (R&D Systems Inc.).

Antibodies

The following antibodies were used for Western Blot: rabbit polyclonal anti-ErbB-2 clone C-18 (sc-284, raised against the C-terminus), mouse monoclonal anti-ErbB-2 clone A-2 (sc-393712, raised against the C-terminus), mouse monoclonal anti-ErbB-2 clone C-3 (sc-377344, raised against the N-terminus), and rabbit polyclonal anti-Histone H3 clone C-16 (sc-8654-R), all from Santa Cruz Biotechnology; rabbit polyclonal anti-pErbB-2 Tyr877 (2241) from Cell Signaling Technology; mouse monoclonal anti-6-Tubulin clone T0198 (T0198) from Sigma-Aldrich; rabbit monoclonal anti-Erk5 clone EP791Y (ab40809) from Abcam; and HRP-conjugated secondary antibodies from Vector Laboratories.

The antibodies used for immunofluorescence (IF) and confocal microscopy were anti-ErbB-2 C-18, anti-ErbB-2 A-2, anti-ErbB-2 C-3, and mouse monoclonal anti-green fluorescence protein (GFP) clone B-2 (SC-9996), all from Santa Cruz Biotechnology, and Alexa Fluor-conjugated secondary antibodies from Invitrogen. The antibodies used for immunohistochemistry (IHC) were anti-ErbB-2 C-18 and anti-ErbB-2 A-2, from Santa Cruz Biotechnology.

Western Blot and SDS-PAGE Molecular Weight (MW) Calculation

Total lysates were obtained from cells growing in complete media or subjected to the different treatments. 10-50 μg of lysates were separated on a 6-12% sodium dodecyl sulfate—polyacrylamide gel electrophoresis (SDS-PAGE), transferred to a nitrocellulose membrane and blotted as described (Beguelin, W. et al. (2010) op. cit.) with the antibodies detailed in each experiment. Signal intensities of phospho-ErbB-2 bands were analyzed by densitometry using Image J software (National Institutes of Health) and normalized to total ErbB-2 protein bands. Experiments assessing total protein content were also repeated three to five times and signal intensities were normalized to 6-tubulin bands, used as loading control. Subcellular protein fractionation kit for cultured cells (78840, Thermo Fisher Scientific Inc., Waltham, Mass., USA) was performed in order to obtain cytoplasmic, membrane, and nuclear protein extracts, according to manufacturer's instructions. Molecular weight (MW) determination was performed as described (Guan, Y. et al. (2015) *An equation to estimate the difference between theoretically predicted and SDS PAGE-displayed molecular weights for an acidic peptide*. Scientific reports 5, 13370). Briefly, for each western blot (WB), a MW standard protein ladder (Amersham ECL Rainbow Marker Full range, GE Healthcare) was loaded along with different protein samples. Then, an Rf value, defined as the migration distance of a protein through the gel divided by the migration distance of the dye front, was calculated for each standard protein. The obtained Rf values were plotted against the log(MW) of its corresponding standard protein to get the linear formula log(MW)=aRf+b (where a is the slope and b is the y-intercept). Finally, the Rf value for each protein sample was then obtained and used for the calculation of the SDS-PAGE-displayed MW of the ErbB-2 protein band.

Hierarchical Clustering

Unsupervised hierarchical clustering of BC cells was carried out on the quantification profiles of p185-, p165- and p95-ErbB-2 from WBs. Normalized signal intensities of the different ErbB-2 isoforms were log 2 transformed and clustering analysis was performed using the R's heatmap.2 function. The heatmap and associated dendrogram were generated with the Euclidean distance and complete linkage clustering method without additional normalization. Color scale reflects the standardized expression of each isoform with red indicating highest expression and green indicating lowest expression.

Inhibition of De Novo N-Linked Glycosylation

BT-474 and MDA-MB-468 cells were treated for 15 h with 10 μg/ml tunicamycin (Enzo Life Sciences, Inc.) or dimethyl sulfoxide (DMSO, Merck). Total cells lysates were processed as indicated for WB analysis using the ErbB-2 C-18 antibody. MW calculation was performed as indicated above.

RNA Isolation and RT-qPCR

Total RNA was isolated from cells treated or transfected as indicated by using TRIzol Reagent (Invitrogen) according to manufacturer's protocol. The assessment of purity and concentration of each RNA sample was performed spectrophotometrically at 260 and 280 nm using NanoDrop 2000 (Thermo Fisher Scientific). For cDNA synthesis, 1 μg of total RNA was reverse transcribed using oligo(dT) primers (Biodynamics) and Superscript III Reverse Transcriptase (Invitrogen) following manufacturer's instructions. Reverse transcriptase (RT)-quantitative PCR (qPCR) was performed as described (Beguelin, W. et al. (2010) op. cit.; Venturutti, L. et al. (2015) op. cit.). Details of primer sequences used for the assessment of total ErbB-2 or transcript 3 (SpT3) mRNA levels are indicated, along with the primers used to amplify glyceraldehyde-3-phosphate dehydrogenase (GAPDH) as a normalization control. RT-qPCRs were performed in a StepOne Real Time PCR System (Applied Biosystems) with FastStart Universal SYBR Green Master mix (Roche) using the following cycling conditions: 40 cycles with 15 s of denaturing at 95° C. and annealing/extension at 60° C. for 1 min.

ErbB-2 Alternative Splicing Analysis

Expression analysis of the canonical SpT1 and the transcript variants SpT2 and SpT3 was performed using a long-range PCR (LR-PCR) and a nested PCR approach. First, cDNAs from all cell lines were subjected to LR-PCR using two sets of primers, one of them amplifies the entire coding region of SpT1, SpT4, and ErbB-2416 (LR-PCR1), and the other the entire coding region of SpT2 and SpT3 (LR-PCR2). Nested PCR was then performed using first-round LR-PCR products and variant specific primers spanning the differential regions of SpT1, SpT2 and SpT3. LR-PCRs were performed with a ready-to-use RANGER Mix 2× (BIOLINE), based on the high-fidelity hot-start RANGER DNA Polymerase. Briefly, after cDNA synthesis, 1 μl of RT-PCR product was amplified in a reaction mixture containing 25 μl of manufacturer's supplied buffer which includes RANGER DNA polymerase along with dNTPs and $MgCl_2$, 0.3 μM of each primer, 5% DMSO and nuclease-free water up to 50 μl. LR-PCR reactions were carried out in a Veriti 96 Well Thermal Cycler (Applied Biosystems) under the following conditions: polymerase activation was at 95° C. for 3 min followed by 35 cycles of amplification (98° C. for 20 s, 55° C. for 15 s, 72° C. for 5 min) and a final extension step at 72° C. for 5 min. The LR-PCR products were run on 0.7% agarose gels, visualized by staining with 0.5 μg/ml ethidium bromide (Invitrogen) and purified with the QIAquick gel extraction kit (QIAGEN) according to manufacturer's instructions. To identify the canonical SpT1, 1 μl of purified LR-PCR1 product was subjected to nested PCR using RANGER DNA polymerase (BIOLINE) and specific primers as indicated above. For the study of SpT2 and SpT3, purified LR-PCR2 products were used for nested PCR with Taq DNA polymerase (Invitrogen) and variant-specific primers. This PCR mixture contained 1 μl of LR-PCR2 product, 200 μM dNTPs, 0.5 μM of each primer, 1.5 mM $MgCl_2$, 0.05 U of Taq DNA polymerase in 10×PCR buffer and nuclease-free water up to 20 μl. Nested PCR reactions for SpT2 and SpT3 were also performed in a Veriti 96 Well Thermal Cycler (Applied Biosystems) under the following conditions: a denaturation step at 94° C. for 2 min, followed by 30 cycles at 94° C. for 30 s, 55° C. for 30 s, 72° C. for 40 s, and a final extension step at 72° C. for 5 min. Expression analysis of SpT4 and ErbB-2Δ16 was performed by conventional PCR using Taq DNA polymerase (Invitrogen) and cDNAs from all cell lines as templates. Cycling conditions were similar to those used in nested PCR for SpT2 and SpT3, setting the annealing temperature at 60° C. Specific primers were designed to span the novel splice junctions between exons 25 and 27 (considering the order of exons in SpT1) for the detection of SpT4, and between exons 15 and 17 (according to SpT1) for ErbB-2Δ16. Nested and conventional PCR products were separated on 1.5-2% agarose gels and visualized under UV light by ethidium bromide staining. For amplicon sequence verification, bands were appropriately excised and purified as indicated, and subjected to Sanger sequencing (Macrogen Inc.). Electropherograms were then examined by Chromas software (Version 2.6.4, Technelysium Pty. Ltd.) and FASTA sequences were analyzed using the National Center for Biotechnology Information (NCBI) Basic Local Alignment Search Tool (BLAST) (https://blast.ncbi.nlm.nih.gov/Blast.cgi). To further explore the relative abundance of SpT4 and ErbB-2Δ16, a competitive PCR approach was designed using cDNAs as templates and two primer sets spanning the sequences comprised between exons 25 and 27 (according to SpT1) for SpT4, and between exons 15 and 17 (according to SpT1) for ErbB-2Δ16. Competitive PCR was performed with Taq DNA polymerase as mentioned above, with an annealing temperature set at 60° C. After gel electrophoresis analysis, bands were quantified using ImageJ software. Negative controls lacking either the template or enzyme were included in all PCR experiments.

siRNA Transfections

Four different siRNAs targeting the common coding region of ErbB-2 transcripts 1 to 4 and ErbB-2Δ16 (ErbB-2 siRNA, siGENOME SMARTpool Human ERBB2) were synthesized by Dharmacon. The siDESIGN Center tool from Dharmacon (http://dharmacon.horizondiscovery.com/design-center/) was used to create custom, variant-specific siRNAs targeting SpT3 (SpT3 siRNA #1 and SpT3 siRNA #2). A Control siRNA from Dharmacon that does not target any known mammalian gene was used as negative control. Cells were transfected with the indicated siRNAs at a final concentration of 100 nM for 48 h by using DharmaFECT1 transfection reagent (Dharmacon) according to manufacturer's instructions. In all experiments, the knockdown effects produced by specific siRNAs were assessed at mRNA and protein levels by RT-qPCR and WB, respectively.

Cell Proliferation

Cell proliferation was evaluated by the incorporation of 1 μCi [$^3$H]-thymidine (PerkinElmer; specific activity 6.7 Ci/mmol) during the last 16 hours of the corresponding treatments as previously described (Beguelin, W. et al. (2010) op. cit.; Rivas, M. A. et al. (2012) *Downregulation of the tumor-suppressor miR-16 via progestin-mediated oncogenic signaling contributes to breast cancer development*. Breast Cancer Res 14, R77).

Preclinical Models

For in vivo blockade of ErbB-2 isoform c expression, two-month-old female NIH(S)-nude mice (La Plata National University, Argentina) were inoculated into their inguinal mammary fat pad with $5\times10^6$ MDA-MB-468 cells resuspended in 1:1 v/v DMEM/F12:Matrigel (Corning). Once tumors were established (volume of 50 $mm^3$), mice were randomly divided into two groups (n=6) and received intratumoral injections of SpT3 siRNA #2 (Custom ERBB2 duplex siRNA, Dharmacon, SEQ ID NO: 2) or Control siRNA (Dharmacon, SEQ ID NO: 31) (1 mg/kg) three times a week for three weeks. For each injection, 20 μg of SpT3 siRNA #2 or Control siRNA were appropriately diluted in 25 μl serum free medium (DMEM/F12), and complexed with 1.5 μl DharmaFECT1 transfection reagent (Dharmacon) previously diluted in 25 μl DMEM/F12, according to manufacturer's instructions. Mice were sacrificed two days after the last treatment. Tumor volumes, growth rates and percentage of growth inhibition were calculated as described (Proietti, C. et al. (2005) *Progestins induce transcriptional activation of signal transducer and activator of transcription 3 (Stat3) via a Jak-and Src-dependent mechanism in breast cancer cells*. MolCell Biol 25, 4826-4840). At necropsy, tumor pieces for molecular studies were stored at −80° C. Tumor pieces and whole organ specimens for histopathological examination were fixed in 10% formalin. Blood samples were also collected for performing hematology tests and evaluating serum biochemistry parameters.

Histopathological Analysis

Hematoxylin and eosin (H&E) staining was performed on 5 μm slide sections of MDA-MB-468 tumors, and used for histopathological examination. Mitotic figure counts were performed in 10 consecutive high power fields (HPF, 400× magnification) using a Leica DM500 light microscope (0.45 mm diameter of the HPF). The identification of well-defined mitotic figures was performed as previously described (Baak, J. P. et al. (2005) *Prospective multicenter validation of the independent prognostic value of the mitotic activity index in lymph node-negative breast cancer patients younger than 55 years*. J Clin Oncol 23, 5993-6001; van Diest, P. J. et al. (1992) *Reproducibility of mitosis counting in 2,469 breast cancer specimens: results from the Multicenter Morphometric Mammary Carcinoma Project*. Hum Pathol 23, 603-607). In brief, the most poorly differentiated peripheral area of the tumor was used for counting mitoses. Necrotic, heavily inflamed, or benign areas were avoided. This area, called the measurement area, was minimally 1×1 mm and maximally 5×5 mm. In the measurement area, at 400× magnification (objective 40, field diameter 450 μm at the specimen level), mitoses were counted in 10 consecutive neighboring fields of vision in the most cellular area. Only certain mitoses were counted, doubtful structures and apoptotic bodies were ignored. Percentage of tumor necrosis was evaluated at 40× magnification using a Leica DM500 light microscope as previously described (Elmore, S. A. et al. (2016) *Recommendations from the INHAND Apoptosis/Necrosis Working Group*. Toxicologic pathology 44, 173-188). Necrotic areas were characterized by cell and nuclear swelling, pale eosinophilic cytoplasm, nuclear dissolution (karyolysis), nuclear fragments (karyorrhexis) and loss of cellular detail with shadows of tumor cells visible to variable extent. Some degree of nuclear condensation (pyknosis) may be present. Adjacent cellular debris and inflammation (neutrophils, macrophages, etc.) may also be present if cell membrane leakage or rupture has occurred.

Immunofluorescence (IF) and Confocal Microscopy in Cell Cultures

ErbB-2 was localized using either a rabbit polyclonal (C-18) or a mouse monoclonal (C-3 or A-2) ErbB-2 antibody (all from Santa Cruz Biotechnology). Secondary antibodies for ErbB-2 C-18 were goat anti-rabbit IgG-Alexa Fluor 488 or donkey anti-rabbit IgG-Alexa Fluor 546. For ErbB-2 C-3 or A-2 a goat anti-mouse IgG-Alexa 488 was used, all from Invitrogen. Negative controls were carried out using PBS instead of primary antibodies. When cells were transfected with hErbB-2ΔNLS, green fluorescent protein (GFP) from this expression vector was visualized by direct fluorescence imaging. Cells were analyzed using a Nikon Eclipse E800 confocal laser microscopy system. A quantitative analysis of confocal images with Image J software was performed to evaluate the percentages of ErbB-2 localized at the nucleus and the cytoplasmic membrane. Segmentation of the whole cell was performed using ErbB-2 images. The cytoplasmic membrane compartment was defined as the difference between the image of the cell and a binary erosion (iterations: 5-25), and the nuclear compartment was defined according to the nuclear stain (DAPI (4',6-diamidino-2-phenylindole) or propidium iodide). An integrated density value (mean fluorescence intensity per unit area) was obtained for total ErbB-2 (tErbB-2), for membrane ErbB-2 (mErbB-2), and for nuclear ErbB-2 (nErbB-2). To compute ErbB-2 cellular distribution, the ratio of integrated density of nErbB-2/tErbB-2 (NErbB-2) and mErbB-2/tErbB-2 (MErbB-2) was calculated for at least 50 cells from each group and an average value was obtained. Quantitative analysis of ErbB-2 subcellular localization is expressed as the percentage of MErbB-2 or NErbB-2.

Immunofluorescence (IF) and Immunohistochemistry (IHC) Analysis of TNBC Patient Tissues IF analysis was performed as described (Schillaci, R. et al. (2012) op. cit.). Briefly, antigen retrieval was performed by immersing the sections in 10 mM sodium citrate buffer pH 6 and microwaving at high power for 4 min. Slides were blocked in Modified Hank's Buffer (MHB) with 5% bovine serum albumin for 30 min and were incubated overnight at 4° C. with the following primary antibodies: rabbit polyclonal ErbB-2 C-18 antibody and mouse monoclonal ErbB-2 A-2 antibody, both from Santa Cruz Biotechnology. Slides were then incubated with anti-rabbit or anti-mouse IgG-Alexa 488 antibody (Invitrogen). Reduction of the autofluorescent background was performed by incubation with Sudan Black B 0.1% (MilliporeSigma). Nuclei were stained with DAPI. Slides were analyzed by a Nikon Eclipse E800 confocal laser microscopy system. Negative controls were carried out with MHB instead of primary antibodies. C4HD tumors from the model of mammary tumors induced by progestins were also used as controls (Beguelin, W. et al. (2010) op. cit.). Slides were independently scored by three pathologists. Score discrepancies were re-evaluated and reconciled on a two-headed microscope. Membrane ErbB-2 (MErbB-2) expression levels detected by IF were semiquantified using the same scores as those used in IHC staining (see below). Nuclear ErbB-2 levels detected by IF were scored considering both the percentage of positive cells and staining intensity. A score of 0 represents faint or no staining in less than 10% of cells, 1+ weak nuclear staining in 10-25%, 2+ moderate staining in 26-50%, and 3+ strong staining in >50% of cells. Scores of 2+ and 3+ were considered positive for NErbB-2 presence (Schillaci, R. et al. (2012) op. cit.).

NErbB-2 was also evaluated by IHC with the ErbB-2 C-18 antibody as follows: heat-induced antigen retrieval was performed in 10 mM Tris, 1 mM EDTA pH 9 for 30 min. Slides were incubated with the ErbB-2 C-18 antibody (dilution 1:200) overnight at 4° C. Sections were subsequently incubated with the anti-rabbit EnVision+ System-HRP Labelled Polymer (K4003, Dako, Agilent) and developed using 3,3'-diaminobenzidine chromogen solution (Cell Marque, MilliporeSigma) according to manufacturer's protocol. The score was performed as detailed for IF.

MErbB-2 expression was evaluated by IHC with c-erb-B2 clone A0485 (Dako), as we already described (Schillaci, R. et al. (2012) op. cit.). MErbB-2 was scored according to the American Society of Clinical Oncology/College of American Pathologists (ASCO/CAP) guidelines (Wolff, A. C. et al. (2013) *Recommendations for human epidermal growth factor receptor 2 testing in breast cancer: American Society of Clinical Oncology/College of American Pathologists clinical practice guideline update*. JClinOncol 31, 3997-4013). Scores 2+ in which FISH confirmed ErbB-2 amplification and 3+ were considered positive for MErbB-2 overexpression. Estrogen (ER) and progesterone receptor (PR) were evaluated by IHC with clone 6F11 (Novocastra Laboratories) and clone hPRa2+hPRa3 (NeoMarkers), respectively and scored as described (Schillaci, R. et al. (2012) op. cit.).

Statistics

Analyses were performed using GraphPad Prism 5 (GraphPad) and STATA version 15 (Stata Corp. LLC). Information on biological replicates and statistical significance are reported in the respective figure legends. When two groups were compared, the unpaired two-tailed Student's t-test was used. When three or more groups were compared, the one-way ANOVA with Tukey's or Dunnett's multiple comparisons test was used. Homoscedasticity of the variances was analyzed in every case. No statistical methods were used a priori to pre-determine sample sizes, but sizes were in line with those indicated in previous reports (Cordo Russo, R. I. et al. (2015) op. cit.; Rivas, M. A. et al. (2012) op. cit.). Two way ANOVA with repeated measures plus Bonferroni post-test was applied to assess statistical significance of differences in tumor growth kinetics among groups as previously described (Proietti, C. J. et al. (2015) *Heregulin Co-opts PR Transcriptional Action Via Stat3 Role As a Coregulator to Drive Cancer Growth*. Mol Endocrinol 29, 1468-1485). Comparison of tumor volumes and percentage of growth inhibition among different groups was performed at the end of each experiment and analyzed by unpaired two-tailed Student's t-test test. Growth rates were calculated as the slopes of growth curves. Briefly, linear regression analysis was performed on tumor growth curves and the slopes were compared by using unpaired two-tailed Student's t-test test to evaluate statistical differences. Correlations between categorical variables were performed using $_{X}2$-test or Fisher's exact test when the number of observations obtained for analysis was small. Specifically, Fisher's exact test was selected when the number of expected values was under five, because it uses the exact hypergeometric distribution to compute the P value (Upton, G. J. G. (1992) *Fisher's exact test*. Journal of the Royal Statistical Society Series A Statistics in Society 155, 395-402). Cumulative survival probabilities were calculated according to the Kaplan-Meier method, and statistical significance was analyzed by log-rank test. Multivariate analysis was performed using the Cox multiple hazards model. Adjustment for significant confounders was done to avoid increased bias and variability, unreliable confidence interval coverage, and problems with the model associated to the small size of our sample (Vittinghoff, E. and McCulloch, C. E. (2007) *Relaxing the rule of ten events per variable in logistic and Cox regression*. Am J Epidemiol 165, 710-718). Only variables that were statistically significant in a univariate model were included in the multivariate analysis. Guidelines for Reporting Recommendations for Tumor Marker Prognostic Studies (REMARK) were followed in this work (McShane, L. M. et al. (2005) *Reporting recommendations for tumor marker prognostic studies*. J Clin Oncol 23, 9067-9072). All tests of statistical significance were two-sided. P values <0.05 were regarded as statistically significant.

REFERENCES CITED

U.S. PATENT DOCUMENTS
7,709,198
8,604,182
8,658,361
8,951,726
7,709,198
8,658,361
7,709,198
10,011,836
8,008,474
7,816,512
7,977,471
9,080,171
5,849,902
10,138,485
5,162,115
5,051,257
U.S. PATENT APPLICATIONS
2019/0024082
2016/0319278
FOREIGN PATENT DOCUMENTS
EP 1527176
WO 2008/104978
WO 98/13526

OTHER PUBLICATIONS

Akinc, A. et al. (2008) A combinatorial library of lipid-like materials for delivery of RNAi therapeutics. Nature biotechnology 26, 561-569.

Al-Ejeh, F. et al. (2014) Kinome profiling reveals breast cancer heterogeneity and identifies targeted therapeutic opportunities for triple negative breast cancer. Oncotarget 5, 3145-3158.

Anido, J. et al. (2006) Biosynthesis of tumorigenic HER2 C-terminal fragments by alternative initiation of translation. EMBO J 25, 3234-3244.

Baak, J. P. et al. (2005) Prospective multicenter validation of the independent prognostic value of the mitotic activity index in lymph node-negative breast cancer patients younger than 55 years. J Clin Oncol 23, 5993-6001.

Beguelin, W. et al. (2010) Progesterone receptor induces ErbB-2 nuclear translocation to promote breast cancer growth via a novel transcriptional effect: ErbB-2 function as a coactivator of Stat3. MolCell Biol 30, 5456-5472.

Biscans, A. et al. (2019) Diverse lipid conjugates for functional extra-hepatic siRNA delivery in vivo. Nucleic acids research 47, 1082-1096.

Blom, N. et al. (2004) Prediction of post-translational glycosylation and phosphorylation of proteins from the amino acid sequence. Proteomics 4, 1633-1649.

Bramsen, J. B. et al. (2010) A screen of chemical modifications identifies position-specific modification by UNA to most potently reduce siRNA off-target effects. Nucleic acids research 38, 5761-5773.

Brand, T. M. et al. (2014) Nuclear epidermal growth factor receptor is a functional molecular target in triple-negative breast cancer. Molecular cancer therapeutics 13, 1356-1368.

Burstein, M. D. et al. (2015) Comprehensive genomic analysis identifies novel subtypes and targets of triple-negative breast cancer. ClinCancer Res. 21, 1688-1698.

Byrne, M. et al. (2013) Novel hydrophobically modified asymmetric RNAi compounds (sd-rxRNA) demonstrate robust efficacy in the eye. J Ocul Pharmacol Ther 29, 855-864.

Castiglioni, F. et al. (2006) Role of exon-16-deleted HER2 in breast carcinomas. Endocr Relat Cancer 13, 221-232.

Centenera, M. M. et al. (2012) Evidence for efficacy of new Hsp90 inhibitors revealed by ex vivo culture of human prostate tumors. Clin Cancer Res 18, 3562-3570.

Cordo Russo, R. I. et al. (2015) Targeting ErbB-2 nuclear localization and function inhibits breast cancer growth and overcomes trastuzumab resistance. Oncogene 34, 3413-3428.

Chernikov, I. V. et al. (2019) Current Development of siRNA Bioconjugates: From Research to the Clinic. Frontiers in pharmacology 10, 444.

Chu, C. Y. and Rana, T. M. (2008) Potent RNAi by short RNA triggers. RNA 14, 1714-1719.

De Paula, D. et al. (2007) Hydrophobization and bioconjugation for enhanced siRNA delivery and targeting. RNA 13, 431-456.

Dean, J. L. et al. (2012) Therapeutic response to CDK4/6 inhibition in breast cancer defined by ex vivo analyses of human tumors. Cell cycle 11, 2756-2761.

Diaz Flaque, M. C. et al. (2013a) Progesterone receptor assembly of a transcriptional complex along with activator protein 1, signal transducer and activator of transcription 3 and ErbB-2 governs breast cancer growth and predicts response to endocrine therapy. Breast Cancer Res 15, R118.

Diaz Flaque, M. C. et al. (2013b) Progestin drives breast cancer growth by inducing p21 (CIP1) expression through the assembly of a transcriptional complex among Stat3, progesterone receptor and ErbB-2. Steroids 78, 559-567.

Didiot, M. C. et al. (2016) Exosome-mediated Delivery of Hydrophobically Modified siRNA for Huntingtin mRNA Silencing. Mol Ther 24, 1836-1847.

Elbashir, S. M. et al. (2001) Duplexes of 21-nucleotide RNAs mediate RNA interference in cultured mammalian cells. Nature 411, 494-498.

Elmore, S. A. et al. (2016) Recommendations from the INHAND Apoptosis/Necrosis Working Group. Toxicologic pathology 44, 173-188.

Emanuelsson, O. et al. (2007) Locating proteins in the cell using TargetP, SignalP and related tools. Nature protocols 2, 953-971.

Fire, A. et al. (1998) Potent and specific genetic interference by double-stranded RNA in Caenorhabditis elegans. Nature 391, 806-811.

Frei, A. P. et al. (2012) Direct identification of ligand-receptor interactions on living cells and tissues. Nature biotechnology 30, 997-1001.

Garrido-Castro, A. C. et al. (2019) Insights into Molecular Classifications of Triple-Negative Breast Cancer: Improving Patient Selection for Treatment. Cancer discovery 9, 176-198.

Gautrey, H. et al. (2015) SRSF3 and hnRNP H1 regulate a splicing hotspot of HER2 in breast cancer cells. RNABiol 12, 1139-1151.

Goldberg, M. S. and Sharp, P. A. (2012) Pyruvate kinase M2-specific siRNA induces apoptosis and tumor regression. J Exp Med 209, 217-224.

Guan, Y. et al. (2015) An equation to estimate the difference between theoretically predicted and SDS PAGE-displayed molecular weights for an acidic peptide. Scientific reports 5, 13370.

Guo, W. et al. (2006) Beta 4 integrin amplifies ErbB2 signaling to promote mammary tumorigenesis. Cell 126, 489-502.

Henderson, I. C. and Patek, A. J. (1998) The relationship between prognostic and predictive factors in the management of breast cancer. Breast Cancer Res Treat 52, 261-288.

Hsu, Y. H. et al. (2014) Definition of PKC-alpha, CDK6, and MET as therapeutic targets in triple-negative breast cancer. Cancer research 74, 4822-4835.

Hutvagner, G. and Zamore, P. D. (2002) A microRNA in a multiple-turnover RNAi enzyme complex. Science 297, 2056-2060. Janas, M. M. et al. (2017) Impact of Oligonucleotide Structure, Chemistry, and Delivery Method on In Vitro Cytotoxicity. Nucleic acid therapeutics 27, 11-22.

Khvorova, A. and Watts, J. K. (2017) The chemical evolution of oligonucleotide therapies of clinical utility. Nature biotechnology 35, 238-248.

Kim, H. P. et al. (2009) Lapatinib, a dual EGFR and HER2 tyrosine kinase inhibitor, downregulates thymidylate synthase by inhibiting the nuclear translocation of EGFR and HER2. PLoSOne 4, e5933.

Kisielow, M. et al. (2002) Isoform-specific knockdown and expression of adaptor protein ShcA using small interfering RNA. The Biochemical journal 363, 1-5.

Kwong, K. Y. and Hung, M. C. (1998) A novel splice variant of HER2 with increased transformation activity. Mol Carcinog 23, 62-68.

Lehmann, B. D. et al. (2011) Identification of human triple-negative breast cancer subtypes and preclinical models for selection of targeted therapies. JClinInvest 121, 2750-2767.

Lehmann, B. D. et al. (2016) Refinement of Triple-Negative Breast Cancer Molecular Subtypes: Implications for Neoadjuvant Chemotherapy Selection. PloS one 11, e0157368.

Li, L. Y. et al. (2011) Nuclear ErbB2 enhances translation and cell growth by activating transcription of ribosomal RNA genes. Cancer Res 71, 4269-4279.

Li, X. et al. (2012) The atypical histone macroH2A1.2 interacts with HER-2 protein in cancer cells. JBiolChem 287, 23171-23183.

Lieberman, J. (2018) Tapping the RNA world for therapeutics. Nature structural & molecular biology 25, 357-364.

Manoharan, M. et al. (2011) Unique gene-silencing and structural properties of 2'-fluoro-modified siRNAs. Angew Chem Int Ed Engl. 50, 2284-2288.

McShane, L. M. et al. (2005) Reporting recommendations for tumor marker prognostic studies. J Clin Oncol 23, 9067-9072.

Mitra, D. et al. (2009) An oncogenic isoform of HER2 associated with locally disseminated breast cancer and trastuzumab resistance. Molecular cancer therapeutics 8, 2152-2162.

Montero, J. C. et al. (2009) Expression of Erk5 in early stage breast cancer and association with disease free survival identifies this kinase as a potential therapeutic target. PLoSOne 4, e5565.

Nielsen, H. (2017) Predicting Secretory Proteins with SignalP. Methods in molecular biology 1611, 59-73.

O'Brien, N. A. et al. (2010) Activated phosphoinositide 3-kinase/AKT signaling confers resistance to trastuzumab but not lapatinib. MolCancer Ther 9, 1489-1502.

Ochnik, A. M. et al. (2014) Antiandrogenic actions of medroxyprogesterone acetate on epithelial cells within normal human breast tissues cultured ex vivo. Menopause 21, 79-88.

Ortiz-Ruiz, M. J. et al. (2014) Therapeutic potential of ERK5 targeting in triple negative breast cancer. Oncotarget 5, 11308-11318.

Page, D. L. et al. (1995) Histologic grading of breast cancer. Let's do it. AmJClinPathol 103, 123-124.

Perou, C. M. et al. (2000) Molecular portraits of human breast tumours. Nature 406, 747-752.

Poeck, H. et al. (2008) 5'-triphosphate-siRNA: turning gene silencing and Rig-I activation against melanoma. Nature Medicine 14, 1256-1263

Prat, A. et al. (2013a) Molecular characterization of basal-like and non-basal-like triple-negative breast cancer. The oncologist 18, 123-133.

Prat, A. et al. (2013b) Characterization of cell lines derived from breast cancers and normal mammary tissues for the study of the intrinsic molecular subtypes. Breast cancer research and treatment 142, 237-255.

Proietti, C. et al. (2005) Progestins induce transcriptional activation of signal transducer and activator of transcription 3 (Stat3) via a Jak- and Src-dependent mechanism in breast cancer cells. MolCell Biol 25, 4826-4840.

Proietti, C. J. et al. (2015) Heregulin Co-opts PR Transcriptional Action Via Stat3 Role As a Coregulator to Drive Cancer Growth. MolEndocrinol 29, 1468-1485.

Proietti, C. J. et al. (2009) Activation of Stat3 by heregulin/ErbB-2 through the co-option of progesterone receptor signaling drives breast cancer growth. MolCell Biol 29, 1249-1265.

Provost, P. et al. (2002) Ribonuclease activity and RNA binding of recombinant human Dicer. The EMBO journal 21, 5864-5874.

Rivas, M. A. et al. (2010) Transactivation of ErbB-2 induced by tumor necrosis factor alpha promotes NF-kappaB activation and breast cancer cell proliferation. Breast Cancer ResTreat 122, 111-124.

Rivas, M. A. et al. (2012) Downregulation of the tumor-suppressor miR-16 via progestin-mediated oncogenic signaling contributes to breast cancer development. Breast Cancer Res 14, R77.

Ross, J. S. et al. (2009) The HER-2 receptor and breast cancer: ten years of targeted anti-HER-2 therapy and personalized medicine. Oncologist 14, 320-368.

Scaltriti, M. et al. (2007) Expression of p95HER2, a truncated form of the HER2 receptor, and response to anti-HER2 therapies in breast cancer. J Natl Cancer Inst 99, 628-638.

Schillaci, R. et al. (2012) Clinical relevance of ErbB-2/HER2 nuclear expression in breast cancer. BMCCancer 12, 74.

Schmid, P. et al. (2018) Atezolizumab and Nab-Paclitaxel in Advanced Triple-Negative Breast Cancer. N Engl J Med 379, 2108-2121.

Singletary, S. E. et al. (2002) Revision of the American Joint Committee on Cancer staging system for breast cancer. JClinOncol 20, 3628-3636.

Slamon, D. J. et al. (1989) Studies of the HER-2/neu proto-oncogene in human breast and ovarian cancer. Science 244, 707-712.

Sun, X. et al. (2008) Asymmetric RNA duplexes mediate RNA interference in mammalian cells. Nature biotechnology 26, 1379-1382.

Turpin, J. et al. (2016) The ErbB2DeltaEx16 splice variant is a major oncogenic driver in breast cancer that promotes a pro-metastatic tumor microenvironment. Oncogene 35, 6053-6064.

Upton, G. J. G. (1992) Fisher's exact test. Journal of the Royal Statistical Society Series A Statistics in Society 155, 395-402.
van Diest, P. J. et al. (1992) Reproducibility of mitosis counting in 2,469 breast cancer specimens: results from the Multicenter Morphometric Mammary Carcinoma Project. Hum Pathol 23, 603-607.
Venturutti, L. et al. (2016) Stat3 regulates ErbB-2 expression and co-opts ErbB-2 nuclear function to induce miR-21 expression, PDCD4 downregulation and breast cancer metastasis. Oncogene 35, 2208-2222.
Vittinghoff, E. and McCulloch, C. E. (2007) Relaxing the rule of ten events per variable in logistic and Cox regression. Am J Epidemiol 165, 710-718.
Wang, F. et al. (2012) RNAscope: a novel in situ RNA analysis platform for formalin-fixed, paraffin-embedded tissues. JMD 14, 22-29.
Wang, S. C. et al. (2004) Binding at and transactivation of the COX-2 promoter by nuclear tyrosine kinase receptor ErbB-2. Cancer Cell 6, 251-261.
Warri, A. M. et al. (1996) Anti-oestrogen stimulation of ERBB2 ectodomain shedding from BT-474 human breast cancer cells with ERBB2 gene amplification. Eur J Cancer 32A, 134-140.
Watanabe, M. et al. (2013) Improvement of mass spectrometry analysis of glycoproteins by MALDI-MS using 3-aminoquinoline/alpha-cyano-4-hydroxycinnamic acid. Analytical and bioanalytical chemistry 405, 4289-4293.
Wolff, A. C. et al. (2013) Recommendations for human epidermal growth factor receptor 2 testing in breast cancer: American Society of Clinical Oncology/College of American Pathologists clinical practice guideline update. JClinOncol 31, 3997-4013.
Xie, X. et al. (2012) Targeted expression of BikDD eliminates breast cancer with virtually no toxicity in noninvasive imaging models. Molecular cancer therapeutics 11, 1915-1924.
Xu, W. et al. (2007) Loss of Hsp90 association up-regulates Src-dependent ErbB2 activity. MolCell Biol 27, 220-228.

The invention claimed is:

1. A double stranded siRNA molecule targeted to ErbB-2 alternative mRNA variant 3 SEQ ID NO: 32), which encodes the non-canonical isoform c of ErbB-2 (SEQ ID NO: 33), wherein said siRNA molecule comprises the sequence selected from SEQ ID NO: 1 or SEQ ID NO: 2, and said siRNA molecule targets the 5' UTR and 5' coding region, from nucleotides 545 to 610, of ErbB-2 alternative mRNA variant 3.

2. The siRNA molecule according to claim 1, wherein said siRNA molecule comprises a duplex region and no overhangs wherein the duplex region comprises a sense strand and an antisense strand, wherein said sense strand and said antisense strand together form said duplex region and said duplex region is 19-30 base pairs in length and said antisense strand comprises a sequence that is complementary to the 5' UTR and 5' coding region, from nucleotides 545 to 610, of the ErbB-2 alternative mRNA variant 3.

3. The siRNA molecule according to claim 1, wherein the sequence selected from SEQ ID NO:1 or SEQ ID NO: 2 is 5' GUGAGAUACUUCAAAGAUU 3' SEQ ID NO: 11.

4. The siRNA molecule according to claim 1, wherein the sequence selected from SEQ ID NO: 1 or SEQ ID NO: 2 is 5' CAAAGAUUCCAGAAGAUAU 3' SEQ ID NO: 21.

5. The siRNA according to claim 2, wherein the sense strand and the antisense strand each comprise one or more chemically-modified nucleotides.

6. The siRNA according to claim 5, wherein the chemically-modified nucleotides include at least one 2'F or 2'OMe modifications.

7. The siRNA according to claim 5, wherein chemically-modified nucleotides include at least one hydrophobic modification.

8. The siRNA according to claim 5, wherein chemically-modified nucleotides are phosphorothioate modified.

9. The siRNA of claim 1, wherein the siRNA is linked to a hydrophobic moiety.

10. A pharmaceutical composition comprising the siRNA molecule according to any one of claims 1-9, together with a pharmaceutically acceptable excipient or carrier.

11. The pharmaceutical composition according to claim 10, further comprising an additional anti-cancer agent.

12. The pharmaceutical composition according to claim 11, wherein the additional anti-cancer agent is selected from the group consisting of radiotherapeutic agents and factors; antibiotics including doxorubicin, daunorubicin, mitomycin, actinomycin D, and bleomycin; chemotherapeutic agents including cisplatin, VP16, adriamycin, verapamil, and podophyllotoxin; tumor necrosis factor; plant alkaloids including taxol, vincristine, and vinblastine; alkylating agents including carmustine, melphalan, cyclophosphamide, chlorambucil, busulfan, and lomustine; chemotherapy treatments with carboplatin, capecitabine and cyclophosphamide; anti-androgen receptor (AR) therapies using bicalutamide or enzalutamide; treatment with the anti-PD-11 antibodies nivolumab, pembrolizumab, atezolizumab, avelumab and durvalumab; endocrine therapy for estrogen receptor-beta-positive TNBC, using toremifene or anastrozole; immunotherapy with the PVX-410 multi-peptide vaccine; treatment with: the anti-EGF-R antibody cetuximab; the Hedgehog signaling inhibitor vismodegib; the anti-vascular endothelial growth factor receptor (VEGF-R) monoclonal antibody bevacizumab; the poly (ADP Ribose) polymerase inhibitors olaparib, talazoparib and veliparib; phosphoinositide 3-kinase (PI3K), AKT and mammalian target of rapamycin (mTOR) inhibitors including the pan-PI3K inhibitor buparlisib (BKM120), the mTOR inhibitor everolimus, and the three AKT isoforms inhibitor Ipatasertib; and MEK Inhibitors including cobimetinib.

13. The pharmaceutical composition according to claim 10, wherein the composition is a medicament for the treatment of breast cancer.

14. The pharmaceutical composition of claim 13, wherein the breast cancer is triple negative breast cancer.

15. A method for the treatment of triple negative breast cancer, comprising administration of a siRNA molecule according to claim 1.

16. A method for the treatment of triple negative breast cancer, comprising administration of a pharmaceutical composition according to claim 10.

17. The siRNA of claim 1, wherein the siRNA is formulated for intravenous administration, subcutaneous administration or intratumoral administration.

18. A method for inhibiting in vitro proliferation of triple negative breast cancer (TNBC) cells, comprising administration of the siRNA molecules according to claim 1.

19. An siRNA molecule according to claim 1, wherein said siRNA molecule comprises a duplex region and at least one overhang, each overhang having up to six or fewer nucleotides, wherein the duplex region comprises a sense strand and an antisense strand, said sense strand and said antisense strand together form said duplex region and said duplex region is 19-30 base pairs in length and said antisense strand comprises a sequence that is complementary to the 5' UTR and 5' coding region, from nucleotides 545 to 610, of the ErbB-2 alternative mRNA variant 3.

20. The siRNA according to claim 19, wherein the sense strand and the antisense strand each comprise one or more chemically-modified nucleotides.

21. The siRNA according to claim 20, wherein the one or more chemically-modified nucleotides are selected from 2'F modification, 2'OMe modification, hydrophobic modification, and phosphorothioate modified nucleotides.

22. The siRNA according to claim 19, wherein the sense strand and the antisense strand each consists of chemically-modified nucleotides.

23. The siRNA according to claim 22, wherein the chemically-modified nucleotides are selected from 2'F modification, 2'OMe modification, hydrophobic modification, and phosphorothioate modified nucleotides.

24. The siRNA of claim 19, wherein the siRNA is linked to a hydrophobic moiety.

25. The siRNA according to claim 2, wherein the sense strand and the antisense strand each consists of chemically-modified nucleotides.

26. The siRNA according to claim 25, wherein the chemically-modified nucleotides are selected from 2'F modification, 2'OMe modification, hydrophobic modification, and phosphorothioate modified nucleotides.

27. The siRNA of claim 2, wherein the siRNA is linked to a hydrophobic moiety.

28. The siRNA according to claim 1 comprising one or more one chemically-modified nucleotides.

29. The siRNA according to claim 28, wherein the one or more chemically-modified nucleotides are selected from 2'F modification, 2'OMe modification, hydrophobic modification, and phosphorothioate modified nucleotides.

30. A pharmaceutical composition comprising the siRNA molecule according to claims 19-29, together with a pharmaceutically acceptable excipient or carrier.

31. The pharmaceutical composition according to claim 30, further comprising an additional anti-cancer agent.

* * * * *